US012655195B2

(12) United States Patent
Levin et al.

(10) Patent No.: US 12,655,195 B2
(45) Date of Patent: Jun. 16, 2026

(54) HLA CLASS II-RESTRICTED DQ T CELL RECEPTORS AGAINST RAS WITH G13D MUTATION

(71) Applicant: The United States of America, as represented by the Secretary, Department of Health and Human Services, Bethesda, MD (US)

(72) Inventors: Noam Levin, Rockville, MD (US); Frank J. Lowery, III, Clarksburg, MD (US); Biman C. Paria, Germantown, MD (US); Steven A. Rosenberg, Potomac, MD (US); Rami Yoseph, Gaithersburg, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 617 days.

(21) Appl. No.: 18/027,981

(22) PCT Filed: Oct. 1, 2021

(86) PCT No.: PCT/US2021/053060
§ 371 (c)(1),
(2) Date: Mar. 23, 2023

(87) PCT Pub. No.: WO2022/072760
PCT Pub. Date: Apr. 7, 2022

(65) Prior Publication Data
US 2023/0365649 A1 Nov. 16, 2023

Related U.S. Application Data

(60) Provisional application No. 63/086,674, filed on Oct. 2, 2020.

(51) Int. Cl.
| | |
|---|---|
| *C07K 14/725* | (2006.01) |
| *A61K 35/17* | (2025.01) |
| *A61K 40/11* | (2025.01) |
| *A61K 40/32* | (2025.01) |
| *A61K 40/42* | (2025.01) |
| *C07K 14/705* | (2006.01) |
| *C12N 5/0783* | (2010.01) |

(52) U.S. Cl.
CPC .......... *C07K 14/7051* (2013.01); *A61K 35/17* (2013.01); *A61K 40/11* (2025.01); *A61K 40/32* (2025.01); *A61K 40/4253* (2025.01); *C12N 5/0636* (2013.01)

(58) Field of Classification Search
None
See application file for complete search history.

(56) References Cited

U.S. PATENT DOCUMENTS

| | | | |
|---|---|---|---|
| 8,034,334 B2 | 10/2011 | Dudley et al. | |
| 8,383,099 B2 | 2/2013 | Dudley et al. | |
| 10,556,940 B2 | 2/2020 | Tran et al. | |
| 10,611,816 B2 | 4/2020 | Tran et al. | |
| 11,306,132 B2 | 4/2022 | Yoseph et al. | |
| 2010/0286143 A1* | 11/2010 | Dias-Santagata .... | C12Q 1/6886 |
| | | | 514/266.4 |
| 2012/0244133 A1 | 9/2012 | Rosenberg et al. | |
| 2014/0134158 A1* | 5/2014 | Bardelli ................. | A61K 31/21 |
| | | | 435/6.12 |
| 2017/0319638 A1 | 11/2017 | Conner et al. | |
| 2019/0374628 A1 | 12/2019 | Eriksen | |

FOREIGN PATENT DOCUMENTS

| | | | | |
|---|---|---|---|---|
| CN | 108395479 A | 8/2018 | | |
| DE | 102019121007 A1 * | 2/2021 | .............. | A61P 35/00 |
| JP | 2018-535647 A | 12/2018 | | |
| JP | 2019-527555 A | 10/2019 | | |
| TW | 201920251 A | 6/2019 | | |
| WO | WO 2016/085904 A1 | 6/2016 | | |
| WO | WO-2017194555 A1 * | 11/2017 | .............. | A61P 35/02 |
| WO | WO-2018067618 A1 * | 4/2018 | .............. | A61K 39/12 |
| WO | 2019/060349 A1 | 3/2019 | | |
| WO | WO-2019069125 A1 * | 4/2019 | .............. | C07K 16/00 |
| WO | WO 2019/112941 A1 | 6/2019 | | |

(Continued)

OTHER PUBLICATIONS

Riley and Baker. The intersection of affinity and specificity in the development andoptimization of T cell receptor based therapeutics. Seminars in Cell & Developmental Biology 84 (2018) 30-41. (Year: 2018).*

Lee et al. Ex Vivo Radiolabeling and In Vivo PET Imaging of T cells Expressing Nuclear Reporter Genes. Springer Protocols, Springer Nature 2018, Reporter Gene Imaging: Methods and Protocols, Methods in Molecular Biology, vol. 1790. (Year: 2018).*

Cafri et al., "Memory T cells targeting oncogenic mutations detected in peripheral blood of epithelial cancer patients", *Nature Communications*, 10: 449, 1-9 (2019).

Charitou et al., "Transcriptional and metabolic rewiring of colorectal cancer cells expressing the oncogenic KRASG13D mutation", *British Journal of Cancer*, 121: 37-50 (2019).

(Continued)

*Primary Examiner* — Julie Wu
*Assistant Examiner* — Amy M. Chattin
(74) *Attorney, Agent, or Firm* — Leydig, Voit & Mayer

(57) ABSTRACT

Disclosed is an isolated or purified T cell receptor (TCR), wherein the TCR has antigenic specificity for a mutated human RAS amino acid sequence with a substitution of glycine at position 13 with aspartic acid. The TCRs may recognize G13D RAS presented by an HLA-DQ heterodimer. Related polypeptides and proteins, as well as related nucleic acids, recombinant expression vectors, host cells, populations of cells, and pharmaceutical compositions are also provided. Also disclosed are methods of detecting the presence of cancer in a mammal and methods of treating or preventing cancer in a mammal.

21 Claims, 43 Drawing Sheets

Figure 1:
Figure 1:
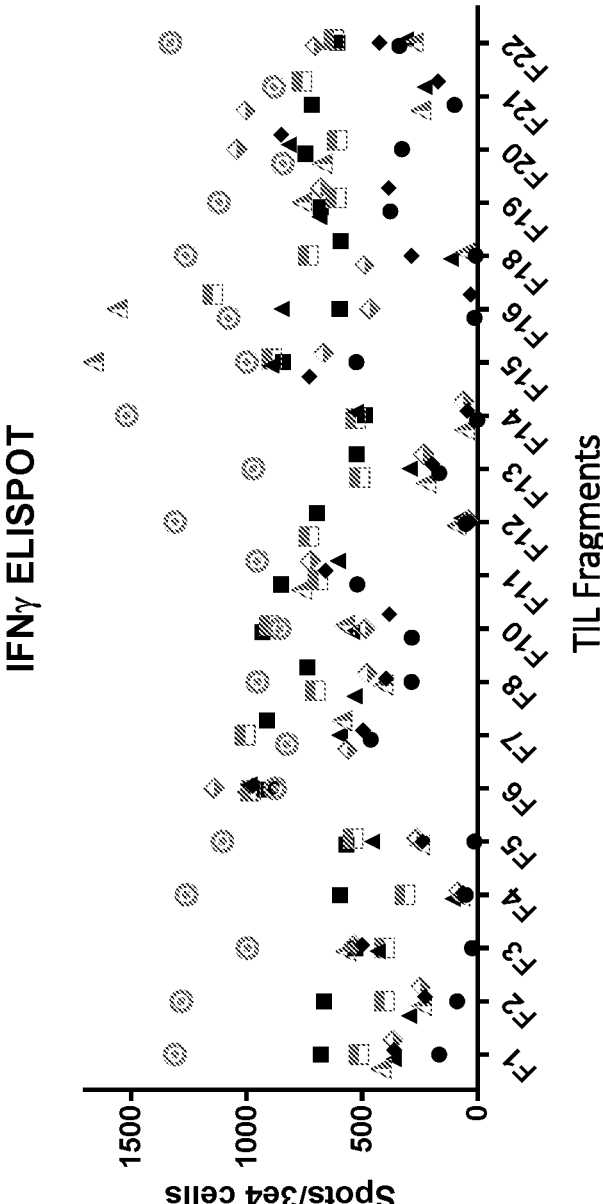

Specification includes a Sequence Listing.

(56) References Cited

FOREIGN PATENT DOCUMENTS

| WO | WO 2019/195492 A1 | 10/2019 | |
| WO | WO-2019246286 A1 * | 12/2019 | .......... C12Q 1/6886 |
| WO | 2020/037239 A1 | 2/2020 | |
| WO | 2020/154617 A1 | 7/2020 | |
| WO | WO-2020145222 A1 * | 7/2020 | ............. A61P 35/00 |
| WO | WO-2020150364 A1 * | 7/2020 | ............. A61K 40/46 |
| WO | WO-2020191365 A1 * | 9/2020 | ............. C40B 30/06 |
| WO | WO-2020257288 A2 * | 12/2020 | ......... C07K 14/7051 |
| WO | WO 2021/163434 A1 | 8/2021 | |
| WO | WO 2021/170684 A1 | 9/2021 | |
| WO | WO-2021250511 A1 * | 12/2021 | ......... A61K 40/4202 |

OTHER PUBLICATIONS

Cohen et al., "Enhanced Antitumor Activity of Murine-Human Hybrid T-Cell Receptor (TCR) in Human Lymphocytes Is Associated with Improved Pairing and TCR/CD3 Stability", *Cancer Research*, 66(17): 8878-8886 (2006).

Cohen et al., "Enhanced Antitumor Activity of T Cells Engineered to Express T Cell Receptors with a Second Disulfide Bond", *Cancer Research*, 67(8): 3898-3903 (2007).

Cox et al., "Drugging the undruggable RAS: Mission possible?", *Nature Reviews Drug Discovery*, 13(11): 828-851 (2014).

Dudley et al., "Generation of tumor-infiltrating lymphocyte cultures for use in adoptive transfer therapy for melanoma patients", *Journal of Immunotherapy*, 26(4): 332-342 (2003).

European Patent Office, International Search Report and Written Opinion issued in the International Patent Application No. PCT/US2021/053060, mailed on Feb. 14, 2022.

Haga-Friedman et al., "Incorporation of Transmembrane Hydrophobic Mutations in the TCR Enhance Its Surface Expression and T Cell Functional Avidity", *Journal of Immunology*, 188(11): 5538-5546 (2012).

Riddell et al., "The use of anti-CD3 and anti-CD28 monoclonal antibodies to clone and expand human antigen-specific T cells", *Journal of Immunological Methods*, 128: 189-201 (1990).

Rive et al., "Recombinant T cell receptors specific for HLA-A*02:01-restricted neoepitopes containing KRAS codon 12 hotspot mutations", *BioRxiv*, 1-23 (2020).

Shiota et al., "Somatic Mosaicism for a NRAS Mutation Associates with Disparate Clinical Features in RAS-associated Leukoproliferative Disease: a Report of Two Cases", *Journal of Clinical Immunology*, 35(5): 454-458 (2015).

Szymczak et al., "Correction of multi-gene deficiency in vivo using a single 'self-cleaving' 2A peptide-based retroviral vector", *Nature Biotechnology*, 22(5): 589-594 (2004).

Tran et al., "Cancer immunotherapy based on mutation-specific CD4+ T cells in a patient with epithelial cancer", *Science*, 344: 641-645 (2014).

Tran et al., "T-Cell Transfer Therapy Targeting Mutant KRAS in Cancer", *The New England Journal of Medicine*, 375(23): 2255-2262 (2016).

Wang et al., "Identification of T-cell Receptors Targeting KRAS-Mutated Human Tumors", *Cancer Immunology Research*, 4(3): 204-214 (2016).

Chatani et al., "Mutated RAS: Targeting the "Untargetable" with T Cells." Clin Cancer Res. ;26(3):537-544. (2020).

Iiizumi et al., "Identification of Novel HLA Class II-Restricted Neoantigens Derived from Driver Mutations", *Cancers*, 11(266), pp. 1-14 (2019).

* cited by examiner

- FL WT
- FL G13D
- WT LP
- G13D LP
- G13D ME Mix
- DMSO
- T cell only
- CD3/CD28

IFNγ ELISPOT

SEQUENCE LISTING

```
<160> NUMBER OF SEQ ID NOS: 253

<210> SEQ ID NO 1
<211> LENGTH: 6
<212> TYPE: PRT
<213> ORGANISM: Homo sapiens

<400> SEQUENCE: 1

Asn Ser Ala Phe Gln Tyr
1               5

<210> SEQ ID NO 2
<211> LENGTH: 6
<212> TYPE: PRT
<213> ORGANISM: Homo sapiens

<400> SEQUENCE: 2

Thr Tyr Ser Ser Gly Asn
1               5

<210> SEQ ID NO 3
<211> LENGTH: 12
<212> TYPE: PRT
<213> ORGANISM: Homo sapiens

<400> SEQUENCE: 3

Cys Ala Met Arg Ala Asn Thr Asp Lys Leu Ile Phe
1               5                   10

<210> SEQ ID NO 4
<211> LENGTH: 5
<212> TYPE: PRT
<213> ORGANISM: Homo sapiens

<400> SEQUENCE: 4

Met Asp His Glu Asn
1               5

<210> SEQ ID NO 5
<211> LENGTH: 6
<212> TYPE: PRT
<213> ORGANISM: Homo sapiens

<400> SEQUENCE: 5

Ser Tyr Asp Val Lys Met
1               5

<210> SEQ ID NO 6
<211> LENGTH: 12
<212> TYPE: PRT
<213> ORGANISM: Homo sapiens

<400> SEQUENCE: 6

Cys Ala Ser Arg Leu Gly Asn Thr Gly Glu Leu Phe
1               5                   10

<210> SEQ ID NO 7
<211> LENGTH: 110
```

```
<212> TYPE: PRT
<213> ORGANISM: Homo sapiens

<400> SEQUENCE: 7

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
        50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro
                100                 105                 110

<210> SEQ ID NO 8
<211> LENGTH: 112
<212> TYPE: PRT
<213> ORGANISM: Homo sapiens

<400> SEQUENCE: 8

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Leu Gly
                85                  90                  95

Asn Thr Gly Glu Leu Phe Phe Gly Glu Gly Ser Arg Leu Thr Val Leu
                100                 105                 110

<210> SEQ ID NO 9
<211> LENGTH: 132
<212> TYPE: PRT
<213> ORGANISM: Homo sapiens

<400> SEQUENCE: 9

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
```

-continued

```
                        85              90              95

Phe Ile Arg Asp Ser Gln Pro Ser Asp Ser Ala Thr Tyr Leu Cys Ala
            100             105             110

Met Arg Ala Asn Thr Asp Lys Leu Ile Phe Gly Thr Gly Thr Arg Leu
        115             120             125

Gln Val Phe Pro
    130
```

```
<210> SEQ ID NO 10
<211> LENGTH: 131
<212> TYPE: PRT
<213> ORGANISM: Artificial Sequence
<220> FEATURE:
<223> OTHER INFORMATION: Synthetic

<400> SEQUENCE: 10

Met Ala Ile Arg Leu Leu Cys Arg Val Ala Phe Cys Phe Leu Ala Val
1               5               10              15

Gly Leu Val Asp Val Lys Val Thr Gln Ser Ser Arg Tyr Leu Val Lys
            20              25              30

Arg Thr Gly Glu Lys Val Phe Leu Glu Cys Val Gln Asp Met Asp His
        35              40              45

Glu Asn Met Phe Trp Tyr Arg Gln Asp Pro Gly Leu Gly Leu Arg Leu
    50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
            85              90              95

Leu Glu Ser Ala Ser Thr Asn Gln Thr Ser Met Tyr Leu Cys Ala Ser
            100             105             110

Arg Leu Gly Asn Thr Gly Glu Leu Phe Phe Gly Glu Gly Ser Arg Leu
        115             120             125

Thr Val Leu
    130
```

```
<210> SEQ ID NO 11
<211> LENGTH: 6
<212> TYPE: PRT
<213> ORGANISM: Homo sapiens

<400> SEQUENCE: 11

Asn Ser Ala Phe Gln Tyr
1               5
```

```
<210> SEQ ID NO 12
<211> LENGTH: 6
<212> TYPE: PRT
<213> ORGANISM: Homo sapiens

<400> SEQUENCE: 12

Thr Tyr Ser Ser Gly Asn
1               5
```

```
<210> SEQ ID NO 13
<211> LENGTH: 12
<212> TYPE: PRT
<213> ORGANISM: Homo sapiens

<400> SEQUENCE: 13

Cys Ala Met Arg Ala Asn Thr Asp Lys Leu Ile Phe
```

-continued

```
1               5               10
```

<210> SEQ ID NO 14
<211> LENGTH: 5
<212> TYPE: PRT
<213> ORGANISM: Homo sapiens

<400> SEQUENCE: 14

```
Met Asp His Glu Asn
1               5
```

<210> SEQ ID NO 15
<211> LENGTH: 6
<212> TYPE: PRT
<213> ORGANISM: Homo sapiens

<400> SEQUENCE: 15

```
Ser Tyr Asp Val Lys Met
1               5
```

<210> SEQ ID NO 16
<211> LENGTH: 12
<212> TYPE: PRT
<213> ORGANISM: Homo sapiens

<400> SEQUENCE: 16

```
Cys Ala Ser Arg Gln Gly Asn Thr Gly Glu Leu Phe
1               5                   10
```

<210> SEQ ID NO 17
<211> LENGTH: 110
<212> TYPE: PRT
<213> ORGANISM: Homo sapiens

<400> SEQUENCE: 17

```
Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
        50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro
                100                 105                 110
```

<210> SEQ ID NO 18
<211> LENGTH: 112
<212> TYPE: PRT
<213> ORGANISM: Homo sapiens

<400> SEQUENCE: 18

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
```

-continued

```
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Gln Gly
                85                  90                  95

Asn Thr Gly Glu Leu Phe Phe Gly Glu Gly Ser Arg Leu Thr Val Leu
            100                 105                 110
```

```
<210> SEQ ID NO 19
<211> LENGTH: 132
<212> TYPE: PRT
<213> ORGANISM: Homo sapiens

<400> SEQUENCE: 19

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Ala Asn Thr Asp Lys Leu Ile Phe Gly Thr Gly Thr Arg Leu
            115                 120                 125

Gln Val Phe Pro
    130
```

```
<210> SEQ ID NO 20
<211> LENGTH: 131
<212> TYPE: PRT
<213> ORGANISM: Artificial Sequence
<220> FEATURE:
<223> OTHER INFORMATION: Synthetic

<400> SEQUENCE: 20

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110
```

-continued

```
Arg Gln Gly Asn Thr Gly Glu Leu Phe Phe Gly Glu Gly Ser Arg Leu
        115                 120                 125

Thr Val Leu
    130

<210> SEQ ID NO 21
<211> LENGTH: 7
<212> TYPE: PRT
<213> ORGANISM: Homo sapiens

<400> SEQUENCE: 21

Thr Ile Ser Gly Asn Glu Tyr
1               5

<210> SEQ ID NO 22
<211> LENGTH: 5
<212> TYPE: PRT
<213> ORGANISM: Homo sapiens

<400> SEQUENCE: 22

Gly Leu Lys Asn Asn
1               5

<210> SEQ ID NO 23
<211> LENGTH: 15
<212> TYPE: PRT
<213> ORGANISM: Homo sapiens

<400> SEQUENCE: 23

Cys Ile Val Arg Val Ala Lys Ser Gly Ala Asn Asn Leu Phe Phe
1               5                   10                  15

<210> SEQ ID NO 24
<211> LENGTH: 5
<212> TYPE: PRT
<213> ORGANISM: Homo sapiens

<400> SEQUENCE: 24

Met Gly His Asp Lys
1               5

<210> SEQ ID NO 25
<211> LENGTH: 6
<212> TYPE: PRT
<213> ORGANISM: Homo sapiens

<400> SEQUENCE: 25

Ser Tyr Gly Val Asn Ser
1               5

<210> SEQ ID NO 26
<211> LENGTH: 14
<212> TYPE: PRT
<213> ORGANISM: Homo sapiens

<400> SEQUENCE: 26

Cys Ala Ser Ser Gly Leu Thr Tyr Thr Asp Thr Gln Tyr Phe
1               5                   10

<210> SEQ ID NO 27
<211> LENGTH: 112
<212> TYPE: PRT
<213> ORGANISM: Homo sapiens
```

<400> SEQUENCE: 27

```
Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Val Ala Lys Ser Gly
                85                  90                  95

Ala Asn Asn Leu Phe Phe Gly Thr Gly Thr Arg Leu Thr Val Ile Pro
            100                 105                 110
```

<210> SEQ ID NO 28
<211> LENGTH: 113
<212> TYPE: PRT
<213> ORGANISM: Homo sapiens

<400> SEQUENCE: 28

```
Glu Ala Asp Ile Tyr Gln Thr Pro Arg Tyr Leu Val Ile Gly Thr Gly
1               5                   10                  15

Lys Lys Ile Thr Leu Glu Cys Ser Gln Thr Met Gly His Asp Lys Met
            20                  25                  30

Tyr Trp Tyr Gln Gln Asp Pro Gly Met Glu Leu His Leu Ile His Tyr
        35                  40                  45

Ser Tyr Gly Val Asn Ser Thr Glu Lys Gly Asp Leu Ser Ser Glu Ser
    50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys Ala Ser Ser Gly Leu
                85                  90                  95

Thr Tyr Thr Asp Thr Gln Tyr Phe Gly Pro Gly Thr Arg Leu Thr Val
            100                 105                 110

Leu
```

<210> SEQ ID NO 29
<211> LENGTH: 129
<212> TYPE: PRT
<213> ORGANISM: Homo sapiens

<400> SEQUENCE: 29

```
Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95
```

-continued

```
Leu Arg Asp Thr Ala Val Tyr Tyr Cys Ile Val Arg Val Ala Lys Ser
            100                 105                 110

Gly Ala Asn Asn Leu Phe Phe Gly Thr Gly Thr Arg Leu Thr Val Ile
        115                 120                 125

Pro

<210> SEQ ID NO 30
<211> LENGTH: 132
<212> TYPE: PRT
<213> ORGANISM: Artificial Sequence
<220> FEATURE:
<223> OTHER INFORMATION: Synthetic

<400> SEQUENCE: 30

Met Ala Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gly Leu Thr Tyr Thr Asp Thr Gln Tyr Phe Gly Pro Gly Thr Arg
        115                 120                 125

Leu Thr Val Leu
    130

<210> SEQ ID NO 31
<211> LENGTH: 6
<212> TYPE: PRT
<213> ORGANISM: Homo sapiens

<400> SEQUENCE: 31

Asn Ser Ala Phe Gln Tyr
1               5

<210> SEQ ID NO 32
<211> LENGTH: 6
<212> TYPE: PRT
<213> ORGANISM: Homo sapiens

<400> SEQUENCE: 32

Thr Tyr Ser Ser Gly Asn
1               5

<210> SEQ ID NO 33
<211> LENGTH: 15
<212> TYPE: PRT
<213> ORGANISM: Homo sapiens

<400> SEQUENCE: 33

Cys Ala Met Ser Tyr Ser Gly Gly Gly Ala Asp Gly Leu Thr Phe
1               5                   10                  15
```

<210> SEQ ID NO 34
<211> LENGTH: 6
<212> TYPE: PRT
<213> ORGANISM: Homo sapiens

<400> SEQUENCE: 34

Asn Ser Ala Phe Gln Tyr
1               5

<210> SEQ ID NO 35
<211> LENGTH: 6
<212> TYPE: PRT
<213> ORGANISM: Homo sapiens

<400> SEQUENCE: 35

Thr Tyr Ser Ser Gly Asn
1               5

<210> SEQ ID NO 36
<211> LENGTH: 13
<212> TYPE: PRT
<213> ORGANISM: Homo sapiens

<400> SEQUENCE: 36

Cys Ala Ser Ser Gln Gly Asn Thr Gly Glu Leu Phe Phe
1               5                   10

<210> SEQ ID NO 37
<211> LENGTH: 113
<212> TYPE: PRT
<213> ORGANISM: Homo sapiens

<400> SEQUENCE: 37

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Ser Tyr Ser Gly Gly
                85                  90                  95

Gly Ala Asp Gly Leu Thr Phe Gly Lys Gly Thr His Leu Ile Ile Gln
            100                 105                 110

Pro

<210> SEQ ID NO 38
<211> LENGTH: 112
<212> TYPE: PRT
<213> ORGANISM: Homo sapiens

<400> SEQUENCE: 38

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe

-continued

```
            35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
                100                 105                 110
```

```
<210> SEQ ID NO 39
<211> LENGTH: 135
<212> TYPE: PRT
<213> ORGANISM: Homo sapiens

<400> SEQUENCE: 39

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Met Ser Tyr Ser Gly Gly Gly Ala Asp Gly Leu Thr Phe Gly Lys Gly
            115                 120                 125

Thr His Leu Ile Ile Gln Pro
    130                 135
```

```
<210> SEQ ID NO 40
<211> LENGTH: 131
<212> TYPE: PRT
<213> ORGANISM: Artificial Sequence
<220> FEATURE:
<223> OTHER INFORMATION: Synthetic

<400> SEQUENCE: 40

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110
```

-continued

```
Ser Gln Gly Asn Thr Gly Glu Leu Phe Phe Gly Glu Gly Ser Arg Leu
        115                 120                 125

Thr Val Leu
    130

<210> SEQ ID NO 41
<211> LENGTH: 6
<212> TYPE: PRT
<213> ORGANISM: Homo sapiens

<400> SEQUENCE: 41

Asp Ser Ser Ser Thr Tyr
1               5

<210> SEQ ID NO 42
<211> LENGTH: 7
<212> TYPE: PRT
<213> ORGANISM: Homo sapiens

<400> SEQUENCE: 42

Ile Phe Ser Asn Met Asp Met
1               5

<210> SEQ ID NO 43
<211> LENGTH: 11
<212> TYPE: PRT
<213> ORGANISM: Homo sapiens

<400> SEQUENCE: 43

Cys Ala Pro Gly Gly Tyr Asn Lys Leu Ile Phe
1               5                   10

<210> SEQ ID NO 44
<211> LENGTH: 5
<212> TYPE: PRT
<213> ORGANISM: Homo sapiens

<400> SEQUENCE: 44

Met Asp His Glu Asn
1               5

<210> SEQ ID NO 45
<211> LENGTH: 6
<212> TYPE: PRT
<213> ORGANISM: Homo sapiens

<400> SEQUENCE: 45

Ser Tyr Asp Val Lys Met
1               5

<210> SEQ ID NO 46
<211> LENGTH: 13
<212> TYPE: PRT
<213> ORGANISM: Homo sapiens

<400> SEQUENCE: 46

Cys Ala Ser Arg Ile Gly Asn Thr Gly Glu Leu Phe Phe
1               5                   10

<210> SEQ ID NO 47
<211> LENGTH: 109
<212> TYPE: PRT
<213> ORGANISM: Homo sapiens
```

-continued

<400> SEQUENCE: 47

```
Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
        35                  40                  45

Ile Phe Ser Asn Met Asp Met Lys Gln Asp Gln Arg Leu Thr Val Leu
    50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Pro Gly Gly Tyr Asn Lys
                85                  90                  95

Leu Ile Phe Gly Ala Gly Thr Arg Leu Ala Val His Pro
            100                 105
```

<210> SEQ ID NO 48
<211> LENGTH: 112
<212> TYPE: PRT
<213> ORGANISM: Homo sapiens

<400> SEQUENCE: 48

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Ile Gly
                85                  90                  95

Asn Thr Gly Glu Leu Phe Phe Gly Glu Gly Ser Arg Leu Thr Val Leu
            100                 105                 110
```

<210> SEQ ID NO 49
<211> LENGTH: 130
<212> TYPE: PRT
<213> ORGANISM: Homo sapiens

<400> SEQUENCE: 49

```
Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Pro
```

-continued

```
                100                 105                 110

Gly Gly Tyr Asn Lys Leu Ile Phe Gly Ala Gly Thr Arg Leu Ala Val
        115                 120                 125

His Pro
    130

<210> SEQ ID NO 50
<211> LENGTH: 131
<212> TYPE: PRT
<213> ORGANISM: Artificial Sequence
<220> FEATURE:
<223> OTHER INFORMATION: Synthetic

<400> SEQUENCE: 50

Met Ala Ile Arg Leu Leu Cys Arg Val Ala Phe Cys Phe Leu Ala Val
1               5                  10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Ile Gly Asn Thr Gly Glu Leu Phe Phe Gly Glu Gly Ser Arg Leu
        115                 120                 125

Thr Val Leu
    130

<210> SEQ ID NO 51
<211> LENGTH: 189
<212> TYPE: PRT
<213> ORGANISM: Homo sapiens

<400> SEQUENCE: 51

Met Thr Glu Tyr Lys Leu Val Val Val Gly Ala Gly Gly Val Gly Lys
1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140
```

-continued

```
Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185
```

```
<210> SEQ ID NO 52
<211> LENGTH: 188
<212> TYPE: PRT
<213> ORGANISM: Homo sapiens

<400> SEQUENCE: 52
```

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

```
<210> SEQ ID NO 53
<211> LENGTH: 189
<212> TYPE: PRT
<213> ORGANISM: Homo sapiens

<400> SEQUENCE: 53
```

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95
```

```
Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 54
<211> LENGTH: 189
<212> TYPE: PRT
<213> ORGANISM: Homo sapiens

<400> SEQUENCE: 54

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
            130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
            180                 185

<210> SEQ ID NO 55
<211> LENGTH: 189
<212> TYPE: PRT
<213> ORGANISM: Homo sapiens

<400> SEQUENCE: 55

Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
            35                  40                  45
```

-continued

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 56
<211> LENGTH: 188
<212> TYPE: PRT
<213> ORGANISM: Homo sapiens

<400> SEQUENCE: 56

Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 57
<211> LENGTH: 189
<212> TYPE: PRT
<213> ORGANISM: Homo sapiens

<400> SEQUENCE: 57

```
Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 58
<211> LENGTH: 189
<212> TYPE: PRT
<213> ORGANISM: Homo sapiens

<400> SEQUENCE: 58

```
Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Pro Thr Arg Thr Val Asp Thr Lys
            115                 120                 125

Gln Ala His Glu Leu Ala Lys Ser Tyr Gly Ile Pro Phe Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

Gly Thr Gln Gly Cys Met Gly Leu Pro Cys Val Val Met
```

```
            180             185

<210> SEQ ID NO 59
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
      Trp

<400> SEQUENCE: 59

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Xaa
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Xaa
            100                 105                 110

Val Xaa Xaa Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 60
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 60

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45
```

```
Gly Lys Glu Val His Ser Gly Val Xaa Thr Asp Pro Gln Ala Tyr Lys
    50              55              60
Glu Ser Asn Tyr Ser Tyr Cys Leu Ser Ser Arg Leu Arg Val Ser Ala
65              70              75              80
Thr Phe Trp His Asn Pro Arg Asn His Phe Arg Cys Gln Val Gln Phe
                85              90              95
His Gly Leu Ser Glu Glu Asp Lys Trp Pro Glu Gly Ser Pro Lys Pro
            100             105             110
Val Thr Gln Asn Ile Ser Ala Glu Ala Trp Gly Arg Ala Asp Cys Gly
        115             120             125
Ile Thr Ser Ala Ser Tyr Gln Gln Gly Val Leu Ser Ala Thr Ile Leu
    130             135             140
Tyr Glu Ile Leu Leu Gly Lys Ala Thr Leu Tyr Ala Val Leu Val Ser
145             150             155             160
Thr Leu Val Val Met Ala Met Val Lys Arg Lys Asn Ser
                165             170
```

<210> SEQ ID NO 61
<211> LENGTH: 137
<212> TYPE: PRT
<213> ORGANISM: Artificial Sequence
<220> FEATURE:
<223> OTHER INFORMATION: Synthetic

<400> SEQUENCE: 61

```
Asn Ile Gln Asn Pro Glu Pro Ala Val Tyr Gln Leu Lys Asp Pro Arg
1               5               10              15
Ser Gln Asp Ser Thr Leu Cys Leu Phe Thr Asp Phe Asp Ser Gln Ile
            20              25              30
Asn Val Pro Lys Thr Met Glu Ser Gly Thr Phe Ile Thr Asp Lys Cys
        35              40              45
Val Leu Asp Met Lys Ala Met Asp Ser Lys Ser Asn Gly Ala Ile Ala
    50              55              60
Trp Ser Asn Gln Thr Ser Phe Thr Cys Gln Asp Ile Phe Lys Glu Thr
65              70              75              80
Asn Ala Thr Tyr Pro Ser Ser Asp Val Pro Cys Asp Ala Thr Leu Thr
                85              90              95
Glu Lys Ser Phe Glu Thr Asp Met Asn Leu Asn Phe Gln Asn Leu Leu
            100             105             110
Val Ile Val Leu Arg Ile Leu Leu Leu Lys Val Ala Gly Phe Asn Leu
        115             120             125
Leu Met Thr Leu Arg Leu Trp Ser Ser
    130             135
```

<210> SEQ ID NO 62
<211> LENGTH: 173
<212> TYPE: PRT
<213> ORGANISM: Artificial Sequence
<220> FEATURE:
<223> OTHER INFORMATION: Synthetic

<400> SEQUENCE: 62

```
Glu Asp Leu Arg Asn Val Thr Pro Pro Lys Val Ser Leu Phe Glu Pro
1               5               10              15
Ser Lys Ala Glu Ile Ala Asn Lys Gln Lys Ala Thr Leu Val Cys Leu
            20              25              30
Ala Arg Gly Phe Phe Pro Asp His Val Glu Leu Ser Trp Trp Val Asn
```

-continued

```
              35                  40                  45
Gly Lys Glu Val His Ser Gly Val Cys Thr Asp Pro Gln Ala Tyr Lys
    50                  55                  60
Glu Ser Asn Tyr Ser Tyr Cys Leu Ser Ser Arg Leu Arg Val Ser Ala
65                  70                  75                  80
Thr Phe Trp His Asn Pro Arg Asn His Phe Arg Cys Gln Val Gln Phe
                85                  90                  95
His Gly Leu Ser Glu Glu Asp Lys Trp Pro Glu Gly Ser Pro Lys Pro
            100                 105                 110
Val Thr Gln Asn Ile Ser Ala Glu Ala Trp Gly Arg Ala Asp Cys Gly
            115                 120                 125
Ile Thr Ser Ala Ser Tyr Gln Gln Gly Val Leu Ser Ala Thr Ile Leu
        130                 135                 140
Tyr Glu Ile Leu Leu Gly Lys Ala Thr Leu Tyr Ala Val Leu Val Ser
145                 150                 155                 160
Thr Leu Val Val Met Ala Met Val Lys Arg Lys Asn Ser
                165                 170
```

<210> SEQ ID NO 63
<211> LENGTH: 137
<212> TYPE: PRT
<213> ORGANISM: Mus musculus

<400> SEQUENCE: 63

```
Asn Ile Gln Asn Pro Glu Pro Ala Val Tyr Gln Leu Lys Asp Pro Arg
1               5                   10                  15
Ser Gln Asp Ser Thr Leu Cys Leu Phe Thr Asp Phe Asp Ser Gln Ile
            20                  25                  30
Asn Val Pro Lys Thr Met Glu Ser Gly Thr Phe Ile Thr Asp Lys Thr
        35                  40                  45
Val Leu Asp Met Lys Ala Met Asp Ser Lys Ser Asn Gly Ala Ile Ala
    50                  55                  60
Trp Ser Asn Gln Thr Ser Phe Thr Cys Gln Asp Ile Phe Lys Glu Thr
65                  70                  75                  80
Asn Ala Thr Tyr Pro Ser Ser Asp Val Pro Cys Asp Ala Thr Leu Thr
                85                  90                  95
Glu Lys Ser Phe Glu Thr Asp Met Asn Leu Asn Phe Gln Asn Leu Ser
            100                 105                 110
Val Met Gly Leu Arg Ile Leu Leu Leu Lys Val Ala Gly Phe Asn Leu
            115                 120                 125
Leu Met Thr Leu Arg Leu Trp Ser Ser
        130                 135
```

<210> SEQ ID NO 64
<211> LENGTH: 173
<212> TYPE: PRT
<213> ORGANISM: Mus musculus

<400> SEQUENCE: 64

```
Glu Asp Leu Arg Asn Val Thr Pro Pro Lys Val Ser Leu Phe Glu Pro
1               5                   10                  15
Ser Lys Ala Glu Ile Ala Asn Lys Gln Lys Ala Thr Leu Val Cys Leu
            20                  25                  30
Ala Arg Gly Phe Phe Pro Asp His Val Glu Leu Ser Trp Trp Val Asn
        35                  40                  45
Gly Lys Glu Val His Ser Gly Val Ser Thr Asp Pro Gln Ala Tyr Lys
```

-continued

```
        50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
                100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

```
<210> SEQ ID NO 65
<211> LENGTH: 269
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (180)..(180)
<223> OTHER INFORMATION: X is Thr or Cys
<220> FEATURE:
<221> NAME/KEY: MISC_FEATURE
<222> LOCATION: (244)..(244)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (246)..(246)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (247)..(247)
<223> OTHER INFORMATION: X is Gly, Ala, Val, Leu, Ile, Pro, Phe, Met, or
     Trp
```

```
<400> SEQUENCE: 65

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
                35                  40                  45

Asn Ser Ala Phe Gln Tyr Phe Met Trp Tyr Arg Gln Tyr Ser Arg Lys
            50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Met Arg Ala Asn Thr Asp Lys Leu Ile Phe Gly Thr Gly Thr Arg Leu
            115                 120                 125

Gln Val Phe Pro Asn Ile Gln Asn Pro Glu Pro Ala Val Tyr Gln Leu
        130                 135                 140

Lys Asp Pro Arg Ser Gln Asp Ser Thr Leu Cys Leu Phe Thr Asp Phe
```

```
        145             150             155             160

Asp Ser Gln Ile Asn Val Pro Lys Thr Met Glu Ser Gly Thr Phe Ile
                165             170             175

Thr Asp Lys Xaa Val Leu Asp Met Lys Ala Met Asp Ser Lys Ser Asn
            180             185             190

Gly Ala Ile Ala Trp Ser Asn Gln Thr Ser Phe Thr Cys Gln Asp Ile
        195             200             205

Phe Lys Glu Thr Asn Ala Thr Tyr Pro Ser Ser Asp Val Pro Cys Asp
    210             215             220

Ala Thr Leu Thr Glu Lys Ser Phe Glu Thr Asp Met Asn Leu Asn Phe
225             230             235             240

Gln Asn Leu Xaa Val Xaa Xaa Leu Arg Ile Leu Leu Leu Lys Val Ala
            245             250             255

Gly Phe Asn Leu Leu Met Thr Leu Arg Leu Trp Ser Ser
        260             265

<210> SEQ ID NO 66
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 66

Met Ala Ile Arg Leu Leu Cys Arg Val Ala Phe Cys Phe Leu Ala Val
1               5               10              15

Gly Leu Val Asp Val Lys Val Thr Gln Ser Ser Arg Tyr Leu Val Lys
            20              25              30

Arg Thr Gly Glu Lys Val Phe Leu Glu Cys Val Gln Asp Met Asp His
        35              40              45

Glu Asn Met Phe Trp Tyr Arg Gln Asp Pro Gly Leu Gly Leu Arg Leu
    50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
            85              90              95

Leu Glu Ser Ala Ser Thr Asn Gln Thr Ser Met Tyr Leu Cys Ala Ser
            100             105             110

Arg Leu Gly Asn Thr Gly Glu Leu Phe Phe Gly Glu Gly Ser Arg Leu
            115             120             125

Thr Val Leu Glu Asp Leu Arg Asn Val Thr Pro Pro Lys Val Ser Leu
    130             135             140

Phe Glu Pro Ser Lys Ala Glu Ile Ala Asn Lys Gln Lys Ala Thr Leu
145             150             155             160

Val Cys Leu Ala Arg Gly Phe Phe Pro Asp His Val Glu Leu Ser Trp
            165             170             175

Trp Val Asn Gly Lys Glu Val His Ser Gly Val Xaa Thr Asp Pro Gln
            180             185             190

Ala Tyr Lys Glu Ser Asn Tyr Ser Tyr Cys Leu Ser Ser Arg Leu Arg
        195             200             205

Val Ser Ala Thr Phe Trp His Asn Pro Arg Asn His Phe Arg Cys Gln
    210             215             220
```

-continued

```
Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
            290                 295                 300
```

```
<210> SEQ ID NO 67
<211> LENGTH: 247
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (158)..(158)
<223> OTHER INFORMATION: X is Thr or Cys
<220> FEATURE:
<221> NAME/KEY: MISC_FEATURE
<222> LOCATION: (222)..(222)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (224)..(224)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (225)..(225)
<223> OTHER INFORMATION: X is Gly, Ala, Val, Leu, Ile, Pro, Phe, Met, or
      Trp

<400> SEQUENCE: 67
```

```
Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro Asn Ile
                100                 105                 110

Gln Asn Pro Glu Pro Ala Val Tyr Gln Leu Lys Asp Pro Arg Ser Gln
            115                 120                 125

Asp Ser Thr Leu Cys Leu Phe Thr Asp Phe Asp Ser Gln Ile Asn Val
            130                 135                 140

Pro Lys Thr Met Glu Ser Gly Thr Phe Ile Thr Asp Lys Xaa Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
                180                 185                 190
```

```
Thr Tyr Pro Ser Ser Asp Val Pro Cys Asp Ala Thr Leu Thr Glu Lys
        195             200             205

Ser Phe Glu Thr Asp Met Asn Leu Asn Phe Gln Asn Leu Xaa Val Xaa
    210             215             220

Xaa Leu Arg Ile Leu Leu Leu Lys Val Ala Gly Phe Asn Leu Leu Met
225             230             235             240

Thr Leu Arg Leu Trp Ser Ser
            245

<210> SEQ ID NO 68
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 68

Asp Val Lys Val Thr Gln Ser Ser Arg Tyr Leu Val Lys Arg Thr Gly
1           5               10              15

Glu Lys Val Phe Leu Glu Cys Val Gln Asp Met Asp His Glu Asn Met
            20              25              30

Phe Trp Tyr Arg Gln Asp Pro Gly Leu Gly Leu Arg Leu Ile Tyr Phe
            35              40              45

Ser Tyr Asp Val Lys Met Lys Glu Lys Gly Asp Ile Pro Glu Gly Tyr
    50              55              60

Ser Val Ser Arg Glu Lys Lys Glu Arg Phe Ser Leu Ile Leu Glu Ser
65              70              75              80

Ala Ser Thr Asn Gln Thr Ser Met Tyr Leu Cys Ala Ser Arg Leu Gly
            85              90              95

Asn Thr Gly Glu Leu Phe Phe Gly Glu Gly Ser Arg Leu Thr Val Leu
            100             105             110

Glu Asp Leu Arg Asn Val Thr Pro Pro Lys Val Ser Leu Phe Glu Pro
        115             120             125

Ser Lys Ala Glu Ile Ala Asn Lys Gln Lys Ala Thr Leu Val Cys Leu
    130             135             140

Ala Arg Gly Phe Phe Pro Asp His Val Glu Leu Ser Trp Trp Val Asn
145             150             155             160

Gly Lys Glu Val His Ser Gly Val Xaa Thr Asp Pro Gln Ala Tyr Lys
            165             170             175

Glu Ser Asn Tyr Ser Tyr Cys Leu Ser Ser Arg Leu Arg Val Ser Ala
            180             185             190

Thr Phe Trp His Asn Pro Arg Asn His Phe Arg Cys Gln Val Gln Phe
            195             200             205

His Gly Leu Ser Glu Glu Asp Lys Trp Pro Glu Gly Ser Pro Lys Pro
    210             215             220

Val Thr Gln Asn Ile Ser Ala Glu Ala Trp Gly Arg Ala Asp Cys Gly
225             230             235             240

Ile Thr Ser Ala Ser Tyr Gln Gln Gly Val Leu Ser Ala Thr Ile Leu
            245             250             255

Tyr Glu Ile Leu Leu Gly Lys Ala Thr Leu Tyr Ala Val Leu Val Ser
            260             265             270

Thr Leu Val Val Met Ala Met Val Lys Arg Lys Asn Ser
            275             280             285
```

-continued

```
<210> SEQ ID NO 69
<211> LENGTH: 269
<212> TYPE: PRT
<213> ORGANISM: Artificial Sequence
<220> FEATURE:
<223> OTHER INFORMATION: Synthetic

<400> SEQUENCE: 69

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Ala Asn Thr Asp Lys Leu Ile Phe Gly Thr Gly Thr Arg Leu
            115                 120                 125

Gln Val Phe Pro Asn Ile Gln Asn Pro Glu Pro Ala Val Tyr Gln Leu
        130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
        210                 215                 220

Ala Thr Leu Thr Glu Lys Ser Phe Glu Thr Asp Met Asn Leu Asn Phe
225                 230                 235                 240

Gln Asn Leu Leu Val Ile Val Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 70
<211> LENGTH: 304
<212> TYPE: PRT
<213> ORGANISM: Artificial Sequence
<220> FEATURE:
<223> OTHER INFORMATION: Synthetic

<400> SEQUENCE: 70

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
```

-continued

```
                35                    40                    45
Glu Asn Met Phe Trp Tyr Arg Gln Asp Pro Gly Leu Gly Leu Arg Leu
    50                    55                    60
Ile Tyr Phe Ser Tyr Asp Val Lys Met Lys Glu Lys Gly Asp Ile Pro
65                    70                    75                    80
Glu Gly Tyr Ser Val Ser Arg Glu Lys Lys Glu Arg Phe Ser Leu Ile
                85                    90                    95
Leu Glu Ser Ala Ser Thr Asn Gln Thr Ser Met Tyr Leu Cys Ala Ser
                100                   105                   110
Arg Leu Gly Asn Thr Gly Glu Leu Phe Phe Gly Glu Gly Ser Arg Leu
                115                   120                   125
Thr Val Leu Glu Asp Leu Arg Asn Val Thr Pro Pro Lys Val Ser Leu
    130                   135                   140
Phe Glu Pro Ser Lys Ala Glu Ile Ala Asn Lys Gln Lys Ala Thr Leu
145                   150                   155                   160
Val Cys Leu Ala Arg Gly Phe Phe Pro Asp His Val Glu Leu Ser Trp
                165                   170                   175
Trp Val Asn Gly Lys Glu Val His Ser Gly Val Cys Thr Asp Pro Gln
                180                   185                   190
Ala Tyr Lys Glu Ser Asn Tyr Ser Tyr Cys Leu Ser Ser Arg Leu Arg
                195                   200                   205
Val Ser Ala Thr Phe Trp His Asn Pro Arg Asn His Phe Arg Cys Gln
    210                   215                   220
Val Gln Phe His Gly Leu Ser Glu Glu Asp Lys Trp Pro Glu Gly Ser
225                   230                   235                   240
Pro Lys Pro Val Thr Gln Asn Ile Ser Ala Glu Ala Trp Gly Arg Ala
                245                   250                   255
Asp Cys Gly Ile Thr Ser Ala Ser Tyr Gln Gln Gly Val Leu Ser Ala
                260                   265                   270
Thr Ile Leu Tyr Glu Ile Leu Leu Gly Lys Ala Thr Leu Tyr Ala Val
                275                   280                   285
Leu Val Ser Thr Leu Val Val Met Ala Met Val Lys Arg Lys Asn Ser
    290                   295                   300
```

```
<210> SEQ ID NO 71
<211> LENGTH: 247
<212> TYPE: PRT
<213> ORGANISM: Artificial Sequence
<220> FEATURE:
<223> OTHER INFORMATION: Synthetic

<400> SEQUENCE: 71

Gln Lys Glu Val Glu Gln Asp Pro Gly Pro Leu Ser Val Pro Glu Gly
1               5                   10                    15
Ala Ile Val Ser Leu Asn Cys Thr Tyr Ser Asn Ser Ala Phe Gln Tyr
                20                    25                    30
Phe Met Trp Tyr Arg Gln Tyr Ser Arg Lys Gly Pro Glu Leu Leu Met
                35                    40                    45
Tyr Thr Tyr Ser Ser Gly Asn Lys Glu Asp Gly Arg Phe Thr Ala Gln
    50                    55                    60
Val Asp Lys Ser Ser Lys Tyr Ile Ser Leu Phe Ile Arg Asp Ser Gln
65                    70                    75                    80
Pro Ser Asp Ser Ala Thr Tyr Leu Cys Ala Met Arg Ala Asn Thr Asp
                85                    90                    95
Lys Leu Ile Phe Gly Thr Gly Thr Arg Leu Gln Val Phe Pro Asn Ile
```

-continued

```
                100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Lys Cys Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
                180                 185                 190

Thr Tyr Pro Ser Ser Asp Val Pro Cys Asp Ala Thr Leu Thr Glu Lys
            195                 200                 205

Ser Phe Glu Thr Asp Met Asn Leu Asn Phe Gln Asn Leu Leu Val Ile
        210                 215                 220

Val Leu Arg Ile Leu Leu Leu Lys Val Ala Gly Phe Asn Leu Leu Met
225                 230                 235                 240

Thr Leu Arg Leu Trp Ser Ser
                245

<210> SEQ ID NO 72
<211> LENGTH: 285
<212> TYPE: PRT
<213> ORGANISM: Artificial Sequence
<220> FEATURE:
<223> OTHER INFORMATION: Synthetic

<400> SEQUENCE: 72

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Leu Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
```

```
                210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
                260                 265                 270

Thr Leu Val Val Met Ala Met Val Lys Arg Lys Asn Ser
            275                 280                 285

<210> SEQ ID NO 73
<211> LENGTH: 269
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (180)..(180)
<223> OTHER INFORMATION: X is Thr or Cys
<220> FEATURE:
<221> NAME/KEY: MISC_FEATURE
<222> LOCATION: (244)..(244)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (246)..(246)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (247)..(247)
<223> OTHER INFORMATION: X is Gly, Ala, Val, Leu, Ile, Pro, Phe, Met, or
      Trp

<400> SEQUENCE: 73

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Ala Asn Thr Asp Lys Leu Ile Phe Gly Thr Gly Thr Arg Leu
            115                 120                 125

Gln Val Phe Pro Asn Ile Gln Asn Pro Glu Pro Ala Val Tyr Gln Leu
        130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Xaa Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
```

```
             195                  200                  205

Phe Lys Glu Thr Asn Ala Thr Tyr Pro Ser Ser Asp Val Pro Cys Asp
    210                  215                  220

Ala Thr Leu Thr Glu Lys Ser Phe Glu Thr Asp Met Asn Leu Asn Phe
225                  230                  235                  240

Gln Asn Leu Xaa Val Xaa Xaa Leu Arg Ile Leu Leu Leu Lys Val Ala
                245                  250                  255

Gly Phe Asn Leu Leu Met Thr Leu Arg Leu Trp Ser Ser
                260                  265

<210> SEQ ID NO 74
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 74

Met Ala Ile Arg Leu Leu Cys Arg Val Ala Phe Cys Phe Leu Ala Val
1                   5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gln Gly Asn Thr Gly Glu Leu Phe Phe Gly Glu Gly Ser Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270
```

-continued

```
Thr Ile Leu Tyr Glu Ile Leu Leu Gly Lys Ala Thr Leu Tyr Ala Val
        275             280             285

Leu Val Ser Thr Leu Val Val Met Ala Met Val Lys Arg Lys Asn Ser
    290             295             300

<210> SEQ ID NO 75
<211> LENGTH: 247
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (158)..(158)
<223> OTHER INFORMATION: X is Thr or Cys
<220> FEATURE:
<221> NAME/KEY: MISC_FEATURE
<222> LOCATION: (222)..(222)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (224)..(224)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (225)..(225)
<223> OTHER INFORMATION: X is Gly, Ala, Val, Leu, Ile, Pro, Phe, Met, or
      Trp

<400> SEQUENCE: 75

Gln Lys Glu Val Glu Gln Asp Pro Gly Pro Leu Ser Val Pro Glu Gly
1               5               10              15

Ala Ile Val Ser Leu Asn Cys Thr Tyr Ser Asn Ser Ala Phe Gln Tyr
        20              25              30

Phe Met Trp Tyr Arg Gln Tyr Ser Arg Lys Gly Pro Glu Leu Leu Met
        35              40              45

Tyr Thr Tyr Ser Ser Gly Asn Lys Glu Asp Gly Arg Phe Thr Ala Gln
    50              55              60

Val Asp Lys Ser Ser Lys Tyr Ile Ser Leu Phe Ile Arg Asp Ser Gln
65              70              75              80

Pro Ser Asp Ser Ala Thr Tyr Leu Cys Ala Met Arg Ala Asn Thr Asp
            85              90              95

Lys Leu Ile Phe Gly Thr Gly Thr Arg Leu Gln Val Phe Pro Asn Ile
            100             105             110

Gln Asn Pro Glu Pro Ala Val Tyr Gln Leu Lys Asp Pro Arg Ser Gln
        115             120             125

Asp Ser Thr Leu Cys Leu Phe Thr Asp Phe Asp Ser Gln Ile Asn Val
    130             135             140

Pro Lys Thr Met Glu Ser Gly Thr Phe Ile Thr Asp Lys Xaa Val Leu
145             150             155             160

Asp Met Lys Ala Met Asp Ser Lys Ser Asn Gly Ala Ile Ala Trp Ser
            165             170             175

Asn Gln Thr Ser Phe Thr Cys Gln Asp Ile Phe Lys Glu Thr Asn Ala
            180             185             190

Thr Tyr Pro Ser Ser Asp Val Pro Cys Asp Ala Thr Leu Thr Glu Lys
            195             200             205

Ser Phe Glu Thr Asp Met Asn Leu Asn Phe Gln Asn Leu Xaa Val Xaa
    210             215             220

Xaa Leu Arg Ile Leu Leu Leu Lys Val Ala Gly Phe Asn Leu Leu Met
225             230             235             240
```

```
Thr Leu Arg Leu Trp Ser Ser
            245

<210> SEQ ID NO 76
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 76

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Gln Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
            130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 77
<211> LENGTH: 269
<212> TYPE: PRT
<213> ORGANISM: Artificial Sequence
<220> FEATURE:
<223> OTHER INFORMATION: Synthetic
```

<400> SEQUENCE: 77

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Met Arg Ala Asn Thr Asp Lys Leu Ile Phe Gly Thr Gly Thr Arg Leu
            115                 120                 125

Gln Val Phe Pro Asn Ile Gln Asn Pro Glu Pro Ala Val Tyr Gln Leu
        130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Cys Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
        210                 215                 220

Ala Thr Leu Thr Glu Lys Ser Phe Glu Thr Asp Met Asn Leu Asn Phe
225                 230                 235                 240

Gln Asn Leu Leu Val Ile Val Leu Arg Ile Leu Leu Leu Lys Val Ala
            245                 250                 255

Gly Phe Asn Leu Leu Met Thr Leu Arg Leu Trp Ser Ser
            260                 265

<210> SEQ ID NO 78
<211> LENGTH: 304
<212> TYPE: PRT
<213> ORGANISM: Artificial Sequence
<220> FEATURE:
<223> OTHER INFORMATION: Synthetic

<400> SEQUENCE: 78

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile

-continued

```
                85                    90                    95

Leu Glu Ser Ala Ser Thr Asn Gln Thr Ser Met Tyr Leu Cys Ala Ser
            100                   105                   110

Arg Gln Gly Asn Thr Gly Glu Leu Phe Phe Gly Glu Gly Ser Arg Leu
            115                   120                   125

Thr Val Leu Glu Asp Leu Arg Asn Val Thr Pro Pro Lys Val Ser Leu
            130                   135                   140

Phe Glu Pro Ser Lys Ala Glu Ile Ala Asn Lys Gln Lys Ala Thr Leu
145                   150                   155                   160

Val Cys Leu Ala Arg Gly Phe Phe Pro Asp His Val Glu Leu Ser Trp
                165                   170                   175

Trp Val Asn Gly Lys Glu Val His Ser Gly Val Cys Thr Asp Pro Gln
                180                   185                   190

Ala Tyr Lys Glu Ser Asn Tyr Ser Tyr Cys Leu Ser Ser Arg Leu Arg
                195                   200                   205

Val Ser Ala Thr Phe Trp His Asn Pro Arg Asn His Phe Arg Cys Gln
            210                   215                   220

Val Gln Phe His Gly Leu Ser Glu Glu Asp Lys Trp Pro Glu Gly Ser
225                   230                   235                   240

Pro Lys Pro Val Thr Gln Asn Ile Ser Ala Glu Ala Trp Gly Arg Ala
                245                   250                   255

Asp Cys Gly Ile Thr Ser Ala Ser Tyr Gln Gln Gly Val Leu Ser Ala
                260                   265                   270

Thr Ile Leu Tyr Glu Ile Leu Leu Gly Lys Ala Thr Leu Tyr Ala Val
                275                   280                   285

Leu Val Ser Thr Leu Val Val Met Ala Met Val Lys Arg Lys Asn Ser
            290                   295                   300

<210> SEQ ID NO 79
<211> LENGTH: 247
<212> TYPE: PRT
<213> ORGANISM: Artificial Sequence
<220> FEATURE:
<223> OTHER INFORMATION: Synthetic

<400> SEQUENCE: 79

Gln Lys Glu Val Glu Gln Asp Pro Gly Pro Leu Ser Val Pro Glu Gly
1               5                   10                   15

Ala Ile Val Ser Leu Asn Cys Thr Tyr Ser Asn Ser Ala Phe Gln Tyr
            20                   25                   30

Phe Met Trp Tyr Arg Gln Tyr Ser Arg Lys Gly Pro Glu Leu Leu Met
            35                   40                   45

Tyr Thr Tyr Ser Ser Gly Asn Lys Glu Asp Gly Arg Phe Thr Ala Gln
            50                   55                   60

Val Asp Lys Ser Ser Lys Tyr Ile Ser Leu Phe Ile Arg Asp Ser Gln
65                   70                   75                   80

Pro Ser Asp Ser Ala Thr Tyr Leu Cys Ala Met Arg Ala Asn Thr Asp
                85                   90                   95

Lys Leu Ile Phe Gly Thr Gly Thr Arg Leu Gln Val Phe Pro Asn Ile
            100                   105                   110

Gln Asn Pro Glu Pro Ala Val Tyr Gln Leu Lys Asp Pro Arg Ser Gln
            115                   120                   125

Asp Ser Thr Leu Cys Leu Phe Thr Asp Phe Asp Ser Gln Ile Asn Val
            130                   135                   140

Pro Lys Thr Met Glu Ser Gly Thr Phe Ile Thr Asp Lys Cys Val Leu
```

```
145              150              155              160

Asp Met Lys Ala Met Asp Ser Lys Ser Asn Gly Ala Ile Ala Trp Ser
             165              170              175

Asn Gln Thr Ser Phe Thr Cys Gln Asp Ile Phe Lys Glu Thr Asn Ala
             180              185              190

Thr Tyr Pro Ser Ser Asp Val Pro Cys Asp Ala Thr Leu Thr Glu Lys
             195              200              205

Ser Phe Glu Thr Asp Met Asn Leu Asn Phe Gln Asn Leu Leu Val Ile
             210              215              220

Val Leu Arg Ile Leu Leu Leu Lys Val Ala Gly Phe Asn Leu Leu Met
225              230              235              240

Thr Leu Arg Leu Trp Ser Ser
             245

<210> SEQ ID NO 80
<211> LENGTH: 285
<212> TYPE: PRT
<213> ORGANISM: Artificial Sequence
<220> FEATURE:
<223> OTHER INFORMATION: Synthetic

<400> SEQUENCE: 80

Asp Val Lys Val Thr Gln Ser Ser Arg Tyr Leu Val Lys Arg Thr Gly
1               5               10              15

Glu Lys Val Phe Leu Glu Cys Val Gln Asp Met Asp His Glu Asn Met
             20              25              30

Phe Trp Tyr Arg Gln Asp Pro Gly Leu Gly Leu Arg Leu Ile Tyr Phe
             35              40              45

Ser Tyr Asp Val Lys Met Lys Glu Lys Gly Asp Ile Pro Glu Gly Tyr
             50              55              60

Ser Val Ser Arg Glu Lys Lys Glu Arg Phe Ser Leu Ile Leu Glu Ser
65              70              75              80

Ala Ser Thr Asn Gln Thr Ser Met Tyr Leu Cys Ala Ser Arg Gln Gly
             85              90              95

Asn Thr Gly Glu Leu Phe Phe Gly Glu Gly Ser Arg Leu Thr Val Leu
             100             105             110

Glu Asp Leu Arg Asn Val Thr Pro Pro Lys Val Ser Leu Phe Glu Pro
             115             120             125

Ser Lys Ala Glu Ile Ala Asn Lys Gln Lys Ala Thr Leu Val Cys Leu
             130             135             140

Ala Arg Gly Phe Phe Pro Asp His Val Glu Leu Ser Trp Trp Val Asn
145             150             155             160

Gly Lys Glu Val His Ser Gly Val Cys Thr Asp Pro Gln Ala Tyr Lys
             165             170             175

Glu Ser Asn Tyr Ser Tyr Cys Leu Ser Ser Arg Leu Arg Val Ser Ala
             180             185             190

Thr Phe Trp His Asn Pro Arg Asn His Phe Arg Cys Gln Val Gln Phe
             195             200             205

His Gly Leu Ser Glu Glu Asp Lys Trp Pro Glu Gly Ser Pro Lys Pro
             210             215             220

Val Thr Gln Asn Ile Ser Ala Glu Ala Trp Gly Arg Ala Asp Cys Gly
225             230             235             240

Ile Thr Ser Ala Ser Tyr Gln Gln Gly Val Leu Ser Ala Thr Ile Leu
             245             250             255

Tyr Glu Ile Leu Leu Gly Lys Ala Thr Leu Tyr Ala Val Leu Val Ser
```

-continued

```
              260              265              270
Thr Leu Val Val Met Ala Met Val Lys Arg Lys Asn Ser
      275              280              285

<210> SEQ ID NO 81
<211> LENGTH: 266
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (177)..(177)
<223> OTHER INFORMATION: X is Thr or Cys
<220> FEATURE:
<221> NAME/KEY: MISC_FEATURE
<222> LOCATION: (241)..(241)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (243)..(243)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (244)..(244)
<223> OTHER INFORMATION: X is Gly, Ala, Val, Leu, Ile, Pro, Phe, Met, or
      Trp

<400> SEQUENCE: 81

Met Arg Leu Val Ala Arg Val Thr Val Phe Leu Thr Phe Gly Thr Ile
1               5                  10                  15

Ile Asp Ala Lys Thr Thr Gln Pro Pro Ser Met Asp Cys Ala Glu Gly
            20                  25                  30

Arg Ala Ala Asn Leu Pro Cys Asn His Ser Thr Ile Ser Gly Asn Glu
        35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
            85                  90                  95

Leu Arg Asp Thr Ala Val Tyr Tyr Cys Ile Val Arg Val Ala Lys Ser
            100                 105                 110

Gly Ala Asn Asn Leu Phe Phe Gly Thr Gly Thr Arg Leu Thr Val Ile
        115                 120                 125

Pro Asn Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Xaa Val Leu Asp Met Lys Ala Met Asp Ser Lys Ser Asn Gly Ala Ile
            180                 185                 190

Ala Trp Ser Asn Gln Thr Ser Phe Thr Cys Gln Asp Ile Phe Lys Glu
        195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Xaa Val Xaa Xaa Leu Arg Ile Leu Leu Leu Lys Val Ala Gly Phe Asn
```

-continued

```
             245              250              255

Leu Leu Met Thr Leu Arg Leu Trp Ser Ser
        260              265
```

```
<210> SEQ ID NO 82
<211> LENGTH: 305
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (189)..(189)
<223> OTHER INFORMATION: X is Ser or Cys
```

```
<400> SEQUENCE: 82

Met Ala Ile Arg Leu Leu Cys Tyr Met Gly Phe Tyr Phe Leu Gly Ala
1               5                  10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gly Leu Thr Tyr Thr Asp Thr Gln Tyr Phe Gly Pro Gly Thr Arg
            115                 120                 125

Leu Thr Val Leu Glu Asp Leu Arg Asn Val Thr Pro Pro Lys Val Ser
        130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Xaa Thr Asp Pro
            180                 185                 190

Gln Ala Tyr Lys Glu Ser Asn Tyr Ser Tyr Cys Leu Ser Ser Arg Leu
            195                 200                 205

Arg Val Ser Ala Thr Phe Trp His Asn Pro Arg Asn His Phe Arg Cys
        210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Thr Leu Val Val Met Ala Met Val Lys Arg Lys Asn
    290                 295                 300

Ser
305
```

<210> SEQ ID NO 83
<211> LENGTH: 249
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (160)..(160)
<223> OTHER INFORMATION: X is Thr or Cys
<220> FEATURE:
<221> NAME/KEY: MISC_FEATURE
<222> LOCATION: (224)..(224)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (226)..(226)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (227)..(227)
<223> OTHER INFORMATION: X is Gly, Ala, Val, Leu, Ile, Pro, Phe, Met, or
      Trp

<400> SEQUENCE: 83

Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
            20                  25                  30

Val Tyr Trp Tyr Arg Gln Ile His Ser Gln Gly Pro Gln Tyr Ile Ile
        35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Val Ala Lys Ser Gly
                85                  90                  95

Ala Asn Asn Leu Phe Phe Gly Thr Gly Thr Arg Leu Thr Val Ile Pro
            100                 105                 110

Asn Ile Gln Asn Pro Glu Pro Ala Val Tyr Gln Leu Lys Asp Pro Arg
        115                 120                 125

Ser Gln Asp Ser Thr Leu Cys Leu Phe Thr Asp Phe Asp Ser Gln Ile
    130                 135                 140

Asn Val Pro Lys Thr Met Glu Ser Gly Thr Phe Ile Thr Asp Lys Xaa
145                 150                 155                 160

Val Leu Asp Met Lys Ala Met Asp Ser Lys Ser Asn Gly Ala Ile Ala
                165                 170                 175

Trp Ser Asn Gln Thr Ser Phe Thr Cys Gln Asp Ile Phe Lys Glu Thr
            180                 185                 190

Asn Ala Thr Tyr Pro Ser Ser Asp Val Pro Cys Asp Ala Thr Leu Thr
        195                 200                 205

Glu Lys Ser Phe Glu Thr Asp Met Asn Leu Asn Phe Gln Asn Leu Xaa
    210                 215                 220

Val Xaa Xaa Leu Arg Ile Leu Leu Leu Lys Val Ala Gly Phe Asn Leu
225                 230                 235                 240

Leu Met Thr Leu Arg Leu Trp Ser Ser
                245

<210> SEQ ID NO 84
<211> LENGTH: 286

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (170)..(170)
<223> OTHER INFORMATION: X is Ser or Cys

<400> SEQUENCE: 84

Glu Ala Asp Ile Tyr Gln Thr Pro Arg Tyr Leu Val Ile Gly Thr Gly
1               5                   10                  15

Lys Lys Ile Thr Leu Glu Cys Ser Gln Thr Met Gly His Asp Lys Met
                20                  25                  30

Tyr Trp Tyr Gln Gln Asp Pro Gly Met Glu Leu His Leu Ile His Tyr
            35                  40                  45

Ser Tyr Gly Val Asn Ser Thr Glu Lys Gly Asp Leu Ser Ser Glu Ser
        50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys Ala Ser Ser Gly Leu
                85                  90                  95

Thr Tyr Thr Asp Thr Gln Tyr Phe Gly Pro Gly Thr Arg Leu Thr Val
            100                 105                 110

Leu Glu Asp Leu Arg Asn Val Thr Pro Pro Lys Val Ser Leu Phe Glu
        115                 120                 125

Pro Ser Lys Ala Glu Ile Ala Asn Lys Gln Lys Ala Thr Leu Val Cys
        130                 135                 140

Leu Ala Arg Gly Phe Phe Pro Asp His Val Glu Leu Ser Trp Trp Val
145                 150                 155                 160

Asn Gly Lys Glu Val His Ser Gly Val Xaa Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
            195                 200                 205

Phe His Gly Leu Ser Glu Glu Asp Lys Trp Pro Glu Gly Ser Pro Lys
        210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
            245                 250                 255

Leu Tyr Glu Ile Leu Leu Gly Lys Ala Thr Leu Tyr Ala Val Leu Val
            260                 265                 270

Ser Thr Leu Val Val Met Ala Met Val Lys Arg Lys Asn Ser
            275                 280                 285

<210> SEQ ID NO 85
<211> LENGTH: 266
<212> TYPE: PRT
<213> ORGANISM: Artificial Sequence
<220> FEATURE:
<223> OTHER INFORMATION: Synthetic

<400> SEQUENCE: 85

Met Arg Leu Val Ala Arg Val Thr Val Phe Leu Thr Phe Gly Thr Ile
1               5                   10                  15

Ile Asp Ala Lys Thr Thr Gln Pro Pro Ser Met Asp Cys Ala Glu Gly
```

-continued

```
                20                  25                  30

Arg Ala Ala Asn Leu Pro Cys Asn His Ser Thr Ile Ser Gly Asn Glu
            35                  40                  45

Tyr Val Tyr Trp Tyr Arg Gln Ile His Ser Gln Gly Pro Gln Tyr Ile
    50                  55                  60

Ile His Gly Leu Lys Asn Asn Glu Thr Asn Glu Met Ala Ser Leu Ile
65                  70                  75                  80

Ile Thr Glu Asp Arg Lys Ser Ser Thr Leu Ile Leu Pro His Ala Thr
                85                  90                  95

Leu Arg Asp Thr Ala Val Tyr Tyr Cys Ile Val Arg Val Ala Lys Ser
                100                 105                 110

Gly Ala Asn Asn Leu Phe Phe Gly Thr Gly Thr Arg Leu Thr Val Ile
            115                 120                 125

Pro Asn Ile Gln Asn Pro Glu Pro Ala Val Tyr Gln Leu Lys Asp Pro
    130                 135                 140

Arg Ser Gln Asp Ser Thr Leu Cys Leu Phe Thr Asp Phe Asp Ser Gln
145                 150                 155                 160

Ile Asn Val Pro Lys Thr Met Glu Ser Gly Thr Phe Ile Thr Asp Lys
                165                 170                 175

Cys Val Leu Asp Met Lys Ala Met Asp Ser Lys Ser Asn Gly Ala Ile
                180                 185                 190

Ala Trp Ser Asn Gln Thr Ser Phe Thr Cys Gln Asp Ile Phe Lys Glu
            195                 200                 205

Thr Asn Ala Thr Tyr Pro Ser Ser Asp Val Pro Cys Asp Ala Thr Leu
    210                 215                 220

Thr Glu Lys Ser Phe Glu Thr Asp Met Asn Leu Asn Phe Gln Asn Leu
225                 230                 235                 240

Leu Val Ile Val Leu Arg Ile Leu Leu Leu Lys Val Ala Gly Phe Asn
                245                 250                 255

Leu Leu Met Thr Leu Arg Leu Trp Ser Ser
            260                 265
```

<210> SEQ ID NO 86
<211> LENGTH: 305
<212> TYPE: PRT
<213> ORGANISM: Artificial Sequence
<220> FEATURE:
<223> OTHER INFORMATION: Synthetic

<400> SEQUENCE: 86

```
Met Ala Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gly Leu Thr Tyr Thr Asp Thr Gln Tyr Phe Gly Pro Gly Thr Arg
```

-continued

```
              115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Ala Tyr Lys Glu Ser Asn Tyr Ser Tyr Cys Leu Ser Ser Arg Leu
                195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Thr Leu Val Val Met Ala Met Val Lys Arg Lys Asn
    290                 295                 300

Ser
305
```

```
<210> SEQ ID NO 87
<211> LENGTH: 249
<212> TYPE: PRT
<213> ORGANISM: Artificial Sequence
<220> FEATURE:
<223> OTHER INFORMATION: Synthetic

<400> SEQUENCE: 87

Asp Ala Lys Thr Thr Gln Pro Pro Ser Met Asp Cys Ala Glu Gly Arg
1               5                   10                  15

Ala Ala Asn Leu Pro Cys Asn His Ser Thr Ile Ser Gly Asn Glu Tyr
                20                  25                  30

Val Tyr Trp Tyr Arg Gln Ile His Ser Gln Gly Pro Gln Tyr Ile Ile
                35                  40                  45

His Gly Leu Lys Asn Asn Glu Thr Asn Glu Met Ala Ser Leu Ile Ile
    50                  55                  60

Thr Glu Asp Arg Lys Ser Ser Thr Leu Ile Leu Pro His Ala Thr Leu
65                  70                  75                  80

Arg Asp Thr Ala Val Tyr Tyr Cys Ile Val Arg Val Ala Lys Ser Gly
                85                  90                  95

Ala Asn Asn Leu Phe Phe Gly Thr Gly Thr Arg Leu Thr Val Ile Pro
                100                 105                 110

Asn Ile Gln Asn Pro Glu Pro Ala Val Tyr Gln Leu Lys Asp Pro Arg
                115                 120                 125

Ser Gln Asp Ser Thr Leu Cys Leu Phe Thr Asp Phe Asp Ser Gln Ile
    130                 135                 140

Asn Val Pro Lys Thr Met Glu Ser Gly Thr Phe Ile Thr Asp Lys Cys
145                 150                 155                 160

Val Leu Asp Met Lys Ala Met Asp Ser Lys Ser Asn Gly Ala Ile Ala
```

-continued

```
                    165                 170                 175

Trp Ser Asn Gln Thr Ser Phe Thr Cys Gln Asp Ile Phe Lys Glu Thr
                180                 185                 190

Asn Ala Thr Tyr Pro Ser Ser Asp Val Pro Cys Asp Ala Thr Leu Thr
                195                 200                 205

Glu Lys Ser Phe Glu Thr Asp Met Asn Leu Asn Phe Gln Asn Leu Leu
            210                 215                 220

Val Ile Val Leu Arg Ile Leu Leu Leu Lys Val Ala Gly Phe Asn Leu
225                 230                 235                 240

Leu Met Thr Leu Arg Leu Trp Ser Ser
                245

<210> SEQ ID NO 88
<211> LENGTH: 286
<212> TYPE: PRT
<213> ORGANISM: Artificial Sequence
<220> FEATURE:
<223> OTHER INFORMATION: Synthetic

<400> SEQUENCE: 88

Glu Ala Asp Ile Tyr Gln Thr Pro Arg Tyr Leu Val Ile Gly Thr Gly
1               5                   10                  15

Lys Lys Ile Thr Leu Glu Cys Ser Gln Thr Met Gly His Asp Lys Met
                20                  25                  30

Tyr Trp Tyr Gln Gln Asp Pro Gly Met Glu Leu His Leu Ile His Tyr
                35                  40                  45

Ser Tyr Gly Val Asn Ser Thr Glu Lys Gly Asp Leu Ser Ser Glu Ser
            50                  55                  60

Thr Val Ser Arg Ile Arg Thr Glu His Phe Pro Leu Thr Leu Glu Ser
65                  70                  75                  80

Ala Arg Pro Ser His Thr Ser Gln Tyr Leu Cys Ala Ser Ser Gly Leu
                85                  90                  95

Thr Tyr Thr Asp Thr Gln Tyr Phe Gly Pro Gly Thr Arg Leu Thr Val
                100                 105                 110

Leu Glu Asp Leu Arg Asn Val Thr Pro Pro Lys Val Ser Leu Phe Glu
            115                 120                 125

Pro Ser Lys Ala Glu Ile Ala Asn Lys Gln Lys Ala Thr Leu Val Cys
            130                 135                 140

Leu Ala Arg Gly Phe Phe Pro Asp His Val Glu Leu Ser Trp Trp Val
145                 150                 155                 160

Asn Gly Lys Glu Val His Ser Gly Val Cys Thr Asp Pro Gln Ala Tyr
                165                 170                 175

Lys Glu Ser Asn Tyr Ser Tyr Cys Leu Ser Ser Arg Leu Arg Val Ser
                180                 185                 190

Ala Thr Phe Trp His Asn Pro Arg Asn His Phe Arg Cys Gln Val Gln
                195                 200                 205

Phe His Gly Leu Ser Glu Glu Asp Lys Trp Pro Glu Gly Ser Pro Lys
            210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
                260                 265                 270

Ser Thr Leu Val Val Met Ala Met Val Lys Arg Lys Asn Ser
```

-continued

```
                275                  280                  285
```

<210> SEQ ID NO 89
<211> LENGTH: 272
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (183)..(183)
<223> OTHER INFORMATION: X is Thr or Cys
<220> FEATURE:
<221> NAME/KEY: MISC_FEATURE
<222> LOCATION: (247)..(247)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (249)..(249)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (250)..(250)
<223> OTHER INFORMATION: X is Gly, Ala, Val, Leu, Ile, Pro, Phe, Met, or
      Trp

<400> SEQUENCE: 89

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Tyr Ser Gly Gly Gly Ala Asp Gly Leu Thr Phe Gly Lys Gly
            115                 120                 125

Thr His Leu Ile Ile Gln Pro Asn Ile Gln Asn Pro Glu Pro Ala Val
        130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Xaa Val Leu Asp Met Lys Ala Met Asp Ser
            180                 185                 190

Lys Ser Asn Gly Ala Ile Ala Trp Ser Asn Gln Thr Ser Phe Thr Cys
            195                 200                 205

Gln Asp Ile Phe Lys Glu Thr Asn Ala Thr Tyr Pro Ser Ser Asp Val
        210                 215                 220

Pro Cys Asp Ala Thr Leu Thr Glu Lys Ser Phe Glu Thr Asp Met Asn
225                 230                 235                 240

Leu Asn Phe Gln Asn Leu Xaa Val Xaa Xaa Leu Arg Ile Leu Leu Leu
                245                 250                 255

Lys Val Ala Gly Phe Asn Leu Leu Met Thr Leu Arg Leu Trp Ser Ser
```

-continued

```
              260             265             270

<210> SEQ ID NO 90
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 90

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Gln Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
        130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
    290                 295                 300

<210> SEQ ID NO 91
<211> LENGTH: 250
<212> TYPE: PRT
<213> ORGANISM: Artificial Sequence
<220> FEATURE:
```

<223> OTHER INFORMATION: Synthetic
<220> FEATURE:
<221> NAME/KEY: MISC_FEATURE
<222> LOCATION: (161)..(161)
<223> OTHER INFORMATION: X is Thr or Cys
<220> FEATURE:
<221> NAME/KEY: MISC_FEATURE
<222> LOCATION: (225)..(225)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (227)..(227)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (228)..(228)
<223> OTHER INFORMATION: X is Gly, Ala, Val, Leu, Ile, Pro, Phe, Met, or
      Trp

<400> SEQUENCE: 91

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Ser Tyr Ser Gly Gly
                85                  90                  95

Gly Ala Asp Gly Leu Thr Phe Gly Lys Gly Thr His Leu Ile Ile Gln
            100                 105                 110

Pro Asn Ile Gln Asn Pro Glu Pro Ala Val Tyr Gln Leu Lys Asp Pro
            115                 120                 125

Arg Ser Gln Asp Ser Thr Leu Cys Leu Phe Thr Asp Phe Asp Ser Gln
    130                 135                 140

Ile Asn Val Pro Lys Thr Met Glu Ser Gly Thr Phe Ile Thr Asp Lys
145                 150                 155                 160

Xaa Val Leu Asp Met Lys Ala Met Asp Ser Lys Ser Asn Gly Ala Ile
                165                 170                 175

Ala Trp Ser Asn Gln Thr Ser Phe Thr Cys Gln Asp Ile Phe Lys Glu
            180                 185                 190

Thr Asn Ala Thr Tyr Pro Ser Ser Asp Val Pro Cys Asp Ala Thr Leu
    195                 200                 205

Thr Glu Lys Ser Phe Glu Thr Asp Met Asn Leu Asn Phe Gln Asn Leu
    210                 215                 220

Xaa Val Xaa Xaa Leu Arg Ile Leu Leu Leu Lys Val Ala Gly Phe Asn
225                 230                 235                 240

Leu Leu Met Thr Leu Arg Leu Trp Ser Ser
            245                 250

<210> SEQ ID NO 92
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE -continued

```
<222> LOCATION: (169)..(169)
<223> OTHER INFORMATION: X is Ser or Cys

<400> SEQUENCE: 92

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 93
<211> LENGTH: 272
<212> TYPE: PRT
<213> ORGANISM: Artificial Sequence
<220> FEATURE:
<223> OTHER INFORMATION: Synthetic

<400> SEQUENCE: 93

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
```

-continued

```
              50              55              60
Gly Pro Glu Leu Leu Met Tyr Thr Tyr Ser Ser Gly Asn Lys Glu Asp
65              70              75              80

Gly Arg Phe Thr Ala Gln Val Asp Lys Ser Ser Lys Tyr Ile Ser Leu
                85              90              95

Phe Ile Arg Asp Ser Gln Pro Ser Asp Ser Ala Thr Tyr Leu Cys Ala
                100             105             110

Met Ser Tyr Ser Gly Gly Gly Ala Asp Gly Leu Thr Phe Gly Lys Gly
            115             120             125

Thr His Leu Ile Ile Gln Pro Asn Ile Gln Asn Pro Glu Pro Ala Val
        130             135             140

Tyr Gln Leu Lys Asp Pro Arg Ser Gln Asp Ser Thr Leu Cys Leu Phe
145             150             155             160

Thr Asp Phe Asp Ser Gln Ile Asn Val Pro Lys Thr Met Glu Ser Gly
                165             170             175

Thr Phe Ile Thr Asp Lys Cys Val Leu Asp Met Lys Ala Met Asp Ser
            180             185             190

Lys Ser Asn Gly Ala Ile Ala Trp Ser Asn Gln Thr Ser Phe Thr Cys
            195             200             205

Gln Asp Ile Phe Lys Glu Thr Asn Ala Thr Tyr Pro Ser Ser Asp Val
        210             215             220

Pro Cys Asp Ala Thr Leu Thr Glu Lys Ser Phe Glu Thr Asp Met Asn
225             230             235             240

Leu Asn Phe Gln Asn Leu Leu Val Ile Val Leu Arg Ile Leu Leu Leu
            245             250             255

Lys Val Ala Gly Phe Asn Leu Leu Met Thr Leu Arg Leu Trp Ser Ser
            260             265             270
```

```
<210> SEQ ID NO 94
<211> LENGTH: 304
<212> TYPE: PRT
<213> ORGANISM: Artificial Sequence
<220> FEATURE:
<223> OTHER INFORMATION: Synthetic

<400> SEQUENCE: 94
```

```
Met Ala Ile Arg Leu Leu Cys Arg Val Ala Phe Cys Phe Leu Ala Val
1               5               10              15

Gly Leu Val Asp Val Lys Val Thr Gln Ser Ser Arg Tyr Leu Val Lys
                20              25              30

Arg Thr Gly Glu Lys Val Phe Leu Glu Cys Val Gln Asp Met Asp His
            35              40              45

Glu Asn Met Phe Trp Tyr Arg Gln Asp Pro Gly Leu Gly Leu Arg Leu
        50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
                85              90              95

Leu Glu Ser Ala Ser Thr Asn Gln Thr Ser Met Tyr Leu Cys Ala Ser
            100             105             110

Ser Gln Gly Asn Thr Gly Glu Leu Phe Phe Gly Glu Gly Ser Arg Leu
            115             120             125

Thr Val Leu Glu Asp Leu Arg Asn Val Thr Pro Pro Lys Val Ser Leu
        130             135             140

Phe Glu Pro Ser Lys Ala Glu Ile Ala Asn Lys Gln Lys Ala Thr Leu
```

```
145              150              155              160

Val Cys Leu Ala Arg Gly Phe Phe Pro Asp His Val Glu Leu Ser Trp
            165              170              175

Trp Val Asn Gly Lys Glu Val His Ser Gly Val Cys Thr Asp Pro Gln
            180              185              190

Ala Tyr Lys Glu Ser Asn Tyr Ser Tyr Cys Leu Ser Ser Arg Leu Arg
            195              200              205

Val Ser Ala Thr Phe Trp His Asn Pro Arg Asn His Phe Arg Cys Gln
    210              215              220

Val Gln Phe His Gly Leu Ser Glu Glu Asp Lys Trp Pro Glu Gly Ser
225              230              235              240

Pro Lys Pro Val Thr Gln Asn Ile Ser Ala Glu Ala Trp Gly Arg Ala
            245              250              255

Asp Cys Gly Ile Thr Ser Ala Ser Tyr Gln Gln Gly Val Leu Ser Ala
            260              265              270

Thr Ile Leu Tyr Glu Ile Leu Leu Gly Lys Ala Thr Leu Tyr Ala Val
            275              280              285

Leu Val Ser Thr Leu Val Val Met Ala Met Val Lys Arg Lys Asn Ser
    290              295              300

<210> SEQ ID NO 95
<211> LENGTH: 250
<212> TYPE: PRT
<213> ORGANISM: Artificial Sequence
<220> FEATURE:
<223> OTHER INFORMATION: Synthetic

<400> SEQUENCE: 95

Gln Lys Glu Val Glu Gln Asp Pro Gly Pro Leu Ser Val Pro Glu Gly
1                5               10              15

Ala Ile Val Ser Leu Asn Cys Thr Tyr Ser Asn Ser Ala Phe Gln Tyr
            20              25              30

Phe Met Trp Tyr Arg Gln Tyr Ser Arg Lys Gly Pro Glu Leu Leu Met
        35              40              45

Tyr Thr Tyr Ser Ser Gly Asn Lys Glu Asp Gly Arg Phe Thr Ala Gln
    50              55              60

Val Asp Lys Ser Ser Lys Tyr Ile Ser Leu Phe Ile Arg Asp Ser Gln
65              70              75              80

Pro Ser Asp Ser Ala Thr Tyr Leu Cys Ala Met Ser Tyr Ser Gly Gly
            85              90              95

Gly Ala Asp Gly Leu Thr Phe Gly Lys Gly Thr His Leu Ile Ile Gln
            100             105             110

Pro Asn Ile Gln Asn Pro Glu Pro Ala Val Tyr Gln Leu Lys Asp Pro
        115             120             125

Arg Ser Gln Asp Ser Thr Leu Cys Leu Phe Thr Asp Phe Asp Ser Gln
    130             135             140

Ile Asn Val Pro Lys Thr Met Glu Ser Gly Thr Phe Ile Thr Asp Lys
145             150             155             160

Cys Val Leu Asp Met Lys Ala Met Asp Ser Lys Ser Asn Gly Ala Ile
            165             170             175

Ala Trp Ser Asn Gln Thr Ser Phe Thr Cys Gln Asp Ile Phe Lys Glu
            180             185             190

Thr Asn Ala Thr Tyr Pro Ser Ser Asp Val Pro Cys Asp Ala Thr Leu
        195             200             205

Thr Glu Lys Ser Phe Glu Thr Asp Met Asn Leu Asn Phe Gln Asn Leu
```

```
          210             215             220

Leu Val Ile Val Leu Arg Ile Leu Leu Lys Val Ala Gly Phe Asn
225                 230             235                 240

Leu Leu Met Thr Leu Arg Leu Trp Ser Ser
            245             250

<210> SEQ ID NO 96
<211> LENGTH: 285
<212> TYPE: PRT
<213> ORGANISM: Artificial Sequence
<220> FEATURE:
<223> OTHER INFORMATION: Synthetic

<400> SEQUENCE: 96

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
        130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
        210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
            275                 280                 285

<210> SEQ ID NO 97
<211> LENGTH: 267
<212> TYPE: PRT
<213> ORGANISM: Artificial Sequence
<220> FEATURE:
<223> OTHER INFORMATION: Synthetic
```

-continued

<220> FEATURE:
<221> NAME/KEY: MISC_FEATURE
<222> LOCATION: (178)..(178)
<223> OTHER INFORMATION: X is Thr or Cys
<220> FEATURE:
<221> NAME/KEY: MISC_FEATURE
<222> LOCATION: (242)..(242)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (244)..(244)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (245)..(245)
<223> OTHER INFORMATION: X is Gly, Ala, Val, Leu, Ile, Pro, Phe, Met, or
      Trp

<400> SEQUENCE: 97

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
        35                  40                  45

Ser Ser Thr Tyr Leu Tyr Trp Tyr Lys Gln Glu Pro Gly Ala Gly Leu
    50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Pro
            100                 105                 110

Gly Gly Tyr Asn Lys Leu Ile Phe Gly Ala Gly Thr Arg Leu Ala Val
        115                 120                 125

His Pro Asn Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
            165                 170                 175

Lys Xaa Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Xaa Val Xaa Xaa Leu Arg Ile Leu Leu Leu Lys Val Ala Gly Phe
        245                 250                 255

Asn Leu Leu Met Thr Leu Arg Leu Trp Ser Ser
            260                 265

<210> SEQ ID NO 98
<211> LENGTH: 304
<212> TYPE: PRT
<213> ORGANISM: Artificial Sequence
<220> FEATURE:
<223> OTHER INFORMATION: Synthetic -continued

```
<220> FEATURE:
<221> NAME/KEY: MISC_FEATURE
<222> LOCATION: (188)..(188)
<223> OTHER INFORMATION: X is Ser or Cys

<400> SEQUENCE: 98

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Arg Ile Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
                180                 185                 190

Ala Tyr Lys Glu Ser Asn Tyr Ser Tyr Cys Leu Ser Ser Arg Leu Arg
                195                 200                 205

Val Ser Ala Thr Phe Trp His Asn Pro Arg Asn His Phe Arg Cys Gln
            210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
            290                 295                 300

<210> SEQ ID NO 99
<211> LENGTH: 246
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (157)..(157)
<223> OTHER INFORMATION: X is Thr or Cys
<220> FEATURE:
<221> NAME/KEY: MISC_FEATURE
<222> LOCATION: (221)..(221)
<223> OTHER INFORMATION: X is Ser, Ala, Val, Leu, Ile, Pro, Phe, Met, or
```

-continued

```
    Trp
<220> FEATURE:
<221> NAME/KEY: MISC_FEATURE
<222> LOCATION: (223)..(223)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (224)..(224)
<223> OTHER INFORMATION: X is Gly, Ala, Val, Leu, Ile, Pro, Phe, Met, or
    Trp

<400> SEQUENCE: 99

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
            20                  25                  30

Tyr Trp Tyr Lys Gln Glu Pro Gly Ala Gly Leu Gln Leu Leu Thr Tyr
        35                  40                  45

Ile Phe Ser Asn Met Asp Met Lys Gln Asp Gln Arg Leu Thr Val Leu
    50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Pro Gly Gly Tyr Asn Lys
                85                  90                  95

Leu Ile Phe Gly Ala Gly Thr Arg Leu Ala Val His Pro Asn Ile Gln
            100                 105                 110

Asn Pro Glu Pro Ala Val Tyr Gln Leu Lys Asp Pro Arg Ser Gln Asp
        115                 120                 125

Ser Thr Leu Cys Leu Phe Thr Asp Phe Asp Ser Gln Ile Asn Val Pro
    130                 135                 140

Lys Thr Met Glu Ser Gly Thr Phe Ile Thr Asp Lys Xaa Val Leu Asp
145                 150                 155                 160

Met Lys Ala Met Asp Ser Lys Ser Asn Gly Ala Ile Ala Trp Ser Asn
                165                 170                 175

Gln Thr Ser Phe Thr Cys Gln Asp Ile Phe Lys Glu Thr Asn Ala Thr
            180                 185                 190

Tyr Pro Ser Ser Asp Val Pro Cys Asp Ala Thr Leu Thr Glu Lys Ser
        195                 200                 205

Phe Glu Thr Asp Met Asn Leu Asn Phe Gln Asn Leu Xaa Val Xaa Xaa
    210                 215                 220

Leu Arg Ile Leu Leu Leu Lys Val Ala Gly Phe Asn Leu Leu Met Thr
225                 230                 235                 240

Leu Arg Leu Trp Ser Ser
                245

<210> SEQ ID NO 100
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 100

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
```

-continued

```
                20                25                30

Phe Trp Tyr Arg Gln Asp Pro Gly Leu Gly Leu Arg Leu Ile Tyr Phe
        35                40                45

Ser Tyr Asp Val Lys Met Lys Glu Lys Gly Asp Ile Pro Glu Gly Tyr
    50                55                60

Ser Val Ser Arg Glu Lys Lys Glu Arg Phe Ser Leu Ile Leu Glu Ser
65                70                75                80

Ala Ser Thr Asn Gln Thr Ser Met Tyr Leu Cys Ala Ser Arg Ile Gly
                85                90                95

Asn Thr Gly Glu Leu Phe Phe Gly Glu Gly Ser Arg Leu Thr Val Leu
            100               105               110

Glu Asp Leu Arg Asn Val Thr Pro Pro Lys Val Ser Leu Phe Glu Pro
        115               120               125

Ser Lys Ala Glu Ile Ala Asn Lys Gln Lys Ala Thr Leu Val Cys Leu
        130               135               140

Ala Arg Gly Phe Phe Pro Asp His Val Glu Leu Ser Trp Trp Val Asn
145               150               155               160

Gly Lys Glu Val His Ser Gly Val Xaa Thr Asp Pro Gln Ala Tyr Lys
            165               170               175

Glu Ser Asn Tyr Ser Tyr Cys Leu Ser Ser Arg Leu Arg Val Ser Ala
            180               185               190

Thr Phe Trp His Asn Pro Arg Asn His Phe Arg Cys Gln Val Gln Phe
            195               200               205

His Gly Leu Ser Glu Glu Asp Lys Trp Pro Glu Gly Ser Pro Lys Pro
        210               215               220

Val Thr Gln Asn Ile Ser Ala Glu Ala Trp Gly Arg Ala Asp Cys Gly
225               230               235               240

Ile Thr Ser Ala Ser Tyr Gln Gln Gly Val Leu Ser Ala Thr Ile Leu
            245               250               255

Tyr Glu Ile Leu Leu Gly Lys Ala Thr Leu Tyr Ala Val Leu Val Ser
            260               265               270

Thr Leu Val Val Met Ala Met Val Lys Arg Lys Asn Ser
        275               280               285
```

<210> SEQ ID NO 101
<211> LENGTH: 267
<212> TYPE: PRT
<213> ORGANISM: Artificial Sequence
<220> FEATURE:
<223> OTHER INFORMATION: Synthetic

<400> SEQUENCE: 101

```
Met Lys Thr Phe Ala Gly Phe Ser Phe Leu Phe Leu Trp Leu Gln Leu
1               5                10                15

Asp Cys Met Ser Arg Gly Glu Asp Val Glu Gln Ser Leu Phe Leu Ser
            20                25                30

Val Arg Glu Gly Asp Ser Ser Val Ile Asn Cys Thr Tyr Thr Asp Ser
        35                40                45

Ser Ser Thr Tyr Leu Tyr Trp Tyr Lys Gln Glu Pro Gly Ala Gly Leu
    50                55                60

Gln Leu Leu Thr Tyr Ile Phe Ser Asn Met Asp Met Lys Gln Asp Gln
65                70                75                80

Arg Leu Thr Val Leu Leu Asn Lys Lys Asp Lys His Leu Ser Leu Arg
                85                90                95

Ile Ala Asp Thr Gln Thr Gly Asp Ser Ala Ile Tyr Phe Cys Ala Pro
```

-continued

```
                100                 105                 110

Gly Gly Tyr Asn Lys Leu Ile Phe Gly Ala Gly Thr Arg Leu Ala Val
            115                 120                 125

His Pro Asn Ile Gln Asn Pro Glu Pro Ala Val Tyr Gln Leu Lys Asp
        130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Cys Val Leu Asp Met Lys Ala Met Asp Ser Lys Ser Asn Gly Ala
                180                 185                 190

Ile Ala Trp Ser Asn Gln Thr Ser Phe Thr Cys Gln Asp Ile Phe Lys
                195                 200                 205

Glu Thr Asn Ala Thr Tyr Pro Ser Ser Asp Val Pro Cys Asp Ala Thr
        210                 215                 220

Leu Thr Glu Lys Ser Phe Glu Thr Asp Met Asn Leu Asn Phe Gln Asn
225                 230                 235                 240

Leu Leu Val Ile Val Leu Arg Ile Leu Leu Leu Lys Val Ala Gly Phe
                245                 250                 255

Asn Leu Leu Met Thr Leu Arg Leu Trp Ser Ser
            260                 265
```

```
<210> SEQ ID NO 102
<211> LENGTH: 304
<212> TYPE: PRT
<213> ORGANISM: Artificial Sequence
<220> FEATURE:
<223> OTHER INFORMATION: Synthetic

<400> SEQUENCE: 102
```

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Ile Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
        130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
```

```
            195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                    245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
                275                 280                 285

Leu Val Ser Thr Leu Val Val Met Ala Met Val Lys Arg Lys Asn Ser
    290                 295                 300

<210> SEQ ID NO 103
<211> LENGTH: 246
<212> TYPE: PRT
<213> ORGANISM: Artificial Sequence
<220> FEATURE:
<223> OTHER INFORMATION: Synthetic

<400> SEQUENCE: 103

Gly Glu Asp Val Glu Gln Ser Leu Phe Leu Ser Val Arg Glu Gly Asp
1               5                   10                  15

Ser Ser Val Ile Asn Cys Thr Tyr Thr Asp Ser Ser Ser Thr Tyr Leu
                20                  25                  30

Tyr Trp Tyr Lys Gln Glu Pro Gly Ala Gly Leu Gln Leu Leu Thr Tyr
                35                  40                  45

Ile Phe Ser Asn Met Asp Met Lys Gln Asp Gln Arg Leu Thr Val Leu
    50                  55                  60

Leu Asn Lys Lys Asp Lys His Leu Ser Leu Arg Ile Ala Asp Thr Gln
65                  70                  75                  80

Thr Gly Asp Ser Ala Ile Tyr Phe Cys Ala Pro Gly Gly Tyr Asn Lys
                85                  90                  95

Leu Ile Phe Gly Ala Gly Thr Arg Leu Ala Val His Pro Asn Ile Gln
                100                 105                 110

Asn Pro Glu Pro Ala Val Tyr Gln Leu Lys Asp Pro Arg Ser Gln Asp
        115                 120                 125

Ser Thr Leu Cys Leu Phe Thr Asp Phe Asp Ser Gln Ile Asn Val Pro
    130                 135                 140

Lys Thr Met Glu Ser Gly Thr Phe Ile Thr Asp Lys Cys Val Leu Asp
145                 150                 155                 160

Met Lys Ala Met Asp Ser Lys Ser Asn Gly Ala Ile Ala Trp Ser Asn
                165                 170                 175

Gln Thr Ser Phe Thr Cys Gln Asp Ile Phe Lys Glu Thr Asn Ala Thr
                180                 185                 190

Tyr Pro Ser Ser Asp Val Pro Cys Asp Ala Thr Leu Thr Glu Lys Ser
        195                 200                 205

Phe Glu Thr Asp Met Asn Leu Asn Phe Gln Asn Leu Leu Val Ile Val
    210                 215                 220

Leu Arg Ile Leu Leu Leu Lys Val Ala Gly Phe Asn Leu Leu Met Thr
225                 230                 235                 240

Leu Arg Leu Trp Ser Ser
                245
```

```
<210> SEQ ID NO 104
<211> LENGTH: 285
<212> TYPE: PRT
<213> ORGANISM: Artificial Sequence
<220> FEATURE:
<223> OTHER INFORMATION: Synthetic

<400> SEQUENCE: 104

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Ile Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 105
<211> LENGTH: 27
<212> TYPE: PRT
<213> ORGANISM: Artificial Sequence
<220> FEATURE:
<223> OTHER INFORMATION: Synthetic

<400> SEQUENCE: 105

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25
```

-continued

```
<210> SEQ ID NO 106
<211> LENGTH: 24
<212> TYPE: PRT
<213> ORGANISM: Homo sapiens

<400> SEQUENCE: 106

Met Thr Glu Tyr Lys Leu Val Val Val Gly Ala Gly Asp Val Gly Lys
1               5                   10                  15

Ser Ala Leu Thr Ile Gln Leu Ile
            20

<210> SEQ ID NO 107
<211> LENGTH: 24
<212> TYPE: PRT
<213> ORGANISM: Homo sapiens

<400> SEQUENCE: 107

Met Thr Glu Tyr Lys Leu Val Val Val Gly Ala Gly Gly Val Gly Lys
1               5                   10                  15

Ser Ala Leu Thr Ile Gln Leu Ile
            20

<210> SEQ ID NO 108
<211> LENGTH: 600
<212> TYPE: PRT
<213> ORGANISM: Artificial Sequence
<220> FEATURE:
<223> OTHER INFORMATION: Synthetic

<400> SEQUENCE: 108

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Leu Gly Asn Thr Gly Glu Leu Phe Phe Gly Glu Gly Ser Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
                180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220
```

-continued

```
Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
            290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Met Lys Ser Leu
                325                 330                 335

Arg Val Leu Leu Val Ile Leu Trp Leu Gln Leu Ser Trp Val Trp Ser
            340                 345                 350

Gln Gln Lys Glu Val Glu Gln Asp Pro Gly Pro Leu Ser Val Pro Glu
            355                 360                 365

Gly Ala Ile Val Ser Leu Asn Cys Thr Tyr Ser Asn Ser Ala Phe Gln
            370                 375                 380

Tyr Phe Met Trp Tyr Arg Gln Tyr Ser Arg Lys Gly Pro Glu Leu Leu
385                 390                 395                 400

Met Tyr Thr Tyr Ser Ser Gly Asn Lys Glu Asp Gly Arg Phe Thr Ala
                405                 410                 415

Gln Val Asp Lys Ser Ser Lys Tyr Ile Ser Leu Phe Ile Arg Asp Ser
            420                 425                 430

Gln Pro Ser Asp Ser Ala Thr Tyr Leu Cys Ala Met Arg Ala Asn Thr
            435                 440                 445

Asp Lys Leu Ile Phe Gly Thr Gly Thr Arg Leu Gln Val Phe Pro Asn
            450                 455                 460

Ile Gln Asn Pro Glu Pro Ala Val Tyr Gln Leu Lys Asp Pro Arg Ser
465                 470                 475                 480

Gln Asp Ser Thr Leu Cys Leu Phe Thr Asp Phe Asp Ser Gln Ile Asn
                485                 490                 495

Val Pro Lys Thr Met Glu Ser Gly Thr Phe Ile Thr Asp Lys Cys Val
                500                 505                 510

Leu Asp Met Lys Ala Met Asp Ser Lys Ser Asn Gly Ala Ile Ala Trp
            515                 520                 525

Ser Asn Gln Thr Ser Phe Thr Cys Gln Asp Ile Phe Lys Glu Thr Asn
            530                 535                 540

Ala Thr Tyr Pro Ser Ser Asp Val Pro Cys Asp Ala Thr Leu Thr Glu
545                 550                 555                 560

Lys Ser Phe Glu Thr Asp Met Asn Leu Asn Phe Gln Asn Leu Leu Val
                565                 570                 575

Ile Val Leu Arg Ile Leu Leu Leu Lys Val Ala Gly Phe Asn Leu Leu
            580                 585                 590

Met Thr Leu Arg Leu Trp Ser Ser
            595                 600
```

<210> SEQ ID NO 109
<211> LENGTH: 600
<212> TYPE: PRT
<213> ORGANISM: Artificial Sequence
<220> FEATURE:

-continued

<223> OTHER INFORMATION: Synthetic

<400> SEQUENCE: 109

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
            100                 105                 110

Arg Gln Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
        130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
            165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
            245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Met Lys Ser Leu
            325                 330                 335

Arg Val Leu Leu Val Ile Leu Trp Leu Gln Leu Ser Trp Val Trp Ser
            340                 345                 350

Gln Gln Lys Glu Val Glu Gln Asp Pro Gly Pro Leu Ser Val Pro Glu
            355                 360                 365

Gly Ala Ile Val Ser Leu Asn Cys Thr Tyr Ser Asn Ser Ala Phe Gln
    370                 375                 380

Tyr Phe Met Trp Tyr Arg Gln Tyr Ser Arg Lys Gly Pro Glu Leu Leu
385                 390                 395                 400
```

-continued

```
Met Tyr Thr Tyr Ser Ser Gly Asn Lys Glu Asp Gly Arg Phe Thr Ala
            405             410             415

Gln Val Asp Lys Ser Ser Lys Tyr Ile Ser Leu Phe Ile Arg Asp Ser
            420             425             430

Gln Pro Ser Asp Ser Ala Thr Tyr Leu Cys Ala Met Arg Ala Asn Thr
            435             440             445

Asp Lys Leu Ile Phe Gly Thr Gly Thr Arg Leu Gln Val Phe Pro Asn
        450             455             460

Ile Gln Asn Pro Glu Pro Ala Val Tyr Gln Leu Lys Asp Pro Arg Ser
465             470             475             480

Gln Asp Ser Thr Leu Cys Leu Phe Thr Asp Phe Asp Ser Gln Ile Asn
            485             490             495

Val Pro Lys Thr Met Glu Ser Gly Thr Phe Ile Thr Asp Lys Cys Val
            500             505             510

Leu Asp Met Lys Ala Met Asp Ser Lys Ser Asn Gly Ala Ile Ala Trp
            515             520             525

Ser Asn Gln Thr Ser Phe Thr Cys Gln Asp Ile Phe Lys Glu Thr Asn
            530             535             540

Ala Thr Tyr Pro Ser Ser Asp Val Pro Cys Asp Ala Thr Leu Thr Glu
545             550             555             560

Lys Ser Phe Glu Thr Asp Met Asn Leu Asn Phe Gln Asn Leu Leu Val
            565             570             575

Ile Val Leu Arg Ile Leu Leu Leu Lys Val Ala Gly Phe Asn Leu Leu
            580             585             590

Met Thr Leu Arg Leu Trp Ser Ser
            595             600

<210> SEQ ID NO 110
<211> LENGTH: 598
<212> TYPE: PRT
<213> ORGANISM: Artificial Sequence
<220> FEATURE:
<223> OTHER INFORMATION: Synthetic

<400> SEQUENCE: 110

Met Ala Ile Arg Leu Leu Cys Tyr Met Gly Phe Tyr Phe Leu Gly Ala
1               5               10              15

Gly Leu Met Glu Ala Asp Ile Tyr Gln Thr Pro Arg Tyr Leu Val Ile
            20              25              30

Gly Thr Gly Lys Lys Ile Thr Leu Glu Cys Ser Gln Thr Met Gly His
            35              40              45

Asp Lys Met Tyr Trp Tyr Gln Gln Asp Pro Gly Met Glu Leu His Leu
        50              55              60

Ile His Tyr Ser Tyr Gly Val Asn Ser Thr Glu Lys Gly Asp Leu Ser
65              70              75              80

Ser Glu Ser Thr Val Ser Arg Ile Arg Thr Glu His Phe Pro Leu Thr
            85              90              95

Leu Glu Ser Ala Arg Pro Ser His Thr Ser Gln Tyr Leu Cys Ala Ser
            100             105             110

Ser Gly Leu Thr Tyr Thr Asp Thr Gln Tyr Phe Gly Pro Gly Thr Arg
            115             120             125

Leu Thr Val Leu Glu Asp Leu Arg Asn Val Thr Pro Pro Lys Val Ser
        130             135             140

Leu Phe Glu Pro Ser Lys Ala Glu Ile Ala Asn Lys Gln Lys Ala Thr
145             150             155             160
```

```
Leu Val Cys Leu Ala Arg Gly Phe Phe Pro Asp His Val Glu Leu Ser
            165                 170                 175

Trp Trp Val Asn Gly Lys Glu Val His Ser Gly Val Cys Thr Asp Pro
            180                 185                 190

Gln Ala Tyr Lys Glu Ser Asn Tyr Ser Tyr Cys Leu Ser Ser Arg Leu
            195                 200                 205

Arg Val Ser Ala Thr Phe Trp His Asn Pro Arg Asn His Phe Arg Cys
        210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Thr Leu Val Val Met Ala Met Val Lys Arg Lys Asn
        290                 295                 300

Ser Arg Ala Lys Arg Ser Gly Ser Gly Ala Thr Asn Phe Ser Leu Leu
305                 310                 315                 320

Lys Gln Ala Gly Asp Val Glu Glu Asn Pro Gly Pro Met Arg Leu Val
                325                 330                 335

Ala Arg Val Thr Val Phe Leu Thr Phe Gly Thr Ile Ile Asp Ala Lys
            340                 345                 350

Thr Thr Gln Pro Pro Ser Met Asp Cys Ala Glu Gly Arg Ala Ala Asn
            355                 360                 365

Leu Pro Cys Asn His Ser Thr Ile Ser Gly Asn Glu Tyr Val Tyr Trp
        370                 375                 380

Tyr Arg Gln Ile His Ser Gln Gly Pro Gln Tyr Ile Ile His Gly Leu
385                 390                 395                 400

Lys Asn Asn Glu Thr Asn Glu Met Ala Ser Leu Ile Ile Thr Glu Asp
                405                 410                 415

Arg Lys Ser Ser Thr Leu Ile Leu Pro His Ala Thr Leu Arg Asp Thr
            420                 425                 430

Ala Val Tyr Tyr Cys Ile Val Arg Val Ala Lys Ser Gly Ala Asn Asn
            435                 440                 445

Leu Phe Phe Gly Thr Gly Thr Arg Leu Thr Val Ile Pro Asn Ile Gln
    450                 455                 460

Asn Pro Glu Pro Ala Val Tyr Gln Leu Lys Asp Pro Arg Ser Gln Asp
465                 470                 475                 480

Ser Thr Leu Cys Leu Phe Thr Asp Phe Asp Ser Gln Ile Asn Val Pro
            485                 490                 495

Lys Thr Met Glu Ser Gly Thr Phe Ile Thr Asp Lys Cys Val Leu Asp
            500                 505                 510

Met Lys Ala Met Asp Ser Lys Ser Asn Gly Ala Ile Ala Trp Ser Asn
        515                 520                 525

Gln Thr Ser Phe Thr Cys Gln Asp Ile Phe Lys Glu Thr Asn Ala Thr
        530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Ile Val
                565                 570                 575

Leu Arg Ile Leu Leu Leu Lys Val Ala Gly Phe Asn Leu Leu Met Thr
```

-continued

```
                580             585             590
Leu Arg Leu Trp Ser Ser
        595

<210> SEQ ID NO 111
<211> LENGTH: 603
<212> TYPE: PRT
<213> ORGANISM: Artificial Sequence
<220> FEATURE:
<223> OTHER INFORMATION: Synthetic

<400> SEQUENCE: 111

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Gln Gly Asn Thr Gly Glu Leu Phe Phe Gly Glu Gly Ser Arg Leu
        115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Met Lys Ser Leu
                325                 330                 335

Arg Val Leu Leu Val Ile Leu Trp Leu Gln Leu Ser Trp Val Trp Ser
```

-continued

```
          340              345              350
Gln Gln Lys Glu Val Glu Gln Asp Pro Gly Pro Leu Ser Val Pro Glu
        355              360              365
Gly Ala Ile Val Ser Leu Asn Cys Thr Tyr Ser Asn Ser Ala Phe Gln
        370              375              380
Tyr Phe Met Trp Tyr Arg Gln Tyr Ser Arg Lys Gly Pro Glu Leu Leu
385              390              395              400
Met Tyr Thr Tyr Ser Ser Gly Asn Lys Glu Asp Gly Arg Phe Thr Ala
                405              410              415
Gln Val Asp Lys Ser Ser Lys Tyr Ile Ser Leu Phe Ile Arg Asp Ser
            420              425              430
Gln Pro Ser Asp Ser Ala Thr Tyr Leu Cys Ala Met Ser Tyr Ser Gly
        435              440              445
Gly Gly Ala Asp Gly Leu Thr Phe Gly Lys Gly Thr His Leu Ile Ile
        450              455              460
Gln Pro Asn Ile Gln Asn Pro Glu Pro Ala Val Tyr Gln Leu Lys Asp
465              470              475              480
Pro Arg Ser Gln Asp Ser Thr Leu Cys Leu Phe Thr Asp Phe Asp Ser
                485              490              495
Gln Ile Asn Val Pro Lys Thr Met Glu Ser Gly Thr Phe Ile Thr Asp
            500              505              510
Lys Cys Val Leu Asp Met Lys Ala Met Asp Ser Lys Ser Asn Gly Ala
            515              520              525
Ile Ala Trp Ser Asn Gln Thr Ser Phe Thr Cys Gln Asp Ile Phe Lys
        530              535              540
Glu Thr Asn Ala Thr Tyr Pro Ser Ser Asp Val Pro Cys Asp Ala Thr
545              550              555              560
Leu Thr Glu Lys Ser Phe Glu Thr Asp Met Asn Leu Asn Phe Gln Asn
                565              570              575
Leu Leu Val Ile Val Leu Arg Ile Leu Leu Leu Lys Val Ala Gly Phe
                580              585              590
Asn Leu Leu Met Thr Leu Arg Leu Trp Ser Ser
            595              600
```

```
<210> SEQ ID NO 112
<211> LENGTH: 598
<212> TYPE: PRT
<213> ORGANISM: Artificial Sequence
<220> FEATURE:
<223> OTHER INFORMATION: Synthetic

<400> SEQUENCE: 112

Met Ala Ile Arg Leu Leu Cys Arg Val Ala Phe Cys Phe Leu Ala Val
1               5              10               15
Gly Leu Val Asp Val Lys Val Thr Gln Ser Ser Arg Tyr Leu Val Lys
            20              25               30
Arg Thr Gly Glu Lys Val Phe Leu Glu Cys Val Gln Asp Met Asp His
        35              40               45
Glu Asn Met Phe Trp Tyr Arg Gln Asp Pro Gly Leu Gly Leu Arg Leu
    50              55               60
Ile Tyr Phe Ser Tyr Asp Val Lys Met Lys Glu Lys Gly Asp Ile Pro
65              70               75               80
Glu Gly Tyr Ser Val Ser Arg Glu Lys Lys Glu Arg Phe Ser Leu Ile
                85              90               95
Leu Glu Ser Ala Ser Thr Asn Gln Thr Ser Met Tyr Leu Cys Ala Ser
```

-continued

```
                     100              105               110
Arg Ile Gly Asn Thr Gly Glu Leu Phe Phe Gly Glu Gly Ser Arg Leu
            115              120              125

Thr Val Leu Glu Asp Leu Arg Asn Val Thr Pro Pro Lys Val Ser Leu
        130              135              140

Phe Glu Pro Ser Lys Ala Glu Ile Ala Asn Lys Gln Lys Ala Thr Leu
145              150              155              160

Val Cys Leu Ala Arg Gly Phe Phe Pro Asp His Val Glu Leu Ser Trp
            165              170              175

Trp Val Asn Gly Lys Glu Val His Ser Gly Val Cys Thr Asp Pro Gln
            180              185              190

Ala Tyr Lys Glu Ser Asn Tyr Ser Tyr Cys Leu Ser Ser Arg Leu Arg
            195              200              205

Val Ser Ala Thr Phe Trp His Asn Pro Arg Asn His Phe Arg Cys Gln
        210              215              220

Val Gln Phe His Gly Leu Ser Glu Glu Asp Lys Trp Pro Glu Gly Ser
225              230              235              240

Pro Lys Pro Val Thr Gln Asn Ile Ser Ala Glu Ala Trp Gly Arg Ala
            245              250              255

Asp Cys Gly Ile Thr Ser Ala Ser Tyr Gln Gln Gly Val Leu Ser Ala
            260              265              270

Thr Ile Leu Tyr Glu Ile Leu Leu Gly Lys Ala Thr Leu Tyr Ala Val
            275              280              285

Leu Val Ser Thr Leu Val Val Met Ala Met Val Lys Arg Lys Asn Ser
        290              295              300

Arg Ala Lys Arg Ser Gly Ser Gly Ala Thr Asn Phe Ser Leu Leu Lys
305              310              315              320

Gln Ala Gly Asp Val Glu Glu Asn Pro Gly Pro Met Lys Thr Phe Ala
            325              330              335

Gly Phe Ser Phe Leu Phe Leu Trp Leu Gln Leu Asp Cys Met Ser Arg
            340              345              350

Gly Glu Asp Val Glu Gln Ser Leu Phe Leu Ser Val Arg Glu Gly Asp
            355              360              365

Ser Ser Val Ile Asn Cys Thr Tyr Thr Asp Ser Ser Ser Thr Tyr Leu
        370              375              380

Tyr Trp Tyr Lys Gln Glu Pro Gly Ala Gly Leu Gln Leu Leu Thr Tyr
385              390              395              400

Ile Phe Ser Asn Met Asp Met Lys Gln Asp Gln Arg Leu Thr Val Leu
            405              410              415

Leu Asn Lys Lys Asp Lys His Leu Ser Leu Arg Ile Ala Asp Thr Gln
            420              425              430

Thr Gly Asp Ser Ala Ile Tyr Phe Cys Ala Pro Gly Gly Tyr Asn Lys
            435              440              445

Leu Ile Phe Gly Ala Gly Thr Arg Leu Ala Val His Pro Asn Ile Gln
        450              455              460

Asn Pro Glu Pro Ala Val Tyr Gln Leu Lys Asp Pro Arg Ser Gln Asp
465              470              475              480

Ser Thr Leu Cys Leu Phe Thr Asp Phe Asp Ser Gln Ile Asn Val Pro
            485              490              495

Lys Thr Met Glu Ser Gly Thr Phe Ile Thr Asp Lys Cys Val Leu Asp
            500              505              510

Met Lys Ala Met Asp Ser Lys Ser Asn Gly Ala Ile Ala Trp Ser Asn
            515              520              525
```

```
Gln Thr Ser Phe Thr Cys Gln Asp Ile Phe Lys Glu Thr Asn Ala Thr
    530                 535                 540

Tyr Pro Ser Ser Asp Val Pro Cys Asp Ala Thr Leu Thr Glu Lys Ser
545                 550                 555                 560

Phe Glu Thr Asp Met Asn Leu Asn Phe Gln Asn Leu Leu Val Ile Val
                565                 570                 575

Leu Arg Ile Leu Leu Leu Lys Val Ala Gly Phe Asn Leu Leu Met Thr
                580                 585                 590

Leu Arg Leu Trp Ser Ser
        595
```

```
<210> SEQ ID NO 113
<211> LENGTH: 23
<212> TYPE: PRT
<213> ORGANISM: Homo sapiens

<400> SEQUENCE: 113

Thr Glu Tyr Lys Leu Val Val Val Gly Ala Gly Gly Val Gly Lys Ser
1               5                   10                  15

Ala Leu Thr Ile Gln Leu Ile
            20
```

```
<210> SEQ ID NO 114
<211> LENGTH: 1800
<212> TYPE: DNA
<213> ORGANISM: Artificial Sequence
<220> FEATURE:
<223> OTHER INFORMATION: Synthetic

<400> SEQUENCE: 114
atggccatcc ggctgctgtg ctatatgggc ttctactttc tgggcgccgg cctgatggag      60
gccgatatct atcagacccc aagatacctg gtcatcggca caggcaagaa gatcaccctg     120
gagtgttccc agacaatggg ccacgataag atgtactggt atcagcagga ccccggcatg     180
gagctgcacc tgatccacta cagctatggc gtgaactcca ccgagaaggg cgacctgagc     240
tccgagagca cagtgtcccg gatcagaacc gagcacttcc ccctgacact ggagtctgcc     300
cggccttctc acaccagcca gtacctgtgc gcctctagcg gcctgaccta tacagatacc     360
cagtacttcg gaccaggaac aaggctgacc gtgctggagg acctgaggaa cgtgaccccca     420 cctaaggtgt ctctgtttga gcccagcaag gccgagatcg ccaataagca gaaggccacc     480
ctggtgtgcc tggccagagg cttctttcct gatcacgtgg agctgtcctg gtgggtgaac     540
ggcaaggagg tgcactctgg cgtgtgcacc gacccacagg cctataagga gtccaattac     600
tcttattgtc tgtcctctag gctgcgcgtg agcgccacat ctggcacaa ccctaggaat      660 cacttccgct gccaggtgca gtttcacggc ctgtccgagg aggataagtg gccagagggc     720
tctcctaagc cagtgaccca gaacatcagc gccgaggcat ggggaagggc agactgtgga     780
atcaccagcg cctcctacca gcagggcgtg ctgtccgcca caatcctgta tgagatcctg     840
ctgggcaagg ccaccctgta cgccgtgctg gtgtctacac tggtggtcat ggctatggtg     900
aagcgcaaga cagccgggc aaagagatct ggaagcggag ccaccaattt ttccctgctg     960
aagcaggcag cgatgtgga ggagaatcca ggacctatga ggctggtggc aagagtgaca    1020
gtgttcctga catttggcac catcatcgat gccaagacca cacagccacc cagcatggac    1080
tgcgcagagg aagggcagc aaacctgccc tgtaatcaca gcaccatctc cggcaacgag    1140
tacgtgtatt ggtacagaca gatccactct cagggccctc agtacatcat ccacggcctg    1200
```

-continued

```
aagaacaatg agacaaatga gatggccagc ctgatcatca ccgaggatag gaagagctcc    1260
acactgatcc tgcctcacgc cacactgagg gacaccgccg tgtactattg catcgtgaga    1320
gtggccaagt ccggcgccaa caatctgttc tttggcacag gcaccaggct gaccgtgatc    1380
ccaaacatcc agaatccaga gcccgccgtg tatcagctga aggacccccg ctctcaggat    1440
agcacactgt gcctgttcac cgactttgat agccagatca acgtgcccaa gacaatggag    1500
tccggcacat tcatcaccga caagtgcgtg ctggacatga aggctatgga ctccaagtct    1560
aacggcgcca tcgcctggtc caatcagaca tctttcacct gccaggatat ctttaaggag    1620
acaaatgcca cctacccttc tagcgacgtg ccatgtgatg ccacactgac cgagaagagc    1680
ttcgagaccg acatgaacct gaattttcag aacctgctgg tcatcgtgct gaggatcctg    1740
ctgctgaagg tggccggctt taatctgctg atgacactgc cctgtggtc ctcttgataa    1800
```

```
<210> SEQ ID NO 115
<211> LENGTH: 1815
<212> TYPE: DNA
<213> ORGANISM: Artificial Sequence
<220> FEATURE:
<223> OTHER INFORMATION: Synthetic

<400> SEQUENCE: 115
```

```
atggccatcc ggctgctgtg cagagtggcc ttctgttttc tggccgtggg cctggtggat      60
gtgaaggtga cccagagctc caggtacctg gtgaagcgca caggcgagaa ggtgttcctg     120
gagtgcgtgc aggacatgga tcacgagaac atgttttggt ataggcagga ccctggactg     180
ggactgaggc tgatctactt cagctatgat gtgaagatga aggagaaggg cgacatccca     240
gagggctact ctgtgagccg ggagaagaag gagcggttca gcctgatcct ggagtccgcc     300
tctaccaacc agacatccat gtatctgtgc gcctctagcc agggcaatac cggcgagctg     360
ttctttggag agggatcccg gctgaccgtg ctggaggatc tgagaaacgt gacacccct      420 aaggtgtctc tgttcgagcc cagcaaggcc gagatcgcca taagcagaa ggccaccctg      480 gtgtgcctgg caaggggctt ctttcctgat cacgtggagc tgtcttggtg ggtgaacggc     540
aaggaggtgc acagcggcgt gtgcaccgac ccacaggcct acaaggagag caattactcc     600
tattgtctgt cctctcggct gagagtgagc gccacatttt ggcacaaccc aaggaatcac     660
ttccgctgcc aggtgcagtt tcacggcctg tctgaggagg ataagtggcc agagggaagc     720
ccaaagccag tgacccagaa catctccgcc gaggcatggg gaagagcaga ctgtggcatc     780
accagcgcct cctaccagca gggcgtgctg tccgccacaa tcctgtacga gatcctgctg     840
ggcaaggcca ccctgtatgc cgtgctggtg tctacactgg tggtcatggc tatggtgaag     900
aggaagaaca gcagggcaaa gcggagcgga agcggagcca ccaatttctc cctgctgaag     960
caggcaggcg atgtggagga gaaccctgga ccaatgatga gagcctgcg cgtgctgctg     1020 gtcatcctgt ggctgcagct gtcctgggtg tggtctcagc agaaggaggt ggagcaggac    1080
ccaggacctc tgagcgtgcc agagggagca atcgtgtccc tgaactgcac ctactccaat    1140
tctgccttcc agtacttcat gtggtaccgg cagtattcca gaaagggccc tgagctgctg    1200
atgtacacct atagctccgg caataaggag gatggccggt tcacagccca ggtggacaag    1260
tctagcaagt acatctccct gtttatcaga gactctcagc caagcgattc cgccacatac    1320
ctgtgcgcaa tgtcttatag cggaggagga gcagacggac tgaccttcgg caagggcaca    1380
cacctgatca tccagcccaa catccagaat ccagagcccg ccgtgtatca gctgaaggac    1440
```

-continued

```
cctaggtctc aggatagcac cctgtgcctg ttcacagact ttgattccca gatcaacgtg    1500
cccaagacaa tggagtctgg cacctttatc acagacaagt gcgtgctgga catgaaggct    1560
atggactcca agtctaacgg cgccatcgcc tggagcaatc agacctcctt cacatgccag    1620
gatatcttta aggagaccaa tgccacatac ccttcctctg acgtgccatg tgatgccacc    1680
ctgacagaga gagcttcga gaccgacatg aacctgaatt ttcagaacct gctggtcatc    1740
gtgctgagga tcctgctgct gaaggtggcc ggcttcaatc tgctgatgac actgcgcctg    1800
tggagctcct gataa                                                     1815

<210> SEQ ID NO 116
<211> LENGTH: 1800
<212> TYPE: DNA
<213> ORGANISM: Artificial Sequence
<220> FEATURE:
<223> OTHER INFORMATION: Synthetic

<400> SEQUENCE: 116
atggccatcc ggctgctgtg cagagtggcc ttctgttttc tggccgtggg cctggtggat     60
gtgaaggtga cccagagctc ccggtatctg gtgaagagaa caggcgagaa ggtgtttctg    120
gagtgcgtgc aggacatgga tcacgagaac atgttctggt acaggcagga cccaggactg    180
ggactgagac tgatctattt ttcctacgat gtgaagatga aggagaaggg cgacatcccc    240
gagggctatt ccgtgtctag ggagaagaag gagcggttca gcctgatcct ggagagcgcc    300
tccaccaacc agacaagcat gtacctgtgc gcctccagga tcggcaatac cggcgagctg    360
ttctttggag agggaagcag gctgaccgtg ctggaggacc tgcgcaacgt gacaccccct    420
aaggtgtccc tgtttgagcc ttctaaggcc gagatcgcca ataagcagaa ggccaccctg    480
gtgtgcctgg caaggggctt ctttccagat cacgtggagc tgtcttggtg ggtgaacggc    540
aaggaggtgc acagcggcgt gtgcaccgac ccacaggcct ataaggagtc taattacagc    600
tattgtctgt ctagccggct gagagtgtcc gccacattct ggcacaaccc caggaatcac    660
tttcgctgcc aggtgcagtt ccacggcctg tctgaggagg ataagtggcc tgagggaagc    720
ccaaagccag tgacccagaa tatctccgcc gaggcatggg gaagggcaga ctgtggaatc    780
acctctgcca gctaccagca gggcgtgctg agcgccacaa tcctgtatga gatcctgctg    840
ggcaaggcca ccctgtacgc cgtgctggtc tccacactgg tggtcatggc tatggtgaag    900
agaaagaact ctagggcaaa gcggagcgga tctggagcaa ccaacttcag cctgctgaag    960
caggcaggcg atgtggagga gaaccctgga ccaatgaaga cattcgccgg cttctctttt    1020
ctgttcctgt ggctgcagct ggattgcatg agccggggag aggacgtgga gcagagcctg    1080
tttctgtccg tgagagaggg cgattcctct gtgatcaatt gtacctatac agacagctcc    1140
tctacctacc tgtattggta caagcaggag cctggagcag gactgcagct gctgacctac    1200
atcttctcca acatggacat gaagcaggat cagaggctga cagtgctgct gaataagaag    1260
gacaagcacc tgagcctgag gatcgcagac acccagacag cggattccgc catctatttt    1320
tgtgccccag cggctacaa caagctgatc ttcggagcag gaaccaggct ggccgtgcac    1380
cctaacatcc agaatcccga gcctgccgtg tatcagctga ggacccacg ctcccaggat    1440 tctaccctgt gcctgtttac agacttcgat tcccagatca atgtgcctaa gacaatggag    1500
tctggcacct ttatcacaga caagtgcgtg ctggacatga aggctatgga cagcaagtcc    1560
aacggcgcca tcgcctggtc taatcagacc agctttacat gccaggatat cttcaaggag    1620
accaacgcca catacccaag ctccgacgtg ccctgtgatg ccaccctgac agagaagagc    1680
```

-continued

--- tttgagaccg acatgaacct gaatttccag aacctgctgg tcatcgtgct gcggatcctg     1740
ctgctgaagg tggccggctt caatctgctg atgacactga gactgtggtc tagctgataa     1800

<210> SEQ ID NO 117
<211> LENGTH: 1806
<212> TYPE: DNA
<213> ORGANISM: Artificial Sequence
<220> FEATURE:
<223> OTHER INFORMATION: Synthetic

<400> SEQUENCE: 117
atggccatcc ggctgctgtg cagagtggcc ttctgttttc tggccgtggg cctggtggac      60
gtgaaggtga cccagagctc caggtacctg gtgaagcgca caggcgagaa ggtgttcctg     120
gagtgcgtgc aggacatgga tcacgagaac atgttttggt ataggcagga tccaggactg     180
ggactgaggc tgatctactt ctcttatgac gtgaagatga aggagaaggg cgatatccct     240
gagggctact ctgtgagccg ggagaagaag gagcggttca gcctgatcct ggagtccgcc     300
tctaccaacc agacaagcat gtacctgtgc gcctcccggc tgggaaatac cggagagctg     360
ttctttggcg agggctcccg gctgacagtg ctggaggatc tccggaatgt gacccccccct     420 aaggtgagcc tgttcgagcc ttccaaggcc gagatcgcca acaagcagaa ggccaccctg     480
gtgtgcctgg caaggggctt cttttccagat cacgtggagc tgtcctggtg ggtgaatggc     540
aaggaggtgc actctggcgt gtgcaccgac ccacaggcct acaaggagtc caactactct     600
tattgtctgt cctctcggct gagagtgagc gccacatttt ggcacaaccc ccggaatcac     660
ttcagatgcc aggtgcagtt tcacggcctg tccgaggagg ataagtggcc tgagggctct     720
ccaaagcccg tgacccagaa catcagcgcc gaggcatggg gaagggcaga ctgtggcatc     780
acctccgcct cttatcagca gggcgtgctg tccgccacaa tcctgtacga gatcctgctg     840
ggcaaggcca ccctgtatgc cgtgctggtg tctacactgg tggtcatggc tatggtgaag     900
agaaagaaca gcagggcaaa gcggagcgga agcggagcaa ccaatttcag cctgctgaag     960
caggcaggcg atgtggagga gaaccctggg cccatgatga aaagcttgcg ggtgctgctg    1020
gtgatccttt ggctccagct aagttgggtc tggtctcaac agaaggaggt ggaacaggac    1080
cccggccccc tgtccgttcc tgagggcgct atcgtgtccc tcaactgcac ttactcaaat    1140
tccgcgttcc agtacttcat gtggtatcgc cagtactccc gcaaggggcc agagctgctg    1200
atgtatacat acagctcggg caacaaggag gacggccgct tcaccgcaca ggtcgataaa    1260
tcgtccaagt acatcagcct ttttattcgt gacagccagc cctctgattc tgctacctac    1320
ctgtgcgcca tgagggccaa cacggacaag ctgatcttcg gcaccggcac ccgcctgcag    1380
gtgttcccta atatccagaa tcccgagccc gcggtgtacc agctgaagga ccccagaagc    1440
caggattcca ccctgtgcct gttcacagac tttgatagcc agatcaacgt gcccaagaca    1500
atggagtccg gcaccttcat cacagacaag tgcgtgctgg acatgaaggc tatggactct    1560
aagagcaacg gcgccatcgc ctggtccaat cagacctctt tcacatgcca ggatatcttt    1620
aaggagacaa acgccacata ccctagctcc gacgtgccat gtgatgccac cctgacagag    1680
aagagcttcg agacagacat gaacctgaat tttcagaacc tgctggtcat cgtgctgagg    1740
atcctgctgc tgaaggtggc cggctttaat ctgctgatga cactgcgcct gtggtctagc    1800
tgataa                                                                1806

<210> SEQ ID NO 118

<211> LENGTH: 1806
<212> TYPE: DNA
<213> ORGANISM: Artificial Sequence
<220> FEATURE:
<223> OTHER INFORMATION: Synthetic

<400> SEQUENCE: 118

```
atggccattc gcctgctgtg ccgagtcgcg ttctgctttc tggccgtggg tttggttgac      60
gtgaaggtca ctcagagctc ccgctacctg gtgaagcgca ccggcgagaa ggtgttcctg     120
gaatgcgtgc aggacatgga tcacgagaat atgtttggt atcgccagga ccccggcctg     180
ggccttaggc tcatctactt ctcttacgat gtaaagatga aagagaaagg tgacatccct     240
gaaggctact ccgtgtccag agagaagaag gagcgtttca gtctaatcct ggagtccgcc     300
tccaccaacc agacatctat gtatctgtgc gcctcacgcc agggcaacac gggggagctg     360
ttcttcggag agggctcccg tctgaccgtc ctggaggatc tccggaatgt gaccccccct     420
aaggtgagcc tgttcgagcc ttccaaggcc gagatcgcca acaagcagaa ggccaccctg     480
gtgtgcctgg caagggggctt ctttccagat cacgtggagc tgtcctggtg ggtgaatggc     540
aaggaggtgc actctggcgt gtgcaccgac ccacaggcct acaaggagtc caactactct     600
tattgtctgt cctctcggct gagagtgagc gccacatttt ggcacaaccc ccggaatcac     660
ttcagatgcc aggtgcagtt tcacggcctg tccgaggagg ataagtggcc tgagggctct     720
ccaaagcccg tgacccagaa catcagcgcc gaggcatggg gaaggggcaga ctgtggcatc     780 acctccgcct cttatcagca gggcgtgctg tccgccacaa tcctgtacga gatcctgctg     840
ggcaaggcca ccctgtatgc cgtgctggtg tctacactgg tggtcatggc tatggtgaag     900
agaaagaaca gcagggcaaa gcggagcgga agcggagcaa ccaatttcag cctgctgaag     960
caggcaggcg atgtggagga gaaccctggg cccatgatga aaagcttgcg ggtgctgctg    1020 gtgatcctt ggctccagct aagttgggtc tggtctcaac agaaggaggt ggaacaggac    1080 cccgccccc tgtccgttcc tgagggcgct atcgtgtccc tcaactgcac ttactcaaat    1140
tccgcgttcc agtacttcat gtggtatcgc cagtactccc gcaaggggcc agagctgctg    1200
atgtatacat acagctcggg caacaaggag gacggccgct tcaccgcaca ggtcgataaa    1260
tcgtccaagt acatcagcct tttttattcgt gacagccagc cctctgattc tgctacctac    1320
ctgtgcgcca tgagggccaa cacggacaag ctgatcttcg gcaccggcac ccgcctgcag    1380
gtgttcccta atatccagaa tcccgagccc gcggtgtacc agctgaagga ccccagaagc    1440
caggattcca ccctgtgcct gttcacagac tttgatagcc agatcaacgt gcccaagaca    1500
atggagtccg gcaccttcat cacagacaag tgcgtgctgg acatgaaggc tatggactct    1560
aagagcaacg gcgccatcgc ctggtccaat cagacctctt tcacatgcca ggatatcttt    1620
aaggagacaa acgccacata ccctagctcc gacgtgccat gtgatgccac cctgacagag    1680
aagagcttcg agacagacat gaacctgaat tttcagaacc tgctggtcat cgtgctgagg    1740
atcctgctgc tgaaggtggc cggctttaat ctgctgatga cactgcgcct gtggtctagc    1800
tgataa                                                               1806
```

<210> SEQ ID NO 119
<211> LENGTH: 7
<212> TYPE: PRT
<213> ORGANISM: Homo sapiens

<400> SEQUENCE: 119

Thr Ile Ser Gly Thr Asp Tyr

```
1               5

<210> SEQ ID NO 120
<211> LENGTH: 5
<212> TYPE: PRT
<213> ORGANISM: Homo sapiens

<400> SEQUENCE: 120

Gly Leu Thr Ser Asn
1               5

<210> SEQ ID NO 121
<211> LENGTH: 14
<212> TYPE: PRT
<213> ORGANISM: Homo sapiens

<400> SEQUENCE: 121

Cys Ile Leu Arg Ala Pro Ser Gly Thr Tyr Lys Tyr Ile Phe
1               5                   10

<210> SEQ ID NO 122
<211> LENGTH: 5
<212> TYPE: PRT
<213> ORGANISM: Homo sapiens

<400> SEQUENCE: 122

Met Asp His Glu Asn
1               5

<210> SEQ ID NO 123
<211> LENGTH: 6
<212> TYPE: PRT
<213> ORGANISM: Homo sapiens

<400> SEQUENCE: 123

Ser Tyr Asp Val Lys Met
1               5

<210> SEQ ID NO 124
<211> LENGTH: 13
<212> TYPE: PRT
<213> ORGANISM: Homo sapiens

<400> SEQUENCE: 124

Cys Ala Ser Arg Gln Gly Asn Thr Gly Glu Leu Phe Phe
1               5                   10

<210> SEQ ID NO 125
<211> LENGTH: 109
<212> TYPE: PRT
<213> ORGANISM: Homo sapiens

<400> SEQUENCE: 125

Lys Thr Thr Gln Pro Asn Ser Met Glu Ser Asn Glu Glu Pro Val
1               5                   10                  15

His Leu Pro Cys Asn His Ser Thr Ile Ser Gly Thr Asp Tyr Ile His
            20                  25                  30

Trp Tyr Arg Gln Leu Pro Ser Gln Gly Pro Glu Tyr Val Ile His Gly
        35                  40                  45

Leu Thr Ser Asn Val Asn Asn Arg Met Ala Ser Leu Ala Ile Ala Glu
    50                  55                  60

Asp Arg Lys Ser Ser Thr Leu Ile Leu His Arg Ala Thr Leu Arg Asp
65                  70                  75                  80
```

-continued

```
Ala Ala Val Tyr Tyr Cys Ile Leu Arg Ala Pro Ser Gly Thr Tyr Lys
            85                  90                  95

Tyr Ile Phe Gly Thr Gly Thr Arg Leu Lys Val Leu Ala
            100                 105

<210> SEQ ID NO 126
<211> LENGTH: 112
<212> TYPE: PRT
<213> ORGANISM: Homo sapiens

<400> SEQUENCE: 126

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Gln Gly
            85                  90                  95

Asn Thr Gly Glu Leu Phe Phe Gly Glu Gly Ser Arg Leu Thr Val Leu
            100                 105                 110

<210> SEQ ID NO 127
<211> LENGTH: 128
<212> TYPE: PRT
<213> ORGANISM: Homo sapiens

<400> SEQUENCE: 127

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
            85                  90                  95

Leu Arg Asp Ala Ala Val Tyr Tyr Cys Ile Leu Arg Ala Pro Ser Gly
            100                 105                 110

Thr Tyr Lys Tyr Ile Phe Gly Thr Gly Thr Arg Leu Lys Val Leu Ala
            115                 120                 125

<210> SEQ ID NO 128
<211> LENGTH: 131
<212> TYPE: PRT
<213> ORGANISM: Homo sapiens

<400> SEQUENCE: 128

Met Ala Ile Arg Leu Leu Cys Arg Val Ala Phe Cys Phe Leu Ala Val
1               5                   10                  15
```

```
Gly Leu Val Asp Val Lys Val Thr Gln Ser Ser Arg Tyr Leu Val Lys
            20              25                  30

Arg Thr Gly Glu Lys Val Phe Leu Glu Cys Val Gln Asp Met Asp His
        35              40                  45

Glu Asn Met Phe Trp Tyr Arg Gln Asp Pro Gly Leu Gly Leu Arg Leu
    50              55                  60

Ile Tyr Phe Ser Tyr Asp Val Lys Met Lys Glu Lys Gly Asp Ile Pro
65              70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gln Gly Asn Thr Gly Glu Leu Phe Phe Gly Glu Gly Ser Arg Leu
        115                 120                 125

Thr Val Leu
    130

<210> SEQ ID NO 129
<211> LENGTH: 6
<212> TYPE: PRT
<213> ORGANISM: Homo sapiens

<400> SEQUENCE: 129

Ala Thr Gly Tyr Pro Ser
1               5

<210> SEQ ID NO 130
<211> LENGTH: 7
<212> TYPE: PRT
<213> ORGANISM: Homo sapiens

<400> SEQUENCE: 130

Ala Thr Lys Ala Asp Asp Lys
1               5

<210> SEQ ID NO 131
<211> LENGTH: 15
<212> TYPE: PRT
<213> ORGANISM: Homo sapiens

<400> SEQUENCE: 131

Cys Ala Leu Arg Leu Ser Gly Ala Gly Ser Tyr Gln Leu Thr Phe
1               5                   10                  15

<210> SEQ ID NO 132
<211> LENGTH: 5
<212> TYPE: PRT
<213> ORGANISM: Homo sapiens

<400> SEQUENCE: 132

Met Asp His Glu Asn
1               5

<210> SEQ ID NO 133
<211> LENGTH: 6
<212> TYPE: PRT
<213> ORGANISM: Homo sapiens

<400> SEQUENCE: 133

Ser Tyr Asp Val Lys Met
1               5
```

<210> SEQ ID NO 134
<211> LENGTH: 13
<212> TYPE: PRT
<213> ORGANISM: Homo sapiens

<400> SEQUENCE: 134

Cys Ala Ser Ser Gln Gly Asn Thr Gly Glu Leu Phe Phe
1               5                   10

<210> SEQ ID NO 135
<211> LENGTH: 113
<212> TYPE: PRT
<213> ORGANISM: Homo sapiens

<400> SEQUENCE: 135

Asn Ser Val Thr Gln Met Glu Gly Pro Val Thr Leu Ser Glu Ala
1               5                   10                  15

Phe Leu Thr Ile Asn Cys Thr Tyr Thr Ala Thr Gly Tyr Pro Ser Leu
                20                  25                  30

Phe Trp Tyr Val Gln Tyr Pro Gly Glu Gly Leu Gln Leu Leu Leu Lys
            35                  40                  45

Ala Thr Lys Ala Asp Asp Lys Gly Ser Asn Lys Gly Phe Glu Ala Thr
        50                  55                  60

Tyr Arg Lys Glu Thr Thr Ser Phe His Leu Glu Lys Gly Ser Val Gln
65                  70                  75                  80

Val Ser Asp Ser Ala Val Tyr Phe Cys Ala Leu Arg Leu Ser Gly Ala
                85                  90                  95

Gly Ser Tyr Gln Leu Thr Phe Gly Lys Gly Thr Lys Leu Ser Val Ile
            100                 105                 110

Pro

<210> SEQ ID NO 136
<211> LENGTH: 112
<212> TYPE: PRT
<213> ORGANISM: Homo sapiens

<400> SEQUENCE: 136

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
            100                 105                 110

<210> SEQ ID NO 137
<211> LENGTH: 133
<212> TYPE: PRT
<213> ORGANISM: Homo sapiens

<400> SEQUENCE: 137

-continued

```
Met Asn Tyr Ser Pro Gly Leu Val Ser Leu Ile Leu Leu Leu Leu Gly
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
        35                  40                  45

Tyr Pro Ser Leu Phe Trp Tyr Val Gln Tyr Pro Gly Glu Gly Leu Gln
    50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Arg
            100                 105                 110

Leu Ser Gly Ala Gly Ser Tyr Gln Leu Thr Phe Gly Lys Gly Thr Lys
            115                 120                 125

Leu Ser Val Ile Pro
    130
```

```
<210> SEQ ID NO 138
<211> LENGTH: 131
<212> TYPE: PRT
<213> ORGANISM: Homo sapiens

<400> SEQUENCE: 138
```

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Gln Gly Asn Thr Gly Glu Leu Phe Phe Gly Glu Gly Ser Arg Leu
            115                 120                 125

Thr Val Leu
    130
```

```
<210> SEQ ID NO 139
<211> LENGTH: 7
<212> TYPE: PRT
<213> ORGANISM: Homo sapiens

<400> SEQUENCE: 139
```

```
Thr Ser Asp Pro Ser Tyr Gly
1               5
```

```
<210> SEQ ID NO 140
<211> LENGTH: 8
<212> TYPE: PRT
<213> ORGANISM: Homo sapiens
```

-continued

<400> SEQUENCE: 140

Gln Gly Ser Tyr Asp Gln Gln Asn
1               5

<210> SEQ ID NO 141
<211> LENGTH: 15
<212> TYPE: PRT
<213> ORGANISM: Homo sapiens

<400> SEQUENCE: 141

Cys Ala Met Arg Glu Arg Ser Gly Thr Ala Ser Lys Leu Thr Phe
1               5                   10                  15

<210> SEQ ID NO 142
<211> LENGTH: 5
<212> TYPE: PRT
<213> ORGANISM: Homo sapiens

<400> SEQUENCE: 142

Met Asp His Glu Asn
1               5

<210> SEQ ID NO 143
<211> LENGTH: 6
<212> TYPE: PRT
<213> ORGANISM: Homo sapiens

<400> SEQUENCE: 143

Ser Tyr Asp Val Lys Met
1               5

<210> SEQ ID NO 144
<211> LENGTH: 15
<212> TYPE: PRT
<213> ORGANISM: Homo sapiens

<400> SEQUENCE: 144

Cys Ala Ser Ser Leu Gly Val Gly Ser Asn Tyr Gly Tyr Thr Phe
1               5                   10                  15

<210> SEQ ID NO 145
<211> LENGTH: 115
<212> TYPE: PRT
<213> ORGANISM: Homo sapiens

<400> SEQUENCE: 145

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
            20                  25                  30

Leu Phe Trp Tyr Lys Gln Pro Ser Ser Gly Glu Met Ile Phe Leu Ile
        35                  40                  45

Tyr Gln Gly Ser Tyr Asp Gln Gln Asn Ala Thr Glu Gly Arg Tyr Ser
        50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Thr Ala Ser Lys Leu Thr Phe Gly Thr Gly Thr Arg Leu Gln
            100                 105                 110

Val Thr Leu

-continued

115

<210> SEQ ID NO 146
<211> LENGTH: 107
<212> TYPE: PRT
<213> ORGANISM: Homo sapiens

<400> SEQUENCE: 146

Ser Arg Tyr Leu Val Lys Arg Thr Gly Glu Lys Val Phe Leu Glu Cys
1               5                   10                  15

Val Gln Asp Met Asp His Glu Asn Met Phe Trp Tyr Arg Gln Asp Pro
            20                  25                  30

Gly Leu Gly Leu Arg Leu Ile Tyr Phe Ser Tyr Asp Val Lys Met Lys
        35                  40                  45

Glu Lys Gly Asp Ile Pro Glu Gly Tyr Ser Val Ser Arg Glu Lys Lys
    50                  55                  60

Glu Arg Phe Ser Leu Ile Leu Glu Ser Ala Ser Thr Asn Gln Thr Ser
65                  70                  75                  80

Met Tyr Leu Cys Ala Ser Ser Leu Gly Val Gly Ser Asn Tyr Gly Tyr
                85                  90                  95

Thr Phe Gly Ser Gly Thr Arg Leu Thr Val Val
            100                 105

<210> SEQ ID NO 147
<211> LENGTH: 136
<212> TYPE: PRT
<213> ORGANISM: Homo sapiens

<400> SEQUENCE: 147

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Arg Ser Gly Thr Ala Ser Lys Leu Thr Phe Gly Thr
        115                 120                 125

Gly Thr Arg Leu Gln Val Thr Leu
    130                 135

<210> SEQ ID NO 148
<211> LENGTH: 133
<212> TYPE: PRT
<213> ORGANISM: Homo sapiens

<400> SEQUENCE: 148

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

```
Arg Thr Gly Glu Lys Val Phe Leu Glu Cys Val Gln Asp Met Asp His
        35              40              45

Glu Asn Met Phe Trp Tyr Arg Gln Asp Pro Gly Leu Gly Leu Arg Leu
    50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
            85              90              95

Leu Glu Ser Ala Ser Thr Asn Gln Thr Ser Met Tyr Leu Cys Ala Ser
            100             105             110

Ser Leu Gly Val Gly Ser Asn Tyr Gly Tyr Thr Phe Gly Ser Gly Thr
        115             120             125

Arg Leu Thr Val Val
    130

<210> SEQ ID NO 149
<211> LENGTH: 6
<212> TYPE: PRT
<213> ORGANISM: Homo sapiens

<400> SEQUENCE: 149

Asn Ser Ala Phe Gln Tyr
1               5

<210> SEQ ID NO 150
<211> LENGTH: 6
<212> TYPE: PRT
<213> ORGANISM: Homo sapiens

<400> SEQUENCE: 150

Thr Tyr Ser Ser Gly Asn
1               5

<210> SEQ ID NO 151
<211> LENGTH: 15
<212> TYPE: PRT
<213> ORGANISM: Homo sapiens

<400> SEQUENCE: 151

Cys Ala Met Ser Tyr Ser Gly Gly Gly Ala Asp Gly Leu Thr Phe
1               5               10              15

<210> SEQ ID NO 152
<211> LENGTH: 5
<212> TYPE: PRT
<213> ORGANISM: Homo sapiens

<400> SEQUENCE: 152

Met Asp His Glu Asn
1               5

<210> SEQ ID NO 153
<211> LENGTH: 6
<212> TYPE: PRT
<213> ORGANISM: Homo sapiens

<400> SEQUENCE: 153

Ser Tyr Asp Val Lys Met
1               5

<210> SEQ ID NO 154
```

```
<211> LENGTH: 13
<212> TYPE: PRT
<213> ORGANISM: Homo sapiens

<400> SEQUENCE: 154

Cys Ala Ser Ser Thr Gly Asn Thr Gly Glu Leu Phe Phe
1               5                   10

<210> SEQ ID NO 155
<211> LENGTH: 113
<212> TYPE: PRT
<213> ORGANISM: Homo sapiens

<400> SEQUENCE: 155

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
        50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Ser Tyr Ser Gly Gly
                85                  90                  95

Gly Ala Asp Gly Leu Thr Phe Gly Lys Gly Thr His Leu Ile Ile Gln
            100                 105                 110

Pro

<210> SEQ ID NO 156
<211> LENGTH: 112
<212> TYPE: PRT
<213> ORGANISM: Homo sapiens

<400> SEQUENCE: 156

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Thr Gly
                85                  90                  95

Asn Thr Gly Glu Leu Phe Phe Gly Glu Gly Ser Arg Leu Thr Val Leu
            100                 105                 110

<210> SEQ ID NO 157
<211> LENGTH: 135
<212> TYPE: PRT
<213> ORGANISM: Homo sapiens

<400> SEQUENCE: 157

Met Met Lys Ser Leu Arg Val Leu Leu Val Ile Leu Trp Leu Gln Leu
1               5                   10                  15
```

-continued

```
Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
                100                 105                 110

Met Ser Tyr Ser Gly Gly Gly Ala Asp Gly Leu Thr Phe Gly Lys Gly
            115                 120                 125

Thr His Leu Ile Ile Gln Pro
    130                 135

<210> SEQ ID NO 158
<211> LENGTH: 131
<212> TYPE: PRT
<213> ORGANISM: Homo sapiens

<400> SEQUENCE: 158

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser Thr Gly Asn Thr Gly Glu Leu Phe Phe Gly Glu Gly Ser Arg Leu
            115                 120                 125

Thr Val Leu
    130

<210> SEQ ID NO 159
<211> LENGTH: 6
<212> TYPE: PRT
<213> ORGANISM: Homo sapiens

<400> SEQUENCE: 159

Asn Ser Ala Phe Gln Tyr
1               5

<210> SEQ ID NO 160
<211> LENGTH: 6
<212> TYPE: PRT
<213> ORGANISM: Homo sapiens

<400> SEQUENCE: 160
```

-continued

```
Thr Tyr Ser Ser Gly Asn
1               5

<210> SEQ ID NO 161
<211> LENGTH: 12
<212> TYPE: PRT
<213> ORGANISM: Homo sapiens

<400> SEQUENCE: 161

Cys Ala Met Arg Ala Asn Thr Asp Lys Leu Ile Phe
1               5                   10

<210> SEQ ID NO 162
<211> LENGTH: 5
<212> TYPE: PRT
<213> ORGANISM: Homo sapiens

<400> SEQUENCE: 162

Met Asp His Glu Asn
1               5

<210> SEQ ID NO 163
<211> LENGTH: 6
<212> TYPE: PRT
<213> ORGANISM: Homo sapiens

<400> SEQUENCE: 163

Ser Tyr Asp Val Lys Met
1               5

<210> SEQ ID NO 164
<211> LENGTH: 13
<212> TYPE: PRT
<213> ORGANISM: Homo sapiens

<400> SEQUENCE: 164

Cys Ala Ser Arg Val Gly Asn Thr Gly Glu Leu Phe Phe
1               5                   10

<210> SEQ ID NO 165
<211> LENGTH: 110
<212> TYPE: PRT
<213> ORGANISM: Homo sapiens

<400> SEQUENCE: 165

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro
            100                 105                 110

<210> SEQ ID NO 166
<211> LENGTH: 112
```

```
<212> TYPE: PRT
<213> ORGANISM: Homo sapiens

<400> SEQUENCE: 166

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Val Gly
                85                  90                  95

Asn Thr Gly Glu Leu Phe Phe Gly Glu Gly Ser Arg Leu Thr Val Leu
            100                 105                 110

<210> SEQ ID NO 167
<211> LENGTH: 132
<212> TYPE: PRT
<213> ORGANISM: Homo sapiens

<400> SEQUENCE: 167

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Ala Asn Thr Asp Lys Leu Ile Phe Gly Thr Gly Thr Arg Leu
        115                 120                 125

Gln Val Phe Pro
    130

<210> SEQ ID NO 168
<211> LENGTH: 131
<212> TYPE: PRT
<213> ORGANISM: Homo sapiens

<400> SEQUENCE: 168

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
```

-continued

```
              50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
               100                 105                 110

Arg Val Gly Asn Thr Gly Glu Leu Phe Phe Gly Glu Gly Ser Arg Leu
          115                 120                 125

Thr Val Leu
       130

<210> SEQ ID NO 169
<211> LENGTH: 7
<212> TYPE: PRT
<213> ORGANISM: Homo sapiens

<400> SEQUENCE: 169

Thr Ser Asp Pro Ser Tyr Gly
1               5

<210> SEQ ID NO 170
<211> LENGTH: 8
<212> TYPE: PRT
<213> ORGANISM: Homo sapiens

<400> SEQUENCE: 170

Gln Gly Ser Tyr Asp Gln Gln Asn
1               5

<210> SEQ ID NO 171
<211> LENGTH: 15
<212> TYPE: PRT
<213> ORGANISM: Homo sapiens

<400> SEQUENCE: 171

Cys Ala Met Arg Glu Arg Thr Gly Thr Ala Ser Lys Leu Thr Phe
1               5                  10                  15

<210> SEQ ID NO 172
<211> LENGTH: 5
<212> TYPE: PRT
<213> ORGANISM: Homo sapiens

<400> SEQUENCE: 172

Met Asp His Glu Asn
1               5

<210> SEQ ID NO 173
<211> LENGTH: 6
<212> TYPE: PRT
<213> ORGANISM: Homo sapiens

<400> SEQUENCE: 173

Ser Tyr Asp Val Lys Met
1               5

<210> SEQ ID NO 174
<211> LENGTH: 14
<212> TYPE: PRT
<213> ORGANISM: Homo sapiens

<400> SEQUENCE: 174
```

-continued

```
Cys Ala Ser Ser Pro Gly Thr Glu Asn Ser Pro Leu His Phe
1               5                   10
```

<210> SEQ ID NO 175
<211> LENGTH: 115
<212> TYPE: PRT
<213> ORGANISM: Homo sapiens

<400> SEQUENCE: 175

```
Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
        50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Thr Gly Thr Ala Ser Lys Leu Thr Phe Gly Thr Gly Thr Arg Leu Gln
                100                 105                 110

Val Thr Leu
        115
```

<210> SEQ ID NO 176
<211> LENGTH: 113
<212> TYPE: PRT
<213> ORGANISM: Homo sapiens

<400> SEQUENCE: 176

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Pro Gly
                85                  90                  95

Thr Glu Asn Ser Pro Leu His Phe Gly Asn Gly Thr Arg Leu Thr Val
                100                 105                 110

Thr
```

<210> SEQ ID NO 177
<211> LENGTH: 136
<212> TYPE: PRT
<213> ORGANISM: Homo sapiens

<400> SEQUENCE: 177

```
Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
```

-continued

```
              20               25               30

Val Gln Glu Lys Glu Ala Val Thr Leu Asp Cys Thr Tyr Asp Thr Ser
              35               40               45

Asp Pro Ser Tyr Gly Leu Phe Trp Tyr Lys Gln Pro Ser Ser Gly Glu
              50               55               60

Met Ile Phe Leu Ile Tyr Gln Gly Ser Tyr Asp Gln Gln Asn Ala Thr
 65               70               75               80

Glu Gly Arg Tyr Ser Leu Asn Phe Gln Lys Ala Arg Lys Ser Ala Asn
              85               90               95

Leu Val Ile Ser Ala Ser Gln Leu Gly Asp Ser Ala Met Tyr Phe Cys
              100              105              110

Ala Met Arg Glu Arg Thr Gly Thr Ala Ser Lys Leu Thr Phe Gly Thr
              115              120              125

Gly Thr Arg Leu Gln Val Thr Leu
    130              135
```

<210> SEQ ID NO 178
<211> LENGTH: 132
<212> TYPE: PRT
<213> ORGANISM: Homo sapiens

<400> SEQUENCE: 178

```
Met Ala Ile Arg Leu Leu Cys Arg Val Ala Phe Cys Phe Leu Ala Val
 1               5               10               15

Gly Leu Val Asp Val Lys Val Thr Gln Ser Ser Arg Tyr Leu Val Lys
              20               25               30

Arg Thr Gly Glu Lys Val Phe Leu Glu Cys Val Gln Asp Met Asp His
              35               40               45

Glu Asn Met Phe Trp Tyr Arg Gln Asp Pro Gly Leu Gly Leu Arg Leu
              50               55               60

Ile Tyr Phe Ser Tyr Asp Val Lys Met Lys Glu Lys Gly Asp Ile Pro
 65               70               75               80

Glu Gly Tyr Ser Val Ser Arg Glu Lys Lys Glu Arg Phe Ser Leu Ile
              85               90               95

Leu Glu Ser Ala Ser Thr Asn Gln Thr Ser Met Tyr Leu Cys Ala Ser
              100              105              110

Ser Pro Gly Thr Glu Asn Ser Pro Leu His Phe Gly Asn Gly Thr Arg
              115              120              125

Leu Thr Val Thr
    130
```

<210> SEQ ID NO 179
<211> LENGTH: 7
<212> TYPE: PRT
<213> ORGANISM: Homo sapiens

<400> SEQUENCE: 179

```
Thr Ser Asp Pro Ser Tyr Gly
 1               5
```

<210> SEQ ID NO 180
<211> LENGTH: 8
<212> TYPE: PRT
<213> ORGANISM: Homo sapiens

<400> SEQUENCE: 180

```
Gln Gly Ser Tyr Asp Gln Gln Asn
 1               5
```

<210> SEQ ID NO 181
<211> LENGTH: 15
<212> TYPE: PRT
<213> ORGANISM: Homo sapiens

<400> SEQUENCE: 181

Cys Ala Met Arg Glu Arg Ser Gly Gly Ser Tyr Ile Pro Thr Phe
1               5               10                  15

<210> SEQ ID NO 182
<211> LENGTH: 5
<212> TYPE: PRT
<213> ORGANISM: Homo sapiens

<400> SEQUENCE: 182

Met Asp His Glu Asn
1               5

<210> SEQ ID NO 183
<211> LENGTH: 6
<212> TYPE: PRT
<213> ORGANISM: Homo sapiens

<400> SEQUENCE: 183

Ser Tyr Asp Val Lys Met
1               5

<210> SEQ ID NO 184
<211> LENGTH: 14
<212> TYPE: PRT
<213> ORGANISM: Homo sapiens

<400> SEQUENCE: 184

Cys Ala Ser Ser Leu Gly Thr Phe Asn Gln Pro Gln His Phe
1               5                   10

<210> SEQ ID NO 185
<211> LENGTH: 115
<212> TYPE: PRT
<213> ORGANISM: Homo sapiens

<400> SEQUENCE: 185

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
            20                  25                  30

Leu Phe Trp Tyr Lys Gln Pro Ser Ser Gly Glu Met Ile Phe Leu Ile
        35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Gly Ser Tyr Ile Pro Thr Phe Gly Arg Gly Thr Ser Leu Ile
            100                 105                 110

Val His Pro
        115

<210> SEQ ID NO 186

-continued

```
<211> LENGTH: 113
<212> TYPE: PRT
<213> ORGANISM: Homo sapiens

<400> SEQUENCE: 186

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Gly
                85                  90                  95

Thr Phe Asn Gln Pro Gln His Phe Gly Asp Gly Thr Arg Leu Ser Ile
            100                 105                 110

Leu

<210> SEQ ID NO 187
<211> LENGTH: 136
<212> TYPE: PRT
<213> ORGANISM: Homo sapiens

<400> SEQUENCE: 187

Met His Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
            35                  40                  45

Asp Pro Ser Tyr Gly Leu Phe Trp Tyr Lys Gln Pro Ser Ser Gly Glu
        50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Arg Ser Gly Gly Ser Tyr Ile Pro Thr Phe Gly Arg
            115                 120                 125

Gly Thr Ser Leu Ile Val His Pro
    130                 135

<210> SEQ ID NO 188
<211> LENGTH: 132
<212> TYPE: PRT
<213> ORGANISM: Homo sapiens

<400> SEQUENCE: 188

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
```

-continued

```
                35                  40                  45
Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Gly Thr Phe Asn Gln Pro Gln His Phe Gly Asp Gly Thr Arg
            115                 120                 125

Leu Ser Ile Leu
        130
```

```
<210> SEQ ID NO 189
<211> LENGTH: 265
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (176)..(176)
<223> OTHER INFORMATION: X is Thr or Cys
<220> FEATURE:
<221> NAME/KEY: MISC_FEATURE
<222> LOCATION: (240)..(240)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (242)..(242)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (243)..(243)
<223> OTHER INFORMATION: X is Gly, Ala, Val, Leu, Ile, Pro, Phe, Met, or
      Trp

<400> SEQUENCE: 189

Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Ala Pro Ser Gly
            100                 105                 110

Thr Tyr Lys Tyr Ile Phe Gly Thr Gly Thr Arg Leu Lys Val Leu Ala
            115                 120                 125

Asn Ile Gln Asn Pro Glu Pro Ala Val Tyr Gln Leu Lys Asp Pro Arg
            130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Xaa
```

-continued

```
                    165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
            195                 200                 205

Asn Ala Thr Tyr Pro Ser Ser Asp Val Pro Cys Asp Ala Thr Leu Thr
            210                 215                 220

Glu Lys Ser Phe Glu Thr Asp Met Asn Leu Asn Phe Gln Asn Leu Xaa
225                 230                 235                 240

Val Xaa Xaa Leu Arg Ile Leu Leu Leu Lys Val Ala Gly Phe Asn Leu
                    245                 250                 255

Leu Met Thr Leu Arg Leu Trp Ser Ser
            260                 265
```

```
<210> SEQ ID NO 190
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 190

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Gln Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
            210                 215                 220

Val Gln Phe His Gly Leu Ser Glu Glu Asp Lys Trp Pro Glu Gly Ser
225                 230                 235                 240
```

```
Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
        290                 295                 300
```

<210> SEQ ID NO 191
<211> LENGTH: 246
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (157)..(157)
<223> OTHER INFORMATION: X is Thr or Cys
<220> FEATURE:
<221> NAME/KEY: MISC_FEATURE
<222> LOCATION: (221)..(221)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (223)..(223)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (224)..(224)
<223> OTHER INFORMATION: X is Gly, Ala, Val, Leu, Ile, Pro, Phe, Met, or
      Trp

<400> SEQUENCE: 191

```
Lys Thr Thr Gln Pro Asn Ser Met Glu Ser Asn Glu Glu Glu Pro Val
1               5                   10                  15

His Leu Pro Cys Asn His Ser Thr Ile Ser Gly Thr Asp Tyr Ile His
            20                  25                  30

Trp Tyr Arg Gln Leu Pro Ser Gln Gly Pro Glu Tyr Val Ile His Gly
            35                  40                  45

Leu Thr Ser Asn Val Asn Asn Arg Met Ala Ser Leu Ala Ile Ala Glu
        50                  55                  60

Asp Arg Lys Ser Ser Thr Leu Ile Leu His Arg Ala Thr Leu Arg Asp
65                  70                  75                  80

Ala Ala Val Tyr Tyr Cys Ile Leu Arg Ala Pro Ser Gly Thr Tyr Lys
                85                  90                  95

Tyr Ile Phe Gly Thr Gly Thr Arg Leu Lys Val Leu Ala Asn Ile Gln
            100                 105                 110

Asn Pro Glu Pro Ala Val Tyr Gln Leu Lys Asp Pro Arg Ser Gln Asp
            115                 120                 125

Ser Thr Leu Cys Leu Phe Thr Asp Phe Asp Ser Gln Ile Asn Val Pro
        130                 135                 140

Lys Thr Met Glu Ser Gly Thr Phe Ile Thr Asp Lys Xaa Val Leu Asp
145                 150                 155                 160

Met Lys Ala Met Asp Ser Lys Ser Asn Gly Ala Ile Ala Trp Ser Asn
                165                 170                 175

Gln Thr Ser Phe Thr Cys Gln Asp Ile Phe Lys Glu Thr Asn Ala Thr
            180                 185                 190

Tyr Pro Ser Ser Asp Val Pro Cys Asp Ala Thr Leu Thr Glu Lys Ser
            195                 200                 205
```

-continued

---

```
Phe Glu Thr Asp Met Asn Leu Asn Phe Gln Asn Leu Xaa Val Xaa Xaa
    210                 215                 220

Leu Arg Ile Leu Leu Leu Lys Val Ala Gly Phe Asn Leu Leu Met Thr
225                 230                 235                 240

Leu Arg Leu Trp Ser Ser
                245
```

```
<210> SEQ ID NO 192
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 192

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Gln Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
            245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 193
```

<211> LENGTH: 265
<212> TYPE: PRT
<213> ORGANISM: Artificial Sequence
<220> FEATURE:
<223> OTHER INFORMATION: Synthetic

<400> SEQUENCE: 193

```
Met Lys Leu Val Thr Ser Ile Thr Val Leu Leu Ser Leu Gly Ile Met
1               5                   10                  15

Gly Asp Ala Lys Thr Thr Gln Pro Asn Ser Met Glu Ser Asn Glu Glu
            20                  25                  30

Glu Pro Val His Leu Pro Cys Asn His Ser Thr Ile Ser Gly Thr Asp
            35                  40                  45

Tyr Ile His Trp Tyr Arg Gln Leu Pro Ser Gln Gly Pro Glu Tyr Val
        50                  55                  60

Ile His Gly Leu Thr Ser Asn Val Asn Asn Arg Met Ala Ser Leu Ala
65                  70                  75                  80

Ile Ala Glu Asp Arg Lys Ser Ser Thr Leu Ile Leu His Arg Ala Thr
                85                  90                  95

Leu Arg Asp Ala Ala Val Tyr Tyr Cys Ile Leu Arg Ala Pro Ser Gly
            100                 105                 110

Thr Tyr Lys Tyr Ile Phe Gly Thr Gly Thr Arg Leu Lys Val Leu Ala
            115                 120                 125

Asn Ile Gln Asn Pro Glu Pro Ala Val Tyr Gln Leu Lys Asp Pro Arg
        130                 135                 140

Ser Gln Asp Ser Thr Leu Cys Leu Phe Thr Asp Phe Asp Ser Gln Ile
145                 150                 155                 160

Asn Val Pro Lys Thr Met Glu Ser Gly Thr Phe Ile Thr Asp Lys Cys
                165                 170                 175

Val Leu Asp Met Lys Ala Met Asp Ser Lys Ser Asn Gly Ala Ile Ala
            180                 185                 190

Trp Ser Asn Gln Thr Ser Phe Thr Cys Gln Asp Ile Phe Lys Glu Thr
            195                 200                 205

Asn Ala Thr Tyr Pro Ser Ser Asp Val Pro Cys Asp Ala Thr Leu Thr
        210                 215                 220

Glu Lys Ser Phe Glu Thr Asp Met Asn Leu Asn Phe Gln Asn Leu Leu
225                 230                 235                 240

Val Ile Val Leu Arg Ile Leu Leu Leu Lys Val Ala Gly Phe Asn Leu
                245                 250                 255

Leu Met Thr Leu Arg Leu Trp Ser Ser
            260                 265
```

<210> SEQ ID NO 194
<211> LENGTH: 304
<212> TYPE: PRT
<213> ORGANISM: Artificial Sequence
<220> FEATURE:
<223> OTHER INFORMATION: Synthetic

<400> SEQUENCE: 194

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
```

-continued

```
         50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
            85              90              95

Leu Glu Ser Ala Ser Thr Asn Gln Thr Ser Met Tyr Leu Cys Ala Ser
            100             105             110

Arg Gln Gly Asn Thr Gly Glu Leu Phe Phe Gly Glu Gly Ser Arg Leu
            115             120             125

Thr Val Leu Glu Asp Leu Arg Asn Val Thr Pro Pro Lys Val Ser Leu
            130             135             140

Phe Glu Pro Ser Lys Ala Glu Ile Ala Asn Lys Gln Lys Ala Thr Leu
145             150             155             160

Val Cys Leu Ala Arg Gly Phe Phe Pro Asp His Val Glu Leu Ser Trp
            165             170             175

Trp Val Asn Gly Lys Glu Val His Ser Gly Val Cys Thr Asp Pro Gln
            180             185             190

Ala Tyr Lys Glu Ser Asn Tyr Ser Tyr Cys Leu Ser Ser Arg Leu Arg
            195             200             205

Val Ser Ala Thr Phe Trp His Asn Pro Arg Asn His Phe Arg Cys Gln
            210             215             220

Val Gln Phe His Gly Leu Ser Glu Glu Asp Lys Trp Pro Glu Gly Ser
225             230             235             240

Pro Lys Pro Val Thr Gln Asn Ile Ser Ala Glu Ala Trp Gly Arg Ala
            245             250             255

Asp Cys Gly Ile Thr Ser Ala Ser Tyr Gln Gln Gly Val Leu Ser Ala
            260             265             270

Thr Ile Leu Tyr Glu Ile Leu Leu Gly Lys Ala Thr Leu Tyr Ala Val
            275             280             285

Leu Val Ser Thr Leu Val Val Met Ala Met Val Lys Arg Lys Asn Ser
            290             295             300
```

<210> SEQ ID NO 195
<211> LENGTH: 246
<212> TYPE: PRT
<213> ORGANISM: Artificial Sequence
<220> FEATURE:
<223> OTHER INFORMATION: Synthetic

<400> SEQUENCE: 195

```
Lys Thr Thr Gln Pro Asn Ser Met Glu Ser Asn Glu Glu Glu Pro Val
1               5               10              15

His Leu Pro Cys Asn His Ser Thr Ile Ser Gly Thr Asp Tyr Ile His
            20              25              30

Trp Tyr Arg Gln Leu Pro Ser Gln Gly Pro Glu Tyr Val Ile His Gly
            35              40              45

Leu Thr Ser Asn Val Asn Asn Arg Met Ala Ser Leu Ala Ile Ala Glu
            50              55              60

Asp Arg Lys Ser Ser Thr Leu Ile Leu His Arg Ala Thr Leu Arg Asp
65              70              75              80

Ala Ala Val Tyr Tyr Cys Ile Leu Arg Ala Pro Ser Gly Thr Tyr Lys
            85              90              95

Tyr Ile Phe Gly Thr Gly Thr Arg Leu Lys Val Leu Ala Asn Ile Gln
            100             105             110

Asn Pro Glu Pro Ala Val Tyr Gln Leu Lys Asp Pro Arg Ser Gln Asp
```

-continued

```
                115                 120                 125
Ser Thr Leu Cys Leu Phe Thr Asp Phe Asp Ser Gln Ile Asn Val Pro
    130                 135                 140

Lys Thr Met Glu Ser Gly Thr Phe Ile Thr Asp Lys Cys Val Leu Asp
145                 150                 155                 160

Met Lys Ala Met Asp Ser Lys Ser Asn Gly Ala Ile Ala Trp Ser Asn
                165                 170                 175

Gln Thr Ser Phe Thr Cys Gln Asp Ile Phe Lys Glu Thr Asn Ala Thr
                180                 185                 190

Tyr Pro Ser Ser Asp Val Pro Cys Asp Ala Thr Leu Thr Glu Lys Ser
                195                 200                 205

Phe Glu Thr Asp Met Asn Leu Asn Phe Gln Asn Leu Leu Val Ile Val
    210                 215                 220

Leu Arg Ile Leu Leu Leu Lys Val Ala Gly Phe Asn Leu Leu Met Thr
225                 230                 235                 240

Leu Arg Leu Trp Ser Ser
                245
```

<210> SEQ ID NO 196
<211> LENGTH: 285
<212> TYPE: PRT
<213> ORGANISM: Artificial Sequence
<220> FEATURE:
<223> OTHER INFORMATION: Synthetic

<400> SEQUENCE: 196

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Gln Gly
                85                  90                  95

Asn Thr Gly Glu Leu Phe Phe Gly Glu Gly Ser Arg Leu Thr Val Leu
                100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
                180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
```

-continued

```
225                230                235                240

Ile Thr Ser Ala Ser Tyr Gln Gln Gly Val Leu Ser Ala Thr Ile Leu
              245                250                255

Tyr Glu Ile Leu Leu Gly Lys Ala Thr Leu Tyr Ala Val Leu Val Ser
          260                265                270

Thr Leu Val Val Met Ala Met Val Lys Arg Lys Asn Ser
          275                280                285

<210> SEQ ID NO 197
<211> LENGTH: 270
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (181)..(181)
<223> OTHER INFORMATION: X is Thr or Cys
<220> FEATURE:
<221> NAME/KEY: MISC_FEATURE
<222> LOCATION: (245)..(245)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (247)..(247)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (248)..(248)
<223> OTHER INFORMATION: X is Gly, Ala, Val, Leu, Ile, Pro, Phe, Met, or
      Trp

<400> SEQUENCE: 197

Met Asn Tyr Ser Pro Gly Leu Val Ser Leu Ile Leu Leu Leu Leu Gly
1                5                10                15

Arg Thr Arg Gly Asn Ser Val Thr Gln Met Glu Gly Pro Val Thr Leu
              20                25                30

Ser Glu Glu Ala Phe Leu Thr Ile Asn Cys Thr Tyr Thr Ala Thr Gly
          35                40                45

Tyr Pro Ser Leu Phe Trp Tyr Val Gln Tyr Pro Gly Glu Gly Leu Gln
      50                55                60

Leu Leu Leu Lys Ala Thr Lys Ala Asp Asp Lys Gly Ser Asn Lys Gly
65                70                75                80

Phe Glu Ala Thr Tyr Arg Lys Glu Thr Thr Ser Phe His Leu Glu Lys
              85                90                95

Gly Ser Val Gln Val Ser Asp Ser Ala Val Tyr Phe Cys Ala Leu Arg
          100                105                110

Leu Ser Gly Ala Gly Ser Tyr Gln Leu Thr Phe Gly Lys Gly Thr Lys
          115                120                125

Leu Ser Val Ile Pro Asn Ile Gln Asn Pro Glu Pro Ala Val Tyr Gln
      130                135                140

Leu Lys Asp Pro Arg Ser Gln Asp Ser Thr Leu Cys Leu Phe Thr Asp
145                150                155                160

Phe Asp Ser Gln Ile Asn Val Pro Lys Thr Met Glu Ser Gly Thr Phe
              165                170                175

Ile Thr Asp Lys Xaa Val Leu Asp Met Lys Ala Met Asp Ser Lys Ser
          180                185                190

Asn Gly Ala Ile Ala Trp Ser Asn Gln Thr Ser Phe Thr Cys Gln Asp
          195                200                205

Ile Phe Lys Glu Thr Asn Ala Thr Tyr Pro Ser Ser Asp Val Pro Cys
```

-continued

```
             210               215               220
Asp Ala Thr Leu Thr Glu Lys Ser Phe Glu Thr Asp Met Asn Leu Asn
225               230               235               240

Phe Gln Asn Leu Xaa Val Xaa Xaa Leu Arg Ile Leu Leu Lys Val
              245               250               255

Ala Gly Phe Asn Leu Leu Met Thr Leu Arg Leu Trp Ser Ser
              260               265               270

<210> SEQ ID NO 198
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 198

Met Ala Ile Arg Leu Leu Cys Arg Val Ala Phe Cys Phe Leu Ala Val
1               5               10               15

Gly Leu Val Asp Val Lys Val Thr Gln Ser Ser Arg Tyr Leu Val Lys
              20               25               30

Arg Thr Gly Glu Lys Val Phe Leu Glu Cys Val Gln Asp Met Asp His
              35               40               45

Glu Asn Met Phe Trp Tyr Arg Gln Asp Pro Gly Leu Gly Leu Arg Leu
              50               55               60

Ile Tyr Phe Ser Tyr Asp Val Lys Met Lys Glu Lys Gly Asp Ile Pro
65               70               75               80

Glu Gly Tyr Ser Val Ser Arg Glu Lys Lys Glu Arg Phe Ser Leu Ile
              85               90               95

Leu Glu Ser Ala Ser Thr Asn Gln Thr Ser Met Tyr Leu Cys Ala Ser
              100               105               110

Ser Gln Gly Asn Thr Gly Glu Leu Phe Phe Gly Glu Gly Ser Arg Leu
              115               120               125

Thr Val Leu Glu Asp Leu Arg Asn Val Thr Pro Pro Lys Val Ser Leu
              130               135               140

Phe Glu Pro Ser Lys Ala Glu Ile Ala Asn Lys Gln Lys Ala Thr Leu
145               150               155               160

Val Cys Leu Ala Arg Gly Phe Phe Pro Asp His Val Glu Leu Ser Trp
              165               170               175

Trp Val Asn Gly Lys Glu Val His Ser Gly Val Xaa Thr Asp Pro Gln
              180               185               190

Ala Tyr Lys Glu Ser Asn Tyr Ser Tyr Cys Leu Ser Ser Arg Leu Arg
              195               200               205

Val Ser Ala Thr Phe Trp His Asn Pro Arg Asn His Phe Arg Cys Gln
              210               215               220

Val Gln Phe His Gly Leu Ser Glu Glu Asp Lys Trp Pro Glu Gly Ser
225               230               235               240

Pro Lys Pro Val Thr Gln Asn Ile Ser Ala Glu Ala Trp Gly Arg Ala
              245               250               255

Asp Cys Gly Ile Thr Ser Ala Ser Tyr Gln Gln Gly Val Leu Ser Ala
              260               265               270

Thr Ile Leu Tyr Glu Ile Leu Leu Gly Lys Ala Thr Leu Tyr Ala Val
              275               280               285
```

```
Leu Val Ser Thr Leu Val Val Met Ala Met Val Lys Arg Lys Asn Ser
    290             295             300
```

<210> SEQ ID NO 199
<211> LENGTH: 250
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (161)..(161)
<223> OTHER INFORMATION: X is Thr or Cys
<220> FEATURE:
<221> NAME/KEY: MISC_FEATURE
<222> LOCATION: (225)..(225)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (227)..(227)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (228)..(228)
<223> OTHER INFORMATION: X is Gly, Ala, Val, Leu, Ile, Pro, Phe, Met, or
      Trp

<400> SEQUENCE: 199

```
Asn Ser Val Thr Gln Met Glu Gly Pro Val Thr Leu Ser Glu Glu Ala
1               5               10              15

Phe Leu Thr Ile Asn Cys Thr Tyr Thr Ala Thr Gly Tyr Pro Ser Leu
                20              25              30

Phe Trp Tyr Val Gln Tyr Pro Gly Glu Gly Leu Gln Leu Leu Leu Lys
            35              40              45

Ala Thr Lys Ala Asp Asp Lys Gly Ser Asn Lys Gly Phe Glu Ala Thr
    50              55              60

Tyr Arg Lys Glu Thr Thr Ser Phe His Leu Glu Lys Gly Ser Val Gln
65              70              75              80

Val Ser Asp Ser Ala Val Tyr Phe Cys Ala Leu Arg Leu Ser Gly Ala
            85              90              95

Gly Ser Tyr Gln Leu Thr Phe Gly Lys Gly Thr Lys Leu Ser Val Ile
            100             105             110

Pro Asn Ile Gln Asn Pro Glu Pro Ala Val Tyr Gln Leu Lys Asp Pro
        115             120             125

Arg Ser Gln Asp Ser Thr Leu Cys Leu Phe Thr Asp Phe Asp Ser Gln
    130             135             140

Ile Asn Val Pro Lys Thr Met Glu Ser Gly Thr Phe Ile Thr Asp Lys
145             150             155             160

Xaa Val Leu Asp Met Lys Ala Met Asp Ser Lys Ser Asn Gly Ala Ile
                165             170             175

Ala Trp Ser Asn Gln Thr Ser Phe Thr Cys Gln Asp Ile Phe Lys Glu
            180             185             190

Thr Asn Ala Thr Tyr Pro Ser Ser Asp Val Pro Cys Asp Ala Thr Leu
            195             200             205

Thr Glu Lys Ser Phe Glu Thr Asp Met Asn Leu Asn Phe Gln Asn Leu
    210             215             220

Xaa Val Xaa Xaa Leu Arg Ile Leu Leu Leu Lys Val Ala Gly Phe Asn
225             230             235             240

Leu Leu Met Thr Leu Arg Leu Trp Ser Ser
                245             250
```

-continued

```
<210> SEQ ID NO 200
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 200

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
        130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
                180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
        210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 201
<211> LENGTH: 270
<212> TYPE: PRT
<213> ORGANISM: Artificial Sequence
<220> FEATURE:
<223> OTHER INFORMATION: Synthetic

<400> SEQUENCE: 201

Met Asn Tyr Ser Pro Gly Leu Val Ser Leu Ile Leu Leu Leu Leu Gly
```

-continued

```
1               5                   10                  15

Arg Thr Arg Gly Asn Ser Val Thr Gln Met Glu Gly Pro Val Thr Leu
            20                  25                  30

Ser Glu Glu Ala Phe Leu Thr Ile Asn Cys Thr Tyr Thr Ala Thr Gly
            35                  40                  45

Tyr Pro Ser Leu Phe Trp Tyr Val Gln Tyr Pro Gly Glu Gly Leu Gln
        50                  55                  60

Leu Leu Leu Lys Ala Thr Lys Ala Asp Asp Lys Gly Ser Asn Lys Gly
65                  70                  75                  80

Phe Glu Ala Thr Tyr Arg Lys Glu Thr Thr Ser Phe His Leu Glu Lys
                85                  90                  95

Gly Ser Val Gln Val Ser Asp Ser Ala Val Tyr Phe Cys Ala Leu Arg
            100                 105                 110

Leu Ser Gly Ala Gly Ser Tyr Gln Leu Thr Phe Gly Lys Gly Thr Lys
            115                 120                 125

Leu Ser Val Ile Pro Asn Ile Gln Asn Pro Glu Pro Ala Val Tyr Gln
        130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Cys Val Leu Asp Met Lys Ala Met Asp Ser Lys Ser
            180                 185                 190

Asn Gly Ala Ile Ala Trp Ser Asn Gln Thr Ser Phe Thr Cys Gln Asp
            195                 200                 205

Ile Phe Lys Glu Thr Asn Ala Thr Tyr Pro Ser Ser Asp Val Pro Cys
        210                 215                 220

Asp Ala Thr Leu Thr Glu Lys Ser Phe Glu Thr Asp Met Asn Leu Asn
225                 230                 235                 240

Phe Gln Asn Leu Leu Val Ile Val Leu Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 202
<211> LENGTH: 304
<212> TYPE: PRT
<213> ORGANISM: Artificial Sequence
<220> FEATURE:
<223> OTHER INFORMATION: Synthetic

<400> SEQUENCE: 202

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
```

-continued

```
               100                105                110
Ser Gln Gly Asn Thr Gly Glu Leu Phe Phe Gly Glu Gly Ser Arg Leu
           115                120                125

Thr Val Leu Glu Asp Leu Arg Asn Val Thr Pro Pro Lys Val Ser Leu
       130                135                140

Phe Glu Pro Ser Lys Ala Glu Ile Ala Asn Lys Gln Lys Ala Thr Leu
145                150                155                160

Val Cys Leu Ala Arg Gly Phe Phe Pro Asp His Val Glu Leu Ser Trp
                165                170                175

Trp Val Asn Gly Lys Glu Val His Ser Gly Val Cys Thr Asp Pro Gln
                180                185                190

Ala Tyr Lys Glu Ser Asn Tyr Ser Tyr Cys Leu Ser Ser Arg Leu Arg
                195                200                205

Val Ser Ala Thr Phe Trp His Asn Pro Arg Asn His Phe Arg Cys Gln
        210                215                220

Val Gln Phe His Gly Leu Ser Glu Glu Asp Lys Trp Pro Glu Gly Ser
225                230                235                240

Pro Lys Pro Val Thr Gln Asn Ile Ser Ala Glu Ala Trp Gly Arg Ala
                245                250                255

Asp Cys Gly Ile Thr Ser Ala Ser Tyr Gln Gln Gly Val Leu Ser Ala
                260                265                270

Thr Ile Leu Tyr Glu Ile Leu Leu Gly Lys Ala Thr Leu Tyr Ala Val
                275                280                285

Leu Val Ser Thr Leu Val Val Met Ala Met Val Lys Arg Lys Asn Ser
        290                295                300
```

<210> SEQ ID NO 203
<211> LENGTH: 250
<212> TYPE: PRT
<213> ORGANISM: Artificial Sequence
<220> FEATURE:
<223> OTHER INFORMATION: Synthetic

<400> SEQUENCE: 203

```
Asn Ser Val Thr Gln Met Glu Gly Pro Val Thr Leu Ser Glu Glu Ala
1                5                10                15

Phe Leu Thr Ile Asn Cys Thr Tyr Thr Ala Thr Gly Tyr Pro Ser Leu
            20                25                30

Phe Trp Tyr Val Gln Tyr Pro Gly Glu Gly Leu Gln Leu Leu Leu Lys
            35                40                45

Ala Thr Lys Ala Asp Asp Lys Gly Ser Asn Lys Gly Phe Glu Ala Thr
    50                55                60

Tyr Arg Lys Glu Thr Thr Ser Phe His Leu Glu Lys Gly Ser Val Gln
65                70                75                80

Val Ser Asp Ser Ala Val Tyr Phe Cys Ala Leu Arg Leu Ser Gly Ala
                85                90                95

Gly Ser Tyr Gln Leu Thr Phe Gly Lys Gly Thr Lys Leu Ser Val Ile
            100                105                110

Pro Asn Ile Gln Asn Pro Glu Pro Ala Val Tyr Gln Leu Lys Asp Pro
            115                120                125

Arg Ser Gln Asp Ser Thr Leu Cys Leu Phe Thr Asp Phe Asp Ser Gln
    130                135                140

Ile Asn Val Pro Lys Thr Met Glu Ser Gly Thr Phe Ile Thr Asp Lys
145                150                155                160

Cys Val Leu Asp Met Lys Ala Met Asp Ser Lys Ser Asn Gly Ala Ile
```

-continued

```
                    165                 170                 175

Ala Trp Ser Asn Gln Thr Ser Phe Thr Cys Gln Asp Ile Phe Lys Glu
                180                 185                 190

Thr Asn Ala Thr Tyr Pro Ser Ser Asp Val Pro Cys Asp Ala Thr Leu
            195                 200                 205

Thr Glu Lys Ser Phe Glu Thr Asp Met Asn Leu Asn Phe Gln Asn Leu
        210                 215                 220

Leu Val Ile Val Leu Arg Ile Leu Leu Leu Lys Val Ala Gly Phe Asn
225                 230                 235                 240

Leu Leu Met Thr Leu Arg Leu Trp Ser Ser
                245                 250

<210> SEQ ID NO 204
<211> LENGTH: 285
<212> TYPE: PRT
<213> ORGANISM: Artificial Sequence
<220> FEATURE:
<223> OTHER INFORMATION: Synthetic

<400> SEQUENCE: 204

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
                35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Gln Gly
                85                  90                  95

Asn Thr Gly Glu Leu Phe Phe Gly Glu Gly Ser Arg Leu Thr Val Leu
                100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
        130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
                180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
        210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
                260                 265                 270

Thr Leu Val Val Met Ala Met Val Lys Arg Lys Asn Ser
```

```
                275              280              285

<210> SEQ ID NO 205
<211> LENGTH: 273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (184)..(184)
<223> OTHER INFORMATION: X is Thr or Cys
<220> FEATURE:
<221> NAME/KEY: MISC_FEATURE
<222> LOCATION: (248)..(248)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (250)..(250)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (251)..(251)
<223> OTHER INFORMATION: X is Gly, Ala, Val, Leu, Ile, Pro, Phe, Met, or
      Trp

<400> SEQUENCE: 205

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Arg Ser Gly Thr Ala Ser Lys Leu Thr Phe Gly Thr
            115                 120                 125

Gly Thr Arg Leu Gln Val Thr Leu Asn Ile Gln Asn Pro Glu Pro Ala
        130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Xaa Val Leu Asp Met Lys Ala Met Asp
            180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
        210                 215                 220

Val Pro Cys Asp Ala Thr Leu Thr Glu Lys Ser Phe Glu Thr Asp Met
225                 230                 235                 240

Asn Leu Asn Phe Gln Asn Leu Xaa Val Xaa Xaa Leu Arg Ile Leu Leu
                245                 250                 255

Leu Lys Val Ala Gly Phe Asn Leu Leu Met Thr Leu Arg Leu Trp Ser
```

-continued

```
                260                 265                 270

Ser

<210> SEQ ID NO 206
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (190)..(190)
<223> OTHER INFORMATION: X is Ser or Cys

<400> SEQUENCE: 206

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Gly Val Gly Ser Asn Tyr Gly Tyr Thr Phe Gly Ser Gly Thr
            115                 120                 125

Arg Leu Thr Val Val Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Xaa Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
        290                 295                 300

Asn Ser
305
```

-continued

```
<210> SEQ ID NO 207
<211> LENGTH: 252
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (163)..(163)
<223> OTHER INFORMATION: X is Thr or Cys
<220> FEATURE:
<221> NAME/KEY: MISC_FEATURE
<222> LOCATION: (227)..(227)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (229)..(229)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (230)..(230)
<223> OTHER INFORMATION: X is Gly, Ala, Val, Leu, Ile, Pro, Phe, Met, or
      Trp

<400> SEQUENCE: 207

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
            20                  25                  30

Leu Phe Trp Tyr Lys Gln Pro Ser Ser Gly Glu Met Ile Phe Leu Ile
        35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Thr Ala Ser Lys Leu Thr Phe Gly Thr Gly Thr Arg Leu Gln
            100                 105                 110

Val Thr Leu Asn Ile Gln Asn Pro Glu Pro Ala Val Tyr Gln Leu Lys
        115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160

Asp Lys Xaa Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
        195                 200                 205

Thr Leu Thr Glu Lys Ser Phe Glu Thr Asp Met Asn Leu Asn Phe Gln
    210                 215                 220

Asn Leu Xaa Val Xaa Xaa Leu Arg Ile Leu Leu Leu Lys Val Ala Gly
225                 230                 235                 240

Phe Asn Leu Leu Met Thr Leu Arg Leu Trp Ser Ser
                245                 250

<210> SEQ ID NO 208
<211> LENGTH: 280
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (164)..(164)
<223> OTHER INFORMATION: X is Ser or Cys

<400> SEQUENCE: 208

Ser Arg Tyr Leu Val Lys Arg Thr Gly Glu Lys Val Phe Leu Glu Cys
1               5                   10                  15

Val Gln Asp Met Asp His Glu Asn Met Phe Trp Tyr Arg Gln Asp Pro
                20                  25                  30

Gly Leu Gly Leu Arg Leu Ile Tyr Phe Ser Tyr Asp Val Lys Met Lys
            35                  40                  45

Glu Lys Gly Asp Ile Pro Glu Gly Tyr Ser Val Ser Arg Glu Lys Lys
        50                  55                  60

Glu Arg Phe Ser Leu Ile Leu Glu Ser Ala Ser Thr Asn Gln Thr Ser
65                  70                  75                  80

Met Tyr Leu Cys Ala Ser Ser Leu Gly Val Gly Ser Asn Tyr Gly Tyr
                85                  90                  95

Thr Phe Gly Ser Gly Thr Arg Leu Thr Val Val Glu Asp Leu Arg Asn
                100                 105                 110

Val Thr Pro Pro Lys Val Ser Leu Phe Glu Pro Ser Lys Ala Glu Ile
            115                 120                 125

Ala Asn Lys Gln Lys Ala Thr Leu Val Cys Leu Ala Arg Gly Phe Phe
        130                 135                 140

Pro Asp His Val Glu Leu Ser Trp Trp Val Asn Gly Lys Glu Val His
145                 150                 155                 160

Ser Gly Val Xaa Thr Asp Pro Gln Ala Tyr Lys Glu Ser Asn Tyr Ser
                165                 170                 175

Tyr Cys Leu Ser Ser Arg Leu Arg Val Ser Ala Thr Phe Trp His Asn
                180                 185                 190

Pro Arg Asn His Phe Arg Cys Gln Val Gln Phe His Gly Leu Ser Glu
            195                 200                 205

Glu Asp Lys Trp Pro Glu Gly Ser Pro Lys Pro Val Thr Gln Asn Ile
        210                 215                 220

Ser Ala Glu Ala Trp Gly Arg Ala Asp Cys Gly Ile Thr Ser Ala Ser
225                 230                 235                 240

Tyr Gln Gln Gly Val Leu Ser Ala Thr Ile Leu Tyr Glu Ile Leu Leu
                245                 250                 255

Gly Lys Ala Thr Leu Tyr Ala Val Leu Val Ser Thr Leu Val Val Met
                260                 265                 270

Ala Met Val Lys Arg Lys Asn Ser
        275                 280

<210> SEQ ID NO 209
<211> LENGTH: 273
<212> TYPE: PRT
<213> ORGANISM: Artificial Sequence
<220> FEATURE:
<223> OTHER INFORMATION: Synthetic

<400> SEQUENCE: 209

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30
```

```
Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
                100                 105                 110

Ala Met Arg Glu Arg Ser Gly Thr Ala Ser Lys Leu Thr Phe Gly Thr
                115                 120                 125

Gly Thr Arg Leu Gln Val Thr Leu Asn Ile Gln Asn Pro Glu Pro Ala
        130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
                180                 185                 190

Ser Lys Ser Asn Gly Ala Ile Ala Trp Ser Asn Gln Thr Ser Phe Thr
                195                 200                 205

Cys Gln Asp Ile Phe Lys Glu Thr Asn Ala Thr Tyr Pro Ser Ser Asp
        210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
                260                 265                 270

Ser
```

<210> SEQ ID NO 210
<211> LENGTH: 306
<212> TYPE: PRT
<213> ORGANISM: Artificial Sequence
<220> FEATURE:
<223> OTHER INFORMATION: Synthetic

<400> SEQUENCE: 210

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110
```

-continued

```
Ser Leu Gly Val Gly Ser Asn Tyr Gly Tyr Thr Phe Gly Ser Gly Thr
    115                 120                 125

Arg Leu Thr Val Val Glu Asp Leu Arg Asn Val Thr Pro Pro Lys Val
    130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
                195                 200                 205

Leu Arg Val Ser Ala Thr Phe Trp His Asn Pro Arg Asn His Phe Arg
    210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr Gln Gln Gly Val Leu
                260                 265                 270

Ser Ala Thr Ile Leu Tyr Glu Ile Leu Leu Gly Lys Ala Thr Leu Tyr
                275                 280                 285

Ala Val Leu Val Ser Thr Leu Val Val Met Ala Met Val Lys Arg Lys
    290                 295                 300

Asn Ser
305
```

```
<210> SEQ ID NO 211
<211> LENGTH: 252
<212> TYPE: PRT
<213> ORGANISM: Artificial Sequence
<220> FEATURE:
<223> OTHER INFORMATION: Synthetic

<400> SEQUENCE: 211

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Thr Ala Ser Lys Leu Thr Phe Gly Thr Gly Thr Arg Leu Gln
                100                 105                 110

Val Thr Leu Asn Ile Gln Asn Pro Glu Pro Ala Val Tyr Gln Leu Lys
            115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160
```

```
Asp Lys Cys Val Leu Asp Met Lys Ala Met Asp Ser Lys Ser Asn Gly
            165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
            195                 200                 205

Thr Leu Thr Glu Lys Ser Phe Glu Thr Asp Met Asn Leu Asn Phe Gln
    210                 215                 220

Asn Leu Leu Val Ile Val Leu Arg Ile Leu Leu Leu Lys Val Ala Gly
225                 230                 235                 240

Phe Asn Leu Leu Met Thr Leu Arg Leu Trp Ser Ser
            245                 250
```

```
<210> SEQ ID NO 212
<211> LENGTH: 280
<212> TYPE: PRT
<213> ORGANISM: Artificial Sequence
<220> FEATURE:
<223> OTHER INFORMATION: Synthetic

<400> SEQUENCE: 212

Ser Arg Tyr Leu Val Lys Arg Thr Gly Glu Lys Val Phe Leu Glu Cys
1               5                   10                  15

Val Gln Asp Met Asp His Glu Asn Met Phe Trp Tyr Arg Gln Asp Pro
            20                  25                  30

Gly Leu Gly Leu Arg Leu Ile Tyr Phe Ser Tyr Asp Val Lys Met Lys
            35                  40                  45

Glu Lys Gly Asp Ile Pro Glu Gly Tyr Ser Val Ser Arg Glu Lys Lys
            50                  55                  60

Glu Arg Phe Ser Leu Ile Leu Glu Ser Ala Ser Thr Asn Gln Thr Ser
65                  70                  75                  80

Met Tyr Leu Cys Ala Ser Ser Leu Gly Val Gly Ser Asn Tyr Gly Tyr
                85                  90                  95

Thr Phe Gly Ser Gly Thr Arg Leu Thr Val Val Glu Asp Leu Arg Asn
            100                 105                 110

Val Thr Pro Pro Lys Val Ser Leu Phe Glu Pro Ser Lys Ala Glu Ile
            115                 120                 125

Ala Asn Lys Gln Lys Ala Thr Leu Val Cys Leu Ala Arg Gly Phe Phe
            130                 135                 140

Pro Asp His Val Glu Leu Ser Trp Trp Val Asn Gly Lys Glu Val His
145                 150                 155                 160

Ser Gly Val Cys Thr Asp Pro Gln Ala Tyr Lys Glu Ser Asn Tyr Ser
                165                 170                 175

Tyr Cys Leu Ser Ser Arg Leu Arg Val Ser Ala Thr Phe Trp His Asn
            180                 185                 190

Pro Arg Asn His Phe Arg Cys Gln Val Gln Phe His Gly Leu Ser Glu
            195                 200                 205

Glu Asp Lys Trp Pro Glu Gly Ser Pro Lys Pro Val Thr Gln Asn Ile
    210                 215                 220

Ser Ala Glu Ala Trp Gly Arg Ala Asp Cys Gly Ile Thr Ser Ala Ser
225                 230                 235                 240

Tyr Gln Gln Gly Val Leu Ser Ala Thr Ile Leu Tyr Glu Ile Leu Leu
            245                 250                 255

Gly Lys Ala Thr Leu Tyr Ala Val Leu Val Ser Thr Leu Val Val Met
            260                 265                 270
```

```
Ala Met Val Lys Arg Lys Asn Ser
      275                 280

<210> SEQ ID NO 213
<211> LENGTH: 272
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (183)..(183)
<223> OTHER INFORMATION: X is Thr or Cys
<220> FEATURE:
<221> NAME/KEY: MISC_FEATURE
<222> LOCATION: (247)..(247)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (249)..(249)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (250)..(250)
<223> OTHER INFORMATION: X is Gly, Ala, Val, Leu, Ile, Pro, Phe, Met, or
      Trp

<400> SEQUENCE: 213

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
                20                  25                  30

Leu Ser Val Pro Glu Gly Ala Ile Val Ser Leu Asn Cys Thr Tyr Ser
          35                  40                  45

Asn Ser Ala Phe Gln Tyr Phe Met Trp Tyr Arg Gln Tyr Ser Arg Lys
      50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
              100                 105                 110

Met Ser Tyr Ser Gly Gly Gly Ala Asp Gly Leu Thr Phe Gly Lys Gly
          115                 120                 125

Thr His Leu Ile Ile Gln Pro Asn Ile Gln Asn Pro Glu Pro Ala Val
      130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
              165                 170                 175

Thr Phe Ile Thr Asp Lys Xaa Val Leu Asp Met Lys Ala Met Asp Ser
          180                 185                 190

Lys Ser Asn Gly Ala Ile Ala Trp Ser Asn Gln Thr Ser Phe Thr Cys
          195                 200                 205

Gln Asp Ile Phe Lys Glu Thr Asn Ala Thr Tyr Pro Ser Ser Asp Val
      210                 215                 220

Pro Cys Asp Ala Thr Leu Thr Glu Lys Ser Phe Glu Thr Asp Met Asn
225                 230                 235                 240

Leu Asn Phe Gln Asn Leu Xaa Val Xaa Xaa Leu Arg Ile Leu Leu Leu
              245                 250                 255
```

-continued

```
Lys Val Ala Gly Phe Asn Leu Leu Met Thr Leu Arg Leu Trp Ser Ser
            260                 265                 270
```

```
<210> SEQ ID NO 214
<211> LENGTH: 304
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 214

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Thr Gly Asn Thr Gly Glu Leu Phe Phe Gly Glu Gly Ser Arg Leu
        115                 120                 125

Thr Val Leu Glu Asp Leu Arg Asn Val Thr Pro Pro Lys Val Ser Leu
            130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
    290                 295                 300
```

```
<210> SEQ ID NO 215
<211> LENGTH: 250
<212> TYPE: PRT
<213> ORGANISM: Artificial Sequence
```

-continued

```
<220> FEATURE:
<223> OTHER INFORMATION: Synthetic
<220> FEATURE:
<221> NAME/KEY: MISC_FEATURE
<222> LOCATION: (161)..(161)
<223> OTHER INFORMATION: X is Thr or Cys
<220> FEATURE:
<221> NAME/KEY: MISC_FEATURE
<222> LOCATION: (225)..(225)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (227)..(227)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (228)..(228)
<223> OTHER INFORMATION: X is Gly, Ala, Val, Leu, Ile, Pro, Phe, Met, or
     Trp

<400> SEQUENCE: 215

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Ser Tyr Ser Gly Gly
                85                  90                  95

Gly Ala Asp Gly Leu Thr Phe Gly Lys Gly Thr His Leu Ile Ile Gln
            100                 105                 110

Pro Asn Ile Gln Asn Pro Glu Pro Ala Val Tyr Gln Leu Lys Asp Pro
        115                 120                 125

Arg Ser Gln Asp Ser Thr Leu Cys Leu Phe Thr Asp Phe Asp Ser Gln
    130                 135                 140

Ile Asn Val Pro Lys Thr Met Glu Ser Gly Thr Phe Ile Thr Asp Lys
145                 150                 155                 160

Xaa Val Leu Asp Met Lys Ala Met Asp Ser Lys Ser Asn Gly Ala Ile
                165                 170                 175

Ala Trp Ser Asn Gln Thr Ser Phe Thr Cys Gln Asp Ile Phe Lys Glu
            180                 185                 190

Thr Asn Ala Thr Tyr Pro Ser Ser Asp Val Pro Cys Asp Ala Thr Leu
        195                 200                 205

Thr Glu Lys Ser Phe Glu Thr Asp Met Asn Leu Asn Phe Gln Asn Leu
    210                 215                 220

Xaa Val Xaa Xaa Leu Arg Ile Leu Leu Leu Lys Val Ala Gly Phe Asn
225                 230                 235                 240

Leu Leu Met Thr Leu Arg Leu Trp Ser Ser
            245                 250

<210> SEQ ID NO 216
<211> LENGTH: 285
<212> TYPE: PRT
<213> ORGANISM: Artificial Sequence
<220> FEATURE:
<223> OTHER INFORMATION: Synthetic
<220> FEATURE:
```

-continued

```
<221> NAME/KEY: MISC_FEATURE
<222> LOCATION: (169)..(169)
<223> OTHER INFORMATION: X is Ser or Cys

<400> SEQUENCE: 216

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Thr Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
                260                 265                 270

Thr Leu Val Val Met Ala Met Val Lys Arg Lys Asn Ser
            275                 280                 285

<210> SEQ ID NO 217
<211> LENGTH: 272
<212> TYPE: PRT
<213> ORGANISM: Artificial Sequence
<220> FEATURE:
<223> OTHER INFORMATION: Synthetic

<400> SEQUENCE: 217

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45
```

-continued

```
Asn Ser Ala Phe Gln Tyr Phe Met Trp Tyr Arg Gln Tyr Ser Arg Lys
    50              55                  60

Gly Pro Glu Leu Leu Met Tyr Thr Tyr Ser Ser Gly Asn Lys Glu Asp
65              70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Ser Tyr Ser Gly Gly Gly Ala Asp Gly Leu Thr Phe Gly Lys Gly
            115                 120                 125

Thr His Leu Ile Ile Gln Pro Asn Ile Gln Asn Pro Glu Pro Ala Val
    130                 135                 140

Tyr Gln Leu Lys Asp Pro Arg Ser Gln Asp Ser Thr Leu Cys Leu Phe
145                 150                 155                 160

Thr Asp Phe Asp Ser Gln Ile Asn Val Pro Lys Thr Met Glu Ser Gly
                165                 170                 175

Thr Phe Ile Thr Asp Lys Cys Val Leu Asp Met Lys Ala Met Asp Ser
            180                 185                 190

Lys Ser Asn Gly Ala Ile Ala Trp Ser Asn Gln Thr Ser Phe Thr Cys
            195                 200                 205

Gln Asp Ile Phe Lys Glu Thr Asn Ala Thr Tyr Pro Ser Ser Asp Val
    210                 215                 220

Pro Cys Asp Ala Thr Leu Thr Glu Lys Ser Phe Glu Thr Asp Met Asn
225                 230                 235                 240

Leu Asn Phe Gln Asn Leu Leu Val Ile Val Leu Arg Ile Leu Leu Leu
                245                 250                 255

Lys Val Ala Gly Phe Asn Leu Leu Met Thr Leu Arg Leu Trp Ser Ser
            260                 265                 270
```

<210> SEQ ID NO 218
<211> LENGTH: 304
<212> TYPE: PRT
<213> ORGANISM: Artificial Sequence
<220> FEATURE:
<223> OTHER INFORMATION: Synthetic

<400> SEQUENCE: 218

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65              70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Thr Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
    130                 135                 140
```

-continued

```
Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
                180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
    290                 295                 300
```

\<210\> SEQ ID NO 219
\<211\> LENGTH: 250
\<212\> TYPE: PRT
\<213\> ORGANISM: Artificial Sequence
\<220\> FEATURE:
\<223\> OTHER INFORMATION: Synthetic

\<400\> SEQUENCE: 219

```
Gln Lys Glu Val Glu Gln Asp Pro Gly Pro Leu Ser Val Pro Glu Gly
1               5               10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
            35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Ser Tyr Ser Gly Gly
                85                  90                  95

Gly Ala Asp Gly Leu Thr Phe Gly Lys Gly Thr His Leu Ile Ile Gln
            100                 105                 110

Pro Asn Ile Gln Asn Pro Glu Pro Ala Val Tyr Gln Leu Lys Asp Pro
        115                 120                 125

Arg Ser Gln Asp Ser Thr Leu Cys Leu Phe Thr Asp Phe Asp Ser Gln
    130                 135                 140

Ile Asn Val Pro Lys Thr Met Glu Ser Gly Thr Phe Ile Thr Asp Lys
145                 150                 155                 160

Cys Val Leu Asp Met Lys Ala Met Asp Ser Lys Ser Asn Gly Ala Ile
                165                 170                 175

Ala Trp Ser Asn Gln Thr Ser Phe Thr Cys Gln Asp Ile Phe Lys Glu
            180                 185                 190

Thr Asn Ala Thr Tyr Pro Ser Ser Asp Val Pro Cys Asp Ala Thr Leu
        195                 200                 205
```

-continued

```
Thr Glu Lys Ser Phe Glu Thr Asp Met Asn Leu Asn Phe Gln Asn Leu
    210                 215                 220
Leu Val Ile Val Leu Arg Ile Leu Leu Leu Lys Val Ala Gly Phe Asn
225                 230                 235                 240
Leu Leu Met Thr Leu Arg Leu Trp Ser Ser
                245                 250

<210> SEQ ID NO 220
<211> LENGTH: 285
<212> TYPE: PRT
<213> ORGANISM: Artificial Sequence
<220> FEATURE:
<223> OTHER INFORMATION: Synthetic

<400> SEQUENCE: 220

Asp Val Lys Val Thr Gln Ser Ser Arg Tyr Leu Val Lys Arg Thr Gly
1               5                   10                  15
Glu Lys Val Phe Leu Glu Cys Val Gln Asp Met Asp His Glu Asn Met
                20                  25                  30
Phe Trp Tyr Arg Gln Asp Pro Gly Leu Gly Leu Arg Leu Ile Tyr Phe
            35                  40                  45
Ser Tyr Asp Val Lys Met Lys Glu Lys Gly Asp Ile Pro Glu Gly Tyr
        50                  55                  60
Ser Val Ser Arg Glu Lys Lys Glu Arg Phe Ser Leu Ile Leu Glu Ser
65                  70                  75                  80
Ala Ser Thr Asn Gln Thr Ser Met Tyr Leu Cys Ala Ser Ser Thr Gly
                85                  90                  95
Asn Thr Gly Glu Leu Phe Phe Gly Glu Gly Ser Arg Leu Thr Val Leu
            100                 105                 110
Glu Asp Leu Arg Asn Val Thr Pro Pro Lys Val Ser Leu Phe Glu Pro
        115                 120                 125
Ser Lys Ala Glu Ile Ala Asn Lys Gln Lys Ala Thr Leu Val Cys Leu
    130                 135                 140
Ala Arg Gly Phe Phe Pro Asp His Val Glu Leu Ser Trp Trp Val Asn
145                 150                 155                 160
Gly Lys Glu Val His Ser Gly Val Cys Thr Asp Pro Gln Ala Tyr Lys
                165                 170                 175
Glu Ser Asn Tyr Ser Tyr Cys Leu Ser Ser Arg Leu Arg Val Ser Ala
            180                 185                 190
Thr Phe Trp His Asn Pro Arg Asn His Phe Arg Cys Gln Val Gln Phe
        195                 200                 205
His Gly Leu Ser Glu Glu Asp Lys Trp Pro Glu Gly Ser Pro Lys Pro
    210                 215                 220
Val Thr Gln Asn Ile Ser Ala Glu Ala Trp Gly Arg Ala Asp Cys Gly
225                 230                 235                 240
Ile Thr Ser Ala Ser Tyr Gln Gln Gly Val Leu Ser Ala Thr Ile Leu
                245                 250                 255
Tyr Glu Ile Leu Leu Gly Lys Ala Thr Leu Tyr Ala Val Leu Val Ser
            260                 265                 270
Thr Leu Val Val Met Ala Met Val Lys Arg Lys Asn Ser
        275                 280                 285

<210> SEQ ID NO 221
<211> LENGTH: 269
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: MISC_FEATURE
<222> LOCATION: (180)..(180)
<223> OTHER INFORMATION: X is Thr or Cys
<220> FEATURE:
<221> NAME/KEY: MISC_FEATURE
<222> LOCATION: (244)..(244)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (246)..(246)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (247)..(247)
<223> OTHER INFORMATION: X is Gly, Ala, Val, Leu, Ile, Pro, Phe, Met, or
      Trp

<400> SEQUENCE: 221

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Ala Asn Thr Asp Lys Leu Ile Phe Gly Thr Gly Thr Arg Leu
            115                 120                 125

Gln Val Phe Pro Asn Ile Gln Asn Pro Glu Pro Ala Val Tyr Gln Leu
        130                 135                 140

Lys Asp Pro Arg Ser Gln Asp Ser Thr Leu Cys Leu Phe Thr Asp Phe
145                 150                 155                 160

Asp Ser Gln Ile Asn Val Pro Lys Thr Met Glu Ser Gly Thr Phe Ile
                165                 170                 175

Thr Asp Lys Xaa Val Leu Asp Met Lys Ala Met Asp Ser Lys Ser Asn
            180                 185                 190

Gly Ala Ile Ala Trp Ser Asn Gln Thr Ser Phe Thr Cys Gln Asp Ile
            195                 200                 205

Phe Lys Glu Thr Asn Ala Thr Tyr Pro Ser Ser Asp Val Pro Cys Asp
        210                 215                 220

Ala Thr Leu Thr Glu Lys Ser Phe Glu Thr Asp Met Asn Leu Asn Phe
225                 230                 235                 240

Gln Asn Leu Xaa Val Xaa Xaa Leu Arg Ile Leu Leu Leu Lys Val Ala
                245                 250                 255

Gly Phe Asn Leu Leu Met Thr Leu Arg Leu Trp Ser Ser
            260                 265

<210> SEQ ID NO 222
<211> LENGTH: 304
<212> TYPE: PRT
<213> ORGANISM: Artificial Sequence
<220> FEATURE:
```

```
<223> OTHER INFORMATION: Synthetic
<220> FEATURE:
<221> NAME/KEY: MISC_FEATURE
<222> LOCATION: (188)..(188)
<223> OTHER INFORMATION: X is Ser or Cys

<400> SEQUENCE: 222

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
            85                  90                  95

Leu Glu Ser Ala Ser Thr Asn Gln Thr Ser Met Tyr Leu Cys Ala Ser
            100                 105                 110

Arg Val Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
    130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
            165                 170                 175

Trp Val Asn Gly Lys Glu Val His Ser Gly Val Xaa Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
            245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
    290                 295                 300

<210> SEQ ID NO 223
<211> LENGTH: 247
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (158)..(158)
<223> OTHER INFORMATION: X is Thr or Cys
<220> FEATURE:
<221> NAME/KEY: MISC_FEATURE
<222> LOCATION: (222)..(222)
```

```
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (224)..(224)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (225)..(225)
<223> OTHER INFORMATION: X is Gly, Ala, Val, Leu, Ile, Pro, Phe, Met, or
      Trp

<400> SEQUENCE: 223

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
            20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
    50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro Asn Ile
            100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Lys Xaa Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Xaa Val Xaa
    210                 215                 220

Xaa Leu Arg Ile Leu Leu Leu Lys Val Ala Gly Phe Asn Leu Leu Met
225                 230                 235                 240

Thr Leu Arg Leu Trp Ser Ser
                245

<210> SEQ ID NO 224
<211> LENGTH: 285
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (169)..(169)
<223> OTHER INFORMATION: X is Ser or Cys

<400> SEQUENCE: 224

Asp Val Lys Val Thr Gln Ser Ser Arg Tyr Leu Val Lys Arg Thr Gly
1               5                   10                  15
```

-continued

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Val Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
            115                 120                 125

Ser Lys Ala Glu Ile Ala Asn Lys Gln Lys Ala Thr Leu Val Cys Leu
        130                 135                 140

Ala Arg Gly Phe Phe Pro Asp His Val Glu Leu Ser Trp Trp Val Asn
145                 150                 155                 160

Gly Lys Glu Val His Ser Gly Val Xaa Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
            195                 200                 205

His Gly Leu Ser Glu Glu Asp Lys Trp Pro Glu Gly Ser Pro Lys Pro
            210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 225
<211> LENGTH: 269
<212> TYPE: PRT
<213> ORGANISM: Artificial Sequence
<220> FEATURE:
<223> OTHER INFORMATION: Synthetic

<400> SEQUENCE: 225

Met Met Lys Ser Leu Arg Val Leu Leu Val Ile Leu Trp Leu Gln Leu
1                   5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
            35                  40                  45

Asn Ser Ala Phe Gln Tyr Phe Met Trp Tyr Arg Gln Tyr Ser Arg Lys
        50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

```
Phe Ile Arg Asp Ser Gln Pro Ser Asp Ser Ala Thr Tyr Leu Cys Ala
        100             105             110

Met Arg Ala Asn Thr Asp Lys Leu Ile Phe Gly Thr Gly Thr Arg Leu
        115             120             125

Gln Val Phe Pro Asn Ile Gln Asn Pro Glu Pro Ala Val Tyr Gln Leu
    130             135             140

Lys Asp Pro Arg Ser Gln Asp Ser Thr Leu Cys Leu Phe Thr Asp Phe
145             150             155             160

Asp Ser Gln Ile Asn Val Pro Lys Thr Met Glu Ser Gly Thr Phe Ile
                165             170             175

Thr Asp Lys Cys Val Leu Asp Met Lys Ala Met Asp Ser Lys Ser Asn
        180             185             190

Gly Ala Ile Ala Trp Ser Asn Gln Thr Ser Phe Thr Cys Gln Asp Ile
        195             200             205

Phe Lys Glu Thr Asn Ala Thr Tyr Pro Ser Ser Asp Val Pro Cys Asp
    210             215             220

Ala Thr Leu Thr Glu Lys Ser Phe Glu Thr Asp Met Asn Leu Asn Phe
225             230             235             240

Gln Asn Leu Leu Val Ile Val Leu Arg Ile Leu Leu Leu Lys Val Ala
                245             250             255

Gly Phe Asn Leu Leu Met Thr Leu Arg Leu Trp Ser Ser
        260             265
```

```
<210> SEQ ID NO 226
<211> LENGTH: 304
<212> TYPE: PRT
<213> ORGANISM: Artificial Sequence
<220> FEATURE:
<223> OTHER INFORMATION: Synthetic

<400> SEQUENCE: 226
```

```
Met Ala Ile Arg Leu Leu Cys Arg Val Ala Phe Cys Phe Leu Ala Val
1               5               10              15

Gly Leu Val Asp Val Lys Val Thr Gln Ser Ser Arg Tyr Leu Val Lys
        20              25              30

Arg Thr Gly Glu Lys Val Phe Leu Glu Cys Val Gln Asp Met Asp His
        35              40              45

Glu Asn Met Phe Trp Tyr Arg Gln Asp Pro Gly Leu Gly Leu Arg Leu
    50              55              60

Ile Tyr Phe Ser Tyr Asp Val Lys Met Lys Glu Lys Gly Asp Ile Pro
65              70              75              80

Glu Gly Tyr Ser Val Ser Arg Glu Lys Lys Glu Arg Phe Ser Leu Ile
                85              90              95

Leu Glu Ser Ala Ser Thr Asn Gln Thr Ser Met Tyr Leu Cys Ala Ser
        100             105             110

Arg Val Gly Asn Thr Gly Glu Leu Phe Phe Gly Glu Gly Ser Arg Leu
        115             120             125

Thr Val Leu Glu Asp Leu Arg Asn Val Thr Pro Pro Lys Val Ser Leu
    130             135             140

Phe Glu Pro Ser Lys Ala Glu Ile Ala Asn Lys Gln Lys Ala Thr Leu
145             150             155             160

Val Cys Leu Ala Arg Gly Phe Phe Pro Asp His Val Glu Leu Ser Trp
                165             170             175

Trp Val Asn Gly Lys Glu Val His Ser Gly Val Cys Thr Asp Pro Gln
        180             185             190
```

-continued

```
Ala Tyr Lys Glu Ser Asn Tyr Ser Tyr Cys Leu Ser Ser Arg Leu Arg
        195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
                275                 280                 285

Leu Val Ser Thr Leu Val Val Met Ala Met Val Lys Arg Lys Asn Ser
        290                 295                 300
```

```
<210> SEQ ID NO 227
<211> LENGTH: 247
<212> TYPE: PRT
<213> ORGANISM: Artificial Sequence
<220> FEATURE:
<223> OTHER INFORMATION: Synthetic

<400> SEQUENCE: 227

Gln Lys Glu Val Glu Gln Asp Pro Gly Pro Leu Ser Val Pro Glu Gly
1               5                   10                  15

Ala Ile Val Ser Leu Asn Cys Thr Tyr Ser Asn Ser Ala Phe Gln Tyr
                20                  25                  30

Phe Met Trp Tyr Arg Gln Tyr Ser Arg Lys Gly Pro Glu Leu Leu Met
        35                  40                  45

Tyr Thr Tyr Ser Ser Gly Asn Lys Glu Asp Gly Arg Phe Thr Ala Gln
        50                  55                  60

Val Asp Lys Ser Ser Lys Tyr Ile Ser Leu Phe Ile Arg Asp Ser Gln
65                  70                  75                  80

Pro Ser Asp Ser Ala Thr Tyr Leu Cys Ala Met Arg Ala Asn Thr Asp
                85                  90                  95

Lys Leu Ile Phe Gly Thr Gly Thr Arg Leu Gln Val Phe Pro Asn Ile
                100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
        130                 135                 140

Pro Lys Thr Met Glu Ser Gly Thr Phe Ile Thr Asp Lys Cys Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
                180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Leu Val Ile
        210                 215                 220

Val Leu Arg Ile Leu Leu Leu Lys Val Ala Gly Phe Asn Leu Leu Met
225                 230                 235                 240

Thr Leu Arg Leu Trp Ser Ser
                245
```

-continued

<210> SEQ ID NO 228
<211> LENGTH: 285
<212> TYPE: PRT
<213> ORGANISM: Artificial Sequence
<220> FEATURE:
<223> OTHER INFORMATION: Synthetic

<400> SEQUENCE: 228

```
Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Arg Val Gly
                85                  90                  95

Asn Thr Gly Glu Leu Phe Phe Gly Glu Gly Ser Arg Leu Thr Val Leu
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Cys Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285
```

<210> SEQ ID NO 229
<211> LENGTH: 273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (184)..(184)
<223> OTHER INFORMATION: X is Thr or Cys
<220> FEATURE:
<221> NAME/KEY: MISC_FEATURE
<222> LOCATION: (248)..(248)
<223> OTHER INFORMATION: X is Ser, Ala, Val, Leu, Ile, Pro, Phe, Met, or -continued

```
    Trp
<220> FEATURE:
<221> NAME/KEY: MISC_FEATURE
<222> LOCATION: (250)..(250)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (251)..(251)
<223> OTHER INFORMATION: X is Gly, Ala, Val, Leu, Ile, Pro, Phe, Met, or
    Trp

<400> SEQUENCE: 229

Met Ser Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
                85                  90                  95

Leu Val Ile Ser Ala Ser Gln Leu Gly Asp Ser Ala Met Tyr Phe Cys
            100                 105                 110

Ala Met Arg Glu Arg Thr Gly Thr Ala Ser Lys Leu Thr Phe Gly Thr
            115                 120                 125

Gly Thr Arg Leu Gln Val Thr Leu Asn Ile Gln Asn Pro Glu Pro Ala
130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
            165                 170                 175

Gly Thr Phe Ile Thr Asp Lys Xaa Val Leu Asp Met Lys Ala Met Asp
            180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Xaa Val Xaa Xaa Leu Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 230
<211> LENGTH: 305
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (189)..(189)
<223> OTHER INFORMATION: X is Ser or Cys

<400> SEQUENCE: 230
```

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Pro Gly Thr Glu Asn Ser Pro Leu His Phe Gly Asn Gly Thr Arg
            115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
            165                 170                 175

Trp Trp Val Asn Gly Lys Glu Val His Ser Gly Val Xaa Thr Asp Pro
            180                 185                 190

Gln Ala Tyr Lys Glu Ser Asn Tyr Ser Tyr Cys Leu Ser Ser Arg Leu
            195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
            245                 250                 255

Ala Asp Cys Gly Ile Thr Ser Ala Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Thr Leu Val Val Met Ala Met Val Lys Arg Lys Asn
    290                 295                 300

Ser
305
```

```
<210> SEQ ID NO 231
<211> LENGTH: 252
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (163)..(163)
<223> OTHER INFORMATION: X is Thr or Cys
<220> FEATURE:
<221> NAME/KEY: MISC_FEATURE
<222> LOCATION: (227)..(227)
<223> OTHER INFORMATION: X is Ser, Ala, Val, Leu, Ile, Pro, Phe, Met, or
      Trp
<220> FEATURE:
<221> NAME/KEY: MISC_FEATURE
```

```
<222> LOCATION: (229)..(229)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (230)..(230)
<223> OTHER INFORMATION: X is Gly, Ala, Val, Leu, Ile, Pro, Phe, Met, or
     Trp

<400> SEQUENCE: 231

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
        50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Thr Gly Thr Ala Ser Lys Leu Thr Phe Gly Thr Gly Thr Arg Leu Gln
                100                 105                 110

Val Thr Leu Asn Ile Gln Asn Pro Glu Pro Ala Val Tyr Gln Leu Lys
            115                 120                 125

Asp Pro Arg Ser Gln Asp Ser Thr Leu Cys Leu Phe Thr Asp Phe Asp
        130                 135                 140

Ser Gln Ile Asn Val Pro Lys Thr Met Glu Ser Gly Thr Phe Ile Thr
145                 150                 155                 160

Asp Lys Xaa Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
                180                 185                 190

Lys Glu Thr Asn Ala Thr Tyr Pro Ser Ser Asp Val Pro Cys Asp Ala
            195                 200                 205

Thr Leu Thr Glu Lys Ser Phe Glu Thr Asp Met Asn Leu Asn Phe Gln
        210                 215                 220

Asn Leu Xaa Val Xaa Xaa Leu Arg Ile Leu Leu Leu Lys Val Ala Gly
225                 230                 235                 240

Phe Asn Leu Leu Met Thr Leu Arg Leu Trp Ser Ser
                245                 250

<210> SEQ ID NO 232
<211> LENGTH: 286
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (170)..(170)
<223> OTHER INFORMATION: X is Ser or Cys

<400> SEQUENCE: 232

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
```

-continued

```
                35                    40                    45
Ser Tyr Asp Val Lys Met Lys Glu Lys Gly Asp Ile Pro Glu Gly Tyr
    50                    55                    60

Ser Val Ser Arg Glu Lys Lys Glu Arg Phe Ser Leu Ile Leu Glu Ser
65                    70                    75                    80

Ala Ser Thr Asn Gln Thr Ser Met Tyr Leu Cys Ala Ser Ser Pro Gly
                85                    90                    95

Thr Glu Asn Ser Pro Leu His Phe Gly Asn Gly Thr Arg Leu Thr Val
                100                   105                   110

Thr Glu Asp Leu Arg Asn Val Thr Pro Pro Lys Val Ser Leu Phe Glu
                115                   120                   125

Pro Ser Lys Ala Glu Ile Ala Asn Lys Gln Lys Ala Thr Leu Val Cys
    130                   135                   140

Leu Ala Arg Gly Phe Phe Pro Asp His Val Glu Leu Ser Trp Trp Val
145                   150                   155                   160

Asn Gly Lys Glu Val His Ser Gly Val Xaa Thr Asp Pro Gln Ala Tyr
                165                   170                   175

Lys Glu Ser Asn Tyr Ser Tyr Cys Leu Ser Ser Arg Leu Arg Val Ser
                180                   185                   190

Ala Thr Phe Trp His Asn Pro Arg Asn His Phe Arg Cys Gln Val Gln
                195                   200                   205

Phe His Gly Leu Ser Glu Glu Asp Lys Trp Pro Glu Gly Ser Pro Lys
    210                   215                   220

Pro Val Thr Gln Asn Ile Ser Ala Glu Ala Trp Gly Arg Ala Asp Cys
225                   230                   235                   240

Gly Ile Thr Ser Ala Ser Tyr Gln Gln Gly Val Leu Ser Ala Thr Ile
                245                   250                   255

Leu Tyr Glu Ile Leu Leu Gly Lys Ala Thr Leu Tyr Ala Val Leu Val
                260                   265                   270

Ser Thr Leu Val Val Met Ala Met Val Lys Arg Lys Asn Ser
                275                   280                   285

<210> SEQ ID NO 233
<211> LENGTH: 273
<212> TYPE: PRT
<213> ORGANISM: Artificial Sequence
<220> FEATURE:
<223> OTHER INFORMATION: Synthetic

<400> SEQUENCE: 233

Met Ser Leu Ser Ser Leu Leu Lys Val Val Thr Ala Ser Leu Trp Leu
1                   5                     10                    15

Gly Pro Gly Ile Ala Gln Lys Ile Thr Gln Thr Gln Pro Gly Met Phe
                20                    25                    30

Val Gln Glu Lys Glu Ala Val Thr Leu Asp Cys Thr Tyr Asp Thr Ser
                35                    40                    45

Asp Pro Ser Tyr Gly Leu Phe Trp Tyr Lys Gln Pro Ser Ser Gly Glu
    50                    55                    60

Met Ile Phe Leu Ile Tyr Gln Gly Ser Tyr Asp Gln Gln Asn Ala Thr
65                    70                    75                    80

Glu Gly Arg Tyr Ser Leu Asn Phe Gln Lys Ala Arg Lys Ser Ala Asn
                85                    90                    95

Leu Val Ile Ser Ala Ser Gln Leu Gly Asp Ser Ala Met Tyr Phe Cys
                100                   105                   110

Ala Met Arg Glu Arg Thr Gly Thr Ala Ser Lys Leu Thr Phe Gly Thr
```

-continued

```
              115                 120                 125

Gly Thr Arg Leu Gln Val Thr Leu Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
                180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
                260                 265                 270

Ser
```

```
<210> SEQ ID NO 234
<211> LENGTH: 305
<212> TYPE: PRT
<213> ORGANISM: Artificial Sequence
<220> FEATURE:
<223> OTHER INFORMATION: Synthetic

<400> SEQUENCE: 234

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Pro Gly Thr Glu Asn Ser Pro Leu His Phe Gly Asn Gly Thr Arg
            115                 120                 125

Leu Thr Val Thr Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Ala Tyr Lys Glu Ser Asn Tyr Ser Tyr Cys Leu Ser Ser Arg Leu
            195                 200                 205
```

-continued

```
Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
            275                 280                 285

Val Leu Val Ser Thr Leu Val Val Met Ala Met Val Lys Arg Lys Asn
    290                 295                 300

Ser
305

<210> SEQ ID NO 235
<211> LENGTH: 252
<212> TYPE: PRT
<213> ORGANISM: Artificial Sequence
<220> FEATURE:
<223> OTHER INFORMATION: Synthetic

<400> SEQUENCE: 235

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Thr Gly Thr Ala Ser Lys Leu Thr Phe Gly Thr Gly Thr Arg Leu Gln
                100                 105                 110

Val Thr Leu Asn Ile Gln Asn Pro Glu Pro Ala Val Tyr Gln Leu Lys
            115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160

Asp Lys Cys Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
            195                 200                 205

Thr Leu Thr Glu Lys Ser Phe Glu Thr Asp Met Asn Leu Asn Phe Gln
    210                 215                 220

Asn Leu Leu Val Ile Val Leu Arg Ile Leu Leu Leu Lys Val Ala Gly
225                 230                 235                 240

Phe Asn Leu Leu Met Thr Leu Arg Leu Trp Ser Ser
            245                 250
```

```
<210> SEQ ID NO 236
<211> LENGTH: 286
<212> TYPE: PRT
<213> ORGANISM: Artificial Sequence
<220> FEATURE:
<223> OTHER INFORMATION: Synthetic

<400> SEQUENCE: 236

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
                20                  25                  30

Phe Trp Tyr Arg Gln Asp Pro Gly Leu Gly Leu Arg Leu Ile Tyr Phe
            35                  40                  45

Ser Tyr Asp Val Lys Met Lys Glu Lys Gly Asp Ile Pro Glu Gly Tyr
        50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Pro Gly
                85                  90                  95

Thr Glu Asn Ser Pro Leu His Phe Gly Asn Gly Thr Arg Leu Thr Val
            100                 105                 110

Thr Glu Asp Leu Arg Asn Val Thr Pro Pro Lys Val Ser Leu Phe Glu
        115                 120                 125

Pro Ser Lys Ala Glu Ile Ala Asn Lys Gln Lys Ala Thr Leu Val Cys
    130                 135                 140

Leu Ala Arg Gly Phe Phe Pro Asp His Val Glu Leu Ser Trp Trp Val
145                 150                 155                 160

Asn Gly Lys Glu Val His Ser Gly Val Cys Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
        195                 200                 205

Phe His Gly Leu Ser Glu Glu Asp Lys Trp Pro Glu Gly Ser Pro Lys
    210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Thr Leu Val Val Met Ala Met Val Lys Arg Lys Asn Ser
        275                 280                 285

<210> SEQ ID NO 237
<211> LENGTH: 273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (184)..(184)
<223> OTHER INFORMATION: X is Thr or Cys
<220> FEATURE:
<221> NAME/KEY: MISC_FEATURE
<222> LOCATION: (248)..(248)
```

-continued

```
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (250)..(250)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (251)..(251)
<223> OTHER INFORMATION: X is Gly, Ala, Val, Leu, Ile, Pro, Phe, Met, or
      Trp

<400> SEQUENCE: 237

Met His Leu Ser Ser Leu Leu Lys Val Val Thr Ala Ser Leu Trp Leu
1               5                   10                  15

Gly Pro Gly Ile Ala Gln Lys Ile Thr Gln Thr Gln Pro Gly Met Phe
            20                  25                  30

Val Gln Glu Lys Glu Ala Val Thr Leu Asp Cys Thr Tyr Asp Thr Ser
        35                  40                  45

Asp Pro Ser Tyr Gly Leu Phe Trp Tyr Lys Gln Pro Ser Ser Gly Glu
    50                  55                  60

Met Ile Phe Leu Ile Tyr Gln Gly Ser Tyr Asp Gln Gln Asn Ala Thr
65                  70                  75                  80

Glu Gly Arg Tyr Ser Leu Asn Phe Gln Lys Ala Arg Lys Ser Ala Asn
            85                  90                  95

Leu Val Ile Ser Ala Ser Gln Leu Gly Asp Ser Ala Met Tyr Phe Cys
            100                 105                 110

Ala Met Arg Glu Arg Ser Gly Gly Ser Tyr Ile Pro Thr Phe Gly Arg
            115                 120                 125

Gly Thr Ser Leu Ile Val His Pro Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
            165                 170                 175

Gly Thr Phe Ile Thr Asp Lys Xaa Val Leu Asp Met Lys Ala Met Asp
            180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Xaa Val Xaa Xaa Leu Arg Ile Leu Leu
            245                 250                 255

Leu Lys Val Ala Gly Phe Asn Leu Leu Met Thr Leu Arg Leu Trp Ser
            260                 265                 270

Ser

<210> SEQ ID NO 238
<211> LENGTH: 305
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (189)..(189)
<223> OTHER INFORMATION: X is Ser or Cys
```

-continued

```
<400> SEQUENCE: 238

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
                100                 105                 110

Ser Leu Gly Thr Phe Asn Gln Pro Gln His Phe Gly Asp Gly Thr Arg
                115                 120                 125

Leu Ser Ile Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Xaa Thr Asp Pro
                180                 185                 190

Gln Ala Tyr Lys Glu Ser Asn Tyr Ser Tyr Cys Leu Ser Ser Arg Leu
                195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Thr Leu Val Val Met Ala Met Val Lys Arg Lys Asn
    290                 295                 300

Ser
305

<210> SEQ ID NO 239
<211> LENGTH: 252
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (163)..(163)
<223> OTHER INFORMATION: X is Thr or Cys
<220> FEATURE:
<221> NAME/KEY: MISC_FEATURE
<222> LOCATION: (227)..(227)
<223> OTHER INFORMATION: X is Ser, Ala, Val, Leu, Ile, Pro, Phe, Met, or
      Trp
<220> FEATURE:
```

<221> NAME/KEY: MISC_FEATURE
<222> LOCATION: (229)..(229)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (230)..(230)
<223> OTHER INFORMATION: X is Gly, Ala, Val, Leu, Ile, Pro, Phe, Met, or
     Trp

<400> SEQUENCE: 239

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Gly Ser Tyr Ile Pro Thr Phe Gly Arg Gly Thr Ser Leu Ile
                100                 105                 110

Val His Pro Asn Ile Gln Asn Pro Glu Pro Ala Val Tyr Gln Leu Lys
            115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160

Asp Lys Xaa Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
            195                 200                 205

Thr Leu Thr Glu Lys Ser Phe Glu Thr Asp Met Asn Leu Asn Phe Gln
    210                 215                 220

Asn Leu Xaa Val Xaa Xaa Leu Arg Ile Leu Leu Leu Lys Val Ala Gly
225                 230                 235                 240

Phe Asn Leu Leu Met Thr Leu Arg Leu Trp Ser Ser
            245                 250

<210> SEQ ID NO 240
<211> LENGTH: 286
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (170)..(170)
<223> OTHER INFORMATION: X is Ser or Cys

<400> SEQUENCE: 240

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

-continued

```
Phe Trp Tyr Arg Gln Asp Pro Gly Leu Gly Leu Arg Leu Ile Tyr Phe
        35              40              45

Ser Tyr Asp Val Lys Met Lys Glu Lys Gly Asp Ile Pro Glu Gly Tyr
    50              55              60

Ser Val Ser Arg Glu Lys Lys Glu Arg Phe Ser Leu Ile Leu Glu Ser
65              70              75              80

Ala Ser Thr Asn Gln Thr Ser Met Tyr Leu Cys Ala Ser Ser Leu Gly
            85              90              95

Thr Phe Asn Gln Pro Gln His Phe Gly Asp Gly Thr Arg Leu Ser Ile
            100             105             110

Leu Glu Asp Leu Arg Asn Val Thr Pro Pro Lys Val Ser Leu Phe Glu
            115             120             125

Pro Ser Lys Ala Glu Ile Ala Asn Lys Gln Lys Ala Thr Leu Val Cys
        130             135             140

Leu Ala Arg Gly Phe Phe Pro Asp His Val Glu Leu Ser Trp Trp Val
145             150             155             160

Asn Gly Lys Glu Val His Ser Gly Val Xaa Thr Asp Pro Gln Ala Tyr
            165             170             175

Lys Glu Ser Asn Tyr Ser Tyr Cys Leu Ser Ser Arg Leu Arg Val Ser
            180             185             190

Ala Thr Phe Trp His Asn Pro Arg Asn His Phe Arg Cys Gln Val Gln
            195             200             205

Phe His Gly Leu Ser Glu Glu Asp Lys Trp Pro Glu Gly Ser Pro Lys
        210             215             220

Pro Val Thr Gln Asn Ile Ser Ala Glu Ala Trp Gly Arg Ala Asp Cys
225             230             235             240

Gly Ile Thr Ser Ala Ser Tyr Gln Gln Gly Val Leu Ser Ala Thr Ile
            245             250             255

Leu Tyr Glu Ile Leu Leu Gly Lys Ala Thr Leu Tyr Ala Val Leu Val
            260             265             270

Ser Thr Leu Val Val Met Ala Met Val Lys Arg Lys Asn Ser
        275             280             285
```

```
<210> SEQ ID NO 241
<211> LENGTH: 273
<212> TYPE: PRT
<213> ORGANISM: Artificial Sequence
<220> FEATURE:
<223> OTHER INFORMATION: Synthetic

<400> SEQUENCE: 241

Met His Leu Ser Ser Leu Leu Lys Val Val Thr Ala Ser Leu Trp Leu
1               5               10              15

Gly Pro Gly Ile Ala Gln Lys Ile Thr Gln Thr Gln Pro Gly Met Phe
            20              25              30

Val Gln Glu Lys Glu Ala Val Thr Leu Asp Cys Thr Tyr Asp Thr Ser
        35              40              45

Asp Pro Ser Tyr Gly Leu Phe Trp Tyr Lys Gln Pro Ser Ser Gly Glu
    50              55              60

Met Ile Phe Leu Ile Tyr Gln Gly Ser Tyr Asp Gln Gln Asn Ala Thr
65              70              75              80

Glu Gly Arg Tyr Ser Leu Asn Phe Gln Lys Ala Arg Lys Ser Ala Asn
            85              90              95

Leu Val Ile Ser Ala Ser Gln Leu Gly Asp Ser Ala Met Tyr Phe Cys
            100             105             110
```

```
Ala Met Arg Glu Arg Ser Gly Gly Ser Tyr Ile Pro Thr Phe Gly Arg
        115                 120                 125

Gly Thr Ser Leu Ile Val His Pro Asn Ile Gln Asn Pro Glu Pro Ala
        130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Cys Val Leu Asp Met Lys Ala Met Asp
                180                 185                 190

Ser Lys Ser Asn Gly Ala Ile Ala Trp Ser Asn Gln Thr Ser Phe Thr
        195                 200                 205

Cys Gln Asp Ile Phe Lys Glu Thr Asn Ala Thr Tyr Pro Ser Ser Asp
        210                 215                 220

Val Pro Cys Asp Ala Thr Leu Thr Glu Lys Ser Phe Glu Thr Asp Met
225                 230                 235                 240

Asn Leu Asn Phe Gln Asn Leu Leu Val Ile Val Leu Arg Ile Leu Leu
                245                 250                 255

Leu Lys Val Ala Gly Phe Asn Leu Leu Met Thr Leu Arg Leu Trp Ser
                260                 265                 270

Ser
```

```
<210> SEQ ID NO 242
<211> LENGTH: 305
<212> TYPE: PRT
<213> ORGANISM: Artificial Sequence
<220> FEATURE:
<223> OTHER INFORMATION: Synthetic

<400> SEQUENCE: 242
```

```
Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
        100                 105                 110

Ser Leu Gly Thr Phe Asn Gln Pro Gln His Phe Gly Asp Gly Thr Arg
        115                 120                 125

Leu Ser Ile Leu Glu Asp Leu Arg Asn Val Thr Pro Pro Lys Val Ser
        130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Cys Thr Asp Pro
                180                 185                 190

Gln Ala Tyr Lys Glu Ser Asn Tyr Ser Tyr Cys Leu Ser Ser Arg Leu
```

-continued

```
            195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr Gln Gln Gly Val Leu Ser
                260                 265                 270

Ala Thr Ile Leu Tyr Glu Ile Leu Leu Gly Lys Ala Thr Leu Tyr Ala
                275                 280                 285

Val Leu Val Ser Thr Leu Val Val Met Ala Met Val Lys Arg Lys Asn
    290                 295                 300

Ser
305

<210> SEQ ID NO 243
<211> LENGTH: 252
<212> TYPE: PRT
<213> ORGANISM: Artificial Sequence
<220> FEATURE:
<223> OTHER INFORMATION: Synthetic

<400> SEQUENCE: 243

Gln Lys Ile Thr Gln Thr Gln Pro Gly Met Phe Val Gln Glu Lys Glu
1               5                   10                  15

Ala Val Thr Leu Asp Cys Thr Tyr Asp Thr Ser Asp Pro Ser Tyr Gly
                20                  25                  30

Leu Phe Trp Tyr Lys Gln Pro Ser Ser Gly Glu Met Ile Phe Leu Ile
            35                  40                  45

Tyr Gln Gly Ser Tyr Asp Gln Gln Asn Ala Thr Glu Gly Arg Tyr Ser
    50                  55                  60

Leu Asn Phe Gln Lys Ala Arg Lys Ser Ala Asn Leu Val Ile Ser Ala
65                  70                  75                  80

Ser Gln Leu Gly Asp Ser Ala Met Tyr Phe Cys Ala Met Arg Glu Arg
                85                  90                  95

Ser Gly Gly Ser Tyr Ile Pro Thr Phe Gly Arg Gly Thr Ser Leu Ile
            100                 105                 110

Val His Pro Asn Ile Gln Asn Pro Glu Pro Ala Val Tyr Gln Leu Lys
        115                 120                 125

Asp Pro Arg Ser Gln Asp Ser Thr Leu Cys Leu Phe Thr Asp Phe Asp
    130                 135                 140

Ser Gln Ile Asn Val Pro Lys Thr Met Glu Ser Gly Thr Phe Ile Thr
145                 150                 155                 160

Asp Lys Cys Val Leu Asp Met Lys Ala Met Asp Ser Lys Ser Asn Gly
                165                 170                 175

Ala Ile Ala Trp Ser Asn Gln Thr Ser Phe Thr Cys Gln Asp Ile Phe
            180                 185                 190

Lys Glu Thr Asn Ala Thr Tyr Pro Ser Ser Asp Val Pro Cys Asp Ala
        195                 200                 205

Thr Leu Thr Glu Lys Ser Phe Glu Thr Asp Met Asn Leu Asn Phe Gln
    210                 215                 220

Asn Leu Leu Val Ile Val Leu Arg Ile Leu Leu Leu Lys Val Ala Gly
225                 230                 235                 240

Phe Asn Leu Leu Met Thr Leu Arg Leu Trp Ser Ser
```

-continued

```
                245                 250

<210> SEQ ID NO 244
<211> LENGTH: 286
<212> TYPE: PRT
<213> ORGANISM: Artificial Sequence
<220> FEATURE:
<223> OTHER INFORMATION: Synthetic

<400> SEQUENCE: 244

Asp Val Lys Val Thr Gln Ser Ser Arg Tyr Leu Val Lys Arg Thr Gly
1               5                   10                  15

Glu Lys Val Phe Leu Glu Cys Val Gln Asp Met Asp His Glu Asn Met
            20                  25                  30

Phe Trp Tyr Arg Gln Asp Pro Gly Leu Gly Leu Arg Leu Ile Tyr Phe
        35                  40                  45

Ser Tyr Asp Val Lys Met Lys Glu Lys Gly Asp Ile Pro Glu Gly Tyr
    50                  55                  60

Ser Val Ser Arg Glu Lys Lys Glu Arg Phe Ser Leu Ile Leu Glu Ser
65                  70                  75                  80

Ala Ser Thr Asn Gln Thr Ser Met Tyr Leu Cys Ala Ser Ser Leu Gly
                85                  90                  95

Thr Phe Asn Gln Pro Gln His Phe Gly Asp Gly Thr Arg Leu Ser Ile
            100                 105                 110

Leu Glu Asp Leu Arg Asn Val Thr Pro Pro Lys Val Ser Leu Phe Glu
            115                 120                 125

Pro Ser Lys Ala Glu Ile Ala Asn Lys Gln Lys Ala Thr Leu Val Cys
    130                 135                 140

Leu Ala Arg Gly Phe Phe Pro Asp His Val Glu Leu Ser Trp Trp Val
145                 150                 155                 160

Asn Gly Lys Glu Val His Ser Gly Val Cys Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
            195                 200                 205

Phe His Gly Leu Ser Glu Glu Asp Lys Trp Pro Glu Gly Ser Pro Lys
    210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Thr Leu Val Val Met Ala Met Val Lys Arg Lys Asn Ser
        275                 280                 285

<210> SEQ ID NO 245
<211> LENGTH: 596
<212> TYPE: PRT
<213> ORGANISM: Artificial Sequence
<220> FEATURE:
<223> OTHER INFORMATION: Synthetic

<400> SEQUENCE: 245

Met Ala Ile Arg Leu Leu Cys Arg Val Ala Phe Cys Phe Leu Ala Val
1               5                   10                  15
```

-continued

```
Gly Leu Val Asp Val Lys Val Thr Gln Ser Ser Arg Tyr Leu Val Lys
         20                  25                  30

Arg Thr Gly Glu Lys Val Phe Leu Glu Cys Val Gln Asp Met Asp His
         35                  40                  45

Glu Asn Met Phe Trp Tyr Arg Gln Asp Pro Gly Leu Gly Leu Arg Leu
         50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                 85                  90                  95

Leu Glu Ser Ala Ser Thr Asn Gln Thr Ser Met Tyr Leu Cys Ala Ser
             100                 105                 110

Arg Gln Gly Asn Thr Gly Glu Leu Phe Phe Gly Glu Gly Ser Arg Leu
             115                 120                 125

Thr Val Leu Glu Asp Leu Arg Asn Val Thr Pro Pro Lys Val Ser Leu
         130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                 165                 170                 175

Trp Val Asn Gly Lys Glu Val His Ser Gly Val Cys Thr Asp Pro Gln
             180                 185                 190

Ala Tyr Lys Glu Ser Asn Tyr Ser Tyr Cys Leu Ser Ser Arg Leu Arg
             195                 200                 205

Val Ser Ala Thr Phe Trp His Asn Pro Arg Asn His Phe Arg Cys Gln
         210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                 245                 250                 255

Asp Cys Gly Ile Thr Ser Ala Ser Tyr Gln Gln Gly Val Leu Ser Ala
             260                 265                 270

Thr Ile Leu Tyr Glu Ile Leu Leu Gly Lys Ala Thr Leu Tyr Ala Val
         275                 280                 285

Leu Val Ser Thr Leu Val Val Met Ala Met Val Lys Arg Lys Asn Ser
         290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Lys Leu Val Thr
                 325                 330                 335

Ser Ile Thr Val Leu Leu Ser Leu Gly Ile Met Gly Asp Ala Lys Thr
             340                 345                 350

Thr Gln Pro Asn Ser Met Glu Ser Asn Glu Glu Glu Pro Val His Leu
         355                 360                 365

Pro Cys Asn His Ser Thr Ile Ser Gly Thr Asp Tyr Ile His Trp Tyr
         370                 375                 380

Arg Gln Leu Pro Ser Gln Gly Pro Glu Tyr Val Ile His Gly Leu Thr
385                 390                 395                 400

Ser Asn Val Asn Asn Arg Met Ala Ser Leu Ala Ile Ala Glu Asp Arg
                 405                 410                 415

Lys Ser Ser Thr Leu Ile Leu His Arg Ala Thr Leu Arg Asp Ala Ala
             420                 425                 430

Val Tyr Tyr Cys Ile Leu Arg Ala Pro Ser Gly Thr Tyr Lys Tyr Ile
```

-continued

```
              435                440                445
Phe Gly Thr Gly Thr Arg Leu Lys Val Leu Ala Asn Ile Gln Asn Pro
    450                455                460

Glu Pro Ala Val Tyr Gln Leu Lys Asp Pro Arg Ser Gln Asp Ser Thr
465                470                475                480

Leu Cys Leu Phe Thr Asp Phe Asp Ser Gln Ile Asn Val Pro Lys Thr
                485                490                495

Met Glu Ser Gly Thr Phe Ile Thr Asp Lys Cys Val Leu Asp Met Lys
                500                505                510

Ala Met Asp Ser Lys Ser Asn Gly Ala Ile Ala Trp Ser Asn Gln Thr
                515                520                525

Ser Phe Thr Cys Gln Asp Ile Phe Lys Glu Thr Asn Ala Thr Tyr Pro
    530                535                540

Ser Ser Asp Val Pro Cys Asp Ala Thr Leu Thr Glu Lys Ser Phe Glu
545                550                555                560

Thr Asp Met Asn Leu Asn Phe Gln Asn Leu Leu Val Ile Val Leu Arg
                565                570                575

Ile Leu Leu Leu Lys Val Ala Gly Phe Asn Leu Leu Met Thr Leu Arg
                580                585                590

Leu Trp Ser Ser
        595
```

<210> SEQ ID NO 246
<211> LENGTH: 601
<212> TYPE: PRT
<213> ORGANISM: Artificial Sequence
<220> FEATURE:
<223> OTHER INFORMATION: Synthetic

<400> SEQUENCE: 246

```
Met Ala Ile Arg Leu Leu Cys Arg Val Ala Phe Cys Phe Leu Ala Val
1               5                10                15

Gly Leu Val Asp Val Lys Val Thr Gln Ser Ser Arg Tyr Leu Val Lys
            20                25                30

Arg Thr Gly Glu Lys Val Phe Leu Glu Cys Val Gln Asp Met Asp His
        35                40                45

Glu Asn Met Phe Trp Tyr Arg Gln Asp Pro Gly Leu Gly Leu Arg Leu
    50                55                60

Ile Tyr Phe Ser Tyr Asp Val Lys Met Lys Glu Lys Gly Asp Ile Pro
65                70                75                80

Glu Gly Tyr Ser Val Ser Arg Glu Lys Lys Glu Arg Phe Ser Leu Ile
                85                90                95

Leu Glu Ser Ala Ser Thr Asn Gln Thr Ser Met Tyr Leu Cys Ala Ser
                100                105                110

Ser Gln Gly Asn Thr Gly Glu Leu Phe Phe Gly Glu Gly Ser Arg Leu
                115                120                125

Thr Val Leu Glu Asp Leu Arg Asn Val Thr Pro Pro Lys Val Ser Leu
    130                135                140

Phe Glu Pro Ser Lys Ala Glu Ile Ala Asn Lys Gln Lys Ala Thr Leu
145                150                155                160

Val Cys Leu Ala Arg Gly Phe Phe Pro Asp His Val Glu Leu Ser Trp
                165                170                175

Trp Val Asn Gly Lys Glu Val His Ser Gly Val Cys Thr Asp Pro Gln
                180                185                190

Ala Tyr Lys Glu Ser Asn Tyr Ser Tyr Cys Leu Ser Ser Arg Leu Arg
```

-continued

```
               195                 200                 205

Val Ser Ala Thr Phe Trp His Asn Pro Arg Asn His Phe Arg Cys Gln
    210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
    290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Asn Tyr Ser Pro
                325                 330                 335

Gly Leu Val Ser Leu Ile Leu Leu Leu Gly Arg Thr Arg Gly Asn
                340                 345                 350

Ser Val Thr Gln Met Glu Gly Pro Val Thr Leu Ser Glu Glu Ala Phe
            355                 360                 365

Leu Thr Ile Asn Cys Thr Tyr Thr Ala Thr Gly Tyr Pro Ser Leu Phe
    370                 375                 380

Trp Tyr Val Gln Tyr Pro Gly Glu Gly Leu Gln Leu Leu Leu Lys Ala
385                 390                 395                 400

Thr Lys Ala Asp Asp Lys Gly Ser Asn Lys Gly Phe Glu Ala Thr Tyr
                405                 410                 415

Arg Lys Glu Thr Thr Ser Phe His Leu Glu Lys Gly Ser Val Gln Val
                420                 425                 430

Ser Asp Ser Ala Val Tyr Phe Cys Ala Leu Arg Leu Ser Gly Ala Gly
            435                 440                 445

Ser Tyr Gln Leu Thr Phe Gly Lys Gly Thr Lys Leu Ser Val Ile Pro
    450                 455                 460

Asn Ile Gln Asn Pro Glu Pro Ala Val Tyr Gln Leu Lys Asp Pro Arg
465                 470                 475                 480

Ser Gln Asp Ser Thr Leu Cys Leu Phe Thr Asp Phe Asp Ser Gln Ile
                485                 490                 495

Asn Val Pro Lys Thr Met Glu Ser Gly Thr Phe Ile Thr Asp Lys Cys
                500                 505                 510

Val Leu Asp Met Lys Ala Met Asp Ser Lys Ser Asn Gly Ala Ile Ala
            515                 520                 525

Trp Ser Asn Gln Thr Ser Phe Thr Cys Gln Asp Ile Phe Lys Glu Thr
    530                 535                 540

Asn Ala Thr Tyr Pro Ser Ser Asp Val Pro Cys Asp Ala Thr Leu Thr
545                 550                 555                 560

Glu Lys Ser Phe Glu Thr Asp Met Asn Leu Asn Phe Gln Asn Leu Leu
                565                 570                 575

Val Ile Val Leu Arg Ile Leu Leu Leu Lys Val Ala Gly Phe Asn Leu
                580                 585                 590

Leu Met Thr Leu Arg Leu Trp Ser Ser
            595                 600
```

<210> SEQ ID NO 247

```
<211> LENGTH: 606
<212> TYPE: PRT
<213> ORGANISM: Artificial Sequence
<220> FEATURE:
<223> OTHER INFORMATION: Synthetic

<400> SEQUENCE: 247

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Gly Val Gly Ser Asn Tyr Gly Tyr Thr Phe Gly Ser Gly Thr
            115                 120                 125

Arg Leu Thr Val Val Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
        290                 295                 300

Asn Ser Arg Ala Lys Arg Ser Gly Ser Gly Ala Thr Asn Phe Ser Leu
305                 310                 315                 320

Leu Lys Gln Ala Gly Asp Val Glu Glu Asn Pro Gly Pro Met Ser Leu
            325                 330                 335

Ser Ser Leu Leu Lys Val Val Thr Ala Ser Leu Trp Leu Gly Pro Gly
            340                 345                 350

Ile Ala Gln Lys Ile Thr Gln Thr Gln Pro Gly Met Phe Val Gln Glu
            355                 360                 365

Lys Glu Ala Val Thr Leu Asp Cys Thr Tyr Asp Thr Ser Asp Pro Ser
370                 375                 380
```

```
Tyr Gly Leu Phe Trp Tyr Lys Gln Pro Ser Ser Gly Glu Met Ile Phe
385                 390                 395                 400

Leu Ile Tyr Gln Gly Ser Tyr Asp Gln Gln Asn Ala Thr Glu Gly Arg
                405                 410                 415

Tyr Ser Leu Asn Phe Gln Lys Ala Arg Lys Ser Ala Asn Leu Val Ile
            420                 425                 430

Ser Ala Ser Gln Leu Gly Asp Ser Ala Met Tyr Phe Cys Ala Met Arg
            435                 440                 445

Glu Arg Ser Gly Thr Ala Ser Lys Leu Thr Phe Gly Thr Gly Thr Arg
        450                 455                 460

Leu Gln Val Thr Leu Asn Ile Gln Asn Pro Glu Pro Ala Val Tyr Gln
465                 470                 475                 480

Leu Lys Asp Pro Arg Ser Gln Asp Ser Thr Leu Cys Leu Phe Thr Asp
                485                 490                 495

Phe Asp Ser Gln Ile Asn Val Pro Lys Thr Met Glu Ser Gly Thr Phe
            500                 505                 510

Ile Thr Asp Lys Cys Val Leu Asp Met Lys Ala Met Asp Ser Lys Ser
            515                 520                 525

Asn Gly Ala Ile Ala Trp Ser Asn Gln Thr Ser Phe Thr Cys Gln Asp
        530                 535                 540

Ile Phe Lys Glu Thr Asn Ala Thr Tyr Pro Ser Ser Asp Val Pro Cys
545                 550                 555                 560

Asp Ala Thr Leu Thr Glu Lys Ser Phe Glu Thr Asp Met Asn Leu Asn
                565                 570                 575

Phe Gln Asn Leu Leu Val Ile Val Leu Arg Ile Leu Leu Leu Lys Val
                580                 585                 590

Ala Gly Phe Asn Leu Leu Met Thr Leu Arg Leu Trp Ser Ser
            595                 600                 605

<210> SEQ ID NO 248
<211> LENGTH: 603
<212> TYPE: PRT
<213> ORGANISM: Artificial Sequence
<220> FEATURE:
<223> OTHER INFORMATION: Synthetic

<400> SEQUENCE: 248

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
                20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Thr Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
        130                 135                 140
```

```
Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
                180                 185                 190

Ala Tyr Lys Glu Ser Asn Tyr Ser Tyr Cys Leu Ser Ser Arg Leu Arg
                195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
                260                 265                 270

Thr Ile Leu Tyr Glu Ile Leu Leu Gly Lys Ala Thr Leu Tyr Ala Val
        275                 280                 285

Leu Val Ser Thr Leu Val Val Met Ala Met Val Lys Arg Lys Asn Ser
        290                 295                 300

Arg Ala Lys Arg Ser Gly Ser Gly Ala Thr Asn Phe Ser Leu Leu Lys
305                 310                 315                 320

Gln Ala Gly Asp Val Glu Glu Asn Pro Gly Pro Met Met Lys Ser Leu
                325                 330                 335

Arg Val Leu Leu Val Ile Leu Trp Leu Gln Leu Ser Trp Val Trp Ser
                340                 345                 350

Gln Gln Lys Glu Val Glu Gln Asp Pro Gly Pro Leu Ser Val Pro Glu
        355                 360                 365

Gly Ala Ile Val Ser Leu Asn Cys Thr Tyr Ser Asn Ser Ala Phe Gln
        370                 375                 380

Tyr Phe Met Trp Tyr Arg Gln Tyr Ser Arg Lys Gly Pro Glu Leu Leu
385                 390                 395                 400

Met Tyr Thr Tyr Ser Ser Gly Asn Lys Glu Asp Gly Arg Phe Thr Ala
                405                 410                 415

Gln Val Asp Lys Ser Ser Lys Tyr Ile Ser Leu Phe Ile Arg Asp Ser
                420                 425                 430

Gln Pro Ser Asp Ser Ala Thr Tyr Leu Cys Ala Met Ser Tyr Ser Gly
                435                 440                 445

Gly Gly Ala Asp Gly Leu Thr Phe Gly Lys Gly Thr His Leu Ile Ile
        450                 455                 460

Gln Pro Asn Ile Gln Asn Pro Glu Pro Ala Val Tyr Gln Leu Lys Asp
465                 470                 475                 480

Pro Arg Ser Gln Asp Ser Thr Leu Cys Leu Phe Thr Asp Phe Asp Ser
                485                 490                 495

Gln Ile Asn Val Pro Lys Thr Met Glu Ser Gly Thr Phe Ile Thr Asp
                500                 505                 510

Lys Cys Val Leu Asp Met Lys Ala Met Asp Ser Lys Ser Asn Gly Ala
                515                 520                 525

Ile Ala Trp Ser Asn Gln Thr Ser Phe Thr Cys Gln Asp Ile Phe Lys
        530                 535                 540

Glu Thr Asn Ala Thr Tyr Pro Ser Ser Asp Val Pro Cys Asp Ala Thr
545                 550                 555                 560
```

-continued

```
Leu Thr Glu Lys Ser Phe Glu Thr Asp Met Asn Leu Asn Phe Gln Asn
                565                 570                 575

Leu Leu Val Ile Val Leu Arg Ile Leu Leu Leu Lys Val Ala Gly Phe
            580                 585                 590

Asn Leu Leu Met Thr Leu Arg Leu Trp Ser Ser
        595                 600

<210> SEQ ID NO 249
<211> LENGTH: 600
<212> TYPE: PRT
<213> ORGANISM: Artificial Sequence
<220> FEATURE:
<223> OTHER INFORMATION: Synthetic

<400> SEQUENCE: 249

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Arg Val Gly Asn Thr Gly Glu Leu Phe Phe Gly Glu Gly Ser Arg Leu
            115                 120                 125

Thr Val Leu Glu Asp Leu Arg Asn Val Thr Pro Pro Lys Val Ser Leu
        130                 135                 140

Phe Glu Pro Ser Lys Ala Glu Ile Ala Asn Lys Gln Lys Ala Thr Leu
145                 150                 155                 160

Val Cys Leu Ala Arg Gly Phe Phe Pro Asp His Val Glu Leu Ser Trp
                165                 170                 175

Trp Val Asn Gly Lys Glu Val His Ser Gly Val Cys Thr Asp Pro Gln
            180                 185                 190

Ala Tyr Lys Glu Ser Asn Tyr Ser Tyr Cys Leu Ser Ser Arg Leu Arg
            195                 200                 205

Val Ser Ala Thr Phe Trp His Asn Pro Arg Asn His Phe Arg Cys Gln
        210                 215                 220

Val Gln Phe His Gly Leu Ser Glu Glu Asp Lys Trp Pro Glu Gly Ser
225                 230                 235                 240

Pro Lys Pro Val Thr Gln Asn Ile Ser Ala Glu Ala Trp Gly Arg Ala
                245                 250                 255

Asp Cys Gly Ile Thr Ser Ala Ser Tyr Gln Gln Gly Val Leu Ser Ala
            260                 265                 270

Thr Ile Leu Tyr Glu Ile Leu Leu Gly Lys Ala Thr Leu Tyr Ala Val
            275                 280                 285

Leu Val Ser Thr Leu Val Val Met Ala Met Val Lys Arg Lys Asn Ser
        290                 295                 300

Arg Ala Lys Arg Ser Gly Ser Gly Ala Thr Asn Phe Ser Leu Leu Lys
305                 310                 315                 320
```

-continued

```
Gln Ala Gly Asp Val Glu Glu Asn Pro Gly Pro Met Met Lys Ser Leu
            325                 330                 335

Arg Val Leu Leu Val Ile Leu Trp Leu Gln Leu Ser Trp Val Trp Ser
            340                 345                 350

Gln Gln Lys Glu Val Glu Gln Asp Pro Gly Pro Leu Ser Val Pro Glu
            355                 360                 365

Gly Ala Ile Val Ser Leu Asn Cys Thr Tyr Ser Asn Ser Ala Phe Gln
    370                 375                 380

Tyr Phe Met Trp Tyr Arg Gln Tyr Ser Arg Lys Gly Pro Glu Leu Leu
385                 390                 395                 400

Met Tyr Thr Tyr Ser Ser Gly Asn Lys Glu Asp Gly Arg Phe Thr Ala
                405                 410                 415

Gln Val Asp Lys Ser Ser Lys Tyr Ile Ser Leu Phe Ile Arg Asp Ser
            420                 425                 430

Gln Pro Ser Asp Ser Ala Thr Tyr Leu Cys Ala Met Arg Ala Asn Thr
            435                 440                 445

Asp Lys Leu Ile Phe Gly Thr Gly Thr Arg Leu Gln Val Phe Pro Asn
    450                 455                 460

Ile Gln Asn Pro Glu Pro Ala Val Tyr Gln Leu Lys Asp Pro Arg Ser
465                 470                 475                 480

Gln Asp Ser Thr Leu Cys Leu Phe Thr Asp Phe Asp Ser Gln Ile Asn
                485                 490                 495

Val Pro Lys Thr Met Glu Ser Gly Thr Phe Ile Thr Asp Lys Cys Val
                500                 505                 510

Leu Asp Met Lys Ala Met Asp Ser Lys Ser Asn Gly Ala Ile Ala Trp
            515                 520                 525

Ser Asn Gln Thr Ser Phe Thr Cys Gln Asp Ile Phe Lys Glu Thr Asn
    530                 535                 540

Ala Thr Tyr Pro Ser Ser Asp Val Pro Cys Asp Ala Thr Leu Thr Glu
545                 550                 555                 560

Lys Ser Phe Glu Thr Asp Met Asn Leu Asn Phe Gln Asn Leu Leu Val
                565                 570                 575

Ile Val Leu Arg Ile Leu Leu Leu Lys Val Ala Gly Phe Asn Leu Leu
            580                 585                 590

Met Thr Leu Arg Leu Trp Ser Ser
            595                 600
```

```
<210> SEQ ID NO 250
<211> LENGTH: 605
<212> TYPE: PRT
<213> ORGANISM: Artificial Sequence
<220> FEATURE:
<223> OTHER INFORMATION: Synthetic

<400> SEQUENCE: 250

Met Ala Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80
```

```
Glu Gly Tyr Ser Val Ser Arg Glu Lys Lys Glu Arg Phe Ser Leu Ile
            85              90              95

Leu Glu Ser Ala Ser Thr Asn Gln Thr Ser Met Tyr Leu Cys Ala Ser
            100             105             110

Ser Pro Gly Thr Glu Asn Ser Pro Leu His Phe Gly Asn Gly Thr Arg
            115             120             125

Leu Thr Val Thr Glu Asp Leu Arg Asn Val Thr Pro Pro Lys Val Ser
    130             135             140

Leu Phe Glu Pro Ser Lys Ala Glu Ile Ala Asn Lys Gln Lys Ala Thr
145             150             155             160

Leu Val Cys Leu Ala Arg Gly Phe Phe Pro Asp His Val Glu Leu Ser
            165             170             175

Trp Trp Val Asn Gly Lys Glu Val His Ser Gly Val Cys Thr Asp Pro
            180             185             190

Gln Ala Tyr Lys Glu Ser Asn Tyr Ser Tyr Cys Leu Ser Ser Arg Leu
            195             200             205

Arg Val Ser Ala Thr Phe Trp His Asn Pro Arg Asn His Phe Arg Cys
    210             215             220

Gln Val Gln Phe His Gly Leu Ser Glu Glu Asp Lys Trp Pro Glu Gly
225             230             235             240

Ser Pro Lys Pro Val Thr Gln Asn Ile Ser Ala Glu Ala Trp Gly Arg
            245             250             255

Ala Asp Cys Gly Ile Thr Ser Ala Ser Tyr Gln Gln Gly Val Leu Ser
            260             265             270

Ala Thr Ile Leu Tyr Glu Ile Leu Leu Gly Lys Ala Thr Leu Tyr Ala
            275             280             285

Val Leu Val Ser Thr Leu Val Val Met Ala Met Val Lys Arg Lys Asn
    290             295             300

Ser Arg Ala Lys Arg Ser Gly Ser Gly Ala Thr Asn Phe Ser Leu Leu
305             310             315             320

Lys Gln Ala Gly Asp Val Glu Glu Asn Pro Gly Pro Met Ser Leu Ser
            325             330             335

Ser Leu Leu Lys Val Val Thr Ala Ser Leu Trp Leu Gly Pro Gly Ile
            340             345             350

Ala Gln Lys Ile Thr Gln Thr Gln Pro Gly Met Phe Val Gln Glu Lys
            355             360             365

Glu Ala Val Thr Leu Asp Cys Thr Tyr Asp Thr Ser Asp Pro Ser Tyr
    370             375             380

Gly Leu Phe Trp Tyr Lys Gln Pro Ser Ser Gly Glu Met Ile Phe Leu
385             390             395             400

Ile Tyr Gln Gly Ser Tyr Asp Gln Gln Asn Ala Thr Glu Gly Arg Tyr
            405             410             415

Ser Leu Asn Phe Gln Lys Ala Arg Lys Ser Ala Asn Leu Val Ile Ser
            420             425             430

Ala Ser Gln Leu Gly Asp Ser Ala Met Tyr Phe Cys Ala Met Arg Glu
            435             440             445

Arg Thr Gly Thr Ala Ser Lys Leu Thr Phe Gly Thr Gly Thr Arg Leu
    450             455             460

Gln Val Thr Leu Asn Ile Gln Asn Pro Glu Pro Ala Val Tyr Gln Leu
465             470             475             480

Lys Asp Pro Arg Ser Gln Asp Ser Thr Leu Cys Leu Phe Thr Asp Phe
            485             490             495

Asp Ser Gln Ile Asn Val Pro Lys Thr Met Glu Ser Gly Thr Phe Ile
```

-continued

```
                500             505             510
Thr Asp Lys Cys Val Leu Asp Met Lys Ala Met Asp Ser Lys Ser Asn
        515             520             525
Gly Ala Ile Ala Trp Ser Asn Gln Thr Ser Phe Thr Cys Gln Asp Ile
    530             535             540
Phe Lys Glu Thr Asn Ala Thr Tyr Pro Ser Ser Asp Val Pro Cys Asp
545             550             555             560
Ala Thr Leu Thr Glu Lys Ser Phe Glu Thr Asp Met Asn Leu Asn Phe
            565             570             575
Gln Asn Leu Leu Val Ile Val Leu Arg Ile Leu Leu Leu Lys Val Ala
            580             585             590
Gly Phe Asn Leu Leu Met Thr Leu Arg Leu Trp Ser Ser
        595             600             605

<210> SEQ ID NO 251
<211> LENGTH: 605
<212> TYPE: PRT
<213> ORGANISM: Artificial Sequence
<220> FEATURE:
<223> OTHER INFORMATION: Synthetic

<400> SEQUENCE: 251

Met Ala Ile Arg Leu Leu Cys Arg Val Ala Phe Cys Phe Leu Ala Val
1           5               10              15
Gly Leu Val Asp Val Lys Val Thr Gln Ser Ser Arg Tyr Leu Val Lys
            20              25              30
Arg Thr Gly Glu Lys Val Phe Leu Glu Cys Val Gln Asp Met Asp His
        35              40              45
Glu Asn Met Phe Trp Tyr Arg Gln Asp Pro Gly Leu Gly Leu Arg Leu
    50              55              60
Ile Tyr Phe Ser Tyr Asp Val Lys Met Lys Glu Lys Gly Asp Ile Pro
65              70              75              80
Glu Gly Tyr Ser Val Ser Arg Glu Lys Lys Glu Arg Phe Ser Leu Ile
            85              90              95
Leu Glu Ser Ala Ser Thr Asn Gln Thr Ser Met Tyr Leu Cys Ala Ser
            100             105             110
Ser Leu Gly Thr Phe Asn Gln Pro Gln His Phe Gly Asp Gly Thr Arg
        115             120             125
Leu Ser Ile Leu Glu Asp Leu Arg Asn Val Thr Pro Pro Lys Val Ser
    130             135             140
Leu Phe Glu Pro Ser Lys Ala Glu Ile Ala Asn Lys Gln Lys Ala Thr
145             150             155             160
Leu Val Cys Leu Ala Arg Gly Phe Phe Pro Asp His Val Glu Leu Ser
            165             170             175
Trp Trp Val Asn Gly Lys Glu Val His Ser Gly Val Cys Thr Asp Pro
            180             185             190
Gln Ala Tyr Lys Glu Ser Asn Tyr Ser Tyr Cys Leu Ser Ser Arg Leu
        195             200             205
Arg Val Ser Ala Thr Phe Trp His Asn Pro Arg Asn His Phe Arg Cys
    210             215             220
Gln Val Gln Phe His Gly Leu Ser Glu Glu Asp Lys Trp Pro Glu Gly
225             230             235             240
Ser Pro Lys Pro Val Thr Gln Asn Ile Ser Ala Glu Ala Trp Gly Arg
            245             250             255
Ala Asp Cys Gly Ile Thr Ser Ala Ser Tyr Gln Gln Gly Val Leu Ser
```

-continued

```
            260              265              270

Ala Thr Ile Leu Tyr Glu Ile Leu Leu Gly Lys Ala Thr Leu Tyr Ala
            275              280              285

Val Leu Val Ser Thr Leu Val Val Met Ala Met Val Lys Arg Lys Asn
            290              295              300

Ser Arg Ala Lys Arg Ser Gly Ser Gly Ala Thr Asn Phe Ser Leu Leu
305              310              315              320

Lys Gln Ala Gly Asp Val Glu Glu Asn Pro Gly Pro Met His Leu Ser
                325              330              335

Ser Leu Leu Lys Val Val Thr Ala Ser Leu Trp Leu Gly Pro Gly Ile
                340              345              350

Ala Gln Lys Ile Thr Gln Thr Gln Pro Gly Met Phe Val Gln Glu Lys
                355              360              365

Glu Ala Val Thr Leu Asp Cys Thr Tyr Asp Thr Ser Asp Pro Ser Tyr
            370              375              380

Gly Leu Phe Trp Tyr Lys Gln Pro Ser Ser Gly Glu Met Ile Phe Leu
385              390              395              400

Ile Tyr Gln Gly Ser Tyr Asp Gln Gln Asn Ala Thr Glu Gly Arg Tyr
                405              410              415

Ser Leu Asn Phe Gln Lys Ala Arg Lys Ser Ala Asn Leu Val Ile Ser
                420              425              430

Ala Ser Gln Leu Gly Asp Ser Ala Met Tyr Phe Cys Ala Met Arg Glu
                435              440              445

Arg Ser Gly Gly Ser Tyr Ile Pro Thr Phe Gly Arg Gly Thr Ser Leu
            450              455              460

Ile Val His Pro Asn Ile Gln Asn Pro Glu Pro Ala Val Tyr Gln Leu
465              470              475              480

Lys Asp Pro Arg Ser Gln Asp Ser Thr Leu Cys Leu Phe Thr Asp Phe
                485              490              495

Asp Ser Gln Ile Asn Val Pro Lys Thr Met Glu Ser Gly Thr Phe Ile
                500              505              510

Thr Asp Lys Cys Val Leu Asp Met Lys Ala Met Asp Ser Lys Ser Asn
                515              520              525

Gly Ala Ile Ala Trp Ser Asn Gln Thr Ser Phe Thr Cys Gln Asp Ile
            530              535              540

Phe Lys Glu Thr Asn Ala Thr Tyr Pro Ser Ser Asp Val Pro Cys Asp
545              550              555              560

Ala Thr Leu Thr Glu Lys Ser Phe Glu Thr Asp Met Asn Leu Asn Phe
                565              570              575

Gln Asn Leu Leu Val Ile Val Leu Arg Ile Leu Leu Leu Lys Val Ala
                580              585              590

Gly Phe Asn Leu Leu Met Thr Leu Arg Leu Trp Ser Ser
                595              600              605
```

```
<210> SEQ ID NO 252
<211> LENGTH: 25
<212> TYPE: PRT
<213> ORGANISM: Homo sapiens

<400> SEQUENCE: 252

Met Thr Glu Tyr Lys Leu Val Val Val Gly Ala Gly Asp Val Gly Lys
1               5               10              15

Ser Ala Leu Thr Ile Gln Leu Ile Gln
            20              25
```

-continued

```
<210> SEQ ID NO 253
<211> LENGTH: 25
<212> TYPE: PRT
<213> ORGANISM: Homo sapiens

<400> SEQUENCE: 253

Met Thr Glu Tyr Lys Leu Val Val Val Gly Ala Gly Gly Val Gly Lys
1               5                   10                  15

Ser Ala Leu Thr Ile Gln Leu Ile Gln
            20                  25
```

1

HLA CLASS II-RESTRICTED DQ T CELL RECEPTORS AGAINST RAS WITH G13D MUTATION

CROSS REFERENCE TO RELATED APPLICATIONS

This application is the U.S. national stage of International Patent Application No. PCT/US2021/053060, filed Oct. 1, 2021, which claims the benefit of U.S. Provisional Patent Application No. 63/086,674, filed Oct. 2, 2020, which is incorporated by reference in its entirety herein.

STATEMENT REGARDING FEDERALLY SPONSORED RESEARCH OR DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 411,903-Byte ASCII (Text) file named "766776_ST25.txt," dated Mar. 22, 2023.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T-cell receptor (TCR) having antigenic specificity for a mutated human RAS amino acid sequence with a substitution of glycine at position 13 with aspartic acid, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 13 is defined by reference to the wild-type human KRAS, wild-type human HRAS, or wild-type human NRAS protein, respectively.

Another embodiment of the invention provides an isolated or purified polypeptide comprising a functional portion of the inventive TCR, wherein the functional portion comprises the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, (l) all of SEQ ID NOs: 31-36, (m) all of SEQ ID NOs: 41-43, (n) all of SEQ ID NOs: 44-46, (o) all of SEQ ID NOs: 41-46, (p) all of SEQ ID NOs: 119-121, (q) all of SEQ ID NOs: 122-124, (r) all of SEQ ID NOs: 119-124, (s) all of SEQ ID NOs: 129-131, (t) all of SEQ ID NOs: 132-134, (u) all of SEQ ID NOs: 129-134, (v) all of SEQ ID NOs: 139-141, (w) all of SEQ ID NOs: 142-144, (x) all of SEQ ID NOs: 139-144, (y) all of SEQ ID NOs: 149-151, (z) all of SEQ ID NOs: 152-154, (aa) all of SEQ ID NOs: 149-154, (bb) all of SEQ ID NOs: 159-161, (cc) all of SEQ ID NOs: 162-164, (dd) all of SEQ ID NOs: 159-164, (ee) all of SEQ ID NOs: 169-171, (ff) all of SEQ ID NOs: 172-174, (gg) all of SEQ ID NOs: 169-174, (hh) all of SEQ ID NOs: 179-181, (ii) all of SEQ ID NOs: 182-184, or (jj) all of SEQ ID NOs: 179-184.

Still another embodiment of the invention provides an isolated or purified protein, comprising: (a) a first polypeptide chain comprising the amino acid sequences of SEQ ID NOs: 1-3 and a second polypeptide chain comprising the amino acid sequences of SEQ ID NOs: 4-6; (b) a first polypeptide chain comprising the amino acid sequences of SEQ ID NOs: 11-13 and a second polypeptide chain comprising the amino acid sequences of SEQ ID NOs: 14-16; (c) a first polypeptide chain comprising the amino acid sequences of SEQ ID NOs: 21-23 and a second polypeptide chain comprising the amino acid sequences of SEQ ID NOs: 24-26; (d) a first polypeptide chain comprising the amino acid sequences of SEQ ID NOs: 31-33 and a second polypeptide chain comprising the amino acid sequences of SEQ ID NOs: 34-36; or (e) a first polypeptide chain comprising the amino acid sequences of SEQ ID NOs: 41-43 and a second polypeptide chain comprising the amino acid sequences of SEQ ID NOs: 44-46; (f) a first polypeptide chain comprising the amino acid sequences of all of SEQ ID NOs: 119-121 and a second polypeptide chain comprising the amino acid sequences of all of SEQ ID NOs: 122-124; (g) a first polypeptide chain comprising the amino acid sequences of all of SEQ ID NOs: 129-131 and a second polypeptide chain comprising the amino acid sequences of all of SEQ ID NOs: 132-134; (h) a first polypeptide chain comprising the amino acid sequences of all of SEQ ID NOs: 139-141 and a second polypeptide chain comprising the amino acid sequences of all of SEQ ID NOs: 142-144; (i) a first polypeptide chain comprising the amino acid sequences of all of SEQ ID NOs: 149-151 and a second polypeptide chain comprising the amino acid sequences of all of SEQ ID NOs: 152-154; (j) a first polypeptide chain comprising the amino acid sequences of all of SEQ ID NOs: 159-161 and a second polypeptide chain comprising the amino acid sequences of all of SEQ ID NOs: 162-164; (k) a first polypeptide chain comprising the amino acid sequences of all of SEQ ID NOs: 169-171 and a second polypeptide chain comprising the amino acid sequences of all of SEQ ID NOs: 172-174; or (l) a first polypeptide chain comprising the amino acid sequences of all of SEQ ID NOs: 179-181 and a second polypeptide chain comprising the amino acid sequences of all of SEQ ID NOs: 182-184.

Further embodiments of the invention provide related nucleic acids, recombinant expression vectors, host cells, populations of cells, and pharmaceutical compositions relating to the inventive TCRs, polypeptides, and proteins.

An embodiment of the invention provides an isolated or purified nucleic acid comprising, from 5' to 3', a first nucleic acid sequence and a second nucleotide sequence, wherein the first and second nucleotide sequence, respectively, encode the amino acid sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 47 and 48; 48 and 47; 49 and 50; 50 and 49; 125 and 126; 126 and 125; 127 and 128; 128 and 127; 135 and 136; 136 and 135; 137 and 138; 138 and 137; 145 and 146; 146 and 145; 147 and 148; 148 and 147; 155 and 156; 156 and 155; 157 and 158; 158 and 157; 165 and 166; 166 and 165; 167 and 168; 168 and 167; 175 and 176; 176 and 175; 177 and 178; 178 and 177; 185 and 186; 186 and 185; 187 and 188; 188 and 187; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; 86 and 85; 87 and 88; 88 and 87; 89 and 90; 90 and 89; 91 and 92; 92 and 91; 93 and 94; 94 and 93; 95 and 96; 96 and 95; 97 and 98; 98 and 97; 99 and 100; 100 and 99; 101 and 102; 102 and 101; 103 and 104; 104 and 103; 189 and 190; 190 and 189; 191 and 192; 192 and 191; 193 and 194; 194 and 193; 195 and 196; 196 and 195; 197 and 198; 198 and 197; 199 and 200; 200 and 199; 201 and 202; 202 and 201; 203 and 204; 204 and 203; 205 and 206; 206 and 205; 207 and 208; 208 and 207; 209 and 210; 210 and 209; 211 and 212; 212 and 211; 213 and 214; 214 and 213; 215 and 216; 216 and 215; 217 and 218; 218 and 217; 219 and 220; 220 and 219; 221 and 222; 222 and 221; 223 and 224; 224 and 223; 225 and 226; 226 and 225; 227 and 228; 228 and 227; 229 and 230; 230 and 229; 231 and 232; 232 and 231; 233 and 234; 234 and 233; 235 and 236; 236 and 235; 237 and 238; 238 and 237; 239 and 240; 240 and 239; 241 and 242; 242 and 241; 243 and 244; or 244 and 243.

Another embodiment of the invention provides a method of producing a host cell expressing a TCR that has antigenic specificity for the peptide of MTEYKLVVVGAGDVGK-SALTIQLIQ (SEQ ID NO: 252), the method comprising contacting a cell with the inventive recombinant expression vector under conditions that allow introduction of the vector into the cell.

Still another embodiment of the invention provides a method of producing the inventive TCR, polypeptide, or protein, the method comprising culturing the inventive host cell or the population of host cells so that the inventive TCR, polypeptide, or protein is produced.

Another embodiment of the invention provides a method of detecting the presence of cancer in mammal, the method comprising: (a) contacting a sample comprising cells of the cancer with the inventive TCR, polypeptide, protein, nucleic acid, recombinant expression vector, host cell, population, or pharmaceutical composition, thereby forming a complex; and (b) detecting the complex, wherein detection of the complex is indicative of the presence of cancer in the mammal.

Another embodiment of the invention provides a method of inducing an immune response against cancer in a mammal, the method comprising administering to the mammal the inventive TCR, polypeptide, protein, nucleic acid, recombinant expression vector, host cell, population, or pharmaceutical composition, in an amount effective to induce the immune response against cancer in the mammal.

Another embodiment of the invention provides a method of treating or preventing cancer in a mammal, the method comprising administering to the mammal the inventive TCR, polypeptide, protein, nucleic acid, recombinant expression vector, host cell, population, or pharmaceutical composition in an amount effective to treat or prevent cancer in the mammal.

BRIEF DESCRIPTION OF THE SEVERAL VIEWS OF THE DRAWING(S)

FIG. 1 is a graph showing IFN-γ secretion (spots/3e4 cells) measured by ELISPOT assay following co-culture of effector cells with target cells. Effector cells were TIL from tumor fragments (numbered F1-F8, F10-F16, and F18-F22) from patient 4400. Target cells were dendritic cells (DC) (i) transfected with mRNA encoding full length (FL) G13D KRAS or the corresponding FL wild-type (WT) KRAS; (ii) pulsed with the G13D 25-mer peptide (G13D LP) or the corresponding WT 25-mer peptide (WT LP); or (iii) pulsed with G13D ME "mix" (containing a combination of three predicted minimal epitopes from the mutated peptide). Effector cells (i) co-cultured with DC treated with DMSO or (ii) cultured alone (T cell only) served as negative controls. Effector cells treated with anti-CD3/CD28 antibodies served as a positive control.

Figure 2A:
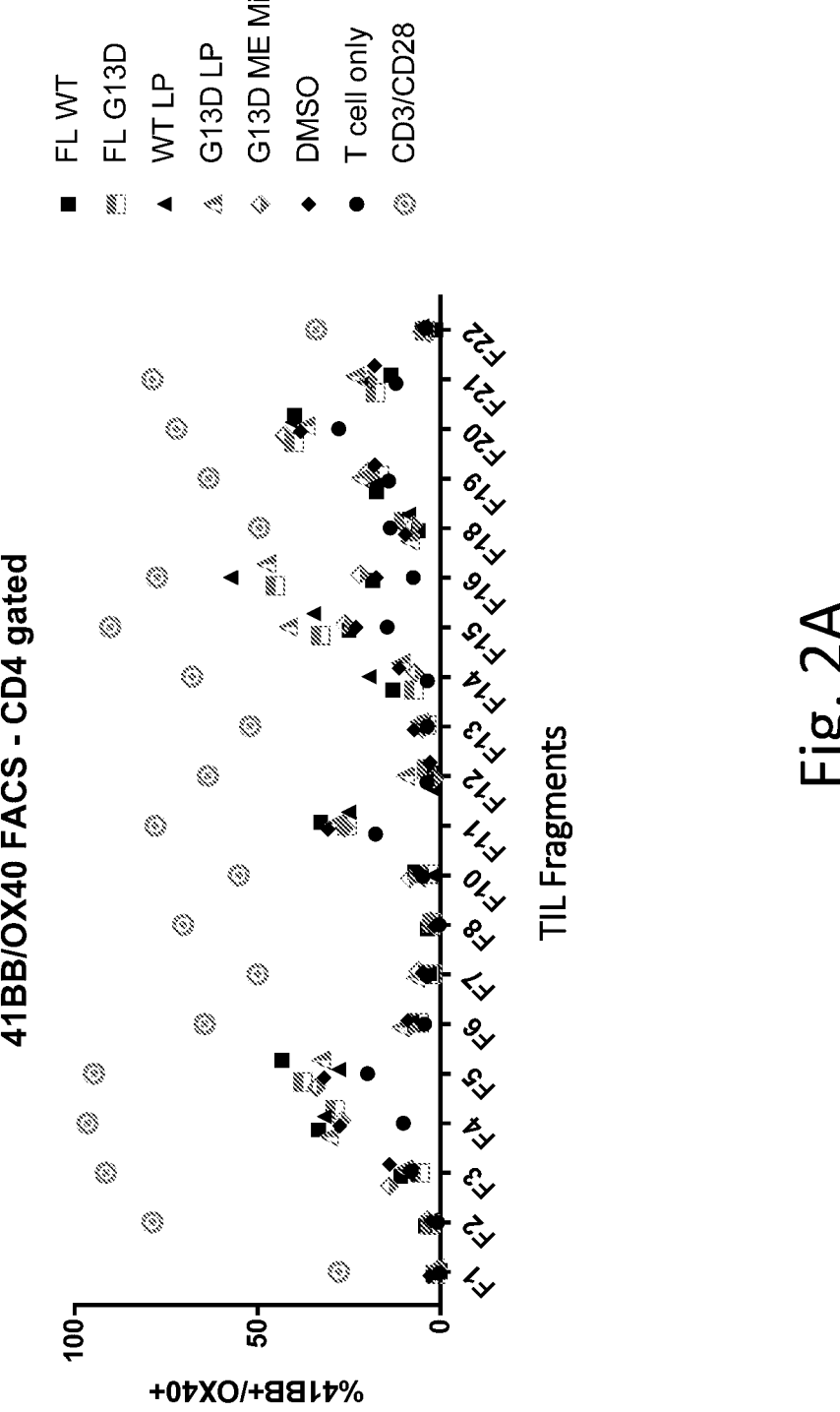
Figure 2B:
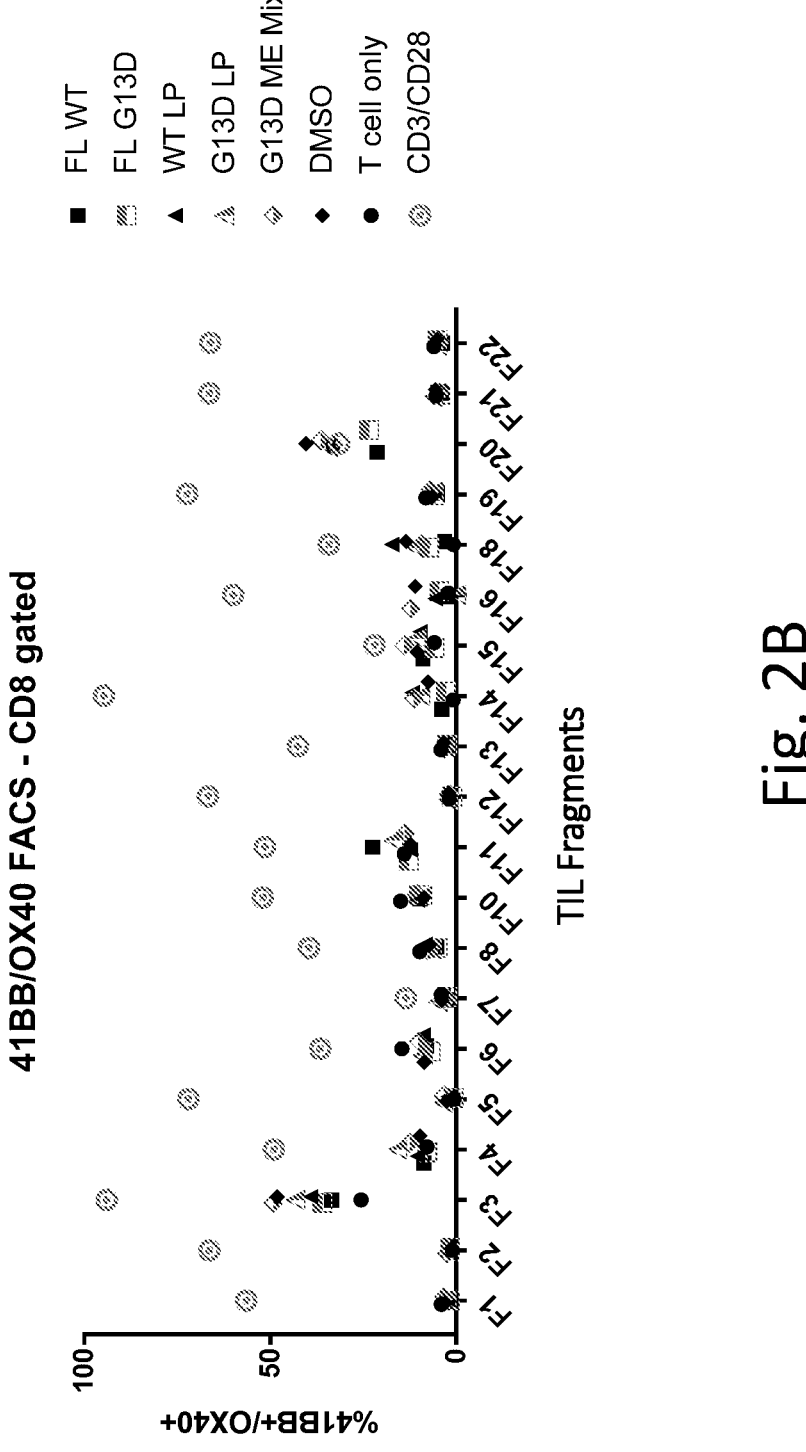

FIGS. 2A-2B are graphs showing the percentage of cells expressing one or both of 4-1BB and OX40 measured by FACS gated on CD4+ cells (FIG. 2A) or CD8+ cells (FIG. 2B) following co-culture of effector cells with target cells. Effector cells, target cells, and controls are as described for FIG. 1.

Figure 3:
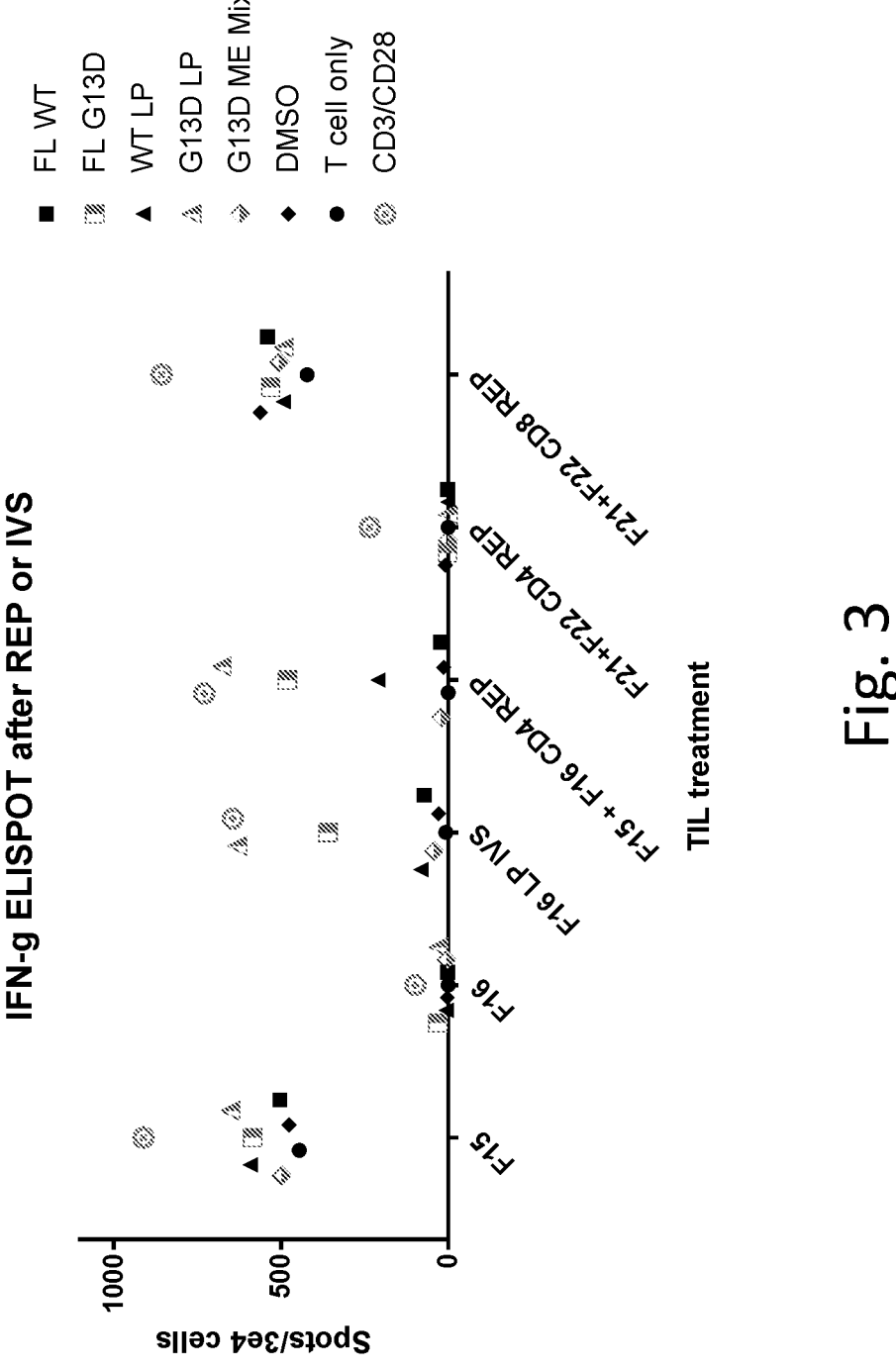

FIG. 3 is a graph showing IFN-γ secretion (spots/3e4 cells) measured by ELISPOT assay following co-culture of effector cells with target cells. Effector cells were (i) TIL from tumor fragments F15 and F16 that were untreated or treated as follows: (a) F16 TIL were stimulated in vitro (IVS) with DC pulsed with G13D 25-mer peptide or (b) F15 and F16 TIL were combined, activated (as described for FIGS. 1 and 2A-2B), sorted for CD4+/41BB+/OX40+ expression, and underwent REP; or (ii) TIL from tumor fragments F21 and F22 that were combined, sorted for CD4+/41BB+/OX40+ or CD8+/41BB+/OX40+ expression, and underwent REP. Target cells and controls are as described for FIG. 1. Reactive cells were single-cell sorted by FACS into a 96-well plate and were sequenced to provide the TCR alpha and TCR beta chains.

Figure 4A:
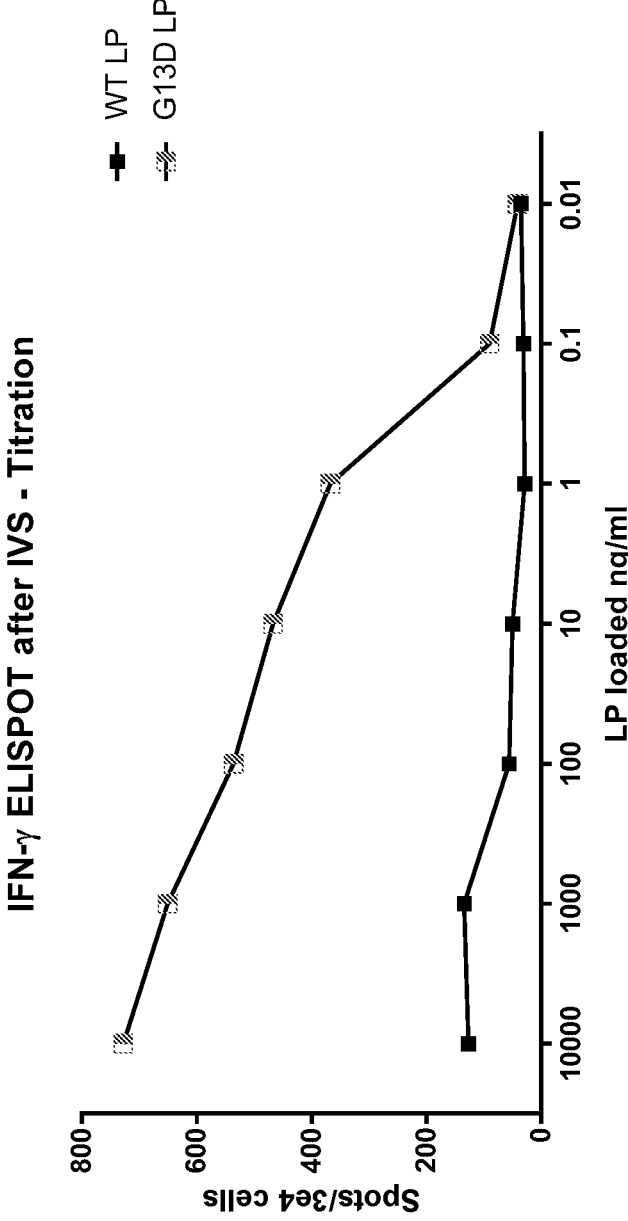
Figure 4B:
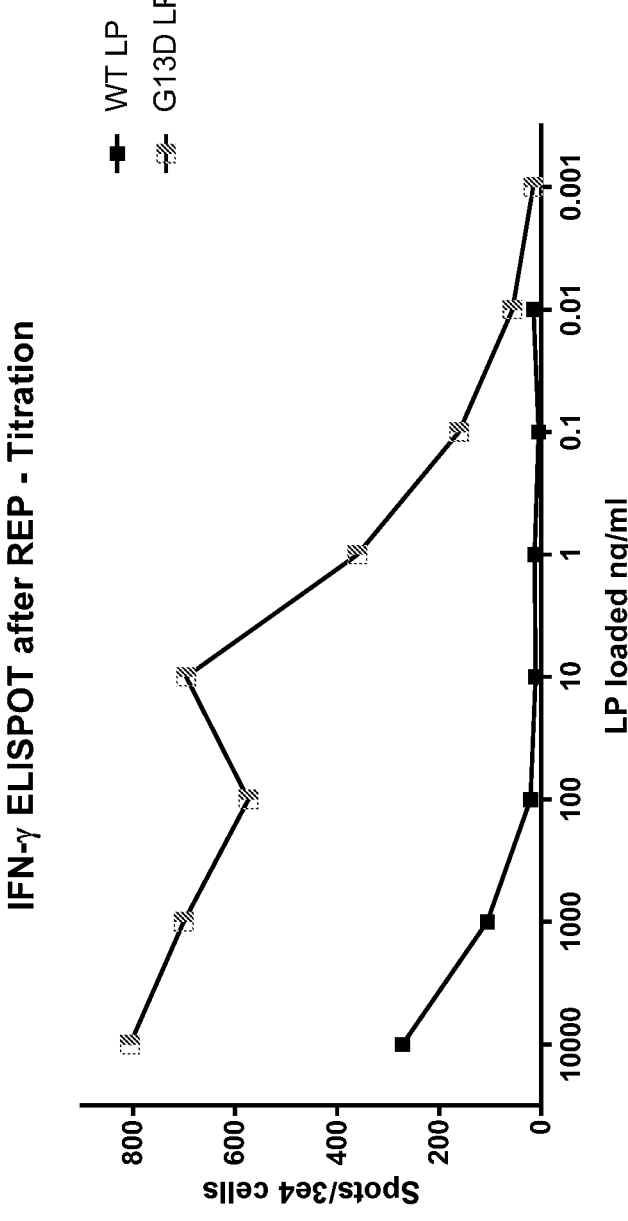

FIGS. 4A-4B are graphs showing the IFN-γ secretion (spots/3e4 cells) measured by ELISPOT assay following co-culture of effector cells with target cells. Target cells were DC pulsed with the indicated concentrations (ng/mL) of G13D 25-mer peptide or the corresponding WT 25-mer peptide. Effector cells were the reactive cells from FIG. 3: TIL from tumor fragment F16 following G13D IVS (FIG. 4A) or TIL from tumor fragments F15 and F16 following activation, sort for CD4+/41BB+/OX40+ and REP (FIG. 4B).

Figure 5:
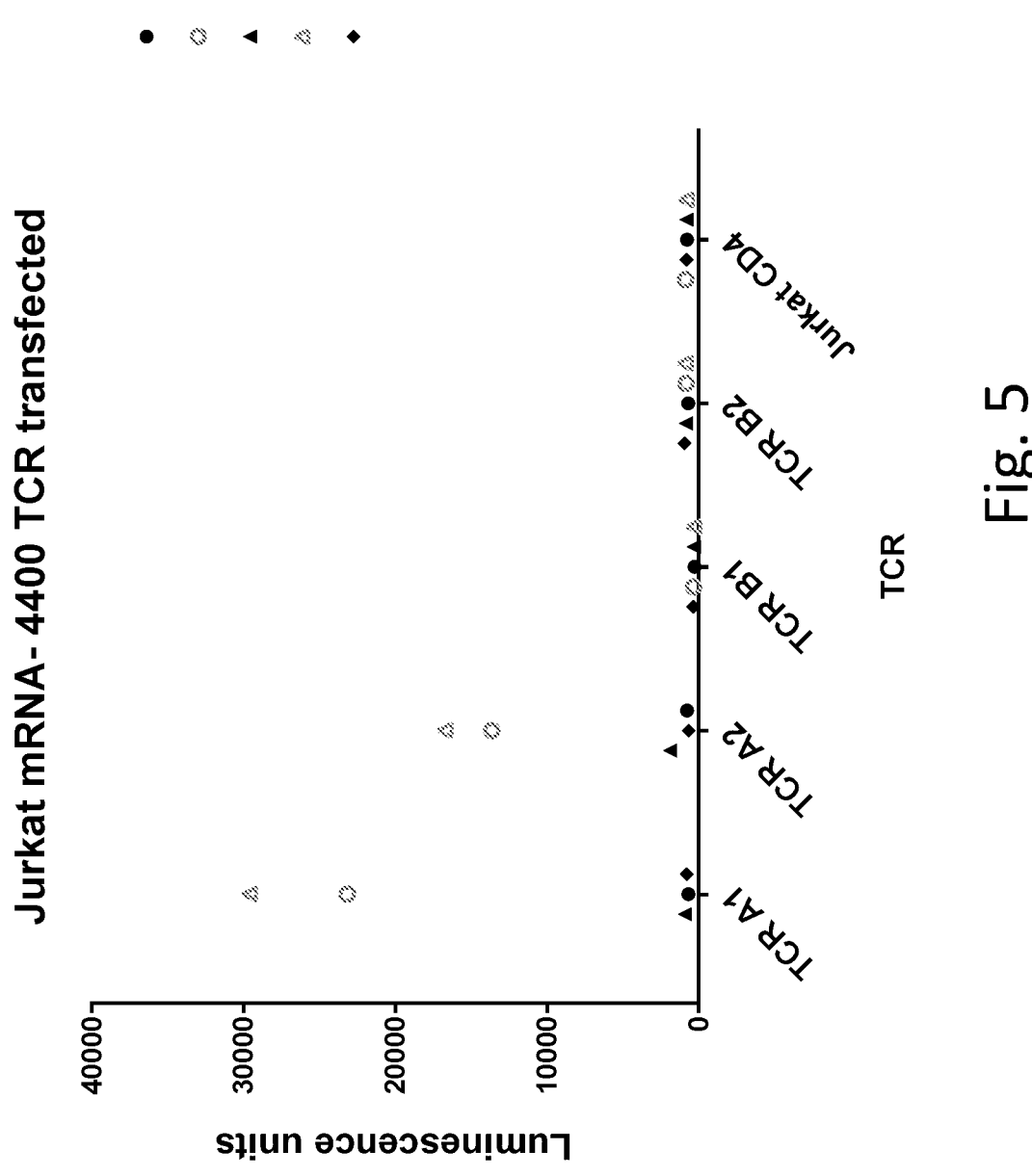

FIG. 5 is a graph showing luciferase expression measured by luminescence units upon co-culture of effector cells with target cells. Effector cells were a Jurkat cell line stably expressing luciferase under the transcriptional control of an NFAT promotor and also stably expressing the CD4 co-receptor; these cells were virally transduced with mRNA encoding TCR alpha and beta chains generated according to the sequencing described for FIG. 3. The TCR was the 4400 TCR-A1 or 4400 TCR-A2 of Example 2 or the 4400 TCR-B1, 4400 TCR-B2. Target cells were DC (i) transfected with full length G13D KRAS mRNA (G13D FL) or the corresponding full length WT KRAS mRNA (WT FL); (ii) pulsed with the G13D 25-mer peptide (G13D Mut LP) or the corresponding WT 25-mer peptide (G13 WT LP) of Example 1. Transfected cells co-cultured with DC treated with DMSO and Jurkat cells without TCR transfection served as negative controls.

Figure 6:
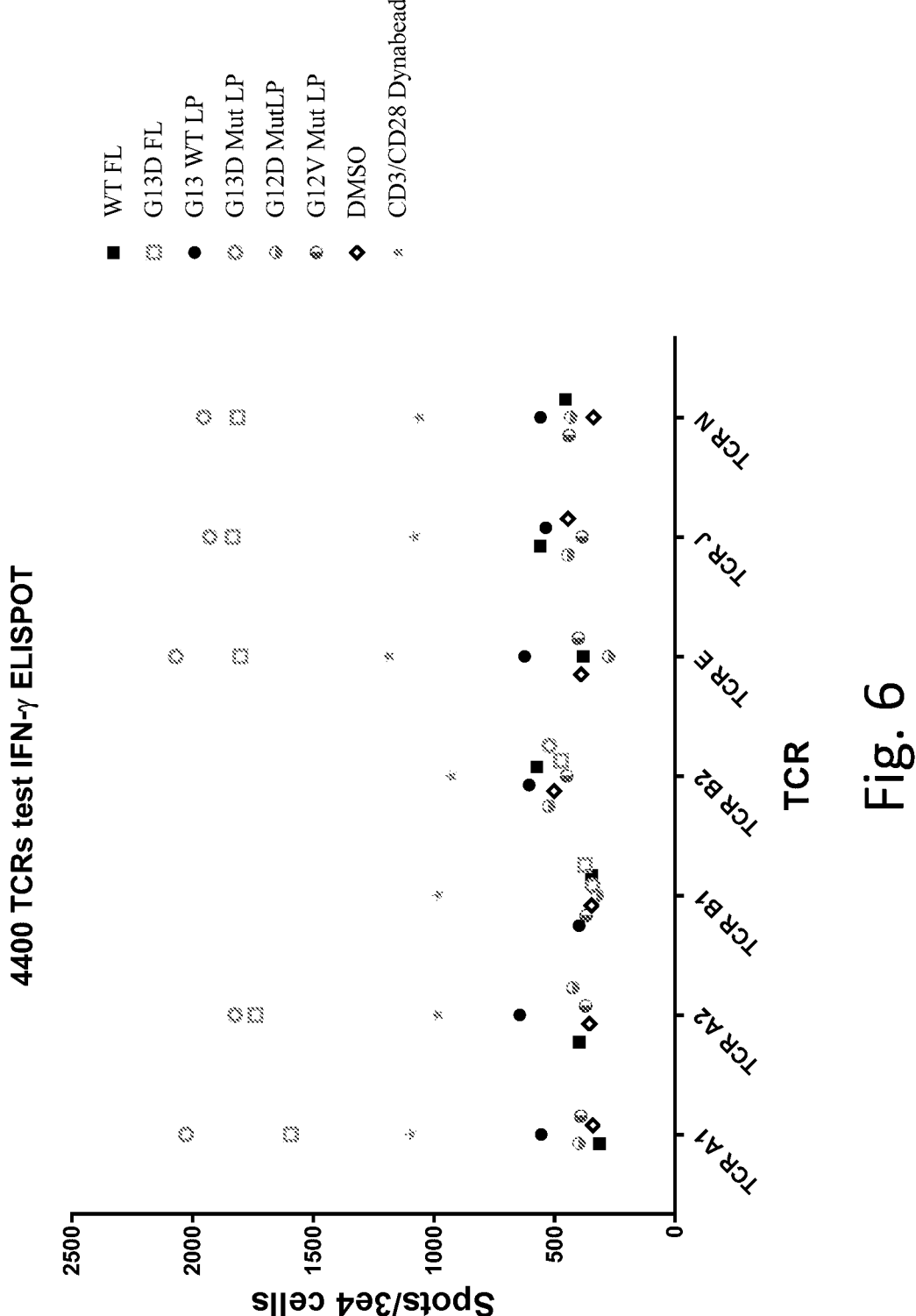

FIG. 6 is a graph showing the IFN-γ secretion (spots/3e4 cells) measured by ELISPOT assay following co-culture of effector cells with target cells. Effector cells were healthy donor PBL independently transduced with the retroviral vector encoding the 4400 TCR-A1, 4400 TCR-A2, 4400 TCR-E, 4400 TCR-J, or 4400 TCR-N of Example 2 or the 4400 TCR-B1, or 4400 TCR-B2. Target cells were DC (i) transduced with full length G13D KRAS mRNA (G13D FL) or the corresponding full length WT KRAS protein (WT FL); (ii) pulsed with G13D 25-mer peptide (G13D Mut LP) or the corresponding WT 25-mer peptide (G13 WT LP) of Example 1; or (iii) pulsed with G12D 25-mer peptide (G12D Mut LP) or G12V 25-mer peptide (G12V Mut LP). Effector cells co-cultured with DC treated with DMSO served as a negative control. Effector cells treated with anti-CD3/CD28 antibodies served as a positive control.

Figure 7A:
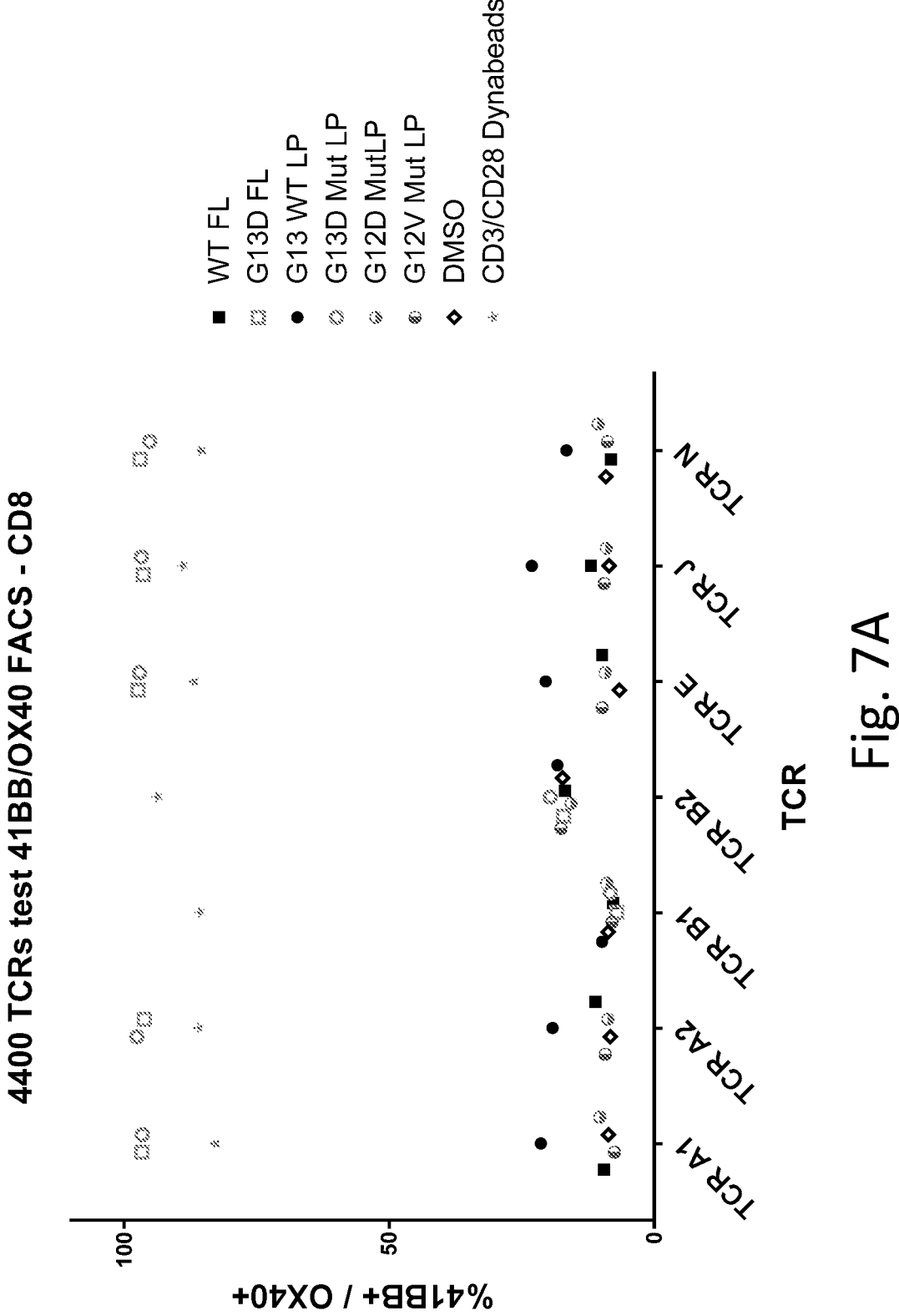
Figure 7B:
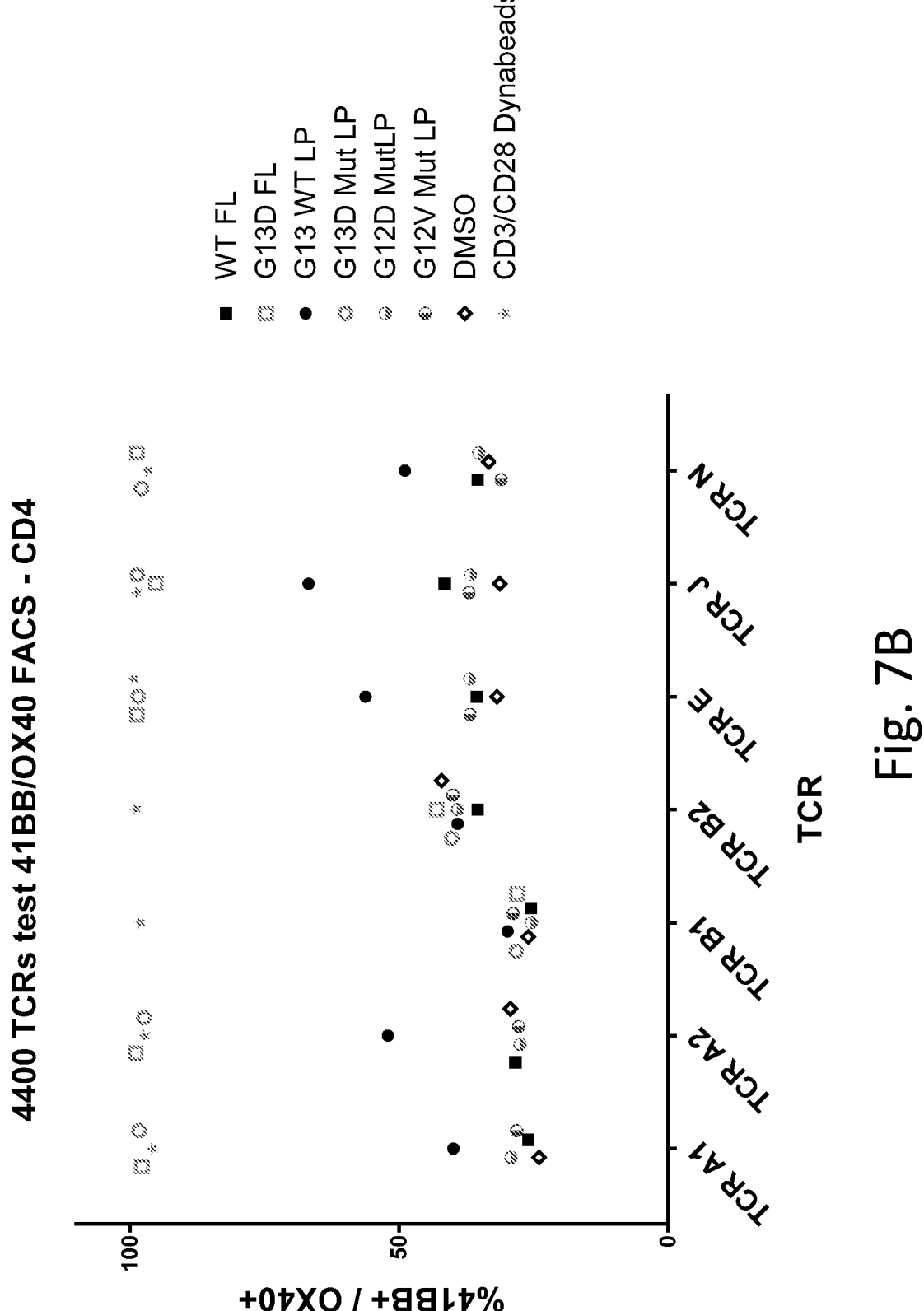

FIGS. 7A-7B are graphs showing the percentage of cells expressing one or both of 4-1BB and OX40 measured by FACS gated on CD8+ cells (FIG. 7A) or CD4+ cells (FIG. 7B) following co-culture of effector cells with target cells. Effector cells, target cells, and controls are as described for FIG. 6.

Figure 8:
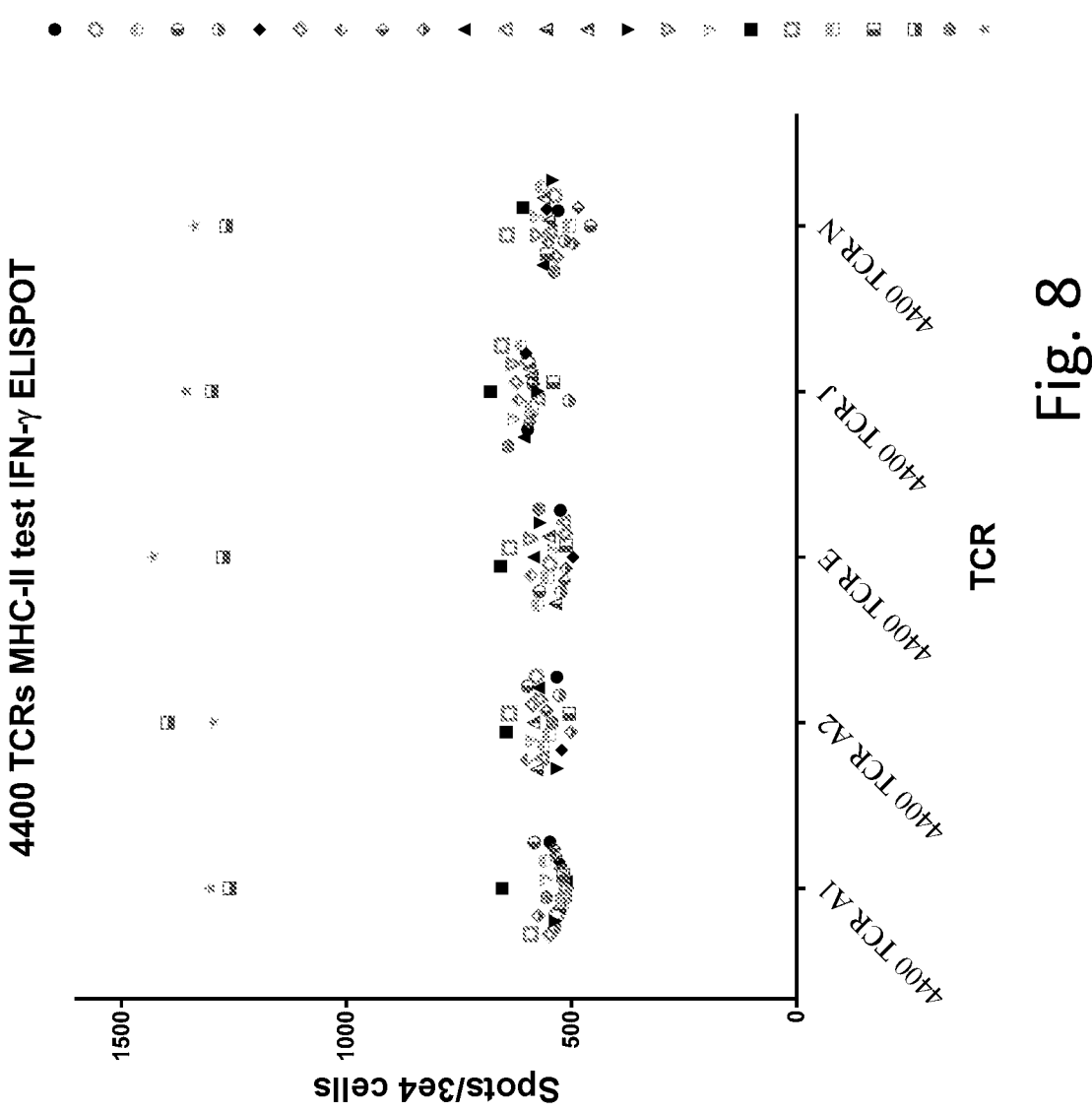

FIG. 8 is a graph showing the IFN-γ secretion (spots/3e4 cells) measured by ELISPOT assay following co-culture of effector cells with target cells. HEK cells (target cells) were untransfected (control) or independently transfected with the HLA heterodimers shown (alpha and beta) and then were pulsed with the G13D 25-mer peptide of Example 1. The effector cells were healthy donor PBL independently transduced with the retroviral vector encoding the 4400 TCR-A1, 4400 TCR-A2, 4400 TCR-E, 4400 TCR-J, or 4400 TCR-N of Example 2. Effector cells cultured in the presence of anti-CD3/anti-CD28 Dynabeads served as a positive control.

Figure 9:
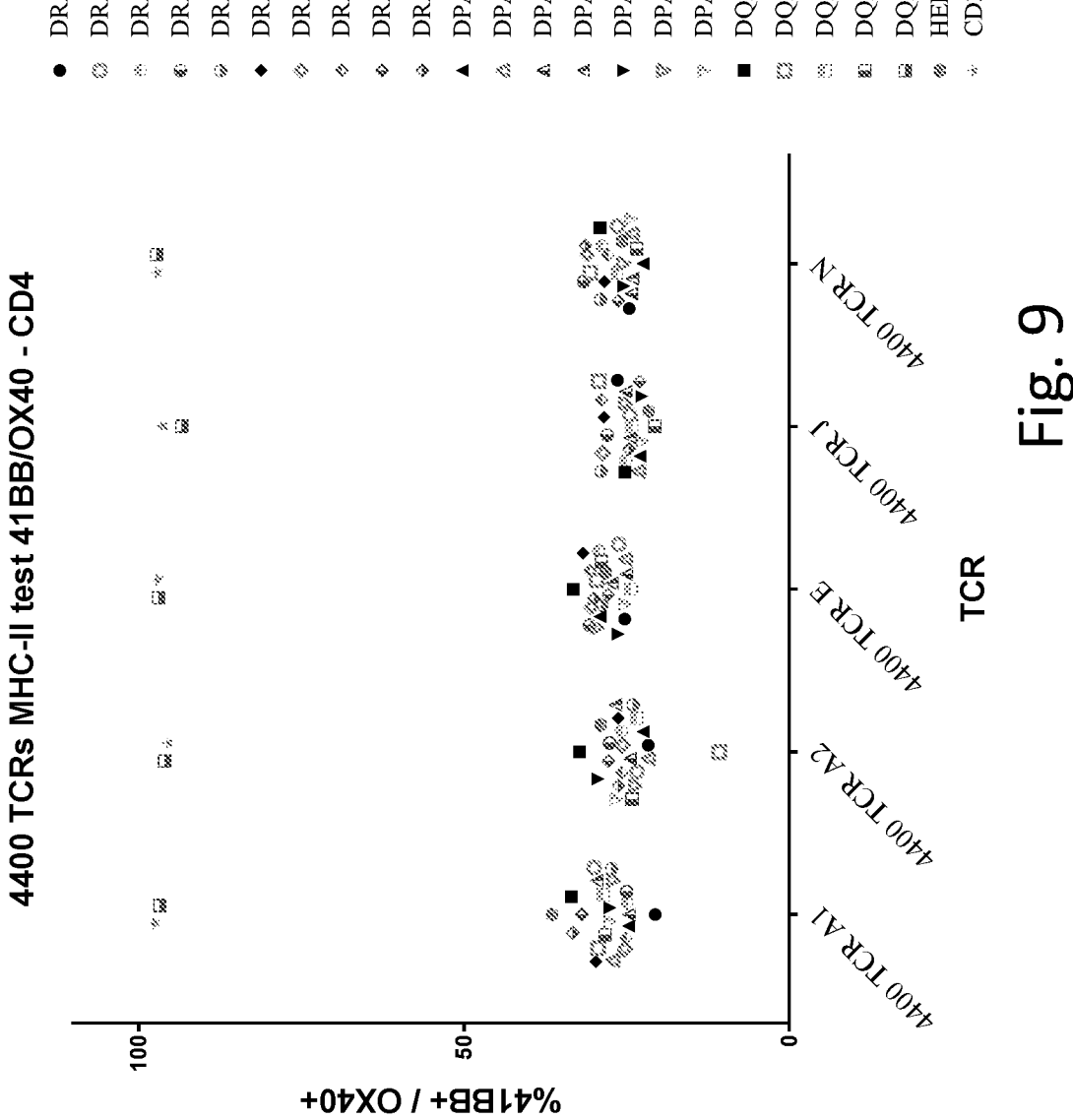

FIG. 9 is a graph showing the percentage of cells expressing one or both of 4-1BB and OX40 measured by FACS gated on CD4+/mTCR+ cells following co-culture of effector cells with target cells. Effector cells, target cells, and controls are as described for FIG. 8.

Figure 10A:
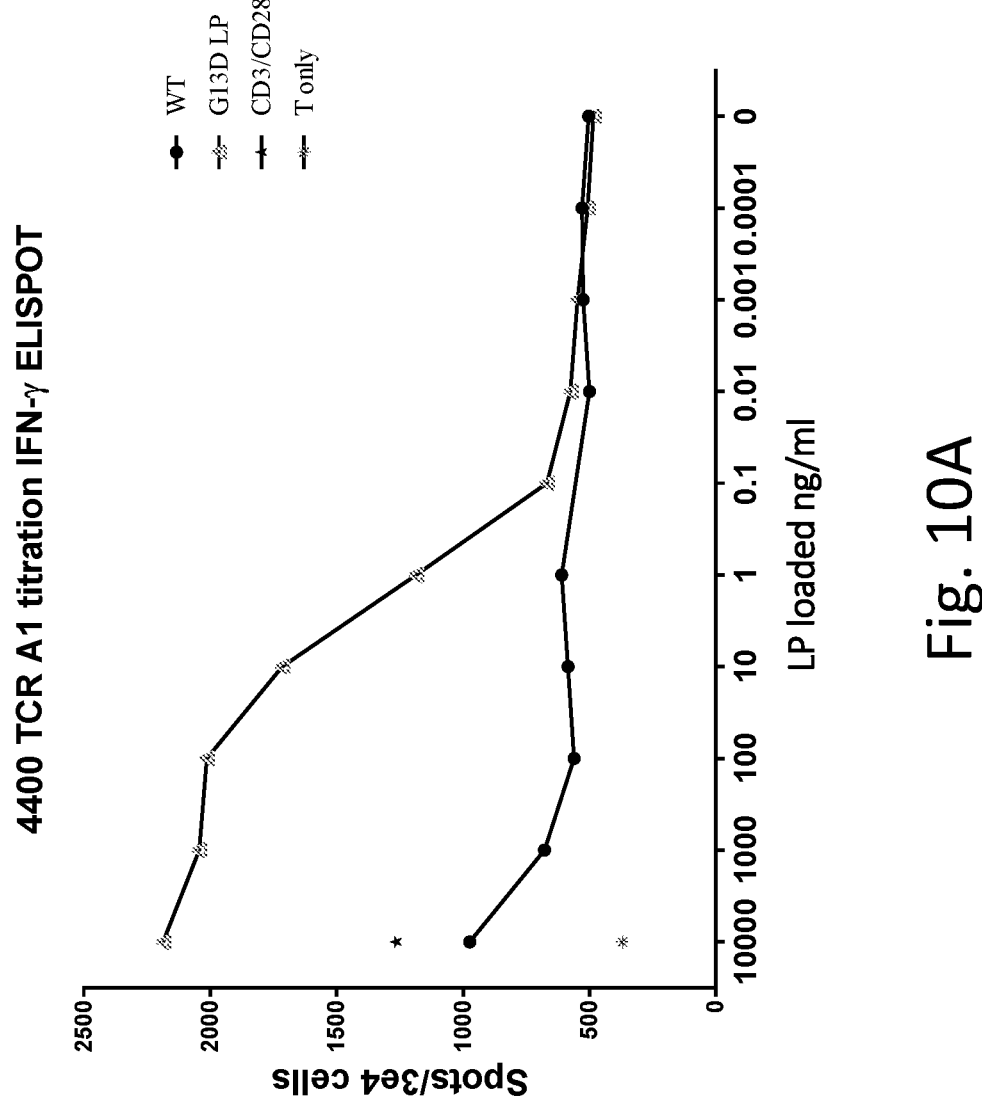
Figure 10B:
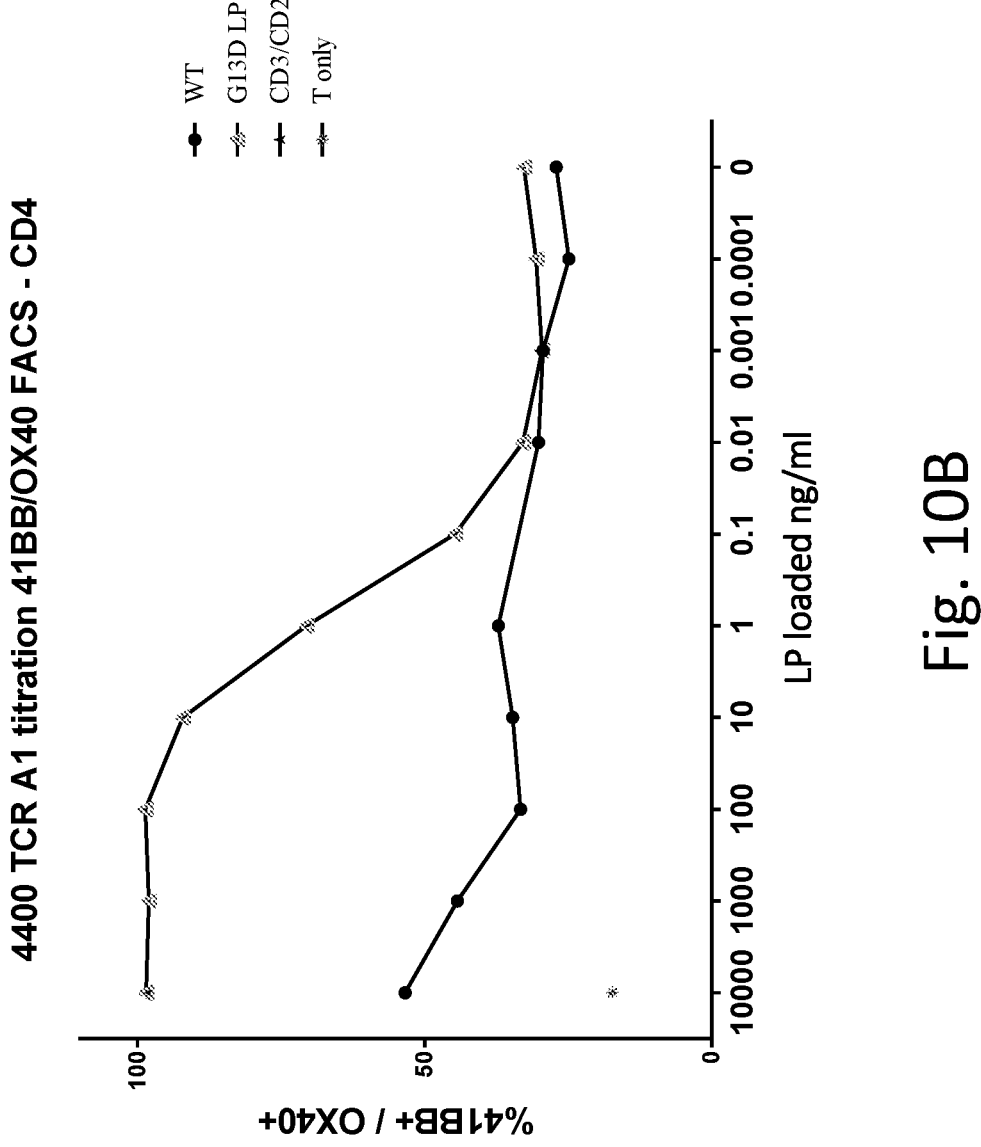
Figure 10C:
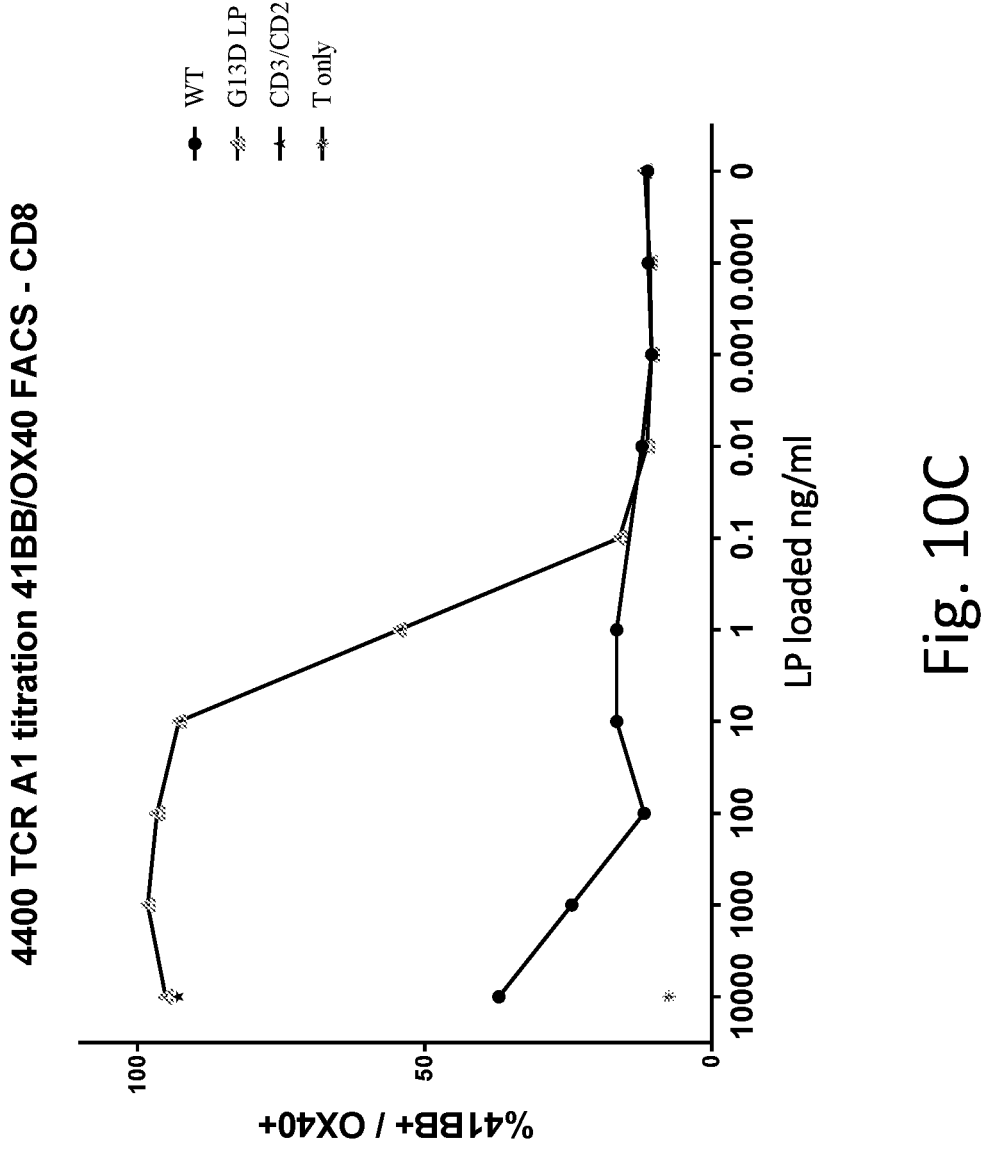

FIGS. 10A-10C are graphs showing the IFN-γ secretion (spots/3e4 cells) measured by ELISPOT assay (FIG. 10A) and the percentage of cells expressing one or both of 4-1BB and OX40 measured by FACS gated on CD4+/mTCR+ cells (FIG. 10B) or CD8+/mTCR+ cells (FIG. 10C) following co-culture of effector cells with target cells. Effector cells were healthy donor PBL transduced with the retroviral vector of Example 2 encoding the 4400 TCR-A1. Target cells were DC pulsed with the indicated concentration (ng/mL) of G13D 25-mer peptide or the corresponding WT 25-mer peptide. Effector cells cultured alone (T only) served as a negative control. Effector cells treated with anti-CD3/CD28 antibodies served as a positive control.

Figure 11A:
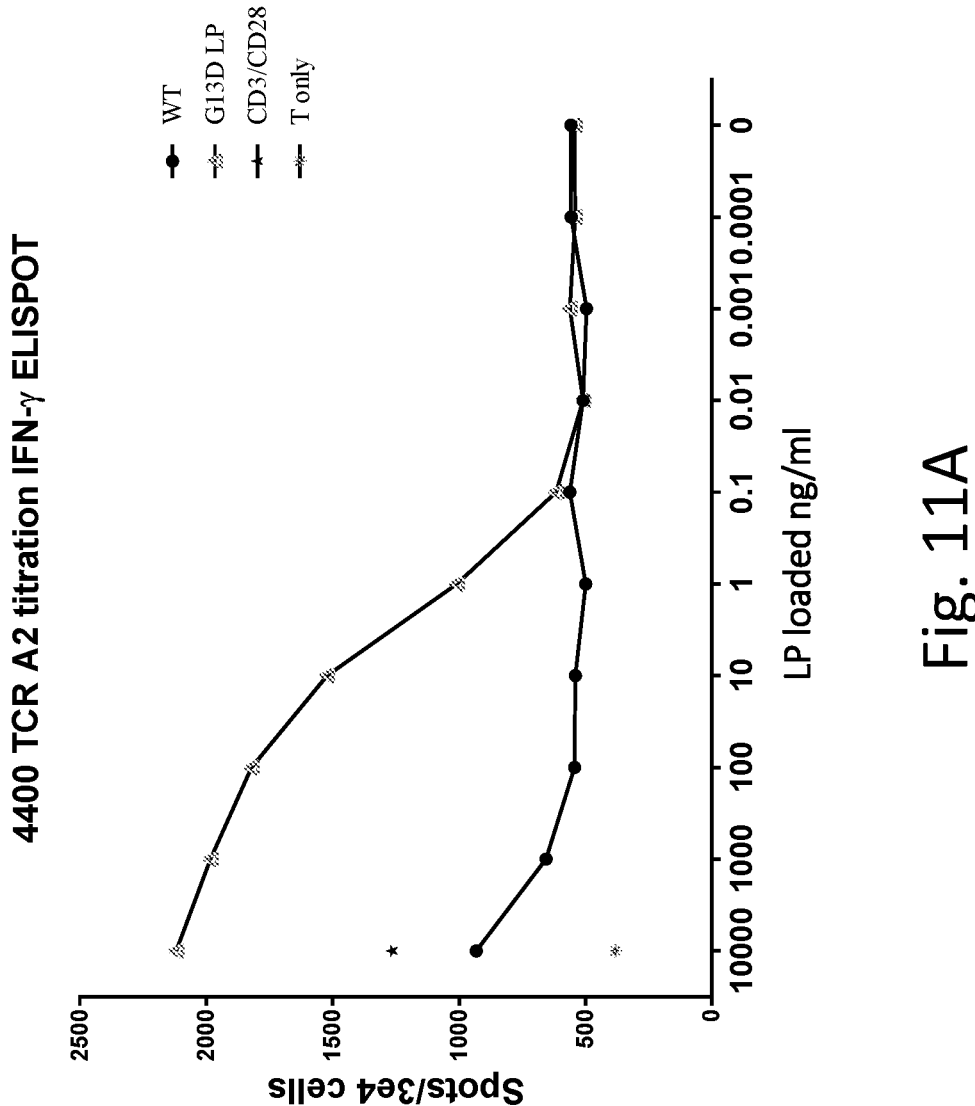
Figure 11B:
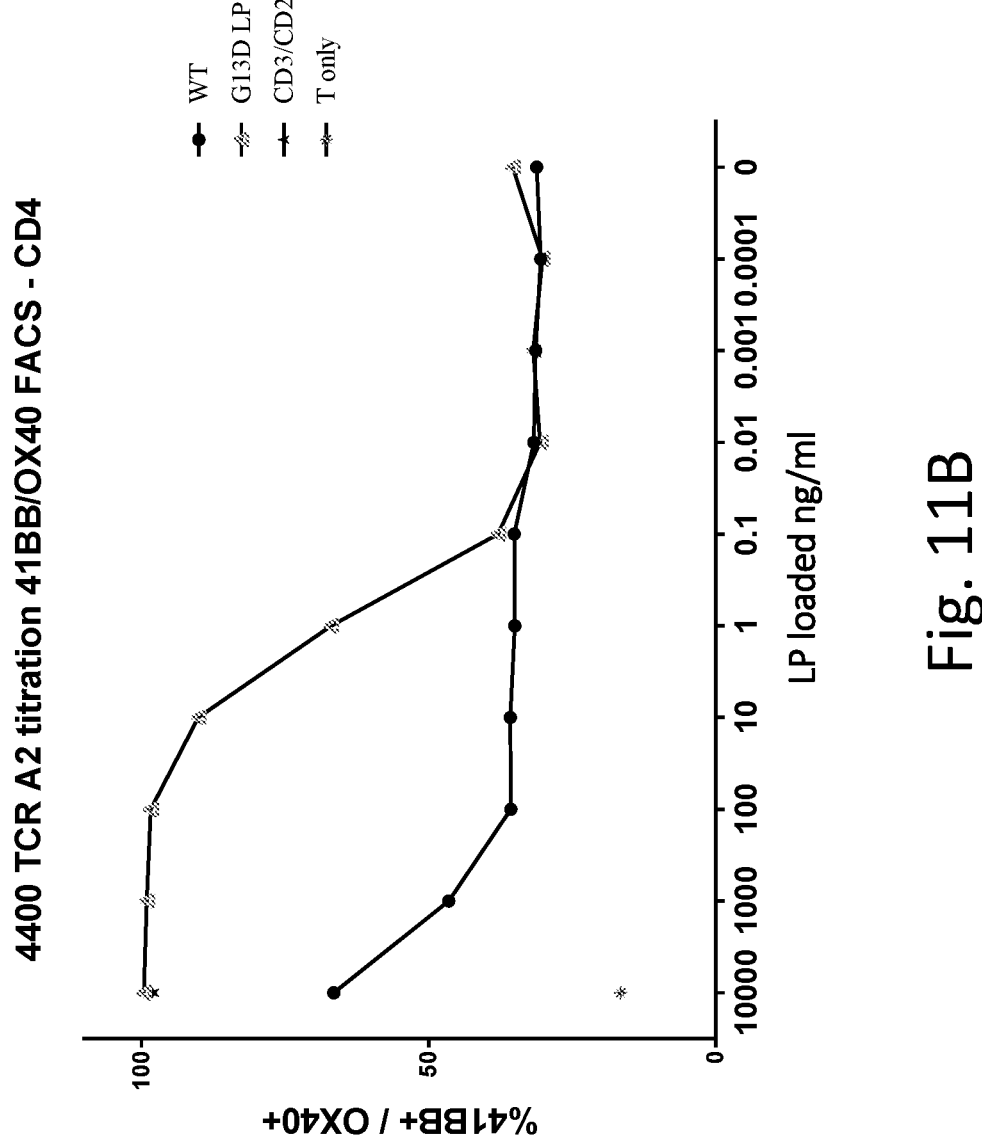
Figure 11C:
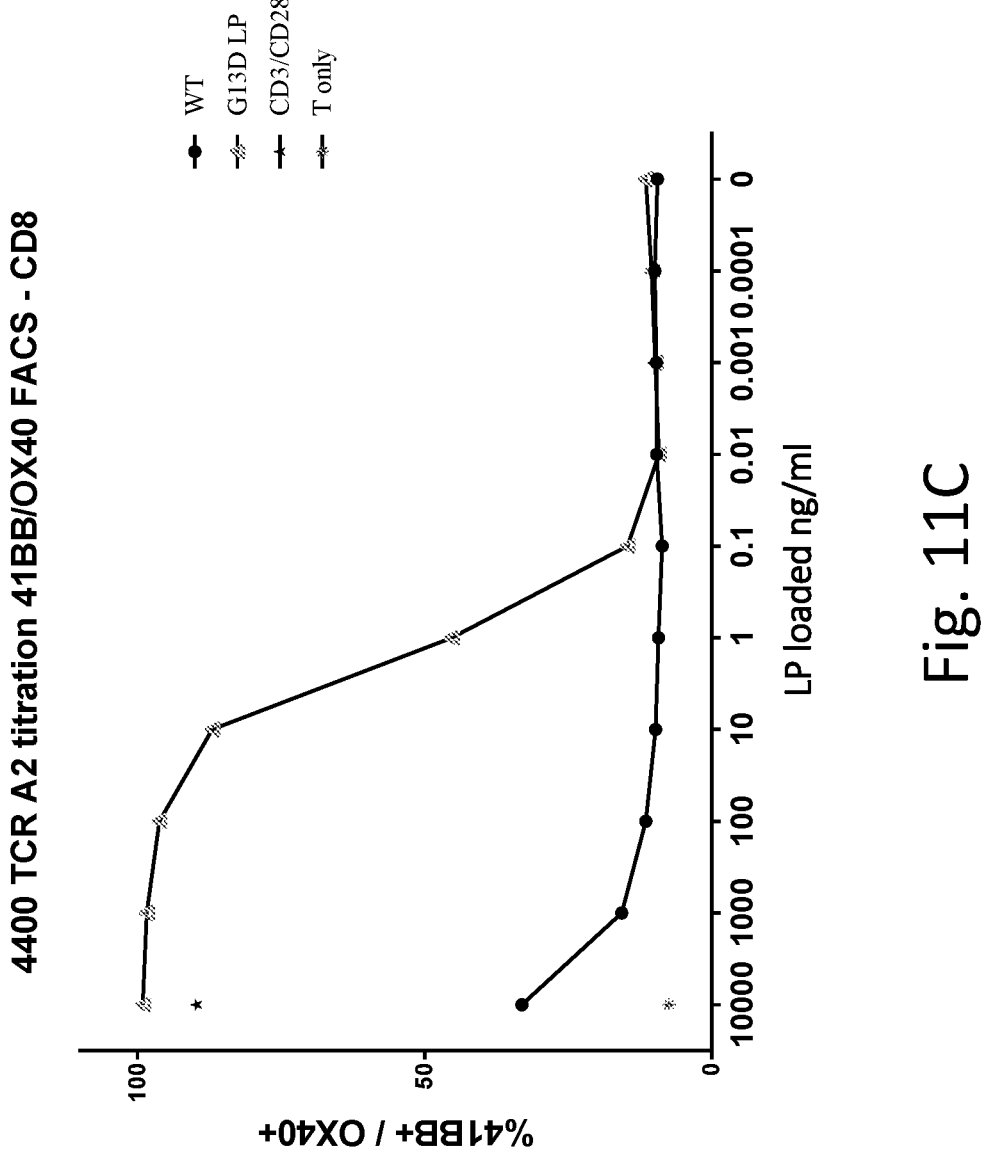

FIGS. 11A-11C are graphs showing the IFN-γ secretion (spots/3e4 cells) measured by ELISPOT assay (FIG. 11A) and the percentage of cells expressing one or both of 4-1BB and OX40 measured by FACS gated on CD4+/mTCR+ cells (FIG. 11B) or CD8+/mTCR+ cells (FIG. 11C) following co-culture of effector cells with target cells. Effector cells were healthy donor PBL transduced with the retroviral vector of Example 2 encoding the 4400 TCR-A2. Target cells and controls are as described for FIGS. 10A-10C.

Figure 12A:
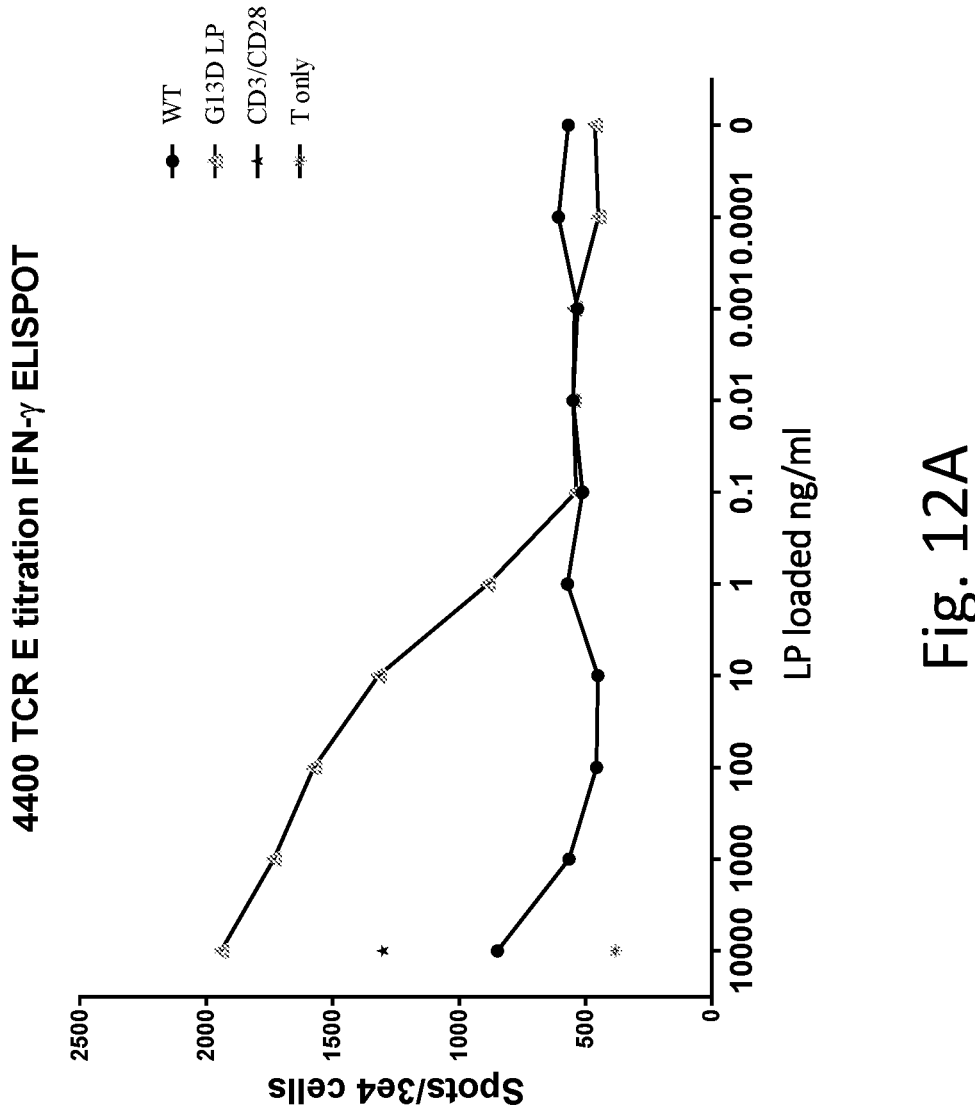
Figure 12B:
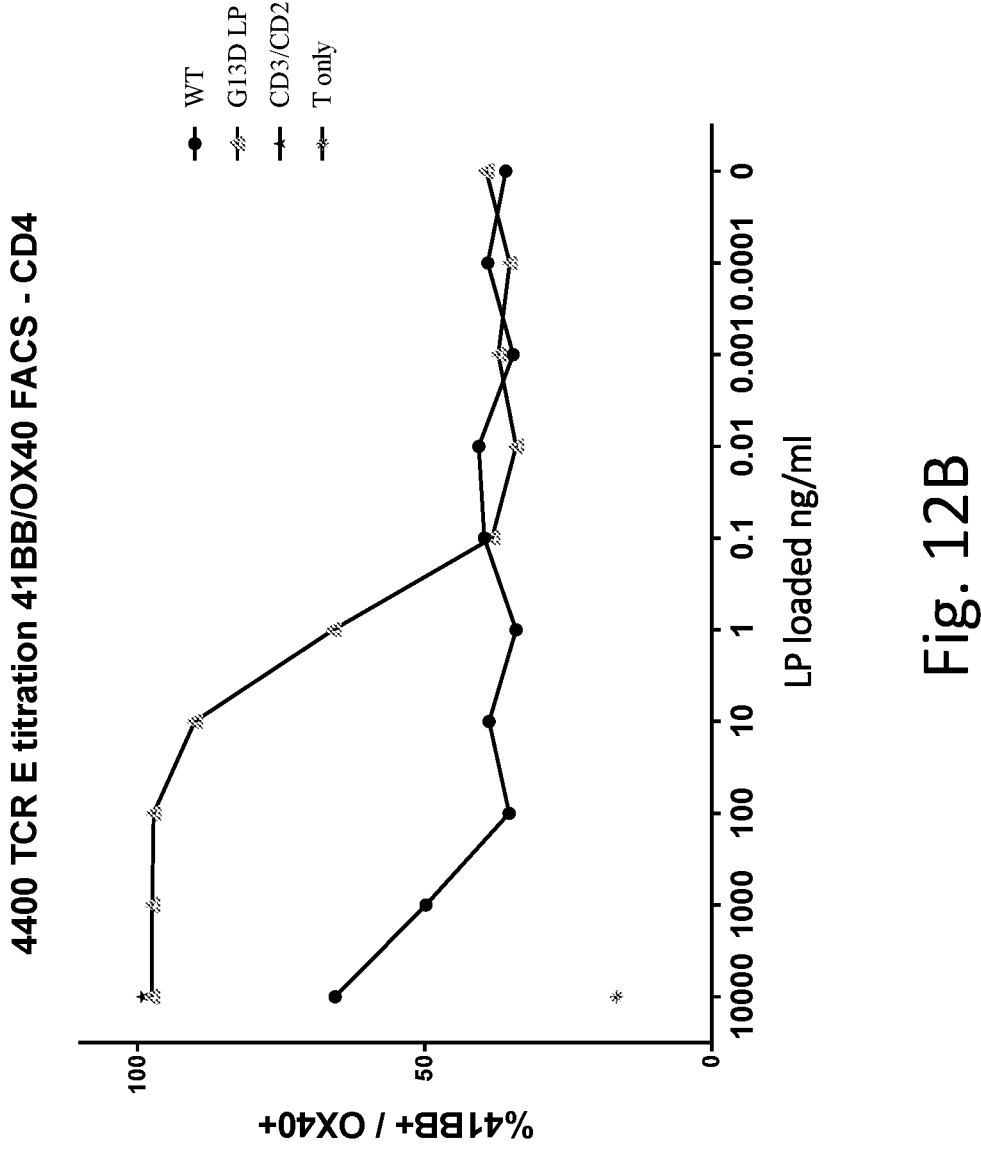
Figure 12C:
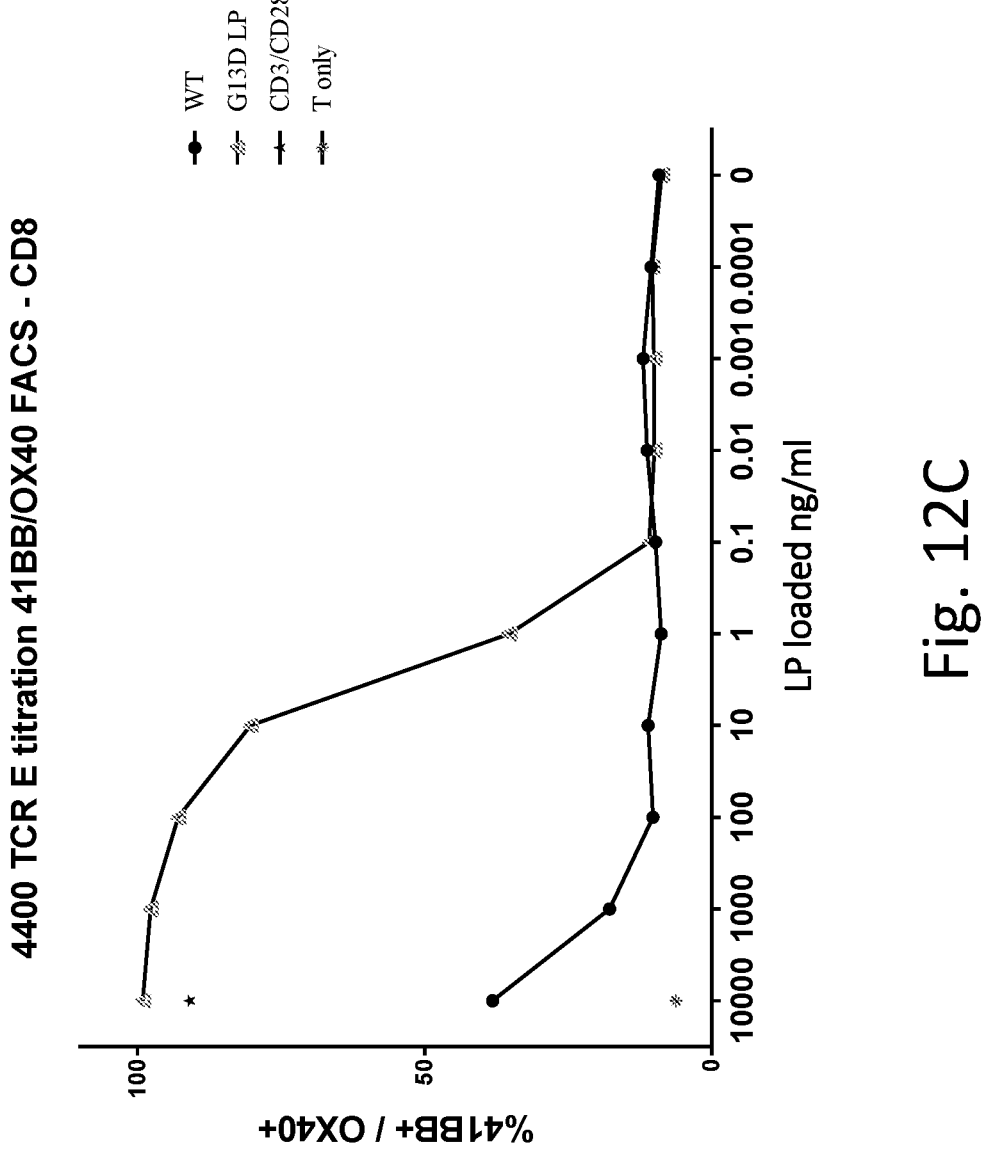

FIGS. 12A-12C are graphs showing the IFN-γ secretion (spots/3e4 cells) measured by ELISPOT assay (FIG. 12A) and the percentage of cells expressing one or both of 4-1BB and OX40 measured by FACS gated on CD4+/mTCR+ cells (FIG. 12B) or CD8+/mTCR+ cells (FIG. 12C) following co-culture of effector cells with target cells. Effector cells were healthy donor PBL transduced with the retroviral vector of Example 2 encoding the 4400 TCR-E. Target cells and controls are as described for FIGS. 10A-10C.

Figure 13A:
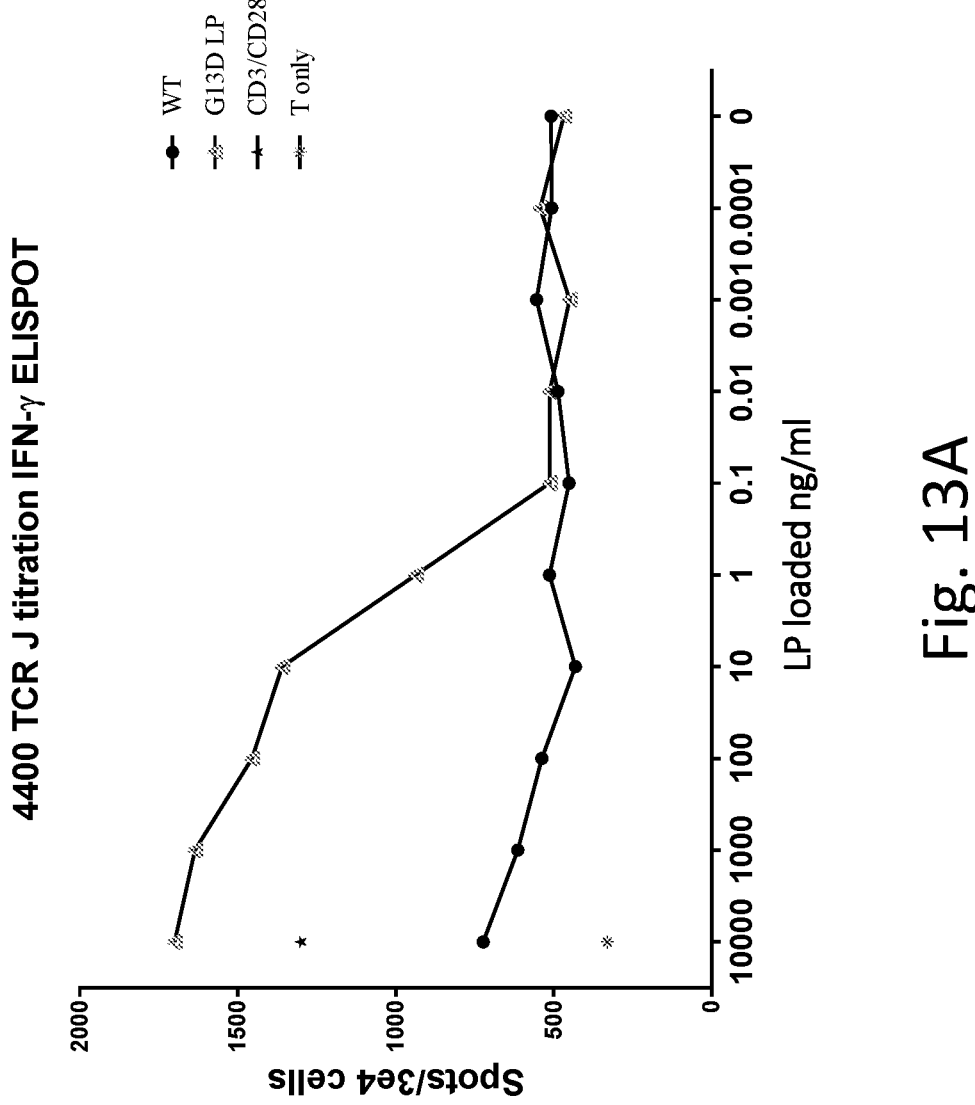
Figure 13B:
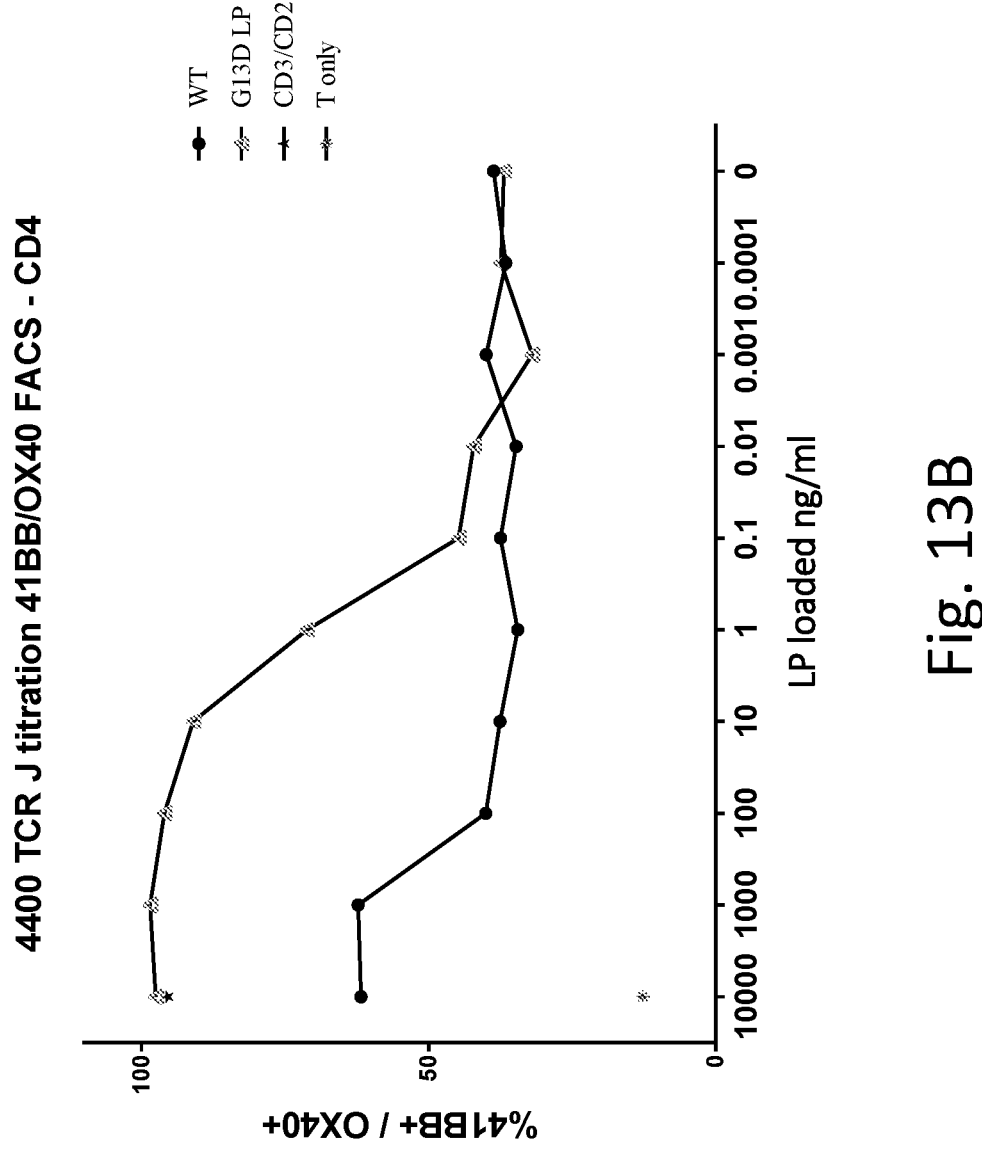
Figure 13C:
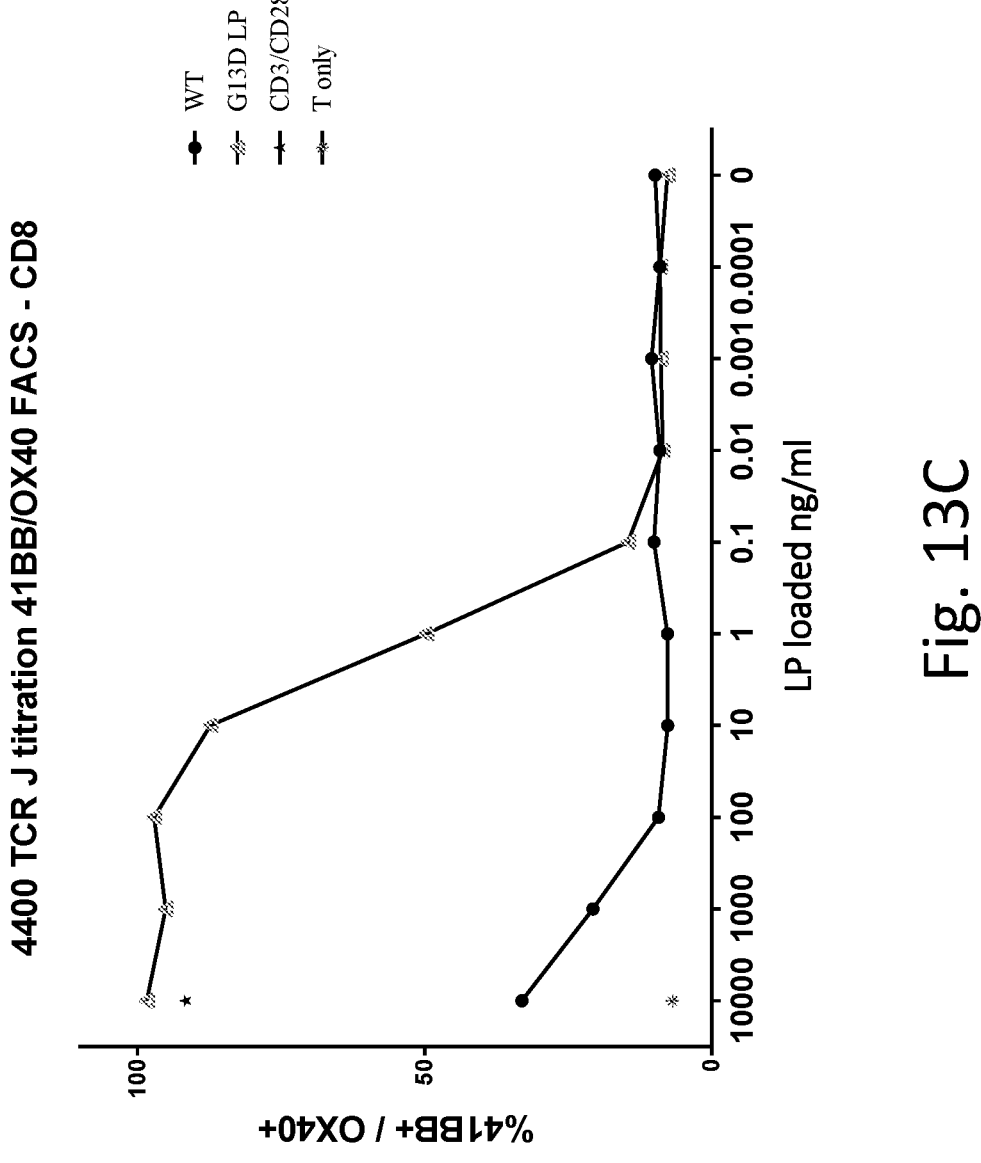

FIGS. 13A-13C are graphs showing the IFN-γ secretion (spots/3e4 cells) measured by ELISPOT assay (FIG. 13A) and the percentage of cells expressing one or both of 4-1BB and OX40 measured by FACS gated on CD4+/mTCR+ cells (FIG. 13B) or CD8+/mTCR+ cells (FIG. 13C) following co-culture of effector cells with target cells. Effector cells were healthy donor PBL transduced with the retroviral vector of Example 2 encoding the 4400 TCR-J. Target cells and controls are as described for FIGS. 10A-10C.

Figure 14A:
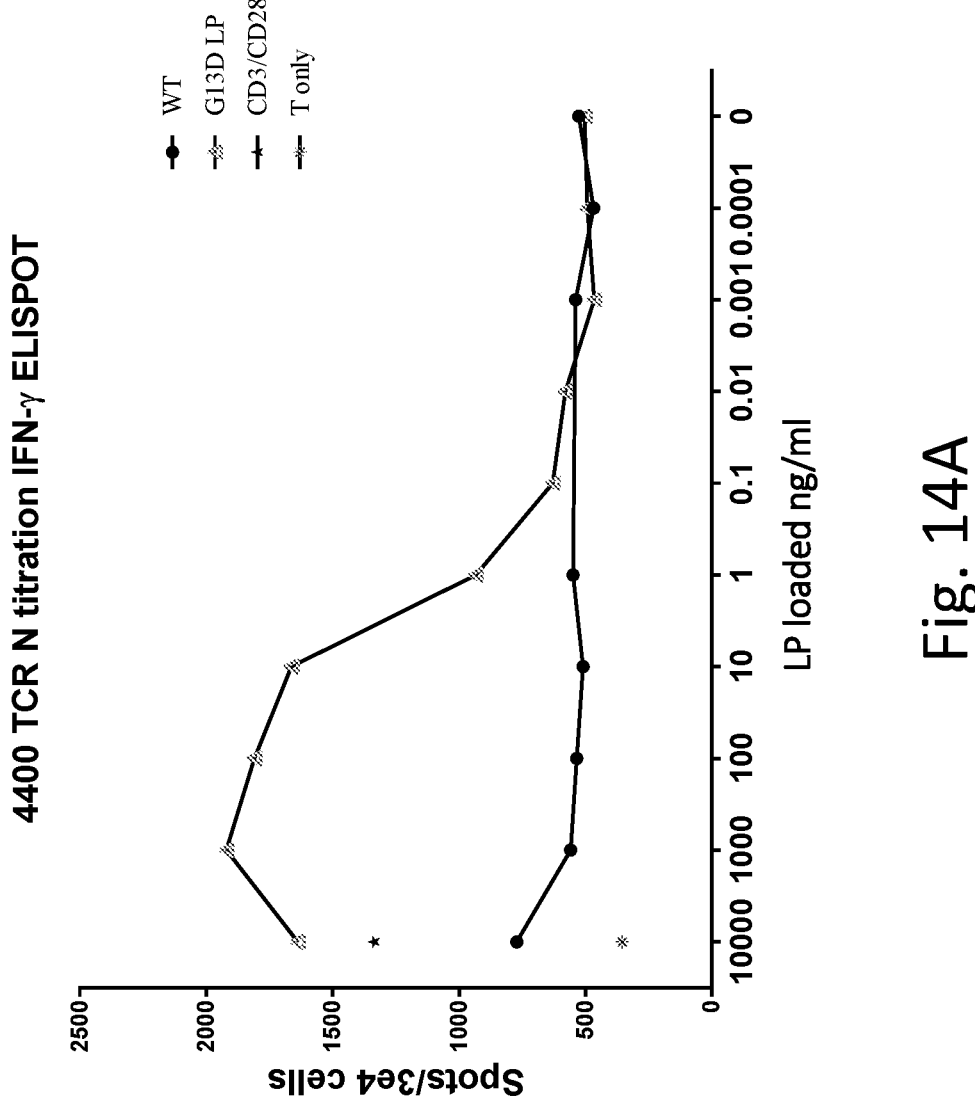
Figure 14B:
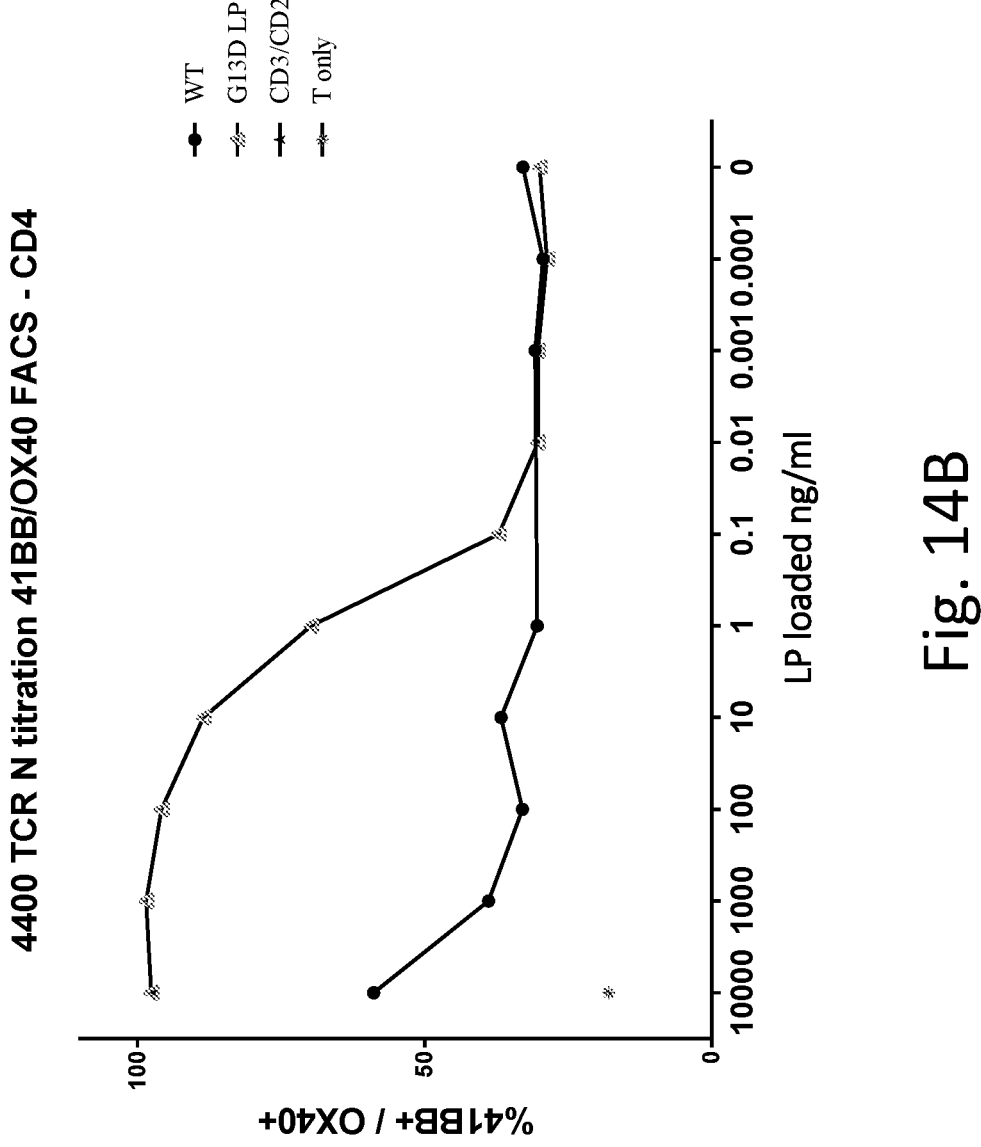
Figure 14C:
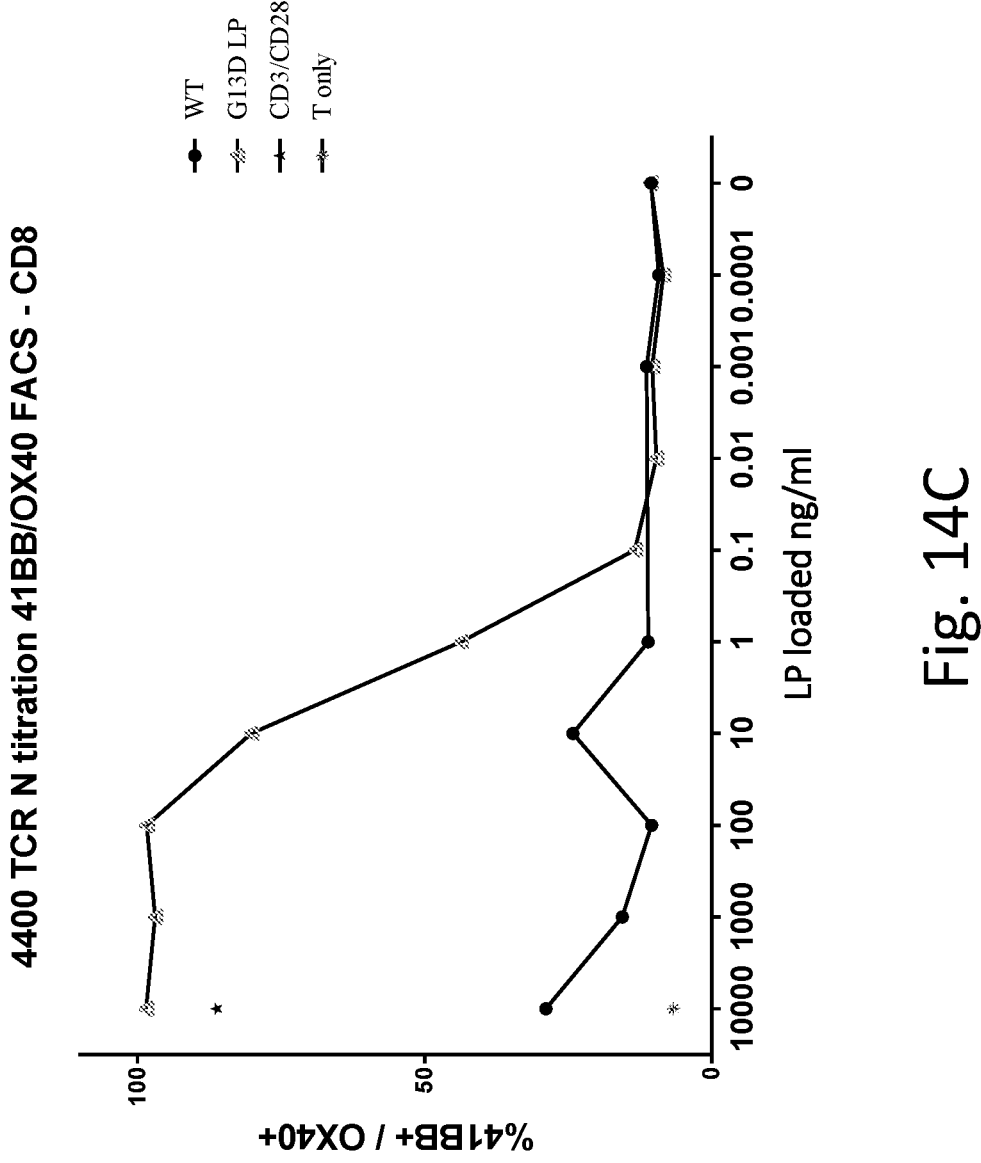

FIGS. 14A-14C are graphs showing the IFN-γ secretion (spots/3e4 cells) measured by ELISPOT assay (FIG. 14A) and the percentage of cells expressing one or both of 4-1BB and OX40 measured by FACS gated on CD4+/mTCR+ cells (FIG. 14B) or CD8+/mTCR+ cells (FIG. 14C) following co-culture of effector cells with target cells. Effector cells were healthy donor PBL transduced with the retroviral vector of Example 2 encoding the 4400 TCR-N. Target cells and controls are as described for FIGS. 10A-10C.

Figure 15:
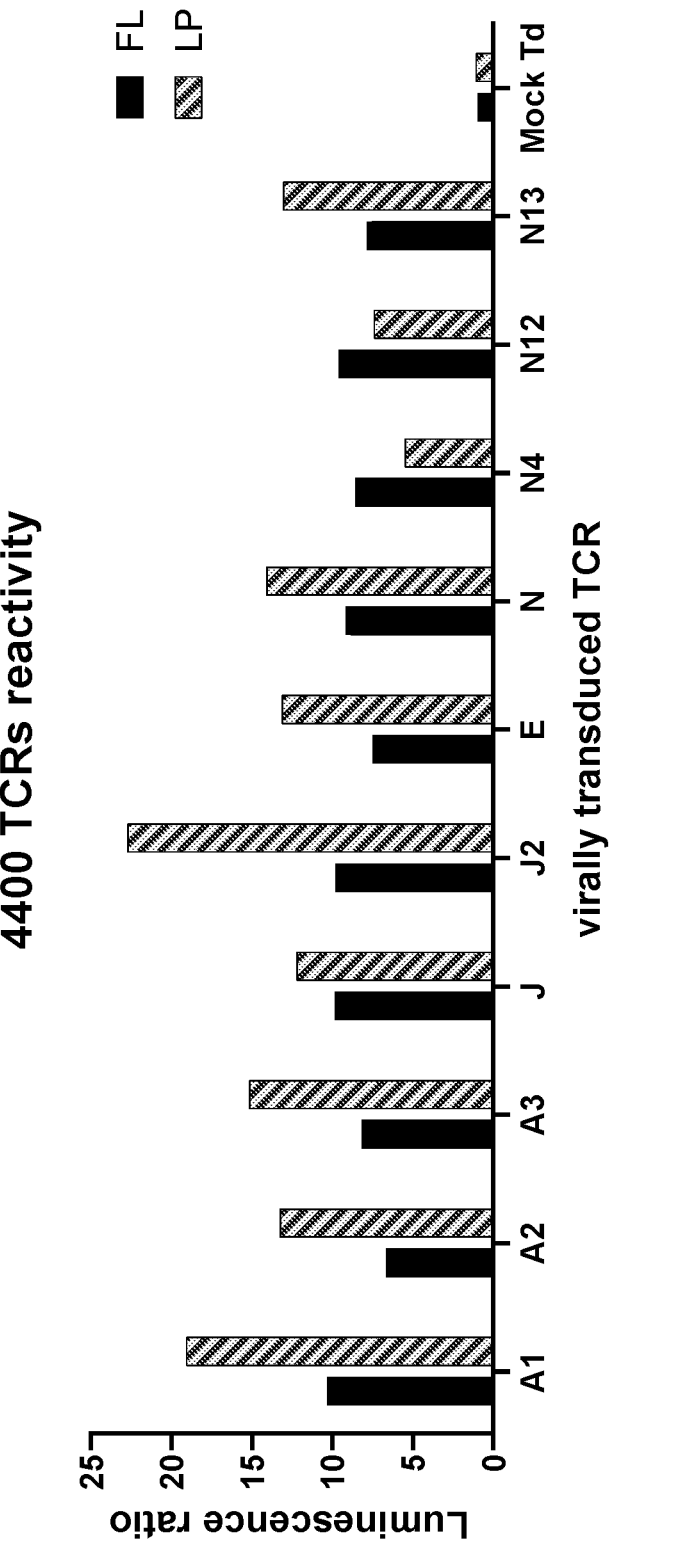

FIG. 15 is a graph showing the luminescence ratio obtained upon co-culture of effector cells with target cells. Effector cells were a Jurkat cell line stably expressing luciferase under the transcriptional control of an NFAT promotor and also stably expressing the CD4 co-receptor; these cells were virally transduced with one of the following TCRs: 4400 TCR-A1, 4400 TCR-A2, 4400 TCR-A3, 4400 TCR-J, 4400 TCR-J2, 4400 TCR-E, 4400 TCR-N, 4400 TCR-N4, 4400 TCR-N12, or 4400 TCR-N13. Target cells were DC (i) transfected with full length G13D KRAS mRNA or the corresponding full length WT KRAS mRNA; (ii) pulsed with the G13D 25-mer peptide or the corresponding WT 25-mer peptide of Example 1. Mock transduction was used as a negative control. The luminescence ratio is the ratio of the luminescence value obtained with G13D full-length gene (FL) to the luminescence value obtained with WT FL or the ratio of the luminescence value obtained with G13D long peptide (LP) to the luminescence value obtained with G13 WT LP.

Figure 16:
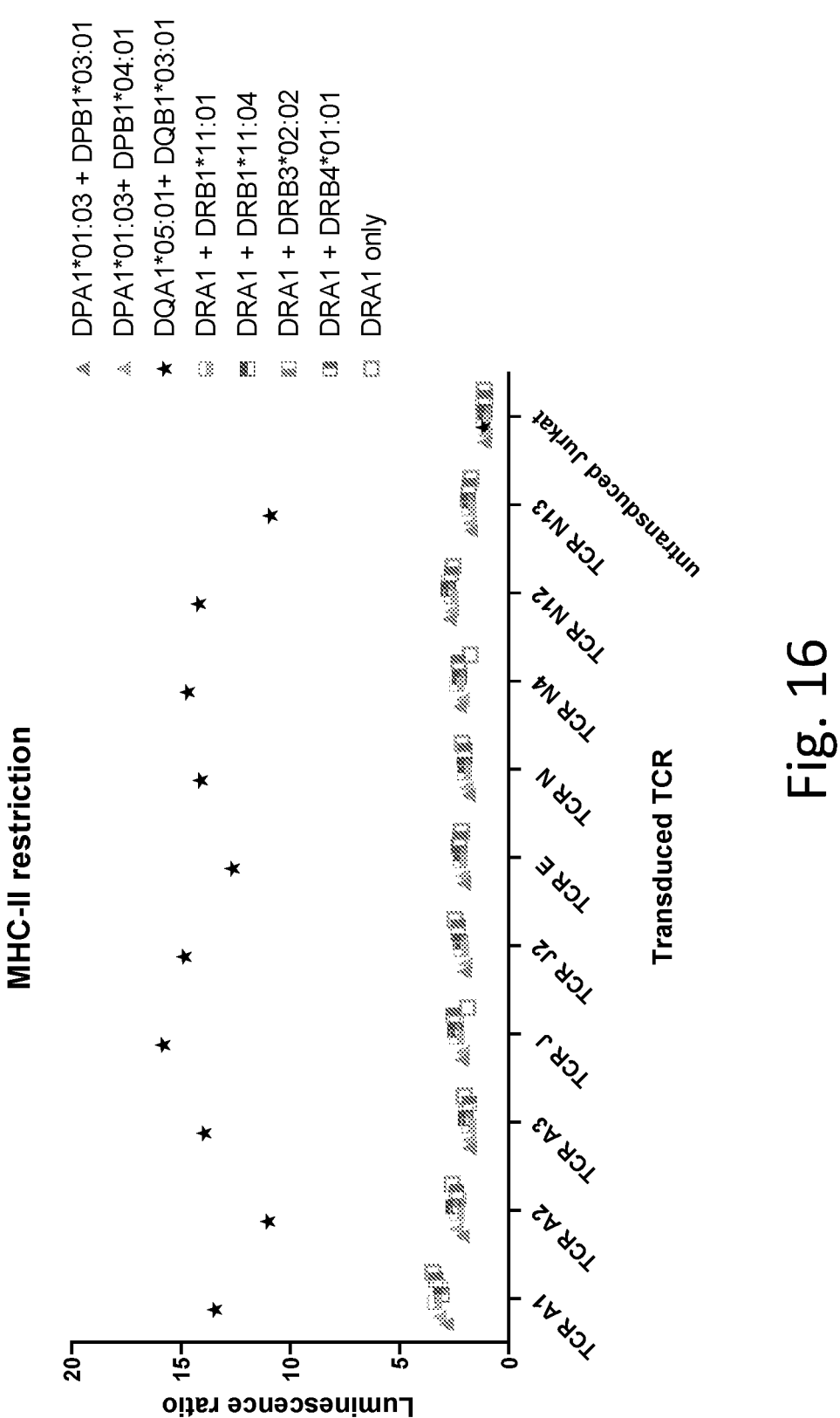

FIG. 16 is a graph showing the luminescence ratio obtained following co-culture of effector cells with target cells. COST cells (target cells) were independently transfected with the HLA heterodimers shown in FIG. 16 (alpha and beta) or with HLA DRA1 only and then were pulsed with the G13D 25-mer peptide of Example 1. The effector cells were the same as those described for FIG. 15. Untransduced Jurkat cells co-cultured with the same target cells served as a negative control. The luminescence ratio is the ratio of the luminescence readout value obtained in the experiment to the average luminescence readout value obtained with the control.

FIGS. 17A-17J are graphs showing the luminescence ratio obtained following co-culture of effector cells with target cells. Effector cells were a Jurkat-NFAT-firefly luciferase CD4+/CD8+ cell line independently virally transduced with one of the following TCRs: 4400 TCR-A1 (17A), 4400 TCR-A2 (17B), 4400 TCR-A3 (17C), 4400 TCR-J (17D), 4400 TCR-J2 (17E), 4400 TCR-E (17F), 4400 TCR-N (17G), 4400 TCR-N4 (17H), 4400 TCR-N12 (17I), or 4400 TCR-N13 (17J). Target cells were DCs loaded with the G13D 25-mer peptide (triangles) or the corresponding WT 25-mer peptide (circles) at one of the concentrations (ng/mL) shown. The luminescence ratio is the ratio of the luminescence readout value obtained in the experiment to the luminescence readout value obtained with the same cells co-cultured with DC loaded with DMSO only.

Figure 17A:
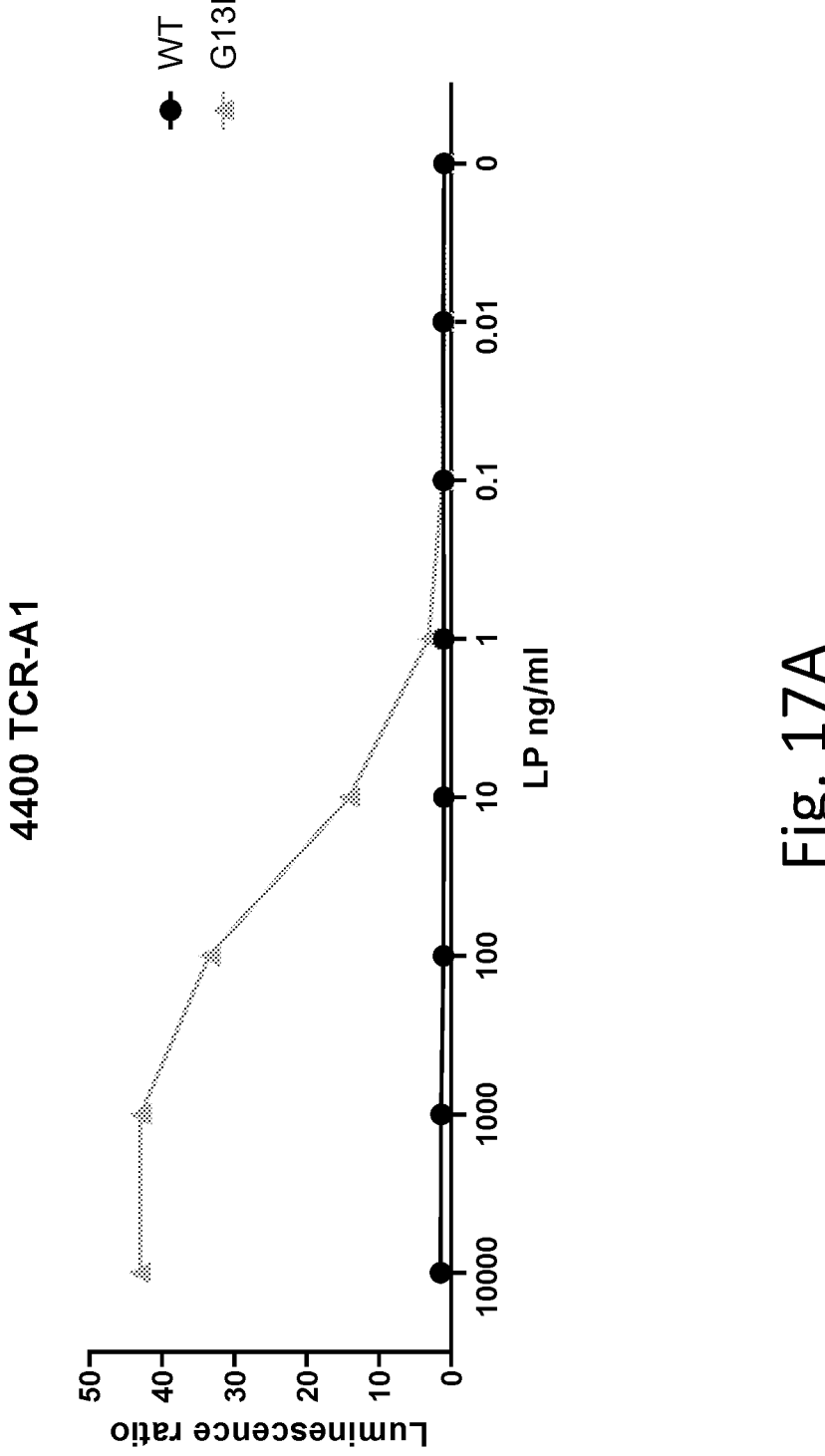
Figure 17B:
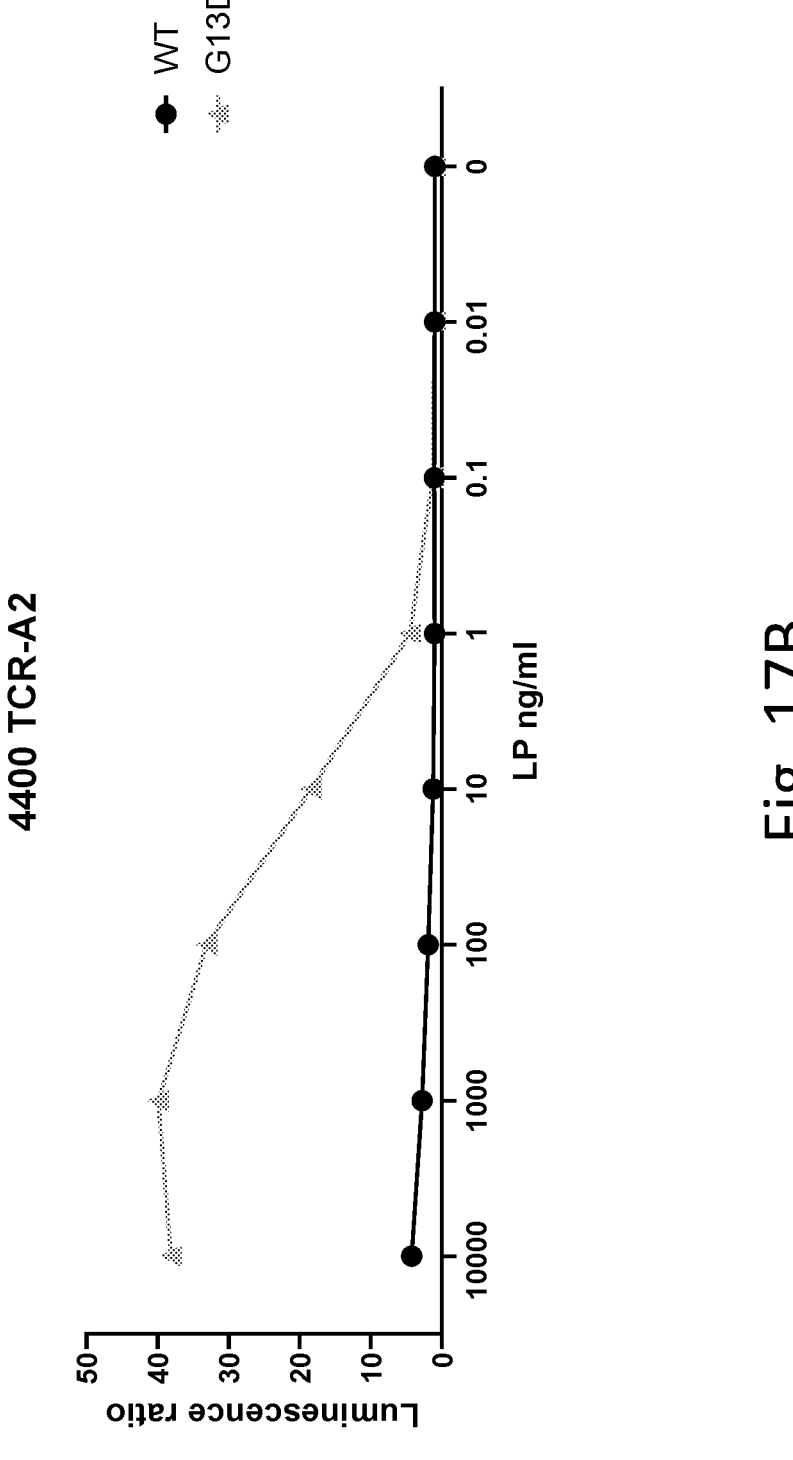
Figure 17C:
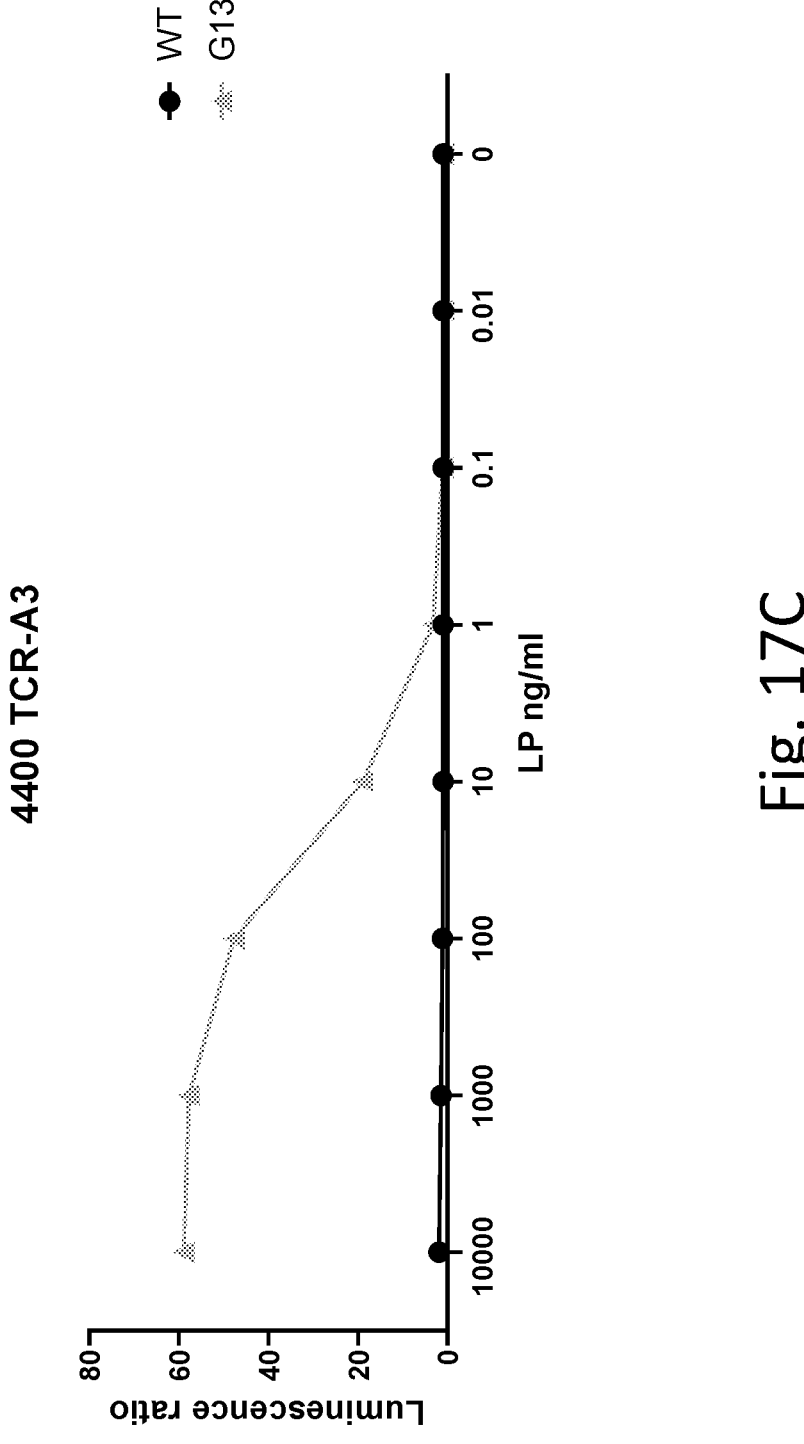
Figure 17D:
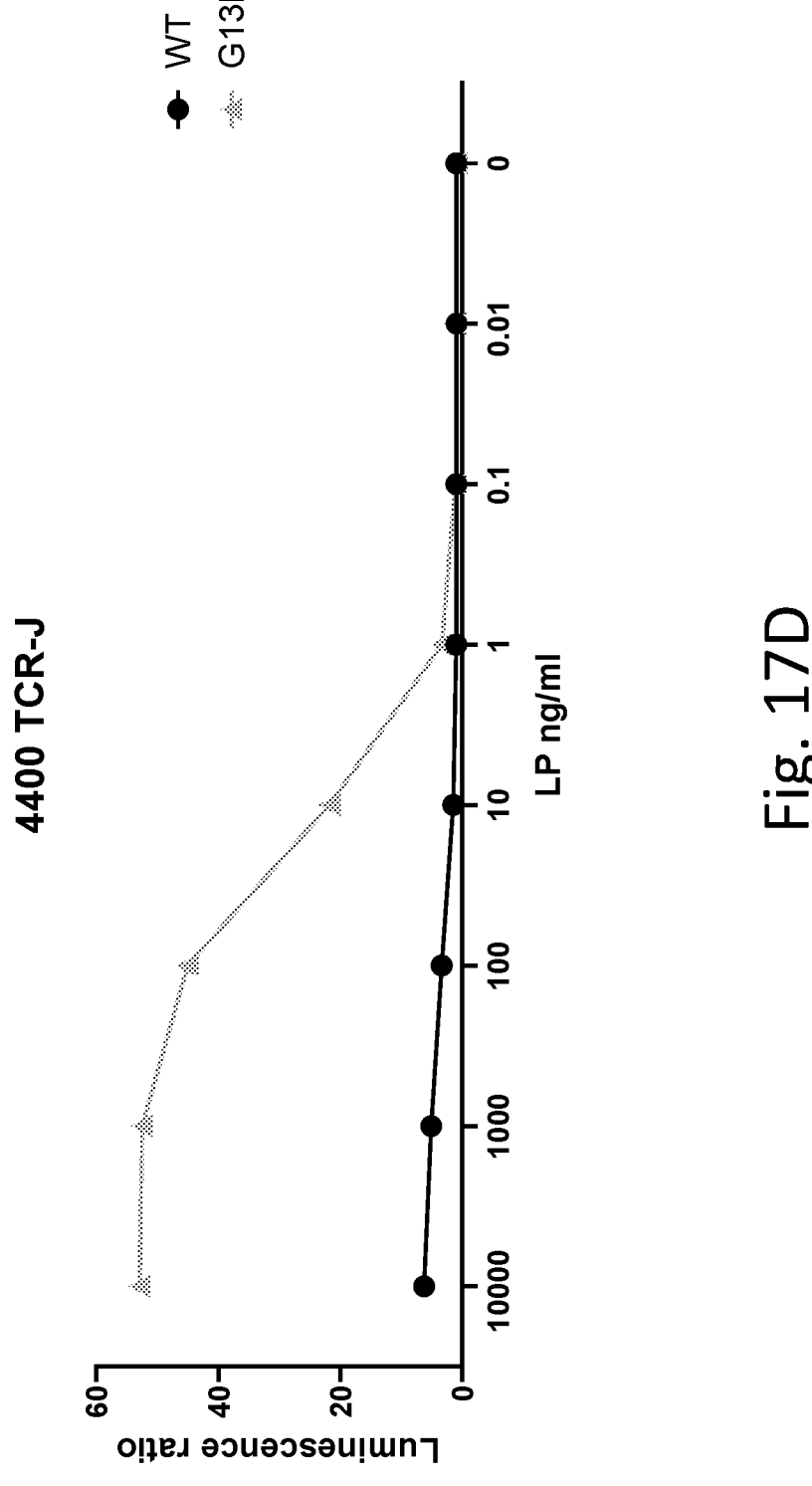
Figure 17E:
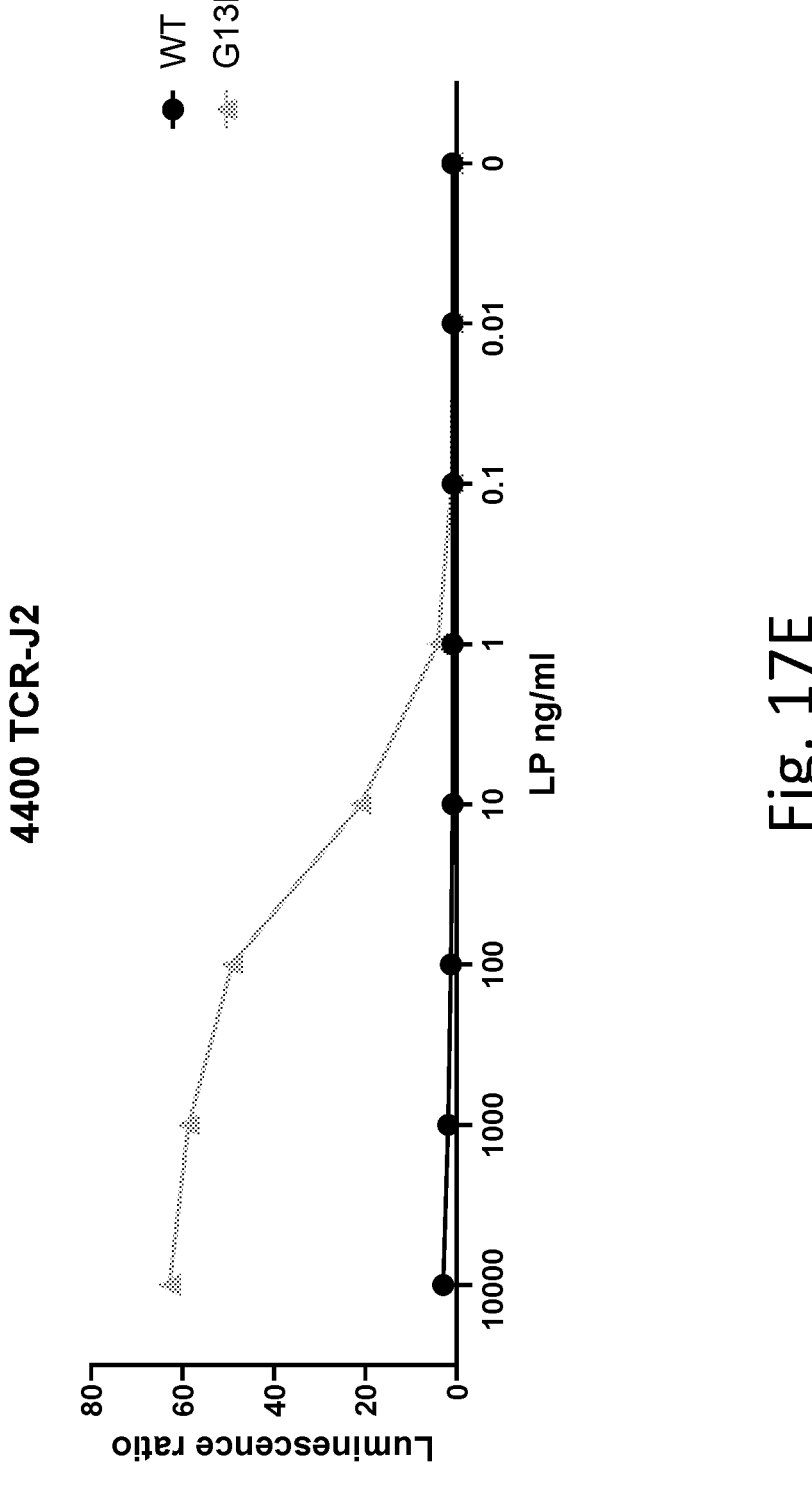
Figure 17F:
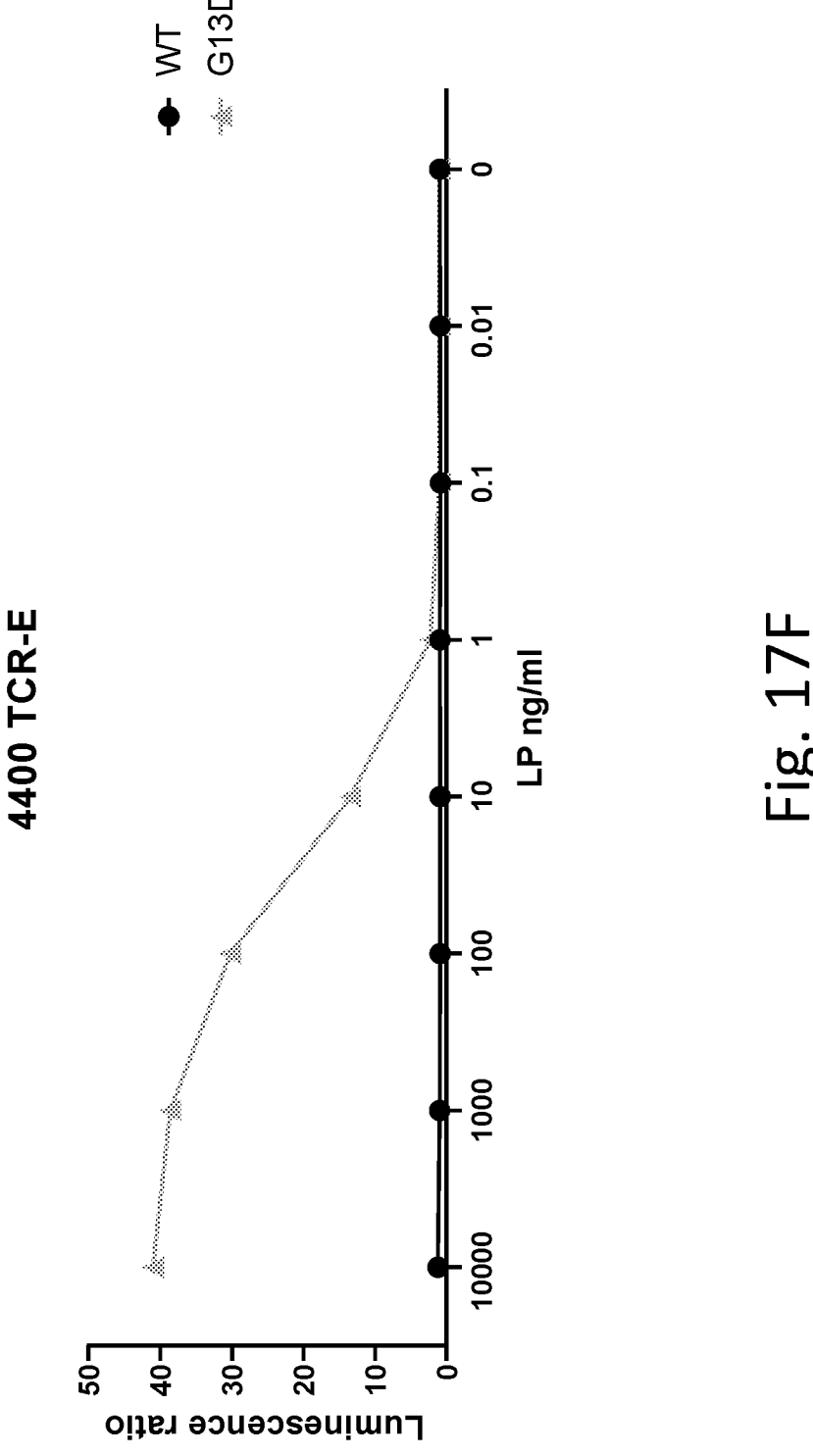
Figure 17G:
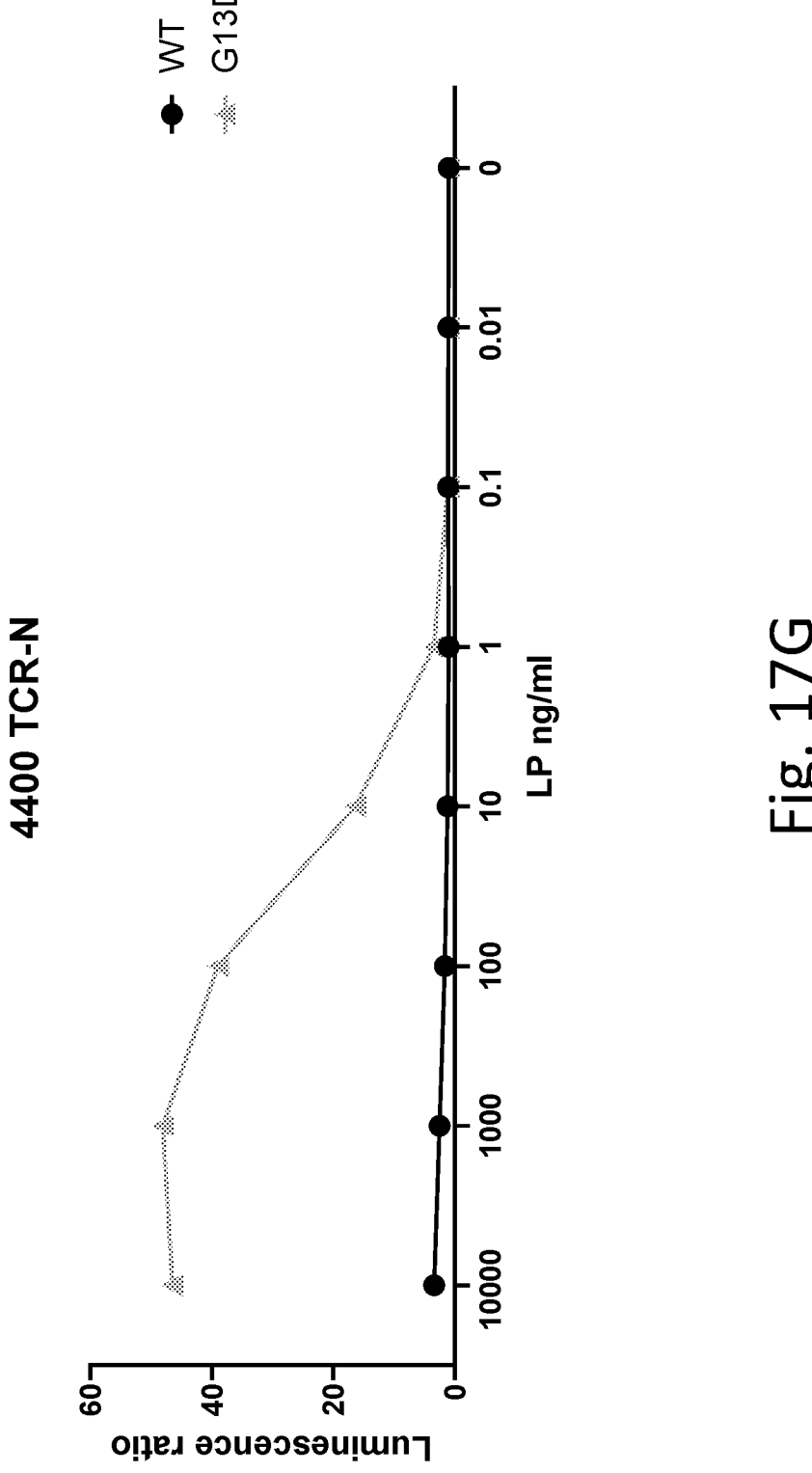
Figure 17H:
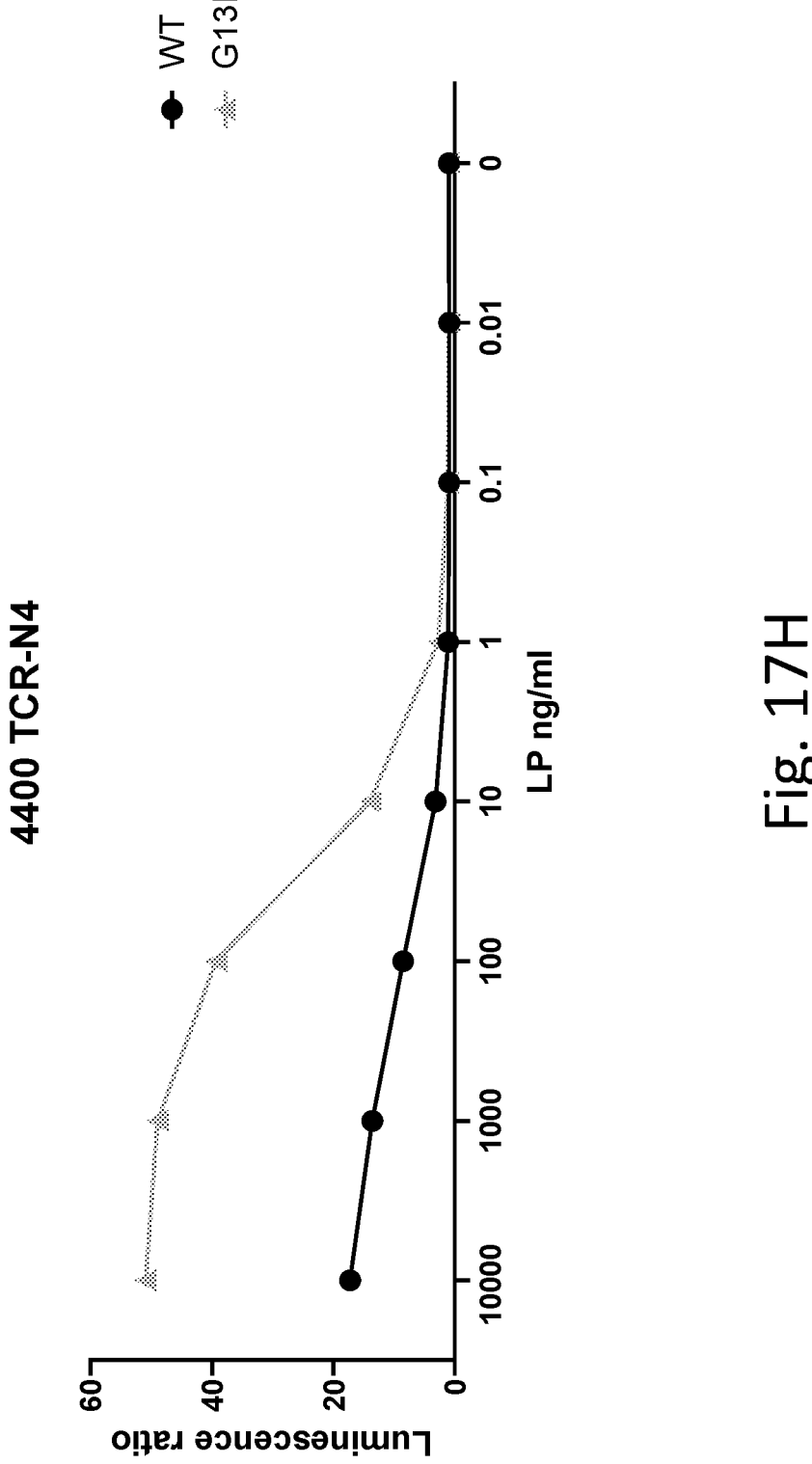
Figure 17I:
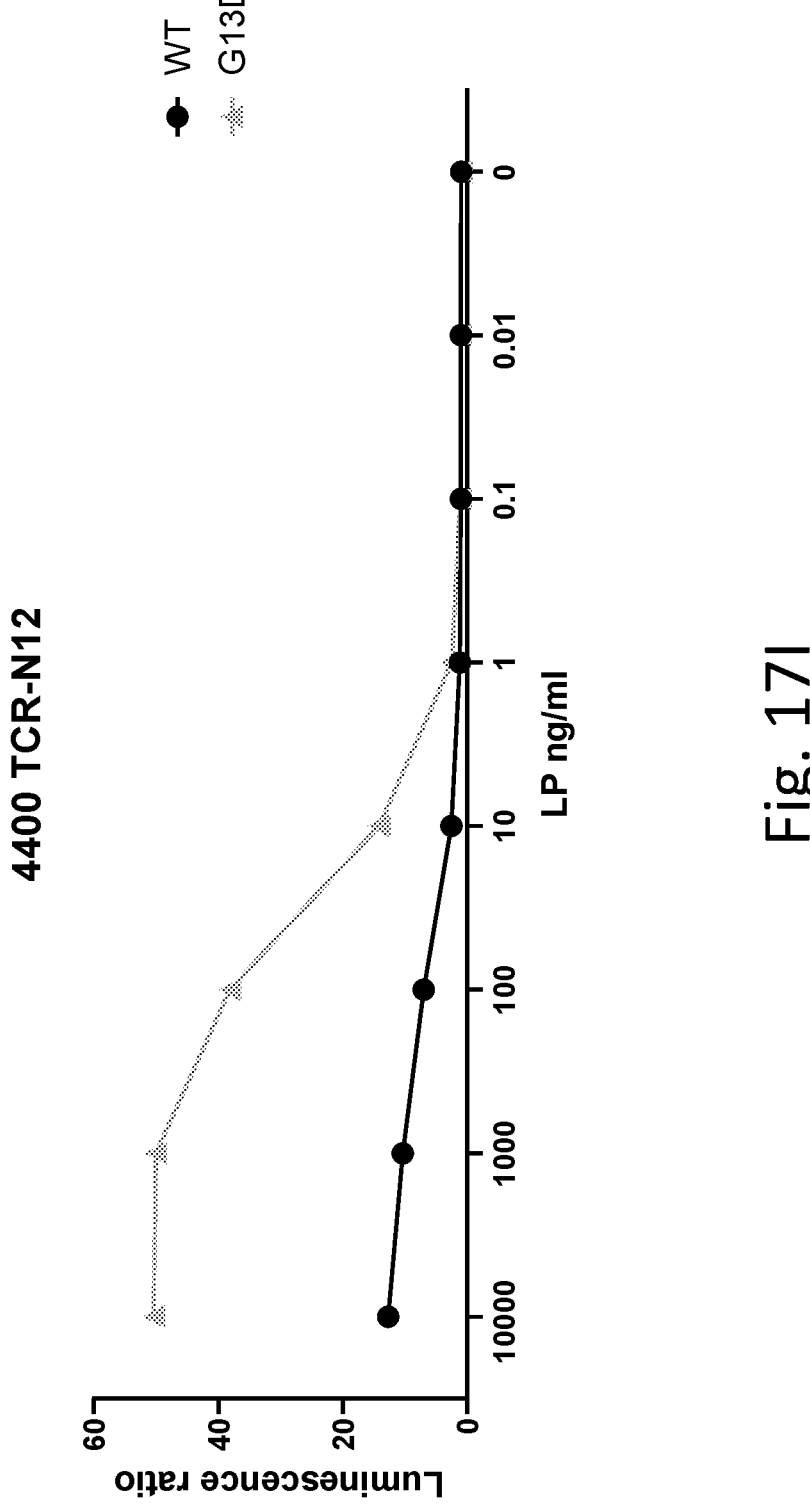
Figure 17J:
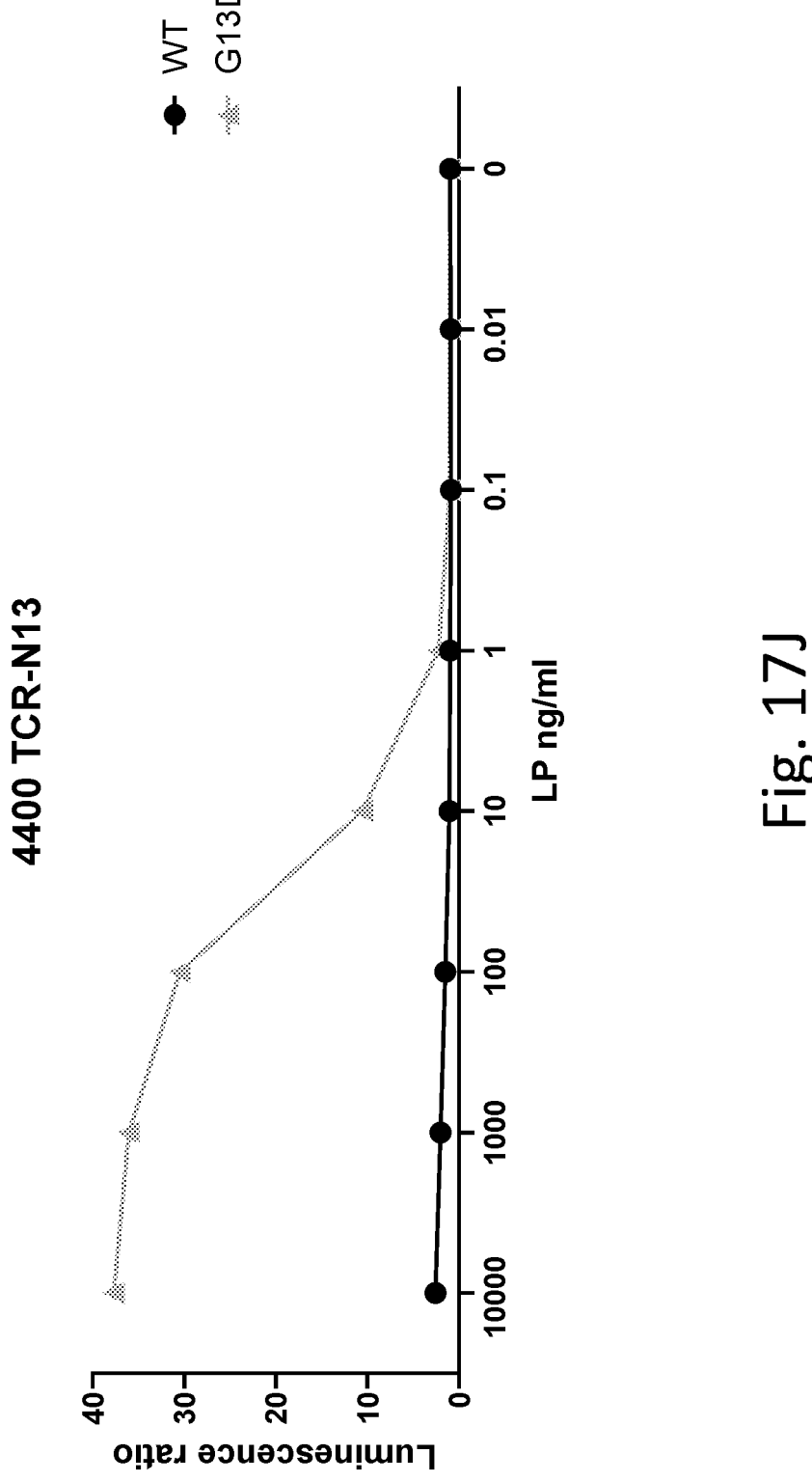
Figure 17K:
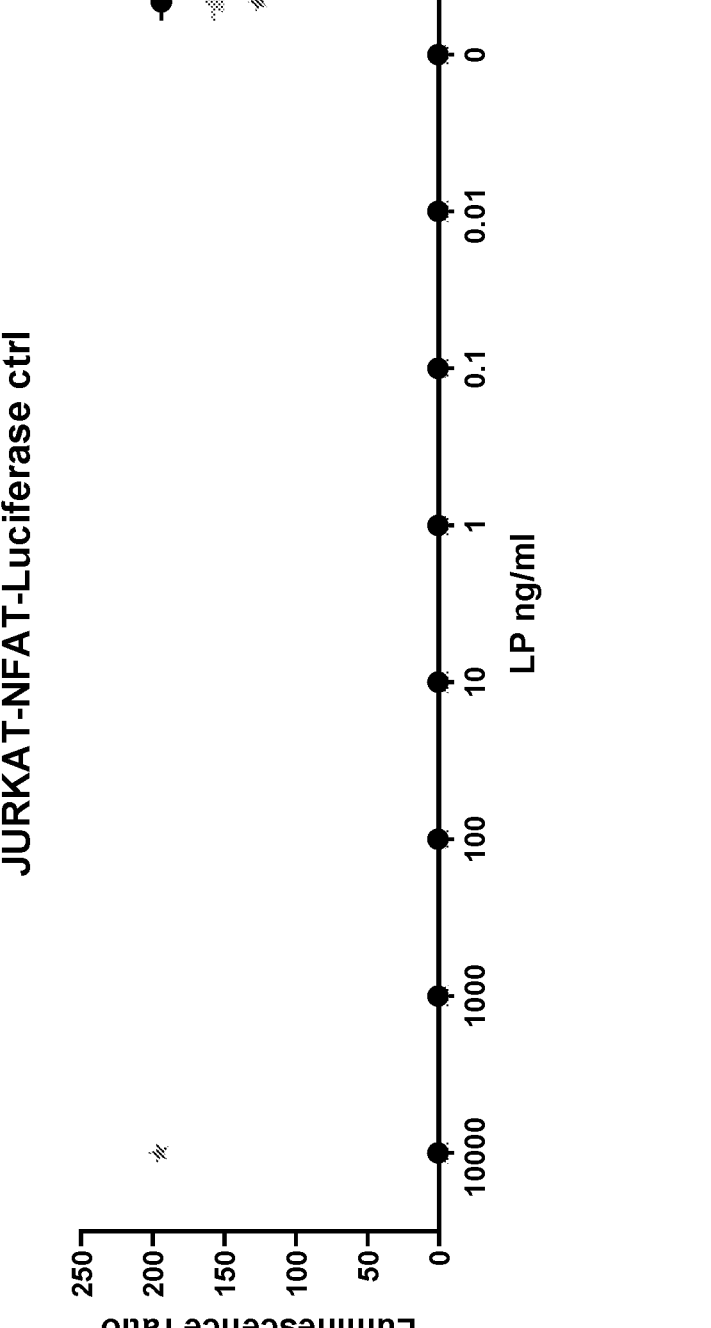

FIG. 17K is a graph showing the luminescence ratio obtained following a control experiment, namely the same experiment as that which was carried out for FIGS. 17A-17J, except that the Jurkat-NFAT firefly luciferase cell line was virally transduced with a control plasmid (a backbone plasmid without the gene encoding a TCR). Effector cells treated with PMA served as an additional control (stars). The luminescence ratio is as defined for FIGS. 17A-17J.

Figure 18:
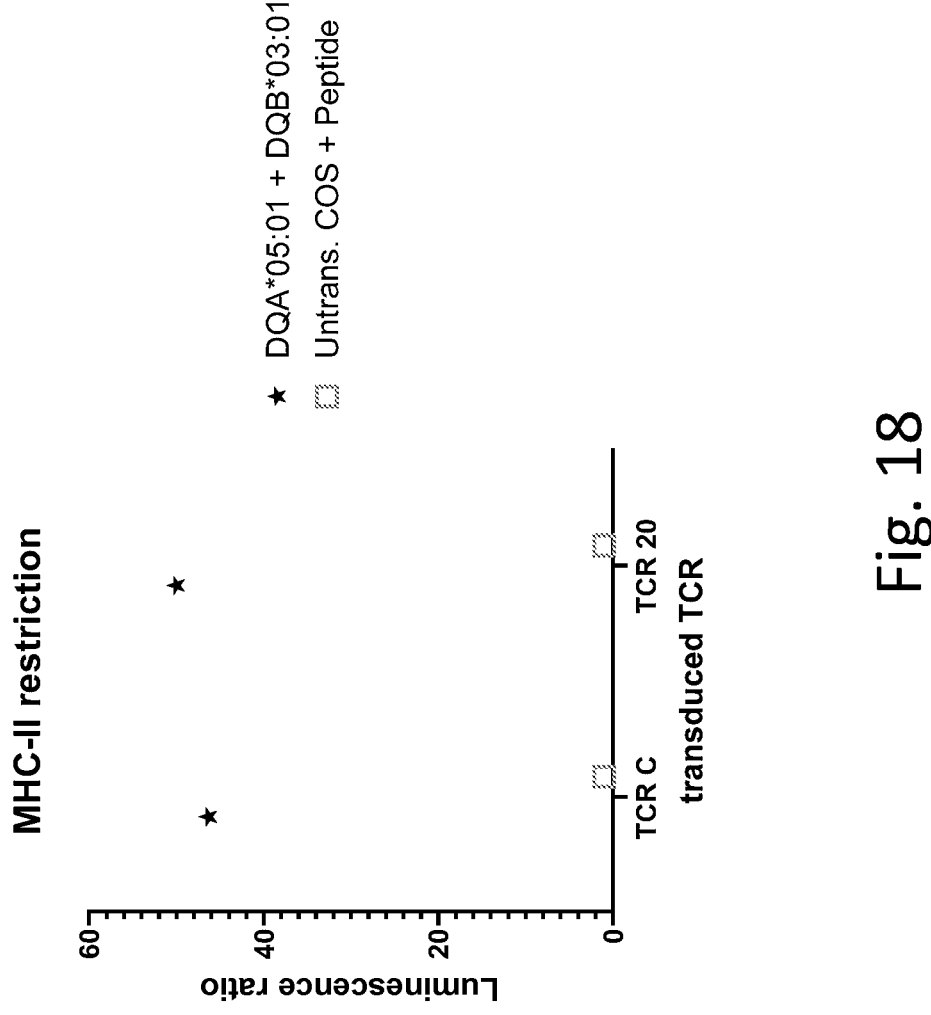

FIG. 18 is a graph showing the luminescence ratio obtained following co-culture of effector cells with target cells. COS7 cells (target cells) were transfected with the HLA-DQA1*05:01 and HLA-DQB1*03:01 heterodimer and then were pulsed with the G13D 25-mer peptide of Example 1. Effector cells were a Jurkat-NFAT-firefly luciferase CD4+/CD8+ cell line independently virally transduced with 4400 TCR-C or 4400 TCR-20. The effector cells were co-cultured with untransfected COS7 loaded with G13D 25-mer peptide as a negative control. The luminescence ratio is the ratio of the luminescence readout value of the experiment to the luminescence readout value of the relevant control.

Figure 19B:
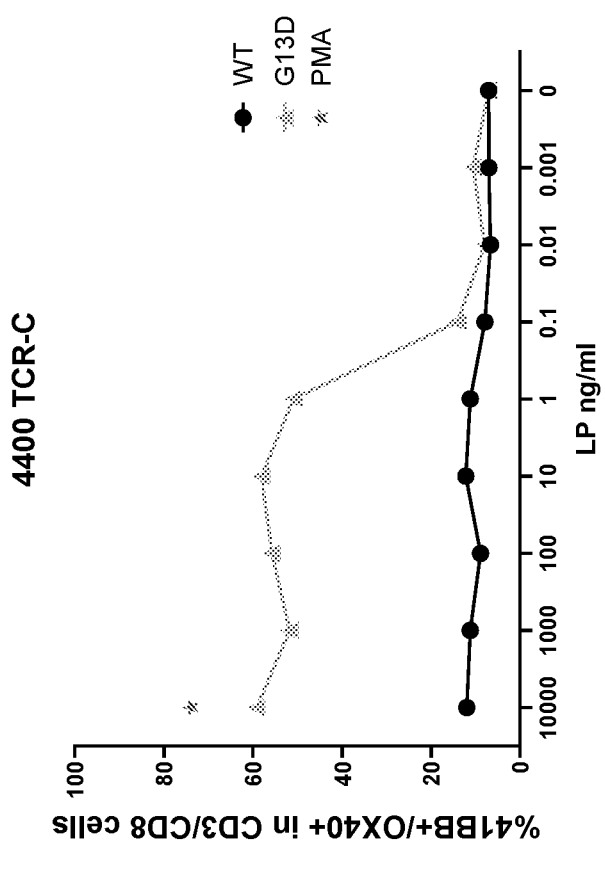
Figure 19A:
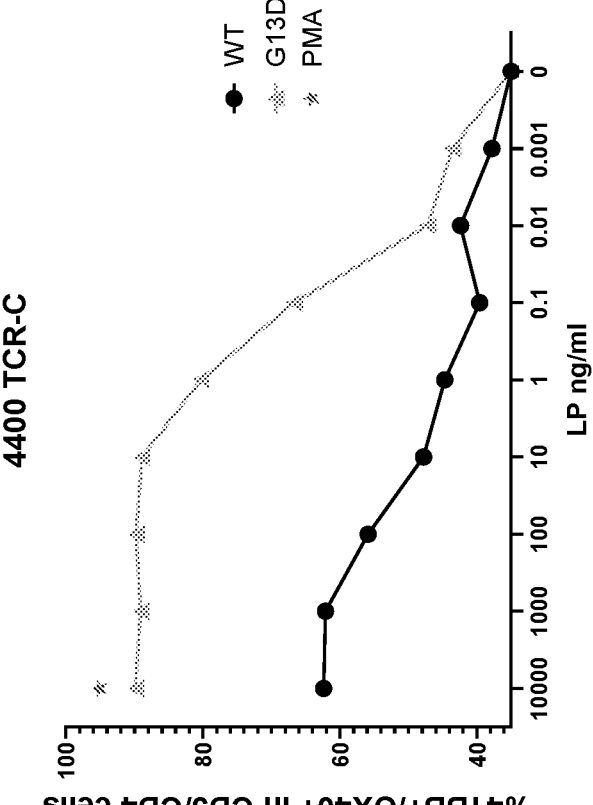
Figure 19D:
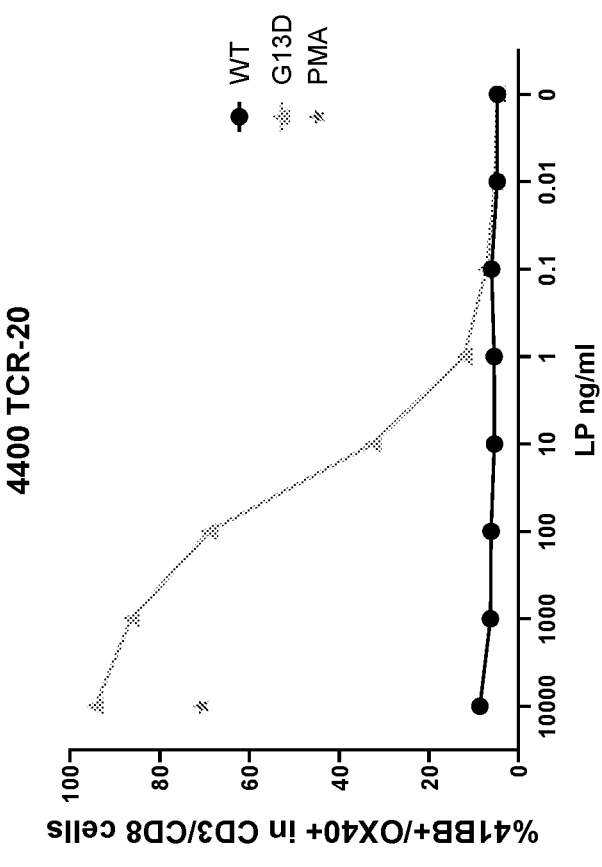
Figure 19C:
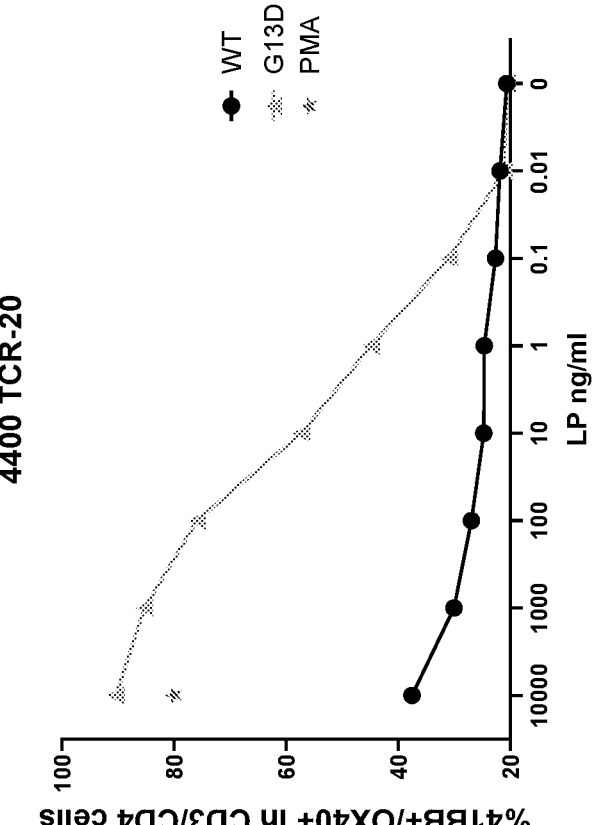

FIGS. 19A-19D are graphs showing the percentage of cells expressing one or both of 4-1BB and OX40 measured by FACS gated on CD8+ cells (FIGS. 19B and 19D) or CD4+ cells (FIGS. 19A and 19C) following co-culture of effector cells with target cells. Effector cells were PBL independently transduced with 4400 TCR-C (FIGS. 19A-19B) or 4400 TCR-20 (FIGS. 19C-19D). Target cells were DC pre-loaded with G13D 25-mer peptide (G13D) or the corresponding WT 25-mer peptide (WT) at one of the various concentrations shown.

DETAILED DESCRIPTION OF THE INVENTION

RAS family proteins belong to the large family of small GTPases. Without being bound to a particular theory or mechanism, it is believed that, when mutated, RAS proteins may be involved in signal transduction early in the oncogenesis of many human cancers. A single amino acid substitution may activate the protein. The mutated RAS protein product may be constitutively activated. Mutated RAS proteins may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers. The human RAS family proteins include KRAS, HRAS, and NRAS.

KRAS is also referred to as GTPase KRas, V-Ki-Ras2 Kirsten rat sarcoma viral oncogene, or KRAS2. There are two transcript variants of KRAS: KRAS variant A and KRAS variant B. Wild-type (WT) KRAS variant A has the amino acid sequence of SEQ ID NO: 51. WT KRAS variant B has the amino acid sequence of SEQ ID NO: 52. Hereinafter, references to "KRAS" (mutated or unmutated (WT)) refer to both variant A and variant B, unless specified otherwise. When activated, mutated KRAS binds to guanosine-5'-triphosphate (GTP) and converts GTP to guanosine 5'-diphosphate (GDP).

HRAS is another member of the RAS protein family. HRAS is also referred to as Harvey Rat Sarcoma Viral Oncoprotein, V-Ha-Ras Harvey Rat Sarcoma Viral Oncogene Homolog, or Ras Family Small GTP Binding Protein H-Ras. WT HRAS has the amino acid sequence of SEQ ID NO: 53.

NRAS is still another member of the RAS protein family. NRAS is also referred to as GTPase NRas, V-Ras Neuroblastoma RAS Viral Oncogene Homolog, or NRAS1. WT NRAS has the amino acid sequence of SEQ ID NO: 54.

An embodiment of the invention provides an isolated or purified TCR, wherein the TCR has antigenic specificity for a mutated human RAS amino acid sequence with a substitution of glycine at position 13 with aspartic acid, wherein the mutated human RAS amino acid sequence is a mutated human KRAS, a mutated human HRAS, or a mutated human NRAS amino acid sequence, and wherein position 13 is defined by reference to the WT human KRAS, WT human HRAS, or WT human NRAS protein, respectively. Hereinafter, references to a "TCR" also refer to functional portions and functional variants of the TCR, unless specified otherwise.

The mutated human RAS amino acid sequence may be a mutated human KRAS amino acid sequence, a mutated human HRAS amino acid sequence, or a mutated human NRAS amino acid sequence. The amino acid sequences of WT human KRAS, NRAS, and HRAS protein each have a length of 188 or 189 amino acid residues and have a high degree of identity to one another. For example, the amino acid sequence of the WT human NRAS protein is 86.8% identical to that of the WT human KRAS protein. Amino acid residues 1-86 of the WT human NRAS protein and the WT human KRAS protein are 100% identical. The amino acid sequence of the WT human HRAS protein is 86.3% identical to that of the WT human KRAS protein. Amino acid residues 1-94 of the WT human HRAS protein and the WT human KRAS protein are 100% identical. Hereinafter, references to "RAS" (mutated or unmutated (WT)) collectively refer to KRAS, HRAS, and NRAS, unless specified otherwise.

In an embodiment of the invention, the mutated human RAS amino acid sequence comprises a human RAS amino acid sequence with a substitution of glycine at position 13 with aspartic acid, wherein position 13 is defined by reference to the corresponding WT RAS protein. The WT RAS protein may be any one of WT KRAS protein (SEQ ID NO: 51 or 52), WT HRAS protein (SEQ ID NO: 53), or WT NRAS protein (SEQ ID NO: 54) because, as explained above, amino acid residues 1-86 of the WT human NRAS protein and the WT human KRAS protein are 100% identical, and amino acid residues 1-94 of the WT human HRAS protein and the WT human KRAS protein are 100% identical. Accordingly, the amino acid residue at position 13 of each of WT KRAS, WT HRAS, and WT NRAS protein is the same, namely, glycine.

The mutated human RAS amino acid sequence has a substitution of glycine at position 13 with aspartic acid. In this regard, embodiments of the invention provide TCRs with antigenic specificity for any human RAS protein, polypeptide or peptide amino acid sequence with a G13D mutation.

Mutations and substitutions of RAS are defined herein by reference to the amino acid sequence of the corresponding WT RAS protein. Thus, mutations and substitutions of RAS are described herein by reference to the amino acid residue present at a particular position in WT RAS protein (namely, position 13), followed by the position number, followed by the amino acid residue with which that residue has been replaced in the particular mutation or substitution under discussion. A RAS amino acid sequence (e.g., a RAS peptide) may comprise fewer than all of the amino acid residues of the full-length, WT RAS protein. Accordingly, position 13 is defined herein by reference to the WT full-length RAS protein (namely, any one of SEQ ID NOs: 51-54) with the understanding that the actual position of the corresponding residue in a particular example of a RAS amino acid sequence may be different. When the positions are as defined by any one of SEQ ID NOs: 51-54, the term "G13" refers to the glycine normally present at position 13 of any one of SEQ ID NOs: 51-54, and "G13D" indicates that the glycine normally present at position 13 of any one of SEQ ID NOs: 51-54 is replaced by aspartic acid. For example, when a particular example of a RAS amino acid sequence is, e.g., TEYKLVVVGAGGVGKSALTIQLI (SEQ ID NO: 113) (an exemplary WT KRAS peptide corresponding to contiguous amino acid residues 2 to 24 of SEQ ID NO: 51), "G13D" refers to a substitution of the underlined glycine in SEQ ID NO: 113 with aspartic acid, even though the actual position of the underlined glycine in SEQ ID NO: 113 is 12. Human RAS amino acid sequences with the G13D mutation are hereinafter referred to as "G13D RAS".

Examples of full-length RAS proteins with the G13D mutation are set forth in Table 1 below.

TABLE 1

| Mutated Full-Length RAS Protein | SEQ ID NO: |
|---|---|
| G13D KRAS variant A | 55 |
| G13D KRAS variant B | 56 |
| G13D HRAS | 57 |
| G13D NRAS | 58 |

In an embodiment of the invention, the TCR has antigenic specificity for a RAS peptide with the G13D mutation described above, wherein the G13D RAS peptide has any length. In an embodiment of the invention, the G13D RAS peptide has any length suitable for binding to any of the HLA Class II molecules described herein. For example, the TCR may have antigenic specificity for a RAS peptide with the G13D mutation, the RAS peptide having a length of about 11 to about 30 amino acid residues, about 12 to about 24 amino acid residues, or about 18 to about 20 amino acid residues. The G13D RAS peptide may comprise any contiguous amino acid residues of mutated RAS protein which include the G13D mutation. In an embodiment of the invention, the TCR may have antigenic specificity for a RAS peptide with the G13D mutation, the mutated RAS peptide having a length of about 30 amino acid residues, about 29 amino acid residues, about 28 amino acid residues, about 27 amino acid residues, about 26 amino acid residues, about 25 amino acid residues, about 24 amino acid residues, about 23 amino acid residues, about 22 amino acid residues, about 21 amino acid residues, about 20 amino acid residues, about 19 amino acid residues, about 18 amino acid residues, about 17 amino acid residues, about 16 amino acid residues, about 15 amino acid residues, about 14 amino acid residues, about 13 amino acid residues, about 12 amino acid residues, about 11 amino acid residues, or a range of any two of the foregoing values. An example of a specific peptide with the G13D mutation, which may be recognized by the inventive TCRs, is MTEYKLVVVGAGDVGKSALTIQLI (SEQ ID NO: 106). Another example of a specific peptide with the G13D mutation, which may be recognized by the inventive TCRs, is MTEYKLVVVGAGDVGKSALTIQLIQ (SEQ ID NO: 252). In an embodiment of the invention, the TCR has antigenic specificity for the mutated human RAS amino acid sequence of SEQ ID NO: 106. In another embodiment of the invention, the TCR has antigenic specificity for the mutated human RAS amino acid sequence of SEQ ID NO: 252. In an embodiment of the invention, the TCR does not have antigenic specificity for the wild-type human RAS amino acid sequence of MTEYKLVVVGAGGVGKSALTIQLI (SEQ ID NO: 107). In another embodiment of the invention, the TCR does not have antigenic specificity for the wild-type human RAS amino acid sequence of MTEYKLVVVGAGGVGKSALTIQLIQ (SEQ ID NO: 253).

In an embodiment of the invention, the inventive TCRs are able to recognize G13D RAS presented by an HLA Class II molecule. In this regard, the TCR may elicit an immune response upon binding to G13D RAS within the context of an HLA Class II molecule. The inventive TCRs are able to recognize G13D RAS that is presented by an HLA Class II molecule and may bind to the HLA Class II molecule in addition to G13D RAS.

In an embodiment of the invention, the HLA Class II molecule is an HLA-DQ heterodimer. The HLA-DQ heterodimer is a cell surface receptor including an α chain and a β chain. The HLA-DQ α chain is encoded by the HLA-DQA1 gene. HLA-DQA1 alleles may include DQA1*01:01, DQA1*01:02, DQA1*01:03, DQA1*01:04, DQA1*02:01, DQA1*03:01, DQA1*03:02, DQA1*03:03, DQA1*04:01, DQA1*05:01, DQA1*05:05, and DQA1*06: 01. The HLA-DQ β chain is encoded by the HLA-DQB1 gene. HLA-DQB1 alleles may include HLA-DQB1*02:01, HLA-DQB1*02:02, HLA-DQB1*02:03, HLA-DQB1*03: 01, HLA-DQB1*03:02, HLA-DQB1*03:03, HLA-DQB1*03:04, HLA-DQB1*03:05, HLA-DQB1*04:01, HLA-DQB1*04:02, HLA-DQB1*05:01, HLA-DQB1*05: 02, HLA-DQB1*05:03, HLA-DQB1*05:04, HLA-DQB1*06:01, HLA-DQB1*06:02, HLA-DQB1*06:03, HLA-DQB1*06:04, HLA-DQB1*06:05, and HLA-DQB1*06:09. In an embodiment of the invention, the HLA Class II molecule is an HLA-DQA1:HLA-DQB1 heterodimer. In an especially preferred embodiment, the HLA Class II molecule is expressed by the HLA-DQA1*05:01:HLA-DQB1*03:01 alleles (namely, an HLA-DQA1*05:01:HLA-DQB1*03:01 heterodimer).

The TCRs of the invention may provide any one or more of a variety of advantages, including when expressed by cells used for adoptive cell transfer. G13D RAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, because the G13D mutation is likely to occur in the early stages of tumorigenesis, the G13D RAS mutation may be expressed on substantially all of a patient's cancer cells. The inventive TCRs may, advantageously, successfully treat or prevent G13D RAS-positive cancers that do not respond to other types of treatment such as, for example, chemotherapy, surgery, or radiation. Additionally, the inventive TCRs may provide highly avid recognition of G13D RAS, which may provide the ability to recognize unmanipulated tumor cells (e.g., tumor cells that have not been treated with interferon (IFN)-γ, transfected with a vector encoding one or both of G13D RAS and and any of the HLA-DQ heterodimers described herein, pulsed with a G13D RAS peptide, or a combination thereof). KRAS mutations are found in about 30% of all cancer patients. The G13D RAS mutation is found in about 13% of cancer patients with a KRAS mutation. Moreover, the HLA-DQA1*05:01:HLA-DQB1*03:01 allele combination is expressed by about 35% of humans with Caucasian ethnicity in the United States and is also commonly expressed by humans of other ethnicities. Accordingly, the inventive TCRs may increase the number of immunotherapy-eligible cancer patients to include those patients that express the HLA-DQA1*05:01:HLA-DQB1*03:01 allele combination who may not be eligible for immunotherapy using TCRs that recognize RAS presented by other MHC molecules. Moreover, the inventive TCRs, polypeptides and proteins comprise human CDR and variable region amino acid sequences, which may reduce the risk of rejection by the human immune system as compared to, e.g., TCRs, polypeptides and proteins comprising mouse CDR and variable region amino acid sequences.

The phrase "antigenic specificity," as used herein, means that the TCR can specifically bind to and immunologically recognize G13D RAS with high avidity. For example, a TCR may be considered to have "antigenic specificity" for G13D RAS if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, HLA Class II molecule positive target cells pulsed with a low concentration of G13D RAS peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative, HLA Class II molecule positive target cells into which a nucleotide sequence encoding G13D RAS has been introduced such that the target cell expresses G13D RAS. Cells expressing the inventive TCRs may also secrete IFN-γ upon co-culture with antigen-negative, HLA Class II molecule positive target cells pulsed with higher concentrations of G13D RAS peptide. The HLA Class II molecule may be any of the HLA Class II molecules described herein.

Alternatively or additionally, a TCR may be considered to have "antigenic specificity" for G13D RAS if T cells expressing the TCR secrete at least twice (e.g., five times) as much IFN-γ upon co-culture with (a) antigen-negative, HLA Class II molecule positive target cells pulsed with a low concentration of G13D RAS peptide or (b) antigen-negative, HLA Class II molecule positive target cells into which a nucleotide sequence encoding G13D RAS has been introduced such that the target cell expresses G13D RAS as compared to the amount of IFN-γ expressed by a negative control. The negative control may be, for example, (i) T cells expressing the TCR, co-cultured with (a) antigen-negative, HLA Class II molecule positive target cells pulsed with the same concentration of an irrelevant peptide (e.g., some other peptide with a different sequence from the G13D RAS peptide) or (b) antigen-negative, HLA Class II molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, HLA Class II molecule positive target cells pulsed with the same concentration of G13D RAS peptide or (b) antigen-negative, HLA Class II molecule positive target cells into which a nucleotide sequence encoding G13D RAS has been introduced such that the target cell expresses G13D RAS. The HLA Class II molecule expressed by the target cells of the negative control would be the same HLA Class II molecule expressed by the target cells that are co-cultured with the T cells being tested. The HLA Class II molecule may be any of the HLA Class II molecules described herein. IFN-γ secretion may be measured by methods known in the art such as, for example, enzyme-linked immunosorbent assay (ELISA).

Alternatively or additionally, a TCR may be considered to have "antigenic specificity" for G13D RAS if at least twice (e.g., five times) as many of the numbers of T cells expressing the TCR secrete IFN-γ upon co-culture with (a) antigen-negative, HLA Class II molecule positive target cells pulsed with a low concentration of G13D RAS peptide or (b) antigen-negative, HLA Class II molecule positive target cells into which a nucleotide sequence encoding G13D RAS has been introduced such that the target cell expresses G13D RAS as compared to the numbers of negative control T cells that secrete IFN-γ. The HLA Class II molecule, concentration of peptide, and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for G13D RAS if T cells expressing the TCR upregulate expression of one or more T-cell activation markers as measured by, for example, flow cytometry after stimulation with target cells expressing G13D RAS. Examples of T-cell activation markers include 4-1BB, OX40, CD107a, CD69, and cytokines that are upregulated upon antigen stimulation (e.g., tumor necrosis factor (TNF), interleukin (IL)-2, etc.).

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for G13D RAS. In some embodiments, the TCR is non-naturally occurring.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 1 (CDR1 of a chain of 4400 TCR-A1), a CDR2 comprising the amino acid sequence of SEQ ID NO: 2 (CDR2 of a chain of 4400 TCR-A1), and a CDR3 comprising the amino acid sequence of SEQ ID NO: 3 (CDR3 of a chain of 4400 TCR-A1), and a second polypeptide chain comprising a CDR1 comprising the amino acid sequence of SEQ ID NO: 4 (CDR1 of β chain of 4400 TCR-A1), a CDR2 comprising the amino acid sequence of SEQ ID NO: 5 (CDR2 of β chain of 4400 TCR-A1), and a CDR3 comprising the amino acid sequence of SEQ ID NO: 6 (CDR3 of β chain of 4400 TCR-A1).

In another embodiment of the invention, the TCR comprises a first polypeptide chain comprising a CDR1 comprising the amino acid sequence of SEQ ID NO: 11 (CDR1 of a chain of 4400 TCR-A2), a CDR2 comprising the amino acid sequence of SEQ ID NO: 12 (CDR2 of a chain of 4400 TCR-A2), and a CDR3 comprising the amino acid sequence of SEQ ID NO: 13 (CDR3 of a chain of 4400 TCR-A2), and a second polypeptide chain comprising a CDR1 comprising the amino acid sequence of SEQ ID NO: 14 (CDR1 of (3 chain of 4400 TCR-A2), a CDR2 comprising the amino acid sequence of SEQ ID NO: 15 (CDR2 of β chain of 4400 TCR-A2), and a CDR3 comprising the amino acid sequence of SEQ ID NO: 16 (CDR3 of β chain of 4400 TCR-A2).

In another embodiment of the invention, the TCR comprises a first polypeptide chain comprising a CDR1 comprising the amino acid sequence of SEQ ID NO: 21 (CDR1 of a chain of 4400 TCR-E), a CDR2 comprising the amino acid sequence of SEQ ID NO: 22 (CDR2 of a chain of 4400 TCR-E), and a CDR3 comprising the amino acid sequence of SEQ ID NO: 23 (CDR3 of a chain of 4400 TCR-E), and a second polypeptide chain comprising a CDR1 comprising the amino acid sequence of SEQ ID NO: 24 (CDR1 of β chain of 4400 TCR-E), a CDR2 comprising the amino acid sequence of SEQ ID NO: 25 (CDR2 of β chain of 4400 TCR-E), and a CDR3 comprising the amino acid sequence of SEQ ID NO: 26 (CDR3 of β chain of 4400 TCR-E).

In another embodiment of the invention, the TCR comprises a first polypeptide chain comprising a CDR1 comprising the amino acid sequence of SEQ ID NO: 31 (CDR1 of a chain of 4400 TCR-J), a CDR2 comprising the amino acid sequence of SEQ ID NO: 32 (CDR2 of a chain of 4400 TCR-J), and a CDR3 comprising the amino acid sequence of SEQ ID NO: 33 (CDR3 of a chain of 4400 TCR-J), and a second polypeptide chain comprising a CDR1 comprising the amino acid sequence of SEQ ID NO: 34 (CDR1 of β chain of 4400 TCR-J), a CDR2 comprising the amino acid sequence of SEQ ID NO: 35 (CDR2 of β chain of 4400 TCR-J), and a CDR3 comprising the amino acid sequence of SEQ ID NO: 36 (CDR3 of β chain of 4400 TCR-J).

In another embodiment of the invention, the TCR comprises a first polypeptide chain comprising a CDR1 comprising the amino acid sequence of SEQ ID NO: 41 (CDR1 of a chain of 4400 TCR-N), a CDR2 comprising the amino acid sequence of SEQ ID NO: 42 (CDR2 of a chain of 4400 TCR-N), and a CDR3 comprising the amino acid sequence of SEQ ID NO: 43 (CDR3 of a chain of 4400 TCR-N), and a second polypeptide chain comprising a CDR1 comprising the amino acid sequence of SEQ ID NO: 44 (CDR1 of β chain of 4400 TCR-N), a CDR2 comprising the amino acid sequence of SEQ ID NO: 45 (CDR2 of β chain of 4400 TCR-N), and a CDR3 comprising the amino acid sequence of SEQ ID NO: 46 (CDR3 of β chain of 4400 TCR-N).

In another embodiment of the invention, the TCR comprises a first polypeptide chain comprising a CDR1 comprising the amino acid sequence of SEQ ID NO: 119 (CDR1 of a chain of 4400 TCR-A3), a CDR2 comprising the amino acid sequence of SEQ ID NO: 120 (CDR2 of a chain of 4400 TCR-A3), and a CDR3 comprising the amino acid sequence of SEQ ID NO: 121 (CDR3 of a chain of 4400 TCR-A3), and a second polypeptide chain comprising a CDR1 comprising the amino acid sequence of SEQ ID NO: 122 (CDR1 of β chain of 4400 TCR-A3), a CDR2 comprising the amino acid sequence of SEQ ID NO: 123 (CDR2 of β chain of 4400 TCR-A3), and a CDR3 comprising the amino acid sequence of SEQ ID NO: 124 (CDR3 of β chain of 4400 TCR-A3).

In another embodiment of the invention, the TCR comprises a first polypeptide chain comprising a CDR1 comprising the amino acid sequence of SEQ ID NO: 129 (CDR1 of a chain of 4400 TCR-J2), a CDR2 comprising the amino acid sequence of SEQ ID NO: 130 (CDR2 of a chain of 4400 TCR-J2), and a CDR3 comprising the amino acid sequence of SEQ ID NO: 131 (CDR3 of a chain of 4400 TCR-J2), and a second polypeptide chain comprising a CDR1 comprising the amino acid sequence of SEQ ID NO: 132 (CDR1 of β chain of 4400 TCR-J2), a CDR2 comprising the amino acid sequence of SEQ ID NO: 133 (CDR2 of β chain of 4400 TCR-J2), and a CDR3 comprising the amino acid sequence of SEQ ID NO: 134 (CDR3 of β chain of 4400 TCR-J2).

In another embodiment of the invention, the TCR comprises a first polypeptide chain comprising a CDR1 comprising the amino acid sequence of SEQ ID NO: 139 (CDR1 of a chain of 4400 TCR-N4), a CDR2 comprising the amino acid sequence of SEQ ID NO: 140 (CDR2 of a chain of 4400 TCR-N4), and a CDR3 comprising the amino acid sequence of SEQ ID NO: 141 (CDR3 of a chain of 4400 TCR-N4), and a second polypeptide chain comprising a CDR1 comprising the amino acid sequence of SEQ ID NO: 142 (CDR1 of β chain of 4400 TCR-N4), a CDR2 comprising the amino acid sequence of SEQ ID NO: 143 (CDR2 of β chain of 4400

TCR-N4), and a CDR3 comprising the amino acid sequence of SEQ ID NO: 144 (CDR3 of β chain of 4400 TCR-N4).

In another embodiment of the invention, the TCR comprises a first polypeptide chain comprising a CDR1 comprising the amino acid sequence of SEQ ID NO: 149 (CDR1 of a chain of 4400 TCR-N12), a CDR2 comprising the amino acid sequence of SEQ ID NO: 150 (CDR2 of a chain of 4400 TCR-N12), and a CDR3 comprising the amino acid sequence of SEQ ID NO: 151 (CDR3 of a chain of 4400 TCR-N12), and a second polypeptide chain comprising a CDR1 comprising the amino acid sequence of SEQ ID NO: 152 (CDR1 of β chain of 4400 TCR-N12), a CDR2 comprising the amino acid sequence of SEQ ID NO: 153 (CDR2 of β chain of 4400 TCR-N12), and a CDR3 comprising the amino acid sequence of SEQ ID NO: 154 (CDR3 of β chain of 4400 TCR-N12).

In another embodiment of the invention, the TCR comprises a first polypeptide chain comprising a CDR1 comprising the amino acid sequence of SEQ ID NO: 159 (CDR1 of a chain of 4400 TCR-N13), a CDR2 comprising the amino acid sequence of SEQ ID NO: 160 (CDR2 of α chain of 4400 TCR-N13), and a CDR3 comprising the amino acid sequence of SEQ ID NO: 161 (CDR3 of α chain of 4400 TCR-N13), and a second polypeptide chain comprising a CDR1 comprising the amino acid sequence of SEQ ID NO: 162 (CDR1 of (3 chain of 4400 TCR-N13), a CDR2 comprising the amino acid sequence of SEQ ID NO: 163 (CDR2 of β chain of 4400 TCR-N13), and a CDR3 comprising the amino acid sequence of SEQ ID NO: 164 (CDR3 of β chain of 4400 TCR-N13).

In another embodiment of the invention, the TCR comprises a first polypeptide chain comprising a CDR1 comprising the amino acid sequence of SEQ ID NO: 169 (CDR1 of α chain of 4400 TCR-C), a CDR2 comprising the amino acid sequence of SEQ ID NO: 170 (CDR2 of α chain of 4400 TCR-C), and a CDR3 comprising the amino acid sequence of SEQ ID NO: 171 (CDR3 of α chain of 4400 TCR-C), and a second polypeptide chain comprising a CDR1 comprising the amino acid sequence of SEQ ID NO: 172 (CDR1 of (3 chain of 4400 TCR-C), a CDR2 comprising the amino acid sequence of SEQ ID NO: 173 (CDR2 of β chain of 4400 TCR-C), and a CDR3 comprising the amino acid sequence of SEQ ID NO: 174 (CDR3 of β chain of 4400 TCR-C).

In another embodiment of the invention, the TCR comprises a first polypeptide chain comprising a CDR1 comprising the amino acid sequence of SEQ ID NO: 179 (CDR1 of α chain of 4400 TCR-20), a CDR2 comprising the amino acid sequence of SEQ ID NO: 180 (CDR2 of α chain of 4400 TCR-20), and a CDR3 comprising the amino acid sequence of SEQ ID NO: 181 (CDR3 of α chain of 4400 TCR-20), and a second polypeptide chain comprising a CDR1 comprising the amino acid sequence of SEQ ID NO: 182 (CDR1 of (3 chain of 4400 TCR-20), a CDR2 comprising the amino acid sequence of SEQ ID NO: 183 (CDR2 of β chain of 4400 TCR-20), and a CDR3 comprising the amino acid sequence of SEQ ID NO: 184 (CDR3 of β chain of 4400 TCR-20).

In this regard, the inventive TCR can comprise any one or more of the amino acid sequences selected from the group consisting of SEQ ID NOs: 1-6, 11-16, 21-26, 31-36, and 41-46. In an embodiment of the invention, the TCR comprises the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26,

15

(j) all of SEQ ID NOs: 31-33, (k) all of SEQ ID NOs: 34-36, (l) all of SEQ ID NOs: 31-36, (m) all of SEQ ID NOs: 41-43, (n) all of SEQ ID NOs: 44-46, (o) all of SEQ ID NOs: 41-46, (p) all of SEQ ID NOs: 119-121, (q) all of SEQ ID NOs: 122-124, (r) all of SEQ ID NOs: 119-124, (s) all of SEQ ID NOs: 129-131, (t) all of SEQ ID NOs: 132-134, (u) all of SEQ ID NOs: 129-134, (v) all of SEQ ID NOs: 139-141, (w) all of SEQ ID NOs: 142-144, (x) all of SEQ ID NOs: 139-144, (y) all of SEQ ID NOs: 149-151, (z) all of SEQ ID NOs: 152-154, (aa) all of SEQ ID NOs: 149-154, (bb) all of SEQ ID NOs: 159-161, (cc) all of SEQ ID NOs: 162-164, (dd) all of SEQ ID NOs: 159-164, (ee) all of SEQ ID NOs: 169-171, (ff) all of SEQ ID NOs: 172-174, (gg) all of SEQ ID NOs: 169-174, (hh) all of SEQ ID NOs: 179-181, (ii) all of SEQ ID NOs: 182-184, or (jj) all of SEQ ID NOs: 179-184. In an especially preferred embodiment, the TCR comprises the amino acid sequences of: (a) all of SEQ ID NOs: 1-6, (b) all of SEQ ID NOs: 11-16, (c) all of SEQ ID NOs: 21-26, (d) all of SEQ ID NOs: 31-36, (e) all of SEQ ID NOs: 41-46, (f) all of SEQ ID NOs: 119-124, (g) all of SEQ ID NOs: 129-134, (h) all of SEQ ID NOs: 139-144, (i) all of SEQ ID NOs: 149-154, (j) all of SEQ ID NOs: 159-164, (k) all of SEQ ID NOs: 169-174, or (l) all of SEQ ID NOs: 179-184.

In an embodiment of the invention, the TCR comprises an amino acid sequence of a variable region of a TCR comprising the CDRs set forth above. In this regard, the TCR can comprise the amino acid sequence of: (1) SEQ ID NO: 7 (predicted sequence of variable region of α chain of 4400 TCR-A1 without N-terminal signal peptide); (2) SEQ ID NO: 8 (predicted sequence of variable region of β chain of 4400 TCR-A1 without N-terminal signal peptide); (3) SEQ ID NO: 9 (variable region of α chain of 4400 TCR-A1 with N-terminal signal peptide); (4) SEQ ID NO: 10 (variable region of β chain of 4400 TCR-A1 with N-terminal signal peptide); (5) SEQ ID NO: 17 (predicted sequence of variable region of a chain of 4400 TCR-A2 without N-terminal signal peptide); (6) SEQ ID NO: 18 (predicted sequence of variable region of β chain of 4400 TCR-A2 without N-terminal signal peptide); (7) SEQ ID NO: 19 (variable region of α chain of 4400 TCR-A2 with N-terminal signal peptide); (8) SEQ ID NO: 20 (variable region of β chain of 4400 TCR-A2 with N-terminal signal peptide); (9) SEQ ID NO: 27 (predicted sequence of variable region of α chain of 4400 TCR-E without N-terminal signal peptide); (10) SEQ ID NO: 28 (predicted sequence of variable region of β chain of 4400 TCR-E without N-terminal signal peptide); (11) SEQ ID NO: 29 (variable region of α chain of 4400 TCR-E with N-terminal signal peptide); (12) SEQ ID NO: 30 (variable region of β chain of 4400 TCR-E with N-terminal signal peptide); (13) SEQ ID NO: 37 (predicted sequence of variable region of α chain of 4400 TCR-J without N-terminal signal peptide); (14) SEQ ID NO: 38 (predicted sequence of variable region of (3 chain of 4400 TCR-J without N-terminal signal peptide); (15) SEQ ID NO: 39 (variable region of α chain of 4400 TCR-J with N-terminal signal peptide); (16) SEQ ID NO: 40 (variable region of β chain of 4400 TCR-J with N-terminal signal peptide); (17) SEQ ID NO: 47 (predicted sequence of variable region of α chain of 4400 TCR-N without N-terminal signal peptide); (18) SEQ ID NO: 48 (predicted sequence of variable region of β chain of 4400 TCR-N without N-terminal signal peptide); (19) SEQ ID NO: 49 (variable region of a chain of 4400 TCR-N with N-terminal signal peptide); (20) SEQ ID NO: 50 (variable region of β chain of 4400 TCR-N with N-terminal signal peptide); (21) SEQ ID NO: 125 (predicted sequence of variable region of α chain of 4400 TCR-A3 without N-terminal signal peptide); (22) SEQ ID NO: 126 (predicted sequence of variable region of β chain of 4400 TCR-A3 without N-terminal signal peptide); (23) SEQ ID NO: 127 (variable region of α chain of 4400 TCR-A3 with N-terminal signal peptide); (24) SEQ ID NO: 128 (variable region of β chain of 4400 TCR-A3 with N-terminal signal peptide); (25) SEQ ID NO: 135 (predicted sequence of variable region of α chain of 4400 TCR-J2 without N-terminal signal peptide); (26) SEQ ID NO: 136 (predicted sequence of variable region of β chain of 4400 TCR-J2 without N-terminal signal peptide); (27) SEQ ID NO: 137 (variable region of α chain of 4400 TCR-J2 with N-terminal signal peptide); (28) SEQ ID NO: 138 (variable region of β chain of 4400 TCR-J2 with N-terminal signal peptide); (29) SEQ ID NO: 145 (predicted sequence of variable region of α chain of 4400 TCR-N4 without N-terminal signal peptide); (30) SEQ ID NO: 146 (predicted sequence of variable region of β chain of 4400 TCR-N4 without N-terminal signal peptide); (31) SEQ ID NO: 147 (variable region of α chain of 4400 TCR-N4 with N-terminal signal peptide); (32) SEQ ID NO: 148 (variable region of β chain of 4400 TCR-N4 with N-terminal signal peptide); (33) SEQ ID NO: 155 (predicted sequence of variable region of α chain of 4400 TCR-N12 without N-terminal signal peptide); (34) SEQ ID NO: 156 (predicted sequence of variable region of β chain of 4400 TCR-N12 without N-terminal signal peptide); (35) SEQ ID NO: 157 (variable region of α chain of 4400 TCR-N12 with N-terminal signal peptide); (36) SEQ ID NO: 158 (variable region of β chain of 4400 TCR-N12 with N-terminal signal peptide); (37) SEQ ID NO: 165 (predicted sequence of variable region of α chain of 4400 TCR-N13 without N-terminal signal peptide); (38) SEQ ID NO: 166 (predicted sequence of variable region of β chain of 4400 TCR-N13 without N-terminal signal peptide); (39) SEQ ID NO: 167 (variable region of α chain of 4400 TCR-N13 with N-terminal signal peptide); (40) SEQ ID NO: 168 (variable region of β chain of 4400 TCR-N13 with N-terminal signal peptide); (41) SEQ ID NO: 175 (predicted sequence of variable region of α chain of 4400 TCR-C without N-terminal signal peptide); (42) SEQ ID NO: 176 (predicted sequence of variable region of β chain of 4400 TCR-C without N-terminal signal peptide); (43) SEQ ID NO: 177 (variable region of α chain of 4400 TCR-C with N-terminal signal peptide); (44) SEQ ID NO: 178 (variable region of β chain of 4400 TCR-C with N-terminal signal peptide); (45) SEQ ID NO: 185 (predicted sequence of variable region of α chain of 4400 TCR-20 without N-terminal signal peptide); (46) SEQ ID NO: 186 (predicted sequence of variable region of β chain of 4400 TCR-20 without N-terminal signal peptide); (47) SEQ ID NO: 187 (variable region of α chain of 4400 TCR-20 with N-terminal signal peptide); (48) SEQ ID NO: 188 (variable region of β chain of 4400 TCR-20 with N-terminal signal peptide); (49) both of SEQ ID NOs: 7 and 8; (50) both of SEQ ID NOs: 9 and 10; (51) both of SEQ ID NOs: 17 and 18; (52) both of SEQ ID NOs: 19 and 20; (53) both of SEQ ID NOs: 27 and 28; (54) both of SEQ ID NOs: 29 and 30; (55) both of SEQ ID NOs: 37 and 38; (56) both of SEQ ID NOs: 39 and 40; (57) both of SEQ ID NOs: 47 and 48; (58) both of SEQ ID NOs: 49 and 50; (59) both of SEQ ID NOs: 125 and 126; (60) both of SEQ ID NOs: 127 and 128; (61) both of SEQ ID NOs: 135 and 136; (62) both of SEQ ID NOs: 137 and 138; (63) both of SEQ ID NOs: 145 and 146; (64) both of SEQ ID NOs: 147 and 148; (65) both of SEQ ID NOs: 155 and 156; (66) both of SEQ ID NOs: 157 and 158; (67) both of SEQ ID NOs: 165 and 166; (68) both of SEQ ID NOs: 167 and 168; (69) both of SEQ ID NOs: 175 and 176; (70)

both of SEQ ID NOs: 177 and 178; (71) both of SEQ ID NOs: 185 and 186; or (72) both of SEQ ID NOs: 187 and 188. Preferably, the TCR comprises the amino acid sequences of (i) both of SEQ ID NOs: 7 and 8, (ii) both of SEQ ID NOs: 9 and 10, (iii) both of SEQ ID NOs: 17 and 18, (iv) both of SEQ ID NOs: 19 and 20, (v) both of SEQ ID NOs: 27 and 28, (vi) both of SEQ ID NOs: 29 and 30, (vii) both of SEQ ID NOs: 37 and 38, (viii) both of SEQ ID NOs: 39 and 40, (ix) both of SEQ ID NOs: 47 and 48, (x) both of SEQ ID NOs: 49 and 50, (xi) both of SEQ ID NOs: 125 and 126, (xii) both of SEQ ID NOs: 127 and 128, (xiii) both of SEQ ID NOs: 135 and 136, (xiv) both of SEQ ID NOs: 137 and 138, (xv) both of SEQ ID NOs: 145 and 146, (xvi) both of SEQ ID NOs: 147 and 148, (xvii) both of SEQ ID NOs: 155 and 156, (xviii) both of SEQ ID NOs: 157 and 158, (xix) both of SEQ ID NOs: 165 and 166, (xx) both of SEQ ID NOs: 167 and 168, (xxi) both of SEQ ID NOs: 175 and 176, (xxii) both of SEQ ID NOs: 177 and 178, (xxiii) both of SEQ ID NOs: 185 and 186, or (xxiv) both of SEQ ID NOs: 187 and 188.

The inventive TCRs may further comprise an α chain constant region and a β chain constant region. The constant region may be derived from any suitable species such as, e.g., human or mouse. In an embodiment of the invention, the TCRs further comprise murine α and β chain constant regions or human α and β chain constant regions. As used herein, the term "murine" or "human," when referring to a TCR or any component of a TCR described herein (e.g., CDR, variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively.

An embodiment of the invention provides a chimeric TCR comprising a human variable region and a murine constant region, wherein the TCR has antigenic specificity for a mutated human RAS amino acid sequence with a substitution of glycine at position 13 with aspartic acid. The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 63 (WT murine α chain constant region), SEQ ID NO: 64 (WT murine β chain constant region), or both SEQ ID NOs: 63 and 64. Preferably, the inventive TCR comprises the amino acid sequences of both of SEQ ID NOs: 63 and 64. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 1-3 and 63, (b) all of SEQ ID NOs: 4-6 and 64, (c) all of SEQ ID NOs: 1-6 and 63-64, (d) all of SEQ ID NOs: 11-13 and 63, (e) all of SEQ ID NOs: 14-16 and 64, (f) all of SEQ ID NOs: 11-16 and 63-64, (g) all of SEQ ID NOs: 21-23 and 63, (h) all of SEQ ID NOs: 24-26 and 64, (i) all of SEQ ID NOs: 21-26 and 63-64, (j) all of SEQ ID NOs: 31-33 and 63, (k) all of SEQ ID NOs: 34-36 and 64, (l) all of SEQ ID NOs: 31-36 and 63-64, (m) all of SEQ ID NOs: 41-43 and 63, (n) all of SEQ ID NOs: 44-46 and 64, (o) all of SEQ ID NOs: 41-46 and 63-64, (p) all of SEQ ID NOs: 119-121 and 63, (q) all of SEQ ID NOs: 122-124 and 64, (r)

all of SEQ ID NOs: 119-124 and 63-64, (s) all of SEQ ID NOs: 129-131 and 63, (t) all of SEQ ID NOs: 132-134 and 64, (u) all of SEQ ID NOs: 129-134 and 63-64, (v) all of SEQ ID NOs: 139-141 and 63, (w) all of SEQ ID NOs: 142-144 and 64, (x) all of SEQ ID NOs: 139-144 and 63-64, (y) all of SEQ ID NOs: 149-151 and 63, (z) all of SEQ ID NOs: 152-154 and 64, (aa) all of SEQ ID NOs: 149-154 and 63-64, (bb) all of SEQ ID NOs: 159-161 and 63, (cc) all of SEQ ID NOs: 162-164 and 64, (dd) all of SEQ ID NOs: 159-164 and 63-64, (ee) all of SEQ ID NOs: 169-171 and 63, (ff) all of SEQ ID NOs: 172-174 and 64, (gg) all of SEQ ID NOs: 169-174 and 63-64, (hh) all of SEQ ID NOs: 179-181 and 63, (ii) all of SEQ ID NOs: 182-184 and 64, or (jj) all of SEQ ID NOs: 179-184 and 63-64.

In another embodiment of the invention, the chimeric TCR may comprise any of the murine constant regions described herein in combination with any of the variable regions described herein with respect to other aspects of the invention. In this regard, the TCR may comprise the amino acid sequences of: (1) both of SEQ ID NOs: 7 and 63, (2) both of SEQ ID NOs: 8 and 64, (3) both of SEQ ID NOs: 9 and 63, (4) both of SEQ ID NOs: 10 and 64, (5) both of SEQ ID NOs: 17 and 63, (6) both of SEQ ID NOs: 18 and 64, (7) both of SEQ ID NOs: 19 and 63, (8) both of SEQ ID NOs: 20 and 64, (9) both of SEQ ID NOs: 27 and 63, (10) both of SEQ ID NOs: 28 and 64, (11) both of SEQ ID NOs: 29 and 63, (12) both of SEQ ID NOs: 30 and 64, (13) both of SEQ ID NOs: 37 and 63, (14) both of SEQ ID NOs: 38 and 64, (15) both of SEQ ID NOs: 39 and 63, (16) both of SEQ ID NOs: 40 and 64, (17) both of SEQ ID NOs: 47 and 63, (17) both of SEQ ID NOs: 48 and 64, (19) both of SEQ ID NOs: 49 and 63, (20) both of SEQ ID NOs: 50 and 64, (21) both of SEQ ID NOs: 125 and 63, both of (22) SEQ ID NOs: 126 and 64, (23) both of SEQ ID NOs: 127 and 63, (24) both of SEQ ID NOs: 128 and 64, (25) both of SEQ ID NOs: 135 and 63, (26) both of SEQ ID NOs: 136 and 64, (27) both of SEQ ID NOs: 137 and 63, (28) both of SEQ ID NOs: 138 and 64, (29) both of SEQ ID NOs: 145 and 63, (30) both of SEQ ID NOs: 146 and 64, (31) both of SEQ ID NOs: 147 and 63, (32) both of SEQ ID NOs: 148 and 64, (33) both of SEQ ID NOs: 155 and 63, (34) both of SEQ ID NOs: 156 and 64, (35) both of SEQ ID NOs: 157 and 63, (36) both of SEQ ID NOs: 158 and 64, (37) both of SEQ ID NOs: 165 and 63, (38) both of SEQ ID NOs: 166 and 64, (39) both of SEQ ID NOs: 167 and 63, (40) both of SEQ ID NOs: 168 and 64, (41) both of SEQ ID NOs: 175 and 63, (42) both of SEQ ID NOs: 176 and 64, (43) both of SEQ ID NOs: 177 and 63, (44) both of SEQ ID NOs: 178 and 64, (45) both of SEQ ID NOs: 185 and 63, (46) both of SEQ ID NOs: 186 and 64, (47) both of SEQ ID NOs: 187 and 63, (48) both of SEQ ID NOs: 188 and 64, (49) all of SEQ ID NOs: 7-8 and 63-64, (50) all of SEQ ID NOs: 9-10 and 63-64, (51) all of SEQ ID NOs: 17-18 and 63-64, (52) all of SEQ ID NOs: 19-20 and 63-64, (53) all of SEQ ID NOs: 27-28 and 63-64, (54) all of SEQ ID NOs: 29-30 and 63-64, (55) all of SEQ ID NOs: 37-38 and 63-64, (56) all of SEQ ID NOs: 39-40 and 63-64, (57) all of SEQ ID NOs: 47-48 and 63-64, (58) all of SEQ ID NOs: 49-50 and 63-64, (59) all of SEQ ID NOs: 125-126 and 63-64, (60) all of SEQ ID NOs: 127-128 and 63-64, (61) all of SEQ ID NOs: 135-136 and 63-64, (62) all of SEQ ID NOs: 137-138 and 63-64, (63) all of SEQ ID NOs: 145-146 and 63-64, (64) all of SEQ ID NOs: 147-148 and 63-64, (65) all of SEQ ID NOs: 155-156 and 63-64, (66) all of SEQ ID NOs: 157-158 and 63-64, (67) all of SEQ ID NOs: 165-166 and 63-64, (68) all of SEQ ID NOs: 167-168 and 63-64, (69) all of SEQ ID NOs: 175-176 and 63-64, (70) all of SEQ ID NOs: 177-178 and 63-64, (71) all of SEQ ID NOs: 185-186 and 63-64, or (72) all of SEQ ID NOs: 187-188 and 63-64.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of G13D RAS' targets, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 59 and 60, respectively, correspond with all or portions of the unsubstituted murine constant region amino acid sequences SEQ ID NOs: 63 and 64, respectively, with SEQ ID NO: 59 having one, two, three, or four amino acid substitution(s) when compared to SEQ ID NO: 63 and SEQ ID NO: 60 having one amino acid substitution when compared to SEQ ID NO: 64. In this regard, an embodiment of the invention provides a TCR comprising the amino acid sequences of (a) SEQ ID NO: 59 (constant region of α chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; (b) SEQ ID NO: 60 (constant region of β chain), wherein X at position 57 is Ser or Cys; or (c) both of SEQ ID NOs: 59 and 60. In an embodiment of the invention, the TCR comprising SEQ ID NO: 59 does not comprise SEQ ID NO: 63 (unsubstituted murine constant region of α chain). In an embodiment of the invention, the TCR comprising SEQ ID NO: 60 does not comprise SEQ ID NO: 64 (unsubstituted murine constant region of β chain).

In an embodiment of the invention, the TCR comprises an α chain comprising a variable region and a constant region and αβ chain comprising a variable region and a constant region. In this regard, the TCR may comprise (a) the amino acid sequence of SEQ ID NO: 65 (α chain of 4400 TCR-A1 with N-terminal signal peptide), wherein: (i) X at position 180 of SEQ ID NO: 65 is Thr or Cys; (ii) X at position 244 of SEQ ID NO: 65 is Ser, Ala, Val, Leu, Ile, Pro, Phe, Met, or Trp; (iii) X at position 246 of SEQ ID NO: 65 is Met, Ala, Val, Leu, Ile, Pro, Phe, or Trp; and (iv) X at position 247 of SEQ ID NO: 65 is Gly, Ala, Val, Leu, Ile, Pro, Phe, Met, or Trp; (b) the amino acid sequence of SEQ ID NO: 66 (β chain of 4400 TCR-A1 with N-terminal signal peptide), wherein X at position 188 of SEQ ID NO: 66 is Ser or Cys; (c) the amino acid sequences of both of SEQ ID NOs: 65 and 66; (d) the amino acid sequence of SEQ ID NO: 67 (predicted sequence of α chain of 4400 TCR-A1 without N-terminal signal peptide), wherein: (i) X at position 158 of SEQ ID NO: 67 is Thr or Cys; (ii) X at position 222 of SEQ ID NO: 67 is Ser, Ala, Val, Leu, Ile, Pro, Phe, Met, or Trp; (iii) X at position 224 of SEQ ID NO: 67 is Met, Ala, Val, Leu, Ile, Pro, Phe, or Trp; and (iv) X at position 225 of SEQ ID NO:

67 is Gly, Ala, Val, Leu, Ile, Pro, Phe, Met, or Trp; (e) the amino acid sequence of SEQ ID NO: 68 (predicted sequence of β chain of 4400 TCR-A1 without N-terminal signal peptide), wherein X at position 169 of SEQ ID NO: 68 is Ser or Cys; (0 the amino acid sequences of both of SEQ ID NOs: 67 and 68; (g) the amino acid sequence of SEQ ID NO: 69 (α chain of cysteine-substituted, LVL-modified 4400 TCR-A1 with N-terminal signal peptide); (h) the amino acid sequence of SEQ ID NO: 70 (β chain of cysteine-substituted, LVL-modified 4400 TCR-A1 with N-terminal signal peptide); (i) the amino acid sequence of SEQ ID NO: 71 (predicted sequence of α chain of cysteine-substituted, LVL-modified 4400 TCR-A1 without N-terminal signal peptide); (j) the amino acid sequence of SEQ ID NO: 72 (predicted sequence of β chain of cysteine-substituted, LVL-modified 4400 TCR-A1 without N-terminal signal peptide); (k) the amino acid sequences of both of SEQ ID NOs: 69 and 70; (l) the amino acid sequences of both of both of SEQ ID NOs: 71 and 72; (m) the amino acid sequence of SEQ ID NO: 73 (α chain of 4400 TCR-A2 with N-terminal signal peptide), wherein: (i) X at position 180 of SEQ ID NO: 73 is Thr or Cys; (ii) X at position 244 of SEQ ID NO: 73 is Ser, Ala, Val, Leu, Ile, Pro, Phe, Met, or Trp; (iii) X at position 246 of SEQ ID NO: 73 is Met, Ala, Val, Leu, Ile, Pro, Phe, or Trp; and (iv) X at position 247 of SEQ ID NO: 73 is Gly, Ala, Val, Leu, Ile, Pro, Phe, Met, or Trp; (n) the amino acid sequence of SEQ ID NO: 74 (β chain of 4400 TCR-A2 with N-terminal signal peptide), wherein X at position 188 of SEQ ID NO: 74 is Ser or Cys; (o) the amino acid sequences of both of SEQ ID NOs: 73 and 74; (p) the amino acid sequence of SEQ ID NO: 75 (predicted sequence of α chain of 4400 TCR-A2 without N-terminal signal peptide), wherein: (i) X at position 158 of SEQ ID NO: 75 is Thr or Cys; (ii) X at position 222 of SEQ ID NO: 75 is Ser, Ala, Val, Leu, Ile, Pro, Phe, Met, or Trp; (iii) X at position 224 of SEQ ID NO: 75 is Met, Ala, Val, Leu, Ile, Pro, Phe, or Trp; and (iv) X at position 225 of SEQ ID NO: 75 is Gly, Ala, Val, Leu, Ile, Pro, Phe, Met, or Trp; (q) the amino acid sequence of SEQ ID NO: 76 (predicted sequence of β chain of 4400 TCR-A2 without N-terminal signal peptide), wherein X at position 169 of SEQ ID NO: 76 is Ser or Cys; (r) the amino acid sequences of both of SEQ ID NOs: 75 and 76; (s) the amino acid sequence of SEQ ID NO: 77 (α chain of cysteine-substituted, LVL-modified 4400 TCR-A2 with N-terminal signal peptide); (t) the amino acid sequence of SEQ ID NO: 78 (β chain of cysteine-substituted, LVL-modified 4400 TCR-A2 with N-terminal signal peptide); (u) the amino acid sequence of SEQ ID NO: 79 (predicted sequence of α chain of cysteine-substituted, LVL-modified 4400 TCR-A2 without N-terminal signal peptide); (v) the amino acid sequence of SEQ ID NO: 80 (predicted sequence of β chain of cysteine-substituted, LVL-modified 4400 TCR-A2 without N-terminal signal peptide); (w) the amino acid sequences of both of SEQ ID NOs: 77 and 78; (x) the amino acid sequences of both of SEQ ID NOs: 79 and 80; (y) the amino acid sequence of SEQ ID NO: 81 (α chain of 4400 TCR-E with N-terminal signal peptide), wherein: (i) X at position 177 of SEQ ID NO: 81 is Thr or Cys; (ii) X at position 241 of SEQ ID NO: 81 is Ser, Ala, Val, Leu, Ile, Pro, Phe, Met, or Trp; (iii) X at position 243 of SEQ ID NO: 81 is Met, Ala, Val, Leu, Ile, Pro, Phe, or Trp; and (iv) X at position 244 of SEQ ID NO: 81 is Gly, Ala, Val, Leu, Ile, Pro, Phe, Met, or Trp; (z) the amino acid sequence of SEQ ID NO: 82 (β chain of 4400 TCR-E with N-terminal signal peptide), wherein X at position 189 of SEQ ID NO: 82 is Ser or Cys; (aa) the amino acid sequences of both of SEQ ID NOs: 81 and 82; (bb) the amino acid sequence of SEQ ID NO: 83 (predicted sequence of α chain of 4400 TCR-E without N-terminal signal peptide), wherein: (i) X at position 160 of SEQ ID NO: 83 is Thr or Cys; (ii) X at position 224 of SEQ ID NO: 83 is Ser, Ala, Val, Leu, Ile, Pro, Phe, Met, or Trp; (iii) X at position 226 of SEQ ID NO: 83 is Met, Ala, Val, Leu, Ile, Pro, Phe, or Trp; and (iv) X at position 227 of SEQ ID NO: 83 is Gly, Ala, Val, Leu, Ile, Pro, Phe, Met, or Trp; (cc) the amino acid sequence of SEQ ID NO: 84 (predicted sequence of β chain of 4400 TCR-E without N-terminal signal peptide), wherein X at position 170 of SEQ ID NO: 84 is Ser or Cys; (dd) the amino acid sequences of both of SEQ ID NOs: 83 and 84; (ee) the amino acid sequence of SEQ ID NO: 85 (α chain of cysteine-substituted, LVL-modified 4400 TCR-E with N-terminal signal peptide); (ff) the amino acid sequence of SEQ ID NO: 86 (β chain of cysteine-substituted, LVL-modified 4400 TCR-E with N-terminal signal peptide); (gg) the amino acid sequence of SEQ ID NO: 87 (predicted sequence of α chain of cysteine-substituted, LVL-modified 4400 TCR-E without N-terminal signal peptide); (hh) the amino acid sequence of SEQ ID NO: 88 (predicted sequence of β chain of cysteine-substituted, LVL-modified 4400 TCR-E without N-terminal signal peptide); (ii) the amino acid sequences of both of SEQ ID NOs: 85 and 86; (jj) the amino acid sequences of both of SEQ ID NOs: 87 and 88; (kk) the amino acid sequence of SEQ ID NO: 89 (α chain of 4400 TCR-J with N-terminal signal peptide), wherein: (i) X at position 183 of SEQ ID NO: 89 is Thr or Cys; (ii) X at position 247 of SEQ ID NO: 89 is Ser, Ala, Val, Leu, Ile, Pro, Phe, Met, or Trp; (iii) X at position 249 of SEQ ID NO: 89 is Met, Ala, Val, Leu, Ile, Pro, Phe, or Trp; and (iv) X at position 250 of SEQ ID NO: 89 is Gly, Ala, Val, Leu, Ile, Pro, Phe, Met, or Trp; (ll) the amino acid sequence of SEQ ID NO: 90 (β chain of 4400 TCR-J with N-terminal signal peptide), wherein X at position 188 of SEQ ID NO: 90 is Ser or Cys; (mm) the amino acid sequences of both of SEQ ID NOs: 89 and 90; (nn) the amino acid sequence of SEQ ID NO: 91 (predicted sequence of α chain of 4400 TCR-J without N-terminal signal peptide), wherein: (i) X at position 161 of SEQ ID NO: 91 is Thr or Cys; (ii) X at position 225 of SEQ ID NO: 91 is Ser, Ala, Val, Leu, Ile, Pro, Phe, Met, or Trp; (iii) X at position 227 of SEQ ID NO: 91 is Met, Ala, Val, Leu, Ile, Pro, Phe, or Trp; and (iv) X at position 228 of SEQ ID NO: 91 is Gly, Ala, Val, Leu, Ile, Pro, Phe, Met, or Trp; (oo) the amino acid sequence of SEQ ID NO: 92 (predicted sequence of β chain of 4400 TCR-J without N-terminal signal peptide), wherein X at position 169 of SEQ ID NO: 92 is Ser or Cys; (pp) the amino acid sequences of both of SEQ ID NOs: 91 and 92; (qq) the amino acid sequence of SEQ ID NO: 93 (α chain of cysteine-substituted, LVL-modified 4400 TCR-J with N-terminal signal peptide); (rr) the amino acid sequence of SEQ ID NO: 94 (β chain of cysteine-substituted, LVL-modified 4400 TCR-J with N-terminal signal peptide); (ss) the amino acid sequence of SEQ ID NO: 95 (predicted sequence of α chain of cysteine-substituted, LVL-modified 4400 TCR-J without N-terminal signal peptide); (tt) the amino acid sequence of SEQ ID NO: 96 (predicted sequence of β chain of cysteine-substituted, LVL-modified 4400 TCR-J without N-terminal signal peptide); (uu) the amino acid sequences of both of SEQ ID NOs: 93 and 94; (vv) the amino acid sequences of both of SEQ ID NOs: 95 and 96; (ww) the amino acid sequence of SEQ ID NO: 97 (α chain of 4400 TCR-N with N-terminal signal peptide), wherein: (i) X at position 178 of SEQ ID NO: 97 is Thr or Cys; (ii) X at position 242 of SEQ ID NO: 97 is Ser, Ala, Val, Leu, Ile, Pro, Phe, Met, or Trp; (iii) X at position 244 of SEQ ID NO: 97 is Met, Ala, Val, Leu, Ile, Pro, Phe, or Trp; and (iv) X at position 245 of SEQ ID NO: 97 is Gly, Ala, Val, Leu, Ile, Pro, Phe, Met, or Trp; (xx) the amino acid sequence of SEQ ID NO: 98 (β chain of 4400 TCR-N with N-terminal signal peptide), wherein X at position 188 of SEQ ID NO: 98 is Ser or Cys; (yy) the amino acid sequences of both of SEQ ID NOs: 97 and 98; (zz) the amino acid sequence of SEQ ID NO: 99 (predicted sequence of α chain of 4400 TCR-N without N-terminal signal peptide), wherein: (i) X at position 157 of SEQ ID NO: 99 is Thr or Cys; (ii) X at position 221 of SEQ ID NO: 99 is Ser, Ala, Val, Leu, Ile, Pro, Phe, Met, or Trp; (iii) X at position 223 of SEQ ID NO: 99 is Met, Ala, Val, Leu, Ile, Pro, Phe, or Trp; and (iv) X at position 224 of SEQ ID NO: 99 is Gly, Ala, Val, Leu, Ile, Pro, Phe, Met, or Trp; (aaa) the amino acid sequence of SEQ ID NO: 100 (predicted sequence of β chain of 4400 TCR-N without N-terminal signal peptide), wherein X at position 169 of SEQ ID NO: 100 is Ser or Cys; (bbb) the amino acid sequences of both of SEQ ID NOs: 99 and 100; (ccc) the amino acid sequence of SEQ ID NO: 101 (α chain of cysteine-substituted, LVL-modified 4400 TCR-N with N-terminal signal peptide); (ddd) the amino acid sequence of SEQ ID NO: 102 (β chain of cysteine-substituted, LVL-modified 4400 TCR-N with N-terminal signal peptide); (eee) the amino acid sequence of SEQ ID NO: 103 (predicted sequence of α chain of cysteine-substituted, LVL-modified 4400 TCR-N without N-terminal signal peptide); (fff) the amino acid sequence of SEQ ID NO: 104 (predicted sequence of β chain of cysteine-substituted, LVL-modified 4400 TCR-N without N-terminal signal peptide); (ggg) the amino acid sequences of both of SEQ ID NOs: 101 and 102; (hhh) the amino acid sequences of both of SEQ ID NOs: 103 and 104; (iii) the amino acid sequence of SEQ ID NO: 189 (α chain of 4400 TCR-A3 with N-terminal signal peptide), wherein: (i) X at position 176 of SEQ ID NO: 189 is Thr or Cys; (ii) X at position 240 of SEQ ID NO: 189 is Ser, Ala, Val, Leu, Ile, Pro, Phe, Met, or Trp; (iii) X at position 242 of SEQ ID NO: 189 is Met, Ala, Val, Leu, Ile, Pro, Phe, or Trp; and (iv) X at position 243 of SEQ ID NO: 189 is Gly, Ala, Val, Leu, Ile, Pro, Phe, Met, or Trp; (jjj) the amino acid sequence of SEQ ID NO: 190 (β chain of 4400 TCR-A3 with N-terminal signal peptide), wherein X at position 188 of SEQ ID NO: 190 is Ser or Cys; (kkk) the amino acid sequences of both of SEQ ID NOs: 189 and 190; (lll) the amino acid sequence of SEQ ID NO: 191 (predicted sequence of α chain of 4400 TCR-A3 without N-terminal signal peptide), wherein: (i) X at position 157 of SEQ ID NO: 191 is Thr or Cys; (ii) X at position 221 of SEQ ID NO: 191 is Ser, Ala, Val, Leu, Ile, Pro, Phe, Met, or Trp; (iii) X at position 223 of SEQ ID NO: 191 is Met, Ala, Val, Leu, Ile, Pro, Phe, or Trp; and (iv) X at position 224 of SEQ ID NO: 191 is Gly, Ala, Val, Leu, Ile, Pro, Phe, Met, or Trp; (mmm) the amino acid sequence of SEQ ID NO: 192 (predicted sequence of β chain of 4400 TCR-A3 without N-terminal signal peptide), wherein X at position 169 of SEQ ID NO: 192 is Ser or Cys; (nnn) the amino acid sequences of both of SEQ ID NOs: 191 and 192; (ooo) the amino acid sequence of SEQ ID NO: 193 (α chain of cysteine-substituted, LVL-modified 4400 TCR-A3 with N-terminal signal peptide); (ppp) the amino acid sequence of SEQ ID NO: 194 (β chain of cysteine-substituted, LVL-modified 4400 TCR-A3 with N-terminal signal peptide); (qqq) the amino acid sequence of SEQ ID NO: 195 (predicted sequence of α chain of cysteine-substituted, LVL-modified 4400 TCR-A3 without N-terminal signal peptide); (rrr) the amino acid sequence of SEQ ID NO: 196 (predicted sequence of β chain of cysteine-substituted, LVL-modified 4400 TCR-A3 without N-terminal signal peptide); (sss) the amino acid sequences of both of SEQ ID NOs: 193 and 194; (ttt) the amino acid sequences of both of SEQ ID NOs: 195 and 196; (uuu) the amino acid sequence of SEQ ID NO: 197 (α chain of 4400 TCR-J2 with N-terminal signal peptide), wherein: (i) X at position 181 of SEQ ID NO: 197 is Thr or Cys; (ii) X at position 245 of SEQ ID NO: 197 is Ser, Ala, Val, Leu, Ile, Pro, Phe, Met, or Trp; (iii) X at position 247 of SEQ ID NO: 197 is Met, Ala, Val, Leu, Ile, Pro, Phe, or Trp; and (iv) X at position 248 of SEQ ID NO: 197 is Gly, Ala, Val, Leu, Ile, Pro, Phe, Met, or Trp; (vvv) the amino acid sequence of SEQ ID NO: 198 (β chain of 4400 TCR-J2 with N-terminal signal peptide), wherein X at position 188 of SEQ ID NO: 198 is Ser or Cys; (www) the amino acid sequences of both of SEQ ID NOs: 197 and 198; (xxx) the amino acid sequence of SEQ ID NO: 199 (predicted sequence of a chain of 4400 TCR-J2 without N-terminal signal peptide), wherein: (i) X at position 161 of SEQ ID NO: 199 is Thr or Cys; (ii) X at position 225 of SEQ ID NO: 199 is Ser, Ala, Val, Leu, Ile, Pro, Phe, Met, or Trp; (iii) X at position 227 of SEQ ID NO: 199 is Met, Ala, Val, Leu, Ile, Pro, Phe, or Trp; and (iv) X at position 228 of SEQ ID NO: 199 is Gly, Ala, Val, Leu, Ile, Pro, Phe, Met, or Trp; (yyy) the amino acid sequence of SEQ ID NO: 200 (predicted sequence of β chain of 4400 TCR-J2 without N-terminal signal peptide), wherein X at position 169 of SEQ ID NO: 200 is Ser or Cys; (zzz) the amino acid sequences of both of SEQ ID NOs: 199 and 200; (aaaa) the amino acid sequence of SEQ ID NO: 201 (α chain of cysteine-substituted, LVL-modified 4400 TCR-J2 with N-terminal signal peptide); (bbbb) the amino acid sequence of SEQ ID NO: 202 (β chain of cysteine-substituted, LVL-modified 4400 TCR-J2 with N-terminal signal peptide); (cccc) the amino acid sequence of SEQ ID NO: 203 (predicted sequence of α chain of cysteine-substituted, LVL-modified 4400 TCR-J2 without N-terminal signal peptide); (dddd) the amino acid sequence of SEQ ID NO: 204 (predicted sequence of β chain of cysteine-substituted, LVL-modified 4400 TCR-J2 without N-terminal signal peptide); (eeee) the amino acid sequences of both of SEQ ID NOs: 201 and 202; (ffff) the amino acid sequences of both of SEQ ID NOs: 203 and 204; (gggg) the amino acid sequence of SEQ ID NO: 205 (α chain of 4400 TCR-N4 with N-terminal signal peptide), wherein: (i) X at position 184 of SEQ ID NO: 205 is Thr or Cys; (ii) X at position 248 of SEQ ID NO: 205 is Ser, Ala, Val, Leu, Ile, Pro, Phe, Met, or Trp; (iii) X at position 250 of SEQ ID NO: 205 is Met, Ala, Val, Leu, Ile, Pro, Phe, or Trp; and (iv) X at position 251 of SEQ ID NO: 205 is Gly, Ala, Val, Leu, Ile, Pro, Phe, Met, or Trp; (hhhh) the amino acid sequence of SEQ ID NO: 206 (β chain of 4400 TCR-N4 with N-terminal signal peptide), wherein X at position 190 of SEQ ID NO: 206 is Ser or Cys; (iiii) the amino acid sequences of both of SEQ ID NOs: 205 and 206; (jjjj) the amino acid sequence of SEQ ID NO: 207 (predicted sequence of α chain of 4400 TCR-N4 without N-terminal signal peptide), wherein: (i) X at position 163 of SEQ ID NO: 207 is Thr or Cys; (ii) X at position 227 of SEQ ID NO: 207 is Ser, Ala, Val, Leu, Ile, Pro, Phe, Met, or Trp; (iii) X at position 229 of SEQ ID NO: 207 is Met, Ala, Val, Leu, Ile, Pro, Phe, or Trp; and (iv) X at position 230 of SEQ ID NO: 207 is Gly, Ala, Val, Leu, Ile, Pro, Phe, Met, or Trp; (kkkk) the amino acid sequence of SEQ ID NO: 208 (predicted sequence of β chain of 4400 TCR-N4 without N-terminal signal peptide), wherein X at position 164 of SEQ ID NO: 208 is Ser or Cys; (llll) the amino acid sequences of both of SEQ ID NOs: 207 and 208; (mmmm) the amino acid sequence of SEQ ID NO: 209 (α chain of cysteine-substituted, LVL-modified 4400 TCR-N4 with N-terminal signal peptide); (nnnn) the amino acid sequence of SEQ ID NO:

210 (β chain of cysteine-substituted, LVL-modified 4400 TCR-N4 with N-terminal signal peptide); (oooo) the amino acid sequence of SEQ ID NO: 211 (predicted sequence of α chain of cysteine-substituted, LVL-modified 4400 TCR-N4 without N-terminal signal peptide); (pppp) the amino acid sequence of SEQ ID NO: 212 (predicted sequence of β chain of cysteine-substituted, LVL-modified 4400 TCR-N4 without N-terminal signal peptide); (qqqq) the amino acid sequences of both of SEQ ID NOs: 209 and 210; (rrrr) the amino acid sequences of both of SEQ ID NOs: 211 and 212; (ssss) the amino acid sequence of SEQ ID NO: 213 (α chain of 4400 TCR-N12 with N-terminal signal peptide), wherein: (i) X at position 183 of SEQ ID NO: 213 is Thr or Cys; (ii) X at position 247 of SEQ ID NO: 213 is Ser, Ala, Val, Leu, Ile, Pro, Phe, Met, or Trp; (iii) X at position 249 of SEQ ID NO: 213 is Met, Ala, Val, Leu, Ile, Pro, Phe, or Trp; and (iv) X at position 250 of SEQ ID NO: 213 is Gly, Ala, Val, Leu, Ile, Pro, Phe, Met, or Trp; (llll) the amino acid sequence of SEQ ID NO: 214 (β chain of 4400 TCR-N12 with N-terminal signal peptide), wherein X at position 188 of SEQ ID NO: 214 is Ser or Cys; (uuuu) the amino acid sequences of both of SEQ ID NOs: 213 and 214; (vvvv) the amino acid sequence of SEQ ID NO: 215 (predicted sequence of α chain of 4400 TCR-N12 without N-terminal signal peptide), wherein: (i) X at position 161 of SEQ ID NO: 215 is Thr or Cys; (ii) X at position 225 of SEQ ID NO: 215 is Ser, Ala, Val, Leu, Ile, Pro, Phe, Met, or Trp; (iii) X at position 227 of SEQ ID NO: 215 is Met, Ala, Val, Leu, Ile, Pro, Phe, or Trp; and (iv) X at position 228 of SEQ ID NO: 215 is Gly, Ala, Val, Leu, Ile, Pro, Phe, Met, or Trp; (wwww) the amino acid sequence of SEQ ID NO: 216 (predicted sequence of β chain of 4400 TCR-N12 without N-terminal signal peptide), wherein X at position 169 of SEQ ID NO: 216 is Ser or Cys; (xxxx) the amino acid sequences of both of SEQ ID NOs: 215 and 216; (yyyy) the amino acid sequence of SEQ ID NO: 217 (α chain of cysteine-substituted, LVL-modified 4400 TCR-N12 with N-terminal signal peptide); (zzzz) the amino acid sequence of SEQ ID NO: 218 (β chain of cysteine-substituted, LVL-modified 4400 TCR-N12 with N-terminal signal peptide); (aaaaa) the amino acid sequence of SEQ ID NO: 219 (predicted sequence of α chain of cysteine-substituted, LVL-modified 4400 TCR-N12 without N-terminal signal peptide); (bbbbb) the amino acid sequence of SEQ ID NO: 220 (predicted sequence of β chain of cysteine-substituted, LVL-modified 4400 TCR-N12 without N-terminal signal peptide); (ccccc) the amino acid sequences of both of SEQ ID NOs: 217 and 218; (ddddd) the amino acid sequences of both of SEQ ID NOs: 219 and 220; (eeeee) the amino acid sequence of SEQ ID NO: 221 (α chain of 4400 TCR-N13 with N-terminal signal peptide), wherein: (i) X at position 180 of SEQ ID NO: 221 is Thr or Cys; (ii) X at position 244 of SEQ ID NO: 221 is Ser, Ala, Val, Leu, Ile, Pro, Phe, Met, or Trp; (iii) X at position 246 of SEQ ID NO: 221 is Met, Ala, Val, Leu, Ile, Pro, Phe, or Trp; and (iv) X at position 247 of SEQ ID NO: 221 is Gly, Ala, Val, Leu, Ile, Pro, Phe, Met, or Trp; (fffff) the amino acid sequence of SEQ ID NO: 222 (β chain of 4400 TCR-N13 with N-terminal signal peptide), wherein X at position 188 of SEQ ID NO: 222 is Ser or Cys; (ggggg) the amino acid sequences of both of SEQ ID NOs: 221 and 222; (hhhhh) the amino acid sequence of SEQ ID NO: 223 (predicted sequence of α chain of 4400 TCR-N13 without N-terminal signal peptide), wherein: (i) X at position 158 of SEQ ID NO: 223 is Thr or Cys; (ii) X at position 222 of SEQ ID NO: 223 is Ser, Ala, Val, Leu, Ile, Pro, Phe, Met, or Trp; (iii) X at position 224 of SEQ ID NO: 223 is Met, Ala, Val, Leu, Ile, Pro, Phe, or Trp; and (iv) X at position 225 of SEQ ID NO: 223 is Gly, Ala, Val, Leu, Ile, Pro, Phe, Met, or Trp; (inn) the amino acid sequence of SEQ ID NO: 224 (predicted sequence of β chain of 4400 TCR-N13 without N-terminal signal peptide), wherein X at position 169 of SEQ ID NO: 224 is Ser or Cys; (jjjjjj) the amino acid sequences of both of SEQ ID NOs: 223 and 224; (kkkkk) the amino acid sequence of SEQ ID NO: 225 (α chain of cysteine-substituted, LVL-modified 4400 TCR-N13 with N-terminal signal peptide); (lllll) the amino acid sequence of SEQ ID NO: 226 (β chain of cysteine-substituted, LVL-modified 4400 TCR-N13 with N-terminal signal peptide); (mmmmm) the amino acid sequence of SEQ ID NO: 227 (predicted sequence of α chain of cysteine-substituted, LVL-modified 4400 TCR-N13 without N-terminal signal peptide); (nnnnn) the amino acid sequence of SEQ ID NO: 228 (predicted sequence of β chain of cysteine-substituted, LVL-modified 4400 TCR-N13 without N-terminal signal peptide); (ooooo) the amino acid sequences of both of SEQ ID NOs: 225 and 226; (ppppp) the amino acid sequences of both of SEQ ID NOs: 227 and 228; (qqqqq) the amino acid sequence of SEQ ID NO: 229 (α chain of 4400 TCR-C with N-terminal signal peptide), wherein: (i) X at position 184 of SEQ ID NO: 229 is Thr or Cys; (ii) X at position 248 of SEQ ID NO: 229 is Ser, Ala, Val, Leu, Ile, Pro, Phe, Met, or Trp; (iii) X at position 250 of SEQ ID NO: 229 is Met, Ala, Val, Leu, Ile, Pro, Phe, or Trp; and (iv) X at position 251 of SEQ ID NO: 229 is Gly, Ala, Val, Leu, Ile, Pro, Phe, Met, or Trp; (rrrrr) the amino acid sequence of SEQ ID NO: 230 (β chain of 4400 TCR-C with N-terminal signal peptide), wherein X at position 189 of SEQ ID NO: 230 is Ser or Cys; (sssss) the amino acid sequences of both of SEQ ID NOs: 229 and 230; (ttttt) the amino acid sequence of SEQ ID NO: 231 (predicted sequence of a chain of 4400 TCR-C without N-terminal signal peptide), wherein: (i) X at position 163 of SEQ ID NO: 231 is Thr or Cys; (ii) X at position 227 of SEQ ID NO: 231 is Ser, Ala, Val, Leu, Ile, Pro, Phe, Met, or Trp; (iii) X at position 229 of SEQ ID NO: 231 is Met, Ala, Val, Ile, Pro, Phe, or Trp; and (iv) X at position 230 of SEQ ID NO: 231 is Gly, Ala, Val, Leu, Ile, Pro, Phe, Met, or Trp; (uuuuu) the amino acid sequence of SEQ ID NO: 232 (predicted sequence of β chain of 4400 TCR-C without N-terminal signal peptide), wherein X at position 170 of SEQ ID NO: 232 is Ser or Cys; (vvvvv) the amino acid sequences of both of SEQ ID NOs: 231 and 232; (wwwww) the amino acid sequence of SEQ ID NO: 233 (a chain of cysteine-substituted, LVL-modified 4400 TCR-C with N-terminal signal peptide); (xxxxx) the amino acid sequence of SEQ ID NO: 234 (β chain of cysteine-substituted, LVL-modified 4400 TCR-C with N-terminal signal peptide); (yyyyy) the amino acid sequence of SEQ ID NO: 235 (predicted sequence of α chain of cysteine-substituted, LVL-modified 4400 TCR-C without N-terminal signal peptide); (zzzzz) the amino acid sequence of SEQ ID NO: 236 (predicted sequence of β chain of cysteine-substituted, LVL-modified 4400 TCR-C without N-terminal signal peptide); (aaaaaa) the amino acid sequences of both of SEQ ID NOs: 233 and 234; (bbbbbb) the amino acid sequences of both of SEQ ID NOs: 235 and 236; (cccccc) the amino acid sequence of SEQ ID NO: 237 (α chain of 4400 TCR-20 with N-terminal signal peptide), wherein: (i) X at position 184 of SEQ ID NO: 237 is Thr or Cys; (ii) X at position 248 of SEQ ID NO: 237 is Ser, Ala, Val, Leu, Ile, Pro, Phe, Met, or Trp; (iii) X at position 250 of SEQ ID NO: 237 is Met, Ala, Val, Leu, Ile, Pro, Phe, or Trp; and (iv) X at position 251 of SEQ ID NO: 237 is Gly, Ala, Val, Leu, Ile, Pro, Phe, Met, or Trp; (dddddd) the amino acid sequence of SEQ ID NO: 238 (β chain of 4400 TCR-20 with N-terminal signal peptide), wherein X at position 189 of SEQ ID NO: 238 is Ser or Cys; (eeeeee) the amino acid sequences of both of SEQ ID NOs: 237 and 238; (ffffff) the amino acid sequence of SEQ ID NO: 239 (predicted sequence of α chain of 4400 TCR-20 without N-terminal signal peptide), wherein: (i) X at position 163 of SEQ ID NO: 239 is Thr or Cys; (ii) X at position 227 of SEQ ID NO: 239 is Ser, Ala, Val, Leu, Ile, Pro, Phe, Met, or Trp; (iii) X at position 229 of SEQ ID NO: 239 is Met, Ala, Val, Leu, Ile, Pro, Phe, or Trp; and (iv) X at position 230 of SEQ ID NO: 239 is Gly, Ala, Val, Leu, Ile, Pro, Phe, Met, or Trp; (gggggg) the amino acid sequence of SEQ ID NO: 240 (predicted sequence of β chain of 4400 TCR-20 without N-terminal signal peptide), wherein X at position 170 of SEQ ID NO: 240 is Ser or Cys; (hhhhhh) the amino acid sequences of both of SEQ ID NOs: 239 and 240; (iiiiii) the amino acid sequence of SEQ ID NO: 241 (α chain of cysteine-substituted, LVL-modified 4400 TCR-20 with N-terminal signal peptide); (jjjjjj) the amino acid sequence of SEQ ID NO: 242 (β chain of cysteine-substituted, LVL-modified 4400 TCR-20 with N-terminal signal peptide); (kkkkkk) the amino acid sequence of SEQ ID NO: 243 (predicted sequence of α chain of cysteine-substituted, LVL-modified 4400 TCR-20 without N-terminal signal peptide); (llllll) the amino acid sequence of SEQ ID NO: 244 (predicted sequence of β chain of cysteine-substituted, LVL-modified 4400 TCR-20 without N-terminal signal peptide); (mmmmmm) the amino acid sequences of both of SEQ ID NOs: 241 and 242; or (nnnnnn) the amino acid sequences of both of SEQ ID NOs: 243 and 244.

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 63 and the native Ser at position 57 (Ser57) of SEQ ID NO: 64 may be substituted with Cys. Preferably, both of the native Thr48 of SEQ ID NO: 63 and the native Ser57 of SEQ ID NO: 64 are substituted with Cys. Examples of cysteine-substituted TCR constant regions sequences are set forth in Table 2. In an embodiment of the invention, the cysteine-substituted TCR comprises (i) SEQ ID NO: 59, (ii) SEQ ID NO: 60, or (iii) both of SEQ ID NOs: 59 and 60, wherein both of SEQ ID NOs: 59 and 60 are as defined in Table 2. The cysteine-substituted TCRs of the invention may include the substituted constant region in addition to any of the CDRs or variable regions described herein.

In an embodiment of the invention, the cysteine-substituted, chimeric TCR comprises a full length α chain and a full-length β chain. Examples of cysteine-substituted, chimeric TCR α chain and β chain sequences are set forth in Table 2. In an embodiment of the invention, the TCR comprises: (1) SEQ ID NO: 59, (2) SEQ ID NO: 60, (3) SEQ ID NO: 65, (4) SEQ ID NO: 66, (5) SEQ ID NO: 67, (6) SEQ ID NO: 68, (7) SEQ ID NO: 73, (8) SEQ ID NO: 74, (9) SEQ ID NO: 75, (10) SEQ ID NO: 76, (11) SEQ ID NO: 81, (12) SEQ ID NO: 82, (13) SEQ ID NO: 83, (14) SEQ ID NO: 84, (15) SEQ ID NO: 89, (16) SEQ ID NO: 90, (17) SEQ ID NO: 91, (18) SEQ ID NO: 92, (19) SEQ ID NO: 97, (20) SEQ ID NO: 98, (21) SEQ ID NO: 99, (22) SEQ ID NO: 100, (23) SEQ ID NO: 189, (24) SEQ ID NO: 190, (25) SEQ ID NO: 191, (26) SEQ ID NO: 192, (27) SEQ ID NO: 197, (28) SEQ ID NO: 198, (29) SEQ ID NO: 199, (30) SEQ ID NO: 200, (31) SEQ ID NO: 205, (32) SEQ ID NO: 206, (33) SEQ ID NO: 207, (34) SEQ ID NO: 208, (35) SEQ ID NO: 213, (36) SEQ ID NO: 214, (37) SEQ ID NO: 215, (38) SEQ ID NO: 216, (39) SEQ ID NO: 221, (40) SEQ ID NO: 222, (41) SEQ ID NO: 223, (42) SEQ ID NO: 224, (43) SEQ ID NO: 229, (44) SEQ ID NO: 230, (45) SEQ ID NO: 231, (46) SEQ ID NO: 232, (47) SEQ ID NO: 237, (48) SEQ ID NO: 238, (49) SEQ ID NO: 239, (50) SEQ ID NO: 240, (51) both of SEQ ID NOs: 59 and 60, (52) both of SEQ ID NOs: 65 and 66, (53) both of SEQ ID NOs: 67 and 68, (54) both of SEQ ID NOs: 73 and 74, (55) both of SEQ ID NOs: 75 and 76, (56) both of SEQ ID NOs: 81 and 82, (57) both of SEQ ID NOs: 83 and 84, (58) both of SEQ ID NOs: 89 and 90, (59) both of SEQ ID NOs: 91 and 92, (60) both of SEQ ID NOs: 97 and 98, (61) both of SEQ ID NOs: 99 and 100, (62) both of SEQ ID NOs: 189 and 190, (63) both of SEQ ID NOs: 191 and 192, (64) both of SEQ ID NOs: 197 and 198, (65) both of SEQ ID NOs: 199 and 200, (66) both of SEQ ID NOs: 205 and 206, (67) both of SEQ ID NOs: 207 and 208, (68) both of SEQ ID NOs: 213 and 214, (69) both of SEQ ID NOs: 215 and 216, (70) both of SEQ ID NOs: 221 and 222, (71) both of SEQ ID NOs: 223 and 224, (72) both of SEQ ID NOs: 229 and 230, (73) both of SEQ ID NOs: 231 and 232, (74) both of SEQ ID NOs: 237 and 238, or (75) both of SEQ ID NOs: 239 and 240, wherein all of SEQ ID NOs: 59-60, 65-68, 73-76, 81-84, 89-92, 97-100, 189-192, 197-200, 205-208, 213-216, 221-224, 229-232, and 237-240 are as defined in Table 2.

TABLE 2

| SEQ ID NO: | Definitions of "X" |
|---|---|
| SEQ ID NO: 59 (constant region α chain) | X at position 48 is Cys, X at position 112 is Ser, X at position 114 is Met, and X at position 115 is Gly. |
| SEQ ID NO: 60 (constant region β chain) | X at position 57 is Cys |
| SEQ ID NO: 65 (4400 TCRA1 α chain with N-terminal signal peptide) | X at position 180 is Cys, X at position 244 is Ser, X at position 246 is Met, and X at position 247 is Gly. |
| SEQ ID NO: 66 (4400 TCR-A1 β chain with N-terminal signal peptide) | X at position 188 is Cys |
| SEQ ID NO: 67 (4400 TCR-A1 α chain predicted sequence without N-terminal signal peptide) | X at position 158 is Cys, X at position 222 is Ser, X at position 224 is Met, and X at position 225 is Gly. |
| SEQ ID NO: 68 (4400 TCR-A1 β chain predicted sequence without N-terminal signal peptide) | X at position 169 is Cys |
| SEQ ID NO: 73 (4400 TCR-A2 α chain with N-terminal signal peptide) | X at position 180 is Cys, X at position 244 is Ser, X at position 246 is Met, and X at position 247 is Gly. |
| SEQ ID NO: 74 (4400 TCR-A2 β chain with N-terminal signal peptide) | X at position 188 is Cys |
| SEQ ID NO: 75 (4400 TCR-A2 α chain predicted sequence without N-terminal signal peptide) | X at position 158 is Cys, X at position 222 is Ser, X at position 224 is Met, and X at position 225 is Gly. |
| SEQ ID NO: 76 (4400 TCR-A2 β chain predicted sequence without N-terminal signal peptide) | X at position 169 is Cys |
| SEQ ID NO: 81 (4400 TCR-E α chain with N-terminal signal peptide) | X at position 177 is Cys, X at position 241 is Ser, X at position 243 is Met, and X at position 244 is Gly. |
| SEQ ID NO: 82 (4400 TCR-E β chain with N-terminal signal peptide) | X at position 189 is Cys |
| SEQ ID NO: 83 (4400 TCR-E α chain predicted sequence without N-terminal signal peptide) | X at position 160 is Cys, X at position 224 is Ser, X at position 226 is Met, and X at position 227 is Gly. |
| SEQ ID NO: 84 (4400 TCR-E β chain predicted sequence without N-terminal signal peptide) | X at position 170 is Cys |
| SEQ ID NO: 89 (4400 TCR-J α chain with N-terminal signal peptide) | X at position 183 is Cys, X at position 247 is Ser, X at position 249 is Met, and X at position 250 is Gly. |
| SEQ ID NO: 90 (4400 TCR-J β chain with N-terminal signal peptide) | X at position 188 is Cys |
| SEQ ID NO: 91 (4400 TCR-J α chain predicted sequence without N-terminal signal peptide) | X at position 161 is Cys, X at position 225 is Ser, X at position 227 is Met, and X at position 228 is Gly. |
| SEQ ID NO: 92 (4400 TCR-J β chain predicted sequence without N-terminal signal peptide) | X at position 169 is Cys |

TABLE 2-continued

| SEQ ID NO: | Definitions of "X" |
|---|---|
| SEQ ID NO: 97<br>(4400 TCR-N α chain with N-terminal signal peptide) | X at position 178 is Cys,<br>X at position 242 is Ser,<br>X at position 244 is Met, and<br>X at position 245 is Gly. |
| SEQ ID NO: 98<br>(4400 TCR-N β chain with N-terminal signal peptide) | X at position 188 is Cys |
| SEQ ID NO: 99<br>(4400 TCR-N α chain predicted sequence without N-terminal signal peptide) | X at position 157 is Cys,<br>X at position 221 is Ser,<br>X at position 223 is Met, and<br>X at position 224 is Gly. |
| SEQ ID NO: 100<br>(4400 TCR-N β chain predicted sequence without N-terminal signal peptide) | X at position 169 is Cys |
| SEQ ID NO: 189<br>(α chain of 4400 TCR-A3 with N-terminal signal peptide) | X at position 176 is Cys;<br>X at position 240 Ser;<br>X at position 242 Met; and<br>X at position 243 Gly. |
| SEQ ID NO: 190<br>(β chain of 4400 TCR-A3 with N-terminal signal peptide) | X at position 188 is Cys |
| SEQ ID NO: 191<br>(predicted sequence of α chain of 4400 TCR-A3 without N-terminal signal peptide) | X at position 157 is Cys;<br>X at position 221 is Ser;<br>X at position 223 is Met; and<br>X at position 224 Gly. |
| SEQ ID NO: 192<br>(predicted sequence of β chain of 4400 TCR-A3 without N-terminal signal peptide) | X at position 169 is Cys |
| SEQ ID NO: 197<br>(α chain of 4400 TCR-J2 with N-terminal signal peptide) | X at position 181 is Cys;<br>X at position 245 is Ser;<br>X at position 247 is Met; and<br>X at position 248 is Gly. |
| SEQ ID NO: 198<br>(β chain of 4400 TCR-J2 with N-terminal signal peptide) | X at position 188 is Cys |
| SEQ ID NO: 199<br>(predicted sequence of α chain of 4400 TCR-J2 without N-terminal signal peptide) | X at position 161 is Cys;<br>X at position 225 is Ser;<br>X at position 227 is Met; and<br>X at position 228 Gly. |
| SEQ ID NO: 200<br>(predicted sequence of β chain of 4400 TCR-J2 without N-terminal signal peptide) | X at position 169 is Cys |
| SEQ ID NO: 205<br>(α chain of 4400 TCR-N4 with N-terminal signal peptide) | X at position 184 is Cys;<br>X at position 248 is Ser;<br>X at position 250 is Met; and<br>X at position 251 is Gly. |
| SEQ ID NO: 206<br>(β chain of 4400 TCR-N4 with N-terminal signal peptide) | X at position 190 is Cys |
| SEQ ID NO: 207<br>(predicted sequence of α chain of 4400 TCR-N4 without N-terminal signal peptide) | X at position 163 is Cys;<br>X at position 227 is Ser;<br>X at position 229 is Met; and<br>X at position 230 is Gly. |
| SEQ ID NO: 208<br>(predicted sequence of β chain of 4400 TCR-N4 without N-terminal signal peptide) | X at position 164 is Cys |
| SEQ ID NO: 213<br>(α chain of 4400 TCR-N12 with N-terminal signal peptide) | X at position 183 is Cys;<br>X at position 247 is Ser;<br>X at position 249 is Met; and<br>X at position 250 is Gly. |
| SEQ ID NO: 214<br>(β chain of 4400 TCR-N12 with N-terminal signal peptide) | X at position 188 is Cys |
| SEQ ID NO: 215<br>(predicted sequence of α chain of 4400 TCR-N12 without N-terminal signal peptide) | X at position 161 is Cys;<br>X at position 225 is Ser;<br>X at position 227 is Met; and<br>X at position 228 is Gly. |
| SEQ ID NO: 216<br>(predicted sequence of β chain of 4400 TCR-N12 without N-terminal signal peptide) | X at position 169 is Cys |
| SEQ ID NO: 221<br>(α chain of 4400 TCR-N13 with N-terminal signal peptide) | X at position 180 is Cys;<br>X at position 244 is Ser;<br>X at position 246 is Met; and<br>X at position 247 is Gly. |
| SEQ ID NO: 222<br>(β chain of 4400 TCR-N13 with N-terminal signal peptide) | X at position 188 is Cys |
| SEQ ID NO: 223<br>(predicted sequence of α chain of 4400 TCR-N13 without N-terminal signal peptide) | X at position 158 is Cys;<br>X at position 222 is Ser;<br>X at position 224 is Met; and<br>X at position 225 is Gly. |
| SEQ ID NO: 224<br>(predicted sequence of β chain of 4400 TCR-N13 without N-terminal signal peptide) | X at position 169 is Cys |

TABLE 2-continued

| SEQ ID NO: | Definitions of "X" |
|---|---|
| SEQ ID NO: 229<br>(α chain of 4400 TCR-C with N-terminal signal peptide) | X at position 184 is Cys;<br>X at position 248 is Ser;<br>X at position 250 is Met; and<br>X at position 251 is Gly. |
| SEQ ID NO: 230<br>(β chain of 4400 TCR-C with N-terminal signal peptide) | X at position 189 is Cys |
| SEQ ID NO: 231<br>(predicted sequence of α chain of 4400 TCR-C without N-terminal signal peptide) | X at position 163 is Cys;<br>X at position 227 is Ser;<br>X at position 229 of is Met; and<br>X at position 230 is Gly. |
| SEQ ID NO: 232<br>(predicted sequence of β chain of 4400 TCR-C without N-terminal signal peptide) | X at position 170 is Cys |
| SEQ ID NO: 237<br>(α chain of 4400 TCR-20 with N-terminal signal peptide) | X at position 184 is Cys;<br>X at position 248 is Ser;<br>X at position 250 is Met; and<br>X at position 251 is Gly. |
| SEQ ID NO: 238<br>(β chain of 4400 TCR-20 with N-terminal signal peptide) | X at position 189 is Cys |
| SEQ ID NO: 239<br>(predicted sequence of α chain of 4400 TCR-20 without N-terminal signal peptide) | X at position 163 is Cys;<br>X at position 227 is Ser;<br>X at position 229 is Met; and<br>X at position 230 is Gly. |
| SEQ ID NO: 240<br>(predicted sequence of β chain of 4400 TCR-20 without N-terminal signal peptide) | X at position 170 is Cys |

In an embodiment of the invention, the substituted amino acid sequence includes substitutions of one, two, or three amino acids in the transmembrane (TM) domain of the constant region of the α chain with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is an LVL-modified TCR in which one, two, or three of the native Ser112, Met114, and Gly115 of SEQ ID NO: 63 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 63 may, independently, be substituted with Ala, Val, Leu, Ile, Pro, Phe, Met, or Trp; preferably with Leu, Ile, or Val. In an embodiment of the invention, the LVL-modified TCR comprises (i) SEQ ID NO: 59, (ii) SEQ ID NO: 60, or (iii) both of SEQ ID NOs: 59 and 60, wherein both of SEQ ID NOs: 59 and 60 are as defined in Table 3. The LVL-modified TCRs of the invention may include the substituted constant region in addition to any of the CDRs or variable regions described herein.

In an embodiment of the invention, the LVL-modified TCR comprises a full length α chain and a full-length β chain. Examples of LVL-modified TCR α chain and β chain sequences are set forth in Table 3. In an embodiment of the invention, the TCR comprises: (1) SEQ ID NO: 59, (2) SEQ ID NO: 60, (3) SEQ ID NO: 65, (4) SEQ ID NO: 66, (5) SEQ ID NO: 67, (6) SEQ ID NO: 68, (7) SEQ ID NO: 73, (8) SEQ ID NO: 74, (9) SEQ ID NO: 75, (10) SEQ ID NO: 76, (11) SEQ ID NO: 81, (12) SEQ ID NO: 82, (13) SEQ ID NO: 83, (14) SEQ ID NO: 84, (15) SEQ ID NO: 89, (16) SEQ ID NO: 90, (17) SEQ ID NO: 91, (18) SEQ ID NO: 92, (19) SEQ ID NO: 97, (20) SEQ ID NO: 98, (21) SEQ ID NO: 99, (22) SEQ ID NO: 100, (23) SEQ ID NO: 189, (24) SEQ ID NO: 190, (25) SEQ ID NO: 191, (26) SEQ ID NO: 192, (27) SEQ ID NO: 197, (28) SEQ ID NO: 198, (29) SEQ ID NO: 199, (30) SEQ ID NO: 200, (31) SEQ ID NO: 205, (32) SEQ ID NO: 206, (33) SEQ ID NO: 207, (34) SEQ ID NO: 208, (35) SEQ ID NO: 213, (36) SEQ ID NO: 214, (37) SEQ ID NO: 215, (38) SEQ ID NO: 216, (39) SEQ ID NO: 221, (40) SEQ ID NO: 222, (41) SEQ ID NO: 223, (42) SEQ ID NO: 224, (43) SEQ ID NO: 229, (44) SEQ ID NO: 230, (45) SEQ ID NO: 231, (46) SEQ ID NO: 232, (47) SEQ ID NO: 237, (48) SEQ ID NO: 238, (49) SEQ ID NO: 239, (50) SEQ ID NO: 240, (51) both of SEQ ID NOs: 59 and 60, (52) both of SEQ ID NOs: 65 and 66, (53) both of SEQ ID NOs: 67 and 68, (54) both of SEQ ID NOs: 73 and 74, (55) both of SEQ ID NOs: 75 and 76, (56) both of SEQ ID NOs: 81 and 82, (57) both of SEQ ID NOs: 83 and 84, (58) both of SEQ ID NOs: 89 and 90, (59) both of SEQ ID NOs: 91 and 92, (60) both of SEQ ID NOs: 97 and 98, (61) both of SEQ ID NOs: 99 and 100, (62) both of SEQ ID NOs: 189 and 190, (63) both of SEQ ID NOs: 191 and 192, (64) both of SEQ ID NOs: 197 and 198, (65) both of SEQ ID NOs: 199 and 200, (66) both of SEQ ID NOs: 205 and 206, (67) both of SEQ ID NOs: 207 and 208, (68) both of SEQ ID NOs: 213 and 214, (69) both of SEQ ID NOs: 215 and 216, (70) both of SEQ ID NOs: 221 and 222, (71) both of SEQ ID NOs: 223 and 224, (72) both of SEQ ID NOs: 229 and 230, (73) both of SEQ ID NOs: 231 and 232, (74) both of SEQ ID NOs: 237 and 238, or (75) both of SEQ ID NOs: 239 and 240, wherein all of SEQ ID NOs: 59-60, 65-68, 73-76, 81-84, 89-92, 97-100, 189-192, 197-200, 205-208, 213-216, 221-224, 229-232, and 237-240 are as defined in Table 3.

TABLE 3

| SEQ ID NO: | Definitions of "X" |
|---|---|
| SEQ ID NO: 59 (constant region α chain) | X at position 48 is Thr;<br>X at position 112 is Ser, Ala, Val, Leu, Ile, Pro, Phe, Met, or Trp; preferably wherein X at position 112 is Leu, Ile, or Val; especially preferably wherein X at position 112 is Leu;<br>X at position 114 is Met, Ala, Val, Leu, Ile, Pro, Phe, or Trp; preferably wherein X at position 114 is Leu, Ile, or Val; especially preferably wherein X at position 114 is Ile; and<br>X at position 115 is Gly, Ala, Val, Leu, Ile, Pro, Phe, Met, or Trp; preferably wherein X at position 115 is Leu, Ile, or Val; especially preferably wherein X at position 115 is Val;<br>wherein SEQ ID NO: 59 does not comprise SEQ ID NO: 63 (unsubstituted α chain constant region) |
| SEQ ID NO: 60 (constant region β chain) | X at position 57 is Ser |
| SEQ ID NO: 65 (4400 TCR-A1 α chain) (with N-terminal signal peptide) | X at position 180 is Thr;<br>X at position 244 is Ser, Ala, Val, Leu, Ile, Pro, Phe, Met, or Trp; preferably wherein X at position 244 is Leu, Ile, or Val; especially preferably wherein X at position 244 is Leu;<br>X at position 246 is Met, Ala, Val, Leu, Ile, Pro, Phe, or Trp; preferably wherein X at position 246 is Leu, Ile, or Val; especially preferably wherein X at position 246 is Ile; and<br>X at position 247 is Gly, Ala, Val, Leu, Ile, Pro, Phe, Met, or Trp; preferably wherein X at position 247 is Leu, Ile, or Val; especially preferably wherein X at position 247 is Val,<br>wherein SEQ ID NO: 65 does not comprise SEQ ID NO: 63 (unsubstituted α chain constant region) |
| SEQ ID NO: 66 (4400 TCR-A1 β chain) (with N-terminal signal peptide) | X at position 188 is Ser |
| SEQ ID NO: 67 (4400 TCR-A1 α chain) (predicted sequence without N-terminal signal peptide) | X at position 158 is Thr;<br>X at position 222 is Ser, Ala, Val, Leu, Ile, Pro, Phe, Met, or Trp; preferably wherein X at position 222 is Leu, Ile, or Val; especially preferably wherein X at position 222 is Leu;<br>X at position 224 is Met, Ala, Val, Leu, Ile, Pro, Phe, or Trp; preferably wherein X at position 224 is Leu, Ile, or Val; especially preferably wherein X at position 224 is Ile; and<br>X at position 225 is Gly, Ala, Val, Leu, Ile, Pro, Phe, Met, or Trp; preferably wherein X at position 225 is Leu, Ile, or Val; especially preferably wherein X at position 225 is Val,<br>wherein SEQ ID NO: 67 does not comprise SEQ ID NO: 63 (unsubstituted α chain constant region) |
| SEQ ID NO: 68 (4400 TCR-A1 β chain) (predicted sequence without N-terminal signal peptide) | X at position 169 is Ser |
| SEQ ID NO: 73 (4400 TCR-A2 α chain with N-terminal signal peptide) | X at position 180 is Thr;<br>X at position 244 is Ser, Ala, Val, Leu, Ile, Pro, Phe, Met, or Trp; preferably wherein X at position 244 is Leu, Ile, or Val; especially preferably wherein X at position 244 is Leu;<br>X at position 246 is Met, Ala, Val, Leu, Ile, Pro, Phe, or Trp; preferably wherein X at position 246 is Leu, Ile, or Val; especially preferably wherein X at position 246 is Ile; and<br>X at position 247 is Gly, Ala, Val, Leu, Ile, Pro, Phe, Met, or Trp; preferably wherein X at position 247 is Leu, Ile, or Val; especially preferably wherein X at position 247 is Val,<br>wherein SEQ ID NO: 73 does not comprise SEQ ID NO: 63 (unsubstituted α chain constant region) |
| SEQ ID NO: 74 (4400 TCR-A2 β chain with N-terminal signal peptide) | X at position 188 is Ser |
| SEQ ID NO: 75 (4400 TCR-A2 α chain predicted sequence without N-terminal signal peptide) | X at position 158 is Thr;<br>X at position 222 is Ser, Ala, Val, Leu, Ile, Pro, Phe, Met, or Trp; preferably wherein X at position 222 is Leu, Ile, or Val; especially preferably wherein X at position 222 is Leu;<br>X at position 224 is Met, Ala, Val, Leu, Ile, Pro, Phe, or Trp; preferably wherein X at position 224 is Leu, Ile, or Val; especially preferably wherein X at position 224 is Ile; and<br>X at position 225 is Gly, Ala, Val, Leu, Ile, Pro, Phe, Met, or Trp; preferably wherein X at position 225 is Leu, Ile, or Val; especially preferably wherein X at position 225 is Val,<br>wherein SEQ ID NO: 75 does not comprise SEQ ID NO: 63 (unsubstituted α chain constant region) |

TABLE 3-continued

| SEQ ID NO: | Definitions of "X" |
|---|---|
| SEQ ID NO: 76 (4400 TCR-A2 β chain predicted sequence without N-terminal signal peptide) | X at position 169 is Ser |
| SEQ ID NO: 81 (4400 TCR-E α chain with N-terminal signal peptide) | X at position 177 is Thr; X at position 241 is Ser, Ala, Val, Leu, Ile, Pro, Phe, Met, or Trp; preferably wherein X at position 241 is Leu, Ile, or Val; especially preferably wherein X at position 241 is Leu; X at position 243 is Met, Ala, Val, Leu, Ile, Pro, Phe, or Trp; preferably wherein X at position 243 is Leu, Ile, or Val; especially preferably wherein X at position 243 is Ile; and X at position 244 is Gly, Ala, Val, Leu, Ile, Pro, Phe, Met, or Trp; preferably wherein X at position 244 is Leu, Ile, or Val; especially preferably wherein X at position 244 is Val, wherein SEQ ID NO: 81 does not comprise SEQ ID NO: 63 (unsubstituted α chain constant region) |
| SEQ ID NO: 82 (4400 TCR-E β chain with N-terminal signal peptide) | X at position 189 is Ser |
| SEQ ID NO: 83 (4400 TCR-E α chain predicted sequence without N-terminal signal peptide) | X at position 160 is Thr; X at position 224 is Ser, Ala, Val, Leu, Ile, Pro, Phe, Met, or Trp; preferably wherein X at position 224 is Leu, Ile, or Val; especially preferably wherein X at position 224 is Leu; X at position 226 is Met, Ala, Val, Leu, Ile, Pro, Phe, or Trp; preferably wherein X at position 226 is Leu, Ile, or Val; especially preferably wherein X at position 226 is Ile; and X at position 227 is Gly, Ala, Val, Leu, Ile, Pro, Phe, Met, or Trp; preferably wherein X at position 227 is Leu, Ile, or Val; especially preferably wherein X at position 227 is Val, wherein SEQ ID NO: 83 does not comprise SEQ ID NO: 63 (unsubstituted α chain constant region) |
| SEQ ID NO: 84 (4400 TCR-E β chain predicted sequence without N-terminal signal peptide) | X at position 170 is Ser |
| SEQ ID NO: 89 (4400 TCR-J α chain with N-terminal signal peptide) | X at position 183 is Thr; X at position 247 is Ser, Ala, Val, Leu, Ile, Pro, Phe, Met, or Trp; preferably wherein X at position 247 is Leu, Ile, or Val; especially preferably wherein X at position 247 is Leu; X at position 249 is Met, Ala, Val, Leu, Ile, Pro, Phe, or Trp; preferably wherein X at position 249 is Leu, Ile, or Val; especially preferably wherein X at position 249 is Ile; and X at position 250 is Gly, Ala, Val, Leu, Ile, Pro, Phe, Met, or Trp; preferably wherein X at position 250 is Leu, Ile, or Val; especially preferably wherein X at position 250 is Val, wherein SEQ ID NO: 89 does not comprise SEQ ID NO: 63 (unsubstituted α chain constant region) |
| SEQ ID NO: 90 (4400 TCR-J β chain with N-terminal signal peptide) | X at position 188 is Ser |
| SEQ ID NO: 91 (4400 TCR-J α chain predicted sequence without N-terminal signal peptide) | X at position 161 is Thr; X at position 225 is Ser, Ala, Val, Leu, Ile, Pro, Phe, Met, or Trp; preferably wherein X at position 225 is Leu, Ile, or Val; especially preferably wherein X at position 225 is Leu; X at position 227 is Met, Ala, Val, Leu, Ile, Pro, Phe, or Trp; preferably wherein X at position 227 is Leu, Ile, or Val; especially preferably wherein X at position 227 is Ile; and X at position 228 is Gly, Ala, Val, Leu, Ile, Pro, Phe, Met, or Trp; preferably wherein X at position 228 is Leu, Ile, or Val; especially preferably wherein X at position 228 is Val, wherein SEQ ID NO: 91 does not comprise SEQ ID NO: 63 (unsubstituted α chain constant region) |
| SEQ ID NO: 92 (4400 TCR-J β chain predicted sequence without N-terminal signal peptide) | X at position 169 is Ser |
| SEQ ID NO: 97 (4400 TCR-N α chain with N-terminal signal peptide) | X at position 178 is Thr; X at position 242 is Ser, Ala, Val, Leu, Ile, Pro, Phe, Met, or Trp; preferably wherein X at position 242 is Leu, Ile, or Val; especially preferably wherein X at position 242 is Leu; X at position 244 is Met, Ala, Val, Leu, Ile, Pro, Phe, or Trp; preferably wherein X at position 244 is Leu, Ile, or Val; |

TABLE 3-continued

| SEQ ID NO: | Definitions of "X" |
| --- | --- |
| | especially preferably wherein X at position 244 is Ile; and<br>X at position 245 is Gly, Ala, Val, Leu, Ile, Pro, Phe, Met, or Trp;<br>preferably wherein X at position 245 is Leu, Ile, or Val;<br>especially preferably wherein X at position 245 is Val,<br>wherein SEQ ID NO: 97 does not comprise SEQ ID NO: 63<br>(unsubstituted α chain constant region) |
| SEQ ID NO: 98<br>(4400 TCR-N β chain<br>with N-terminal signal<br>peptide) | X at position 188 is Ser |
| SEQ ID NO: 99<br>(4400 TCR-N α chain<br>predicted sequence<br>without N-terminal<br>signal peptide) | X at position 157 is Thr;<br>X at position 221 is Ser, Ala, Val, Leu, Ile, Pro, Phe, Met, or Trp;<br>preferably wherein X at position 221 is Leu, Ile, or Val;<br>especially preferably wherein X at position 221 is Leu;<br>X at position 223 is Met, Ala, Val, Leu, Ile, Pro, Phe, or Trp;<br>preferably wherein X at position 223 is Leu, Ile, or Val;<br>especially preferably wherein X at position 223 is Ile; and<br>X at position 224 is Gly, Ala, Val, Leu, Ile, Pro, Phe, Met, or Trp;<br>preferably wherein X at position 224 is Leu, Ile, or Val;<br>especially preferably wherein X at position 224 is Val,<br>wherein SEQ ID NO: 99 does not comprise SEQ ID NO: 63<br>(unsubstituted α chain constant region) |
| SEQ ID NO: 100<br>(4400 TCR-N β chain<br>predicted sequence<br>without N-terminal<br>signal peptide) | X at position 169 is Ser |
| SEQ ID NO: 189<br>(α chain of 4400<br>TCR-A3 with N-<br>terminal signal<br>peptide) | X at position 176 is Thr;<br>X at position 240 is Ser, Ala, Val, Leu, Ile, Pro, Phe, Met, or Trp;<br>preferably wherein X at position 240 is Leu, Ile, or Val;<br>especially preferably wherein X at position 240 is Leu;<br>X at position 242 is Met, Ala, Val, Leu, Ile, Pro, Phe, or Trp;<br>preferably wherein X at position 242 is Leu, Ile, or Val;<br>especially preferably wherein X at position 242 is Ile; and<br>X at position 243 is Gly, Ala, Val, Leu, Ile, Pro, Phe, Met, or Trp;<br>preferably wherein X at position 243 is Leu, Ile, or Val;<br>especially preferably wherein X at position 243 is Val,<br>wherein SEQ ID NO: 189 does not comprise SEQ ID NO: 63<br>(unsubstituted α chain constant region) |
| SEQ ID NO: 190<br>(β chain of 4400<br>TCR-A3 with N-<br>terminal signal<br>peptide) | X at position 188 is Ser |
| SEQ ID NO: 191<br>(predicted sequence<br>of α chain of 4400<br>TCR-A3 without N-<br>terminal signal<br>peptide) | X at position 157 is Thr;<br>X at position 221 is Ser, Ala, Val, Leu, Ile, Pro, Phe, Met, or Trp;<br>preferably wherein X at position 221 is Leu, Ile, or Val;<br>especially preferably wherein X at position 221 is Leu;<br>X at position 223 is Met, Ala, Val, Leu, Ile, Pro, Phe, or Trp;<br>preferably wherein X at position 223 is Leu, Ile, or Val;<br>especially preferably wherein X at position 223 is Ile; and<br>X at position 224 is Gly, Ala, Val, Leu, Ile, Pro, Phe, Met, or Trp;<br>preferably wherein X at position 224 is Leu, Ile, or Val;<br>especially preferably wherein X at position 224 is Val,<br>wherein SEQ ID NO: 191 does not comprise SEQ ID NO: 63<br>(unsubstituted α chain constant region) |
| SEQ ID NO: 192<br>(predicted sequence<br>of β chain of 4400<br>TCR-A3 without N-<br>terminal signal<br>peptide) | X at position 169 is Ser |
| SEQ ID NO: 197<br>(α chain of 4400<br>TCR-J2 with N-<br>terminal signal<br>peptide) | X at position 181 is Thr;<br>X at position 245 is Ser, Ala, Val, Leu, Ile, Pro, Phe, Met, or Trp;<br>preferably wherein X at position 245 is Leu, Ile, or Val;<br>especially preferably wherein X at position 245 is Leu;<br>X at position 247 is Met, Ala, Val, Leu, Ile, Pro, Phe, or Trp;<br>preferably wherein X at position 247 is Leu, Ile, or Val;<br>especially preferably wherein X at position 247 is Ile; and<br>X at position 248 is Gly, Ala, Val, Leu, Ile, Pro, Phe, Met, or Trp;<br>preferably wherein X at position 248 is Leu, Ile, or Val;<br>especially preferably wherein X at position 248 is Val,<br>wherein SEQ ID NO: 197 does not comprise SEQ ID NO: 63<br>(unsubstituted α chain constant region) |

TABLE 3-continued

| SEQ ID NO: | Definitions of "X" |
|---|---|
| SEQ ID NO: 198 (β chain of 4400 TCR-J2 with N-terminal signal peptide) | X at position 188 is Ser |
| SEQ ID NO: 199 (predicted sequence of α chain of 4400 TCR-J2 without N-terminal signal peptide) | X at position 161 is Thr;<br>X at position 225 is Ser, Ala, Val, Leu, Ile, Pro, Phe, Met, or Trp;<br>preferably wherein X at position 225 is Leu, Ile, or Val;<br>especially preferably wherein X at position 225 is Leu;<br>X at position 227 is Met, Ala, Val, Leu, Ile, Pro, Phe, or Trp;<br>preferably wherein X at position 227 is Leu, Ile, or Val;<br>especially preferably wherein X at position 227 is Ile; and<br>X at position 228 is Gly, Ala, Val, Leu, Ile, Pro, Phe, Met, or Trp;<br>preferably wherein X at position 228 is Leu, Ile, or Val;<br>especially preferably wherein X at position 228 is Val,<br>wherein SEQ ID NO: 199 does not comprise SEQ ID NO: 63<br>(unsubstituted α chain constant region) |
| SEQ ID NO: 200 (predicted sequence of β chain of 4400 TCR-J2 without N-terminal signal peptide) | X at position 169 is Ser |
| SEQ ID NO: 205 (α chain of 4400 TCR-N4 with N-terminal signal peptide) | X at position 184 is Thr;<br>X at position 248 is Ser, Ala, Val, Leu, Ile, Pro, Phe, Met, or Trp;<br>preferably wherein X at position 248 is Leu, Ile, or Val;<br>especially preferably wherein X at position 248 is Leu;<br>X at position 250 is Met, Ala, Val, Leu, Ile, Pro, Phe, or Trp;<br>preferably wherein X at position 250 is Leu, Ile, or Val;<br>especially preferably wherein X at position 250 is Ile; and<br>X at position 251 is Gly, Ala, Val, Leu, Ile, Pro, Phe, Met, or Trp;<br>preferably wherein X at position 251 is Leu, Ile, or Val;<br>especially preferably wherein X at position 251 is Val,<br>wherein SEQ ID NO: 205 does not comprise SEQ ID NO: 63<br>(unsubstituted α chain constant region) |
| SEQ ID NO: 206 (β chain of 4400 TCR-N4 with N-terminal signal peptide) | X at position 190 is Ser |
| SEQ ID NO: 207 (predicted sequence of α chain of 4400 TCR-N4 without N-terminal signal peptide) | X at position 163 is Thr;<br>X at position 227 is Ser, Ala, Val, Leu, Ile, Pro, Phe, Met, or Trp;<br>preferably wherein X at position 227 is Leu, Ile, or Val;<br>especially preferably wherein X at position 227 is Leu;<br>X at position 229 is Met, Ala, Val, Leu, Ile, Pro, Phe, or Trp;<br>preferably wherein X at position 229 is Leu, Ile, or Val;<br>especially preferably wherein X at position 229 is Ile; and<br>X at position 230 is Gly, Ala, Val, Leu, Ile, Pro, Phe, Met, or Trp;<br>preferably wherein X at position 230 is Leu, Ile, or Val;<br>especially preferably wherein X at position 230 is Val,<br>wherein SEQ ID NO: 207 does not comprise SEQ ID NO: 63<br>(unsubstituted α chain constant region) |
| SEQ ID NO: 208 (predicted sequence of β chain of 4400 TCR-N4 without N-terminal signal peptide) | X at position 164 is Ser |
| SEQ ID NO: 213 (α chain of 4400 TCR-N12 with N-terminal signal peptide) | X at position 183 is Thr;<br>X at position 247 is Ser, Ala, Val, Leu, Ile, Pro, Phe, Met, or Trp;<br>preferably wherein X at position 247 is Leu, Ile, or Val;<br>especially preferably wherein X at position 247 is Leu;<br>X at position 249 is Met, Ala, Val, Leu, Ile, Pro, Phe, or Trp;<br>preferably wherein X at position 249 is Leu, Ile, or Val;<br>especially preferably wherein X at position 249 is Ile; and<br>X at position 250 is Gly, Ala, Val, Leu, Ile, Pro, Phe, Met, or Trp;<br>preferably wherein X at position 250 is Leu, Ile, or Val;<br>especially preferably wherein X at position 250 is Val,<br>wherein SEQ ID NO: 213 does not comprise SEQ ID NO: 63<br>(unsubstituted α chain constant region) |
| SEQ ID NO: 214 (β chain of 4400 TCR-N12 with N-terminal signal peptide) | X at position 188 is Ser |
| SEQ ID NO: 215 (predicted sequence of α chain of 4400 | X at position 161 is Thr;<br>X at position 225 is Ser, Ala, Val, Leu, Ile, Pro, Phe, Met, or Trp;<br>preferably wherein X at position 225 is Leu, Ile, or Val; |

TABLE 3-continued

| SEQ ID NO: | Definitions of "X" |
| --- | --- |
| TCR-N12 without N-terminal signal peptide) | especially preferably wherein X at position 225 is Leu;<br>X at position 227 is Met, Ala, Val, Leu, Ile, Pro, Phe, or Trp;<br>preferably wherein X at position 227 is Leu, Ile, or Val;<br>especially preferably wherein X at position 227 is Ile; and<br>X at position 228 is Gly, Ala, Val, Leu, Ile, Pro, Phe, Met, or Trp;<br>preferably wherein X at position 228 is Leu, Ile, or Val;<br>especially preferably wherein X at position 228 is Val,<br>wherein SEQ ID NO: 215 does not comprise SEQ ID NO: 63<br>(unsubstituted α chain constant region) |
| SEQ ID NO: 216 (predicted sequence of β chain of 4400 TCR-N12 without N-terminal signal peptide) | X at position 169 is Ser |
| SEQ ID NO: 221 (α chain of 4400 TCR-N13 with N-terminal signal peptide) | X at position 180 is Thr;<br>X at position 244 is Ser, Ala, Val, Leu, Ile, Pro, Phe, Met, or Trp;<br>preferably wherein X at position 244 is Leu, Ile, or Val;<br>especially preferably wherein X at position 244 is Leu;<br>X at position 246 is Met, Ala, Val, Leu, Ile, Pro, Phe, or Trp;<br>preferably wherein X at position 246 is Leu, Ile, or Val;<br>especially preferably wherein X at position 246 is Ile; and<br>X at position 247 is Gly, Ala, Val, Leu, Ile, Pro, Phe, Met, or Trp;<br>preferably wherein X at position 247 is Leu, Ile, or Val;<br>especially preferably wherein X at position 247 is Val,<br>wherein SEQ ID NO: 221 does not comprise SEQ ID NO: 63<br>(unsubstituted α chain constant region) |
| SEQ ID NO: 222 (β chain of 4400 TCR-N13 with N-terminal signal peptide) | X at position 188 is Ser |
| SEQ ID NO: 223 (predicted sequence of α chain of 4400 TCR-N13 without N-terminal signal peptide) | X at position 158 is Thr;<br>X at position 222 is Ser, Ala, Val, Leu, Ile, Pro, Phe, Met, or Trp;<br>preferably wherein X at position 222 is Leu, Ile, or Val;<br>especially preferably wherein X at position 222 is Leu;<br>X at position 224 is Met, Ala, Val, Leu, Ile, Pro, Phe, or Trp;<br>preferably wherein X at position 224 is Leu, Ile, or Val;<br>especially preferably wherein X at position 224 is Ile; and<br>X at position 225 is Gly, Ala, Val, Leu, Ile, Pro, Phe, Met, or Trp;<br>preferably wherein X at position 225 is Leu, Ile, or Val;<br>especially preferably wherein X at position 225 is Val,<br>wherein SEQ ID NO: 223 does not comprise SEQ ID NO: 63<br>(unsubstituted α chain constant region) |
| SEQ ID NO: 224 (predicted sequence of β chain of 4400 TCR-N13 without N-terminal signal peptide) | X at position 169 is Ser |
| SEQ ID NO: 229 (α chain of 4400 TCR-C with N-terminal signal peptide) | X at position 184 is Thr;<br>X at position 248 is Ser, Ala, Val, Leu, Ile, Pro, Phe, Met, or Trp;<br>preferably wherein X at position 248 is Leu, Ile, or Val;<br>especially preferably wherein X at position 248 is Leu;<br>X at position 250 is Met, Ala, Val, Leu, Ile, Pro, Phe, or Trp;<br>preferably wherein X at position 250 is Leu, Ile, or Val;<br>especially preferably wherein X at position 250 is Ile; and<br>X at position 251 is Gly, Ala, Val, Leu, Ile, Pro, Phe, Met, or Trp;<br>preferably wherein X at position 251 is Leu, Ile, or Val;<br>especially preferably wherein X at position 251 is Val,<br>wherein SEQ ID NO: 229 does not comprise SEQ ID NO: 63<br>(unsubstituted α chain constant region) |
| SEQ ID NO: 230 (β chain of 4400 TCR-C with N-terminal signal peptide) | X at position 189 is Ser |
| SEQ ID NO: 231 (predicted sequence of α chain of 4400 TCR-C without N-terminal signal peptide) | X at position 163 is Thr;<br>X at position 227 is Ser, Ala, Val, Leu, Ile, Pro, Phe, Met, or Trp;<br>preferably wherein X at position 227 is Leu, Ile, or Val;<br>especially preferably wherein X at position 227 is Leu;<br>X at position 229 is Met, Ala, Val, Leu, Ile, Pro, Phe, or Trp;<br>preferably wherein X at position 229 is Leu, Ile, or Val;<br>especially preferably wherein X at position 229 is Ile; and<br>X at position 230 is Gly, Ala, Val, Leu, Ile, Pro, Phe, Met, or Trp;<br>preferably wherein X at position 230 is Leu, Ile, or Val; |

TABLE 3-continued

| SEQ ID NO: | Definitions of "X" |
|---|---|
| | especially preferably wherein X at position 230 is Val, wherein SEQ ID NO: 231 does not comprise SEQ ID NO: 63 (unsubstituted α chain constant region) |
| SEQ ID NO: 232 (predicted sequence of β chain of 4400 TCR-C without N-terminal signal peptide) | X at position 170 is Ser |
| SEQ ID NO: 237 (α chain of 4400 TCR-20 with N-terminal signal peptide) | X at position 184 is Thr; X at position 248 is Ser, Ala, Val, Leu, Ile, Pro, Phe, Met, or Trp; preferably wherein X at position 248 is Leu, Ile, or Val; especially preferably wherein X at position 248 is Leu; X at position 250 is Met, Ala, Val, Leu, Ile, Pro, Phe, or Trp; preferably wherein X at position 250 is Leu, Ile, or Val; especially preferably wherein X at position 250 is Ile; and X at position 251 is Gly, Ala, Val, Leu, Ile, Pro, Phe, Met, or Trp; preferably wherein X at position 251 is Leu, Ile, or Val; especially preferably wherein X at position 251 is Val, wherein SEQ ID NO: 237 does not comprise SEQ ID NO: 63 (unsubstituted α chain constant region) |
| SEQ ID NO: 238 (β chain of 4400 TCR-20 with N-terminal signal peptide) | X at position 189 is Ser |
| SEQ ID NO: 239 (predicted sequence of α chain of 4400 TCR-20 without N-terminal signal peptide) | X at position 163 is Thr; X at position 227 is Ser, Ala, Val, Leu, Ile, Pro, Phe, Met, or Trp; preferably wherein X at position 227 is Leu, Ile, or Val; especially preferably wherein X at position 227 is Leu; X at position 229 is Met, Ala, Val, Leu, Ile, Pro, Phe, or Trp; preferably wherein X at position 229 is Leu, Ile, or Val; especially preferably wherein X at position 229 is Ile; and X at position 230 is Gly, Ala, Val, Leu, Ile, Pro, Phe, Met, or Trp; preferably wherein X at position 230 is Leu, Ile, or Val; especially preferably wherein X at position 230 is Val, wherein SEQ ID NO: 239 does not comprise SEQ ID NO: 63 (unsubstituted α chain constant region) |
| SEQ ID NO: 240 (predicted sequence of β chain of 4400 TCR-20 without N-terminal signal peptide) | X at position 170 is Ser |

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of the α chain with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 63 is substituted with Cys; one, two, or three of the native Ser112, Met114, and Gly115 of SEQ ID NO: 63 are, independently, substituted with Ala, Val, Leu, Ile, Pro, Phe, Met, or Trp; preferably with Leu, Ile, or Val; and the native Ser57 of SEQ ID NO: 64 is substituted with Cys. Preferably, all three of the native Ser112, Met114, and Gly115 of SEQ ID NO: 63 may, independently, be substituted with Ala, Val, Leu, Ile, Pro, Phe, Met, or Trp; preferably with Leu, Ile, or Val. In an embodiment of the invention, the cysteine-substituted, LVL-modified TCR comprises (i) SEQ ID NO: 59, (ii) SEQ ID NO: 60, or (iii) both of SEQ ID NOs: 59 and 60, wherein both of SEQ ID NOs: 59 and 60 are as defined in Table 4. The cysteine-substituted, LVL-modified TCRs of the invention may include the substituted constant region in addition to any of the CDRs or variable regions described herein.

In an embodiment, the cysteine-substituted, LVL-modified TCR comprises a full-length α chain and a full-length β chain. Examples of cysteine-substituted, LVL-modified TCR α chain and β chain sequences are set forth in Tables 4 and 7. In an embodiment of the invention, the TCR comprises: (1) SEQ ID NO: 59, (2) SEQ ID NO: 60, (3) SEQ ID NO: 65, (4) SEQ ID NO: 66, (5) SEQ ID NO: 67, (6) SEQ ID NO: 68, (7) SEQ ID NO: 69, (8) SEQ ID NO: 70, (9) SEQ ID NO: 71, (10) SEQ ID NO: 72, (11) SEQ ID NO: 73, (12) SEQ ID NO: 74, (13) SEQ ID NO: 75, (14) SEQ ID NO: 76, (15) SEQ ID NO: 77, (16) SEQ ID NO: 78, (17) SEQ ID NO: 79, (18) SEQ ID NO: 80, (19) SEQ ID NO: 81, (20) SEQ ID NO: 82, (21) SEQ ID NO: 83, (22) SEQ ID NO: 84, (23) SEQ ID NO: 85, (24) SEQ ID NO: 86, (25) SEQ ID NO: 87, (26) SEQ ID NO: 88, (27) SEQ ID NO: 89, (28) SEQ ID NO: 90, (29) SEQ ID NO: 91, (30) SEQ ID NO: 92, (31) SEQ ID NO: 93, (32) SEQ ID NO: 94, (33) SEQ ID NO: 95, (34) SEQ ID NO: 96, (35) SEQ ID NO: 97, (36) SEQ ID NO: 98, (37) SEQ ID NO: 99, (38) SEQ ID NO: 100, (39) SEQ ID NO: 101, (40) SEQ ID NO: 102, (41) SEQ ID NO: 103, (42) SEQ ID NO: 104, (43) SEQ ID NO: 189, (44) SEQ ID NO: 190, (45) SEQ ID NO: 191, (46) SEQ ID NO: 192, (47) SEQ ID NO: 193, (48) SEQ ID NO: 194, (49) SEQ ID NO: 195, (50) SEQ ID NO: 196, (51) SEQ ID NO: 197, (52) SEQ ID NO: 198, (53) SEQ ID NO: 199, (54) SEQ ID NO: 200, (55) SEQ ID NO: 201, (56) SEQ ID NO:

202, (57) SEQ ID NO: 203, (58) SEQ ID NO: 204, (59) SEQ ID NO: 205, (60) SEQ ID NO: 206, (61) SEQ ID NO: 207, (62) SEQ ID NO: 208, (63) SEQ ID NO: 209, (64) SEQ ID NO: 210, (65) SEQ ID NO: 211, (66) SEQ ID NO: 212, (67) SEQ ID NO: 213, (68) SEQ ID NO: 214, (69) SEQ ID NO: 215, (70) SEQ ID NO: 216, (71) SEQ ID NO: 217, (72) SEQ ID NO: 218, (73) SEQ ID NO: 219, (74) SEQ ID NO: 220, (75) SEQ ID NO: 221, (76) SEQ ID NO: 222, (77) SEQ ID NO: 223, (78) SEQ ID NO: 224, (79) SEQ ID NO: 225, (80) SEQ ID NO: 226, (81) SEQ ID NO: 227, (82) SEQ ID NO: 228, (83) SEQ ID NO: 229, (84) SEQ ID NO: 230, (85) SEQ ID NO: 231, (86) SEQ ID NO: 232, (87) SEQ ID NO: 233, (88) SEQ ID NO: 234, (89) SEQ ID NO: 235, (90) SEQ ID NO: 236, (91) SEQ ID NO: 237, (92) SEQ ID NO: 238, (93) SEQ ID NO: 239, (94) SEQ ID NO: 240, (95) SEQ ID NO: 241, (96) SEQ ID NO: 242, (97) SEQ ID NO: 243, (98) SEQ ID NO: 244, (99) both of SEQ ID NOs: 59 and 60, (100) both of SEQ ID NOs: 65 and 66, (101) both of SEQ ID NOs: 67 and 68, (102) both of SEQ ID NOs: 69 and 70, (103) both of SEQ ID NOs: 71 and 72, (104) both of SEQ ID NOs: 73 and 74, (105) both of SEQ ID NOs: 75 and 76, (106) both of SEQ ID NOs: 77 and 78, (107) both of SEQ ID NOs: 79 and 80, (108) both of SEQ ID NOs: 81 and 82, (109) both of SEQ ID NOs: 83 and 84, (110) both of SEQ ID NOs: 85 and 86, (111) both of SEQ ID NOs: 87 and 88, (112) both of SEQ ID NOs: 89 and 90, (113) both of SEQ ID NOs: 91 and 92, (114) both of SEQ ID NOs: 93 and 94, (115) both of SEQ ID NOs: 95 and 96, (116) both of SEQ ID NOs: 97 and 98, (117) both of SEQ ID NOs: 99 and 100, (118) both of SEQ ID NOs: 101 and 102, (119) both of SEQ ID NOs: 103 and 104, (120) both of SEQ ID NOs: 189 and 190, (121) both of SEQ ID NOs: 191 and 192, (122) both of SEQ ID NOs: 193 and 194, (123) both of SEQ ID NOs: 195 and 196, (124) both of SEQ ID NOs: 197 and 198, (125) both of SEQ ID NOs: 199 and 200, (126) both of SEQ ID NOs: 201 and 202, (127) both of SEQ ID NOs: 203 and 204, (128) both of SEQ ID NOs: 205 and 206, (129) both of SEQ ID NOs: 207 and 208, (130) both of SEQ ID NOs: 209 and 210, (131) both of SEQ ID NOs: 211 and 212, (132) both of SEQ ID NOs: 213 and 214, (133) both of SEQ ID NOs: 215 and 216, (134) both of SEQ ID NOs: 217 and 218, (135) both of SEQ ID NOs: 219 and 220, (136) both of SEQ ID NOs: 221 and 222, (137) both of SEQ ID NOs: 223 and 224, (138) both of SEQ ID NOs: 225 and 226, (139) both of SEQ ID NOs: 227 and 228, (140) both of SEQ ID NOs: 229 and 230, (141) both of SEQ ID NOs: 231 and 232, (142) both of SEQ ID NOs: 233 and 234, (143) both of SEQ ID NOs: 235 and 236, (144) both of SEQ ID NOs: 237 and 238, (145) both of SEQ ID NOs: 239 and 240, (146) both of SEQ ID NOs: 241 and 242, or (147) both of SEQ ID NOs: 243 and 244, wherein all of SEQ ID NOs: 59-60, 65-68, 73-76, 81-84, 89-92, 97-100, 189-192, 197-200, 205-208, 213-216, 221-224, 229-232, and 237-240 are as defined in Table 4.

TABLE 4

| SEQ ID NO: | Definitions of "X" |
| --- | --- |
| SEQ ID NO: 59 (constant region α chain) | X at position 48 is Cys; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; and especially preferably wherein X at position 115 is Val, wherein SEQ ID NO: 49 does not simultaneously comprise all of Ser at position 112, Met at position 114, and Gly at position 115. |
| SEQ ID NO: 60 (constant region β chain) | X at position 57 is Cys |
| SEQ ID NO: 65 (4400 TCR-A1 α chain) (with N-terminal signal peptide) | X at position 180 is Cys; X at position 244 is Ser, Ala, Val, Leu, Ile, Pro, Phe, Met, or Trp; preferably wherein X at position 244 is Leu, Ile, or Val; especially preferably wherein X at position 244 is Leu; X at position 246 is Met, Ala, Val, Leu, Ile, Pro, Phe, or Trp; preferably wherein X at position 246 is Leu, Ile, or Val; especially preferably wherein X at position 246 is Ile; and X at position 247 is Gly, Ala, Val, Leu, Ile, Pro, Phe, Met, or Trp; preferably wherein X at position 247 is Leu, Ile, or Val; and especially preferably wherein X at position 247 is Val, wherein SEQ ID NO: 65 does not simultaneously comprise all of Ser at position 244, Met at position 246, and Gly at position 247. |
| SEQ ID NO: 66 (4400 TCR-A1 β chain) (with N-terminal signal peptide) | X at position 188 is Cys |
| SEQ ID NO: 67 (4400 TCR-A1 α chain) (predicted sequence without N-terminal signal peptide) | X at position 158 is Cys; X at position 222 is Ser, Ala, Val, Leu, Ile, Pro, Phe, Met, or Trp; preferably wherein X at position 222 is Leu, Ile, or Val; especially preferably wherein X at position 222 is Leu; X at position 224 is Met, Ala, Val, Leu, Ile, Pro, Phe, or Trp; preferably wherein X at position 224 is Leu, Ile, or Val; especially preferably wherein X at position 224 is Ile; and X at position 225 is Gly, Ala, Val, Leu, Ile, Pro, Phe, Met, or Trp; preferably wherein X at position 225 is Leu, Ile, or Val; and especially preferably wherein X at position 225 is Val, wherein SEQ ID NO: 67 does not simultaneously comprise all of Ser at position 222, Met at position 224, and Gly at position 225. |

TABLE 4-continued

| SEQ ID NO: | Definitions of "X" |
| --- | --- |
| SEQ ID NO: 68 (4400 TCR-A1 β chain) (predicted sequence without N-terminal signal peptide) | X at position 169 is Cys |
| SEQ ID NO: 73 (4400 TCR-A2 α chain with N-terminal signal peptide) | X at position 180 is Cys; X at position 244 is Ser, Ala, Val, Leu, Ile, Pro, Phe, Met, or Trp; preferably wherein X at position 244 is Leu, Ile, or Val; especially preferably wherein X at position 244 is Leu; X at position 246 is Met, Ala, Val, Leu, Ile, Pro, Phe, or Trp; preferably wherein X at position 246 is Leu, Ile, or Val; especially preferably wherein X at position 246 is Ile; and X at position 247 is Gly, Ala, Val, Leu, Ile, Pro, Phe, Met, or Trp; preferably wherein X at position 247 is Leu, Ile, or Val; and especially preferably wherein X at position 247 is Val, wherein SEQ ID NO: 73 does not simultaneously comprise all of Ser at position 244, Met at position 246, and Gly at position 247. |
| SEQ ID NO: 74 (4400 TCR-A2 β chain with N-terminal signal peptide) | X at position 188 is Cys |
| SEQ ID NO: 75 (4400 TCR-A2 α chain predicted sequence without N-terminal signal peptide) | X at position 158 is Cys; X at position 222 is Ser, Ala, Val, Leu, Ile, Pro, Phe, Met, or Trp; preferably wherein X at position 222 is Leu, Ile, or Val; especially preferably wherein X at position 222 is Leu; X at position 224 is Met, Ala, Val, Leu, Ile, Pro, Phe, or Trp; preferably wherein X at position 224 is Leu, Ile, or Val; especially preferably wherein X at position 224 is Ile; and X at position 225 is Gly, Ala, Val, Leu, Ile, Pro, Phe, Met, or Trp; preferably wherein X at position 225 is Leu, Ile, or Val; and especially preferably wherein X at position 225 is Val, wherein SEQ ID NO: 75 does not simultaneously comprise all of Ser at position 222, Met at position 224, and Gly at position 225. |
| SEQ ID NO: 76 (4400 TCR-A2 β chain predicted sequence without N-terminal signal peptide) | X at position 169 is Cys |
| SEQ ID NO: 81 (4400 TCR-E α chain with N-terminal signal peptide) | X at position 177 is Cys; X at position 241 is Ser, Ala, Val, Leu, Ile, Pro, Phe, Met, or Trp; preferably wherein X at position 241 is Leu, Ile, or Val; especially preferably wherein X at position 241 is Leu; X at position 243 is Met, Ala, Val, Leu, Ile, Pro, Phe, or Trp; preferably wherein X at position 243 is Leu, Ile, or Val; especially preferably wherein X at position 243 is Ile; and X at position 244 is Gly, Ala, Val, Leu, Ile, Pro, Phe, Met, or Trp; preferably wherein X at position 244 is Leu, Ile, or Val; and especially preferably wherein X at position 244 is Val, wherein SEQ ID NO: 81 does not simultaneously comprise all of Ser at position 241, Met at position 243, and Gly at position 244. |
| SEQ ID NO: 82 (4400 TCR-E β chain with N-terminal signal peptide) | X at position 189 is Cys |
| SEQ ID NO: 83 (4400 TCR-E α chain predicted sequence without N-terminal signal peptide) | X at position 160 is Cys; X at position 224 is Ser, Ala, Val, Leu, Ile, Pro, Phe, Met, or Trp; preferably wherein X at position 224 is Leu, Ile, or Val; especially preferably wherein X at position 224 is Leu; X at position 226 is Met, Ala, Val, Leu, Ile, Pro, Phe, or Trp; preferably wherein X at position 226 is Leu, Ile, or Val; especially preferably wherein X at position 226 is Ile; and X at position 227 is Gly, Ala, Val, Leu, Ile, Pro, Phe, Met, or Trp; preferably wherein X at position 227 is Leu, Ile, or Val; and especially preferably wherein X at position 227 is Val, wherein SEQ ID NO: 83 does not simultaneously comprise all of Ser at position 224, Met at position 226, and Gly at position 227. |
| SEQ ID NO: 84 (4400 TCR-E β chain predicted sequence without N-terminal signal peptide) | X at position 170 is Cys |
| SEQ ID NO: 89 (4400 TCR-J α chain with N-terminal signal peptide) | X at position 183 is Cys; X at position 247 is Ser, Ala, Val, Leu, Ile, Pro, Phe, Met, or Trp; preferably wherein X at position 247 is Leu, Ile, or Val; especially preferably wherein X at position 247 is Leu; X at position 249 is Met, Ala, Val, Leu, Ile, Pro, Phe, or Trp; preferably wherein X at position 249 is Leu, Ile, or Val; especially preferably wherein X at position 249 is Ile; and |

TABLE 4-continued

| SEQ ID NO: | Definitions of "X" |
| --- | --- |
| | X at position 250 is Gly, Ala, Val, Leu, Ile, Pro, Phe, Met, or Trp; preferably wherein X at position 250 is Leu, Ile, or Val; and especially preferably wherein X at position 250 is Val, wherein SEQ ID NO: 89 does not simultaneously comprise all of Ser at position 247, Met at position 249, and Gly at position 250. |
| SEQ ID NO: 90 (4400 TCR-J β chain with N-terminal signal peptide) | X at position 188 is Cys |
| SEQ ID NO: 91 (4400 TCR-J α chain predicted sequence without N-terminal signal peptide) | X at position 161 is Cys; X at position 225 is Ser, Ala, Val, Leu, Ile, Pro, Phe, Met, or Trp; preferably wherein X at position 225 is Leu, Ile, or Val; especially preferably wherein X at position 225 is Leu; X at position 227 is Met, Ala, Val, Leu, Ile, Pro, Phe, or Trp; preferably wherein X at position 227 is Leu, Ile, or Val; especially preferably wherein X at position 227 is Ile; and X at position 228 is Gly, Ala, Val, Leu, Ile, Pro, Phe, Met, or Trp; preferably wherein X at position 228 is Leu, Ile, or Val; and especially preferably wherein X at position 228 is Val, wherein SEQ ID NO: 91 does not simultaneously comprise all of Ser at position 225, Met at position 227, and Gly at position 228. |
| SEQ ID NO: 92 (4400 TCR-J β chain predicted sequence without N-terminal signal peptide) | X at position 169 is Cys |
| SEQ ID NO: 97 (4400 TCR-N α chain with N-terminal signal peptide) | X at position 178 is Cys; X at position 242 is Ser, Ala, Val, Leu, Ile, Pro, Phe, Met, or Trp; preferably wherein X at position 242 is Leu, Ile, or Val; especially preferably wherein X at position 242 is Leu; X at position 244 is Met, Ala, Val, Leu, Ile, Pro, Phe, or Trp; preferably wherein X at position 244 is Leu, Ile, or Val; especially preferably wherein X at position 244 is Ile; and X at position 245 is Gly, Ala, Val, Leu, Ile, Pro, Phe, Met, or Trp; preferably wherein X at position 245 is Leu, Ile, or Val; and especially preferably wherein X at position 245 is Val, wherein SEQ ID NO: 97 does not simultaneously comprise all of Ser at position 242, Met at position 244, and Gly at position 245. |
| SEQ ID NO: 98 (4400 TCR-N β chain with N-terminal signal peptide) | X at position 188 is Cys |
| SEQ ID NO: 99 (4400 TCR-N α chain predicted sequence without N-terminal signal peptide) | X at position 157 is Cys; X at position 221 is Ser, Ala, Val, Leu, Ile, Pro, Phe, Met, or Trp; preferably wherein X at position 221 is Leu, Ile, or Val; especially preferably wherein X at position 221 is Leu; X at position 223 is Met, Ala, Val, Leu, Ile, Pro, Phe, or Trp; preferably wherein X at position 223 is Leu, Ile, or Val; especially preferably wherein X at position 223 is Ile; and X at position 224 is Gly, Ala, Val, Leu, Ile, Pro, Phe, Met, or Trp; preferably wherein X at position 224 is Leu, Ile, or Val; and especially preferably wherein X at position 224 is Val, wherein SEQ ID NO: 99 does not simultaneously comprise all of Ser at position 221, Met at position 223, and Gly at position 224. |
| SEQ ID NO: 100 (4400 TCR-N β chain predicted sequence without N-terminal signal peptide) | X at position 169 is Cys |
| SEQ ID NO: 189 (α chain of 4400 TCR-A3 with N-terminal signal peptide) | X at position 176 is Cys; X at position 240 is Ser, Ala, Val, Leu, Ile, Pro, Phe, Met, or Trp; preferably wherein X at position 240 is Leu, Ile, or Val; especially preferably wherein X at position 240 is Leu; X at position 242 is Met, Ala, Val, Leu, Ile, Pro, Phe, or Trp; preferably wherein X at position 242 is Leu, Ile, or Val; especially preferably wherein X at position 242 is Ile; and X at position 243 is Gly, Ala, Val, Leu, Ile, Pro, Phe, Met, or Trp; preferably wherein X at position 243 is Leu, Ile, or Val; and especially preferably wherein X at position 243 is Val, wherein SEQ ID NO: 189 does not simultaneously comprise all of Ser at position 240, Met at position 242, and Gly at position 243. |

TABLE 4-continued

| SEQ ID NO: | Definitions of "X" |
|---|---|
| SEQ ID NO: 190 (β chain of 4400 TCR-A3 with N-terminal signal peptide) | X at position 188 is Cys |
| SEQ ID NO: 191 (predicted sequence of α chain of 4400 TCR-A3 without N-terminal signal peptide) | X at position 157 is Cys; X at position 221 is Ser, Ala, Val, Leu, Ile, Pro, Phe, Met, or Trp; preferably wherein X at position 221 is Leu, Ile, or Val; especially preferably wherein X at position 221 is Leu; X at position 223 is Met, Ala, Val, Leu, Ile, Pro, Phe, or Trp; preferably wherein X at position 223 is Leu, Ile, or Val; especially preferably wherein X at position 223 is Ile; and X at position 224 is Gly, Ala, Val, Leu, Ile, Pro, Phe, Met, or Trp; preferably wherein X at position 224 is Leu, Ile, or Val; and especially preferably wherein X at position 224 is Val, wherein SEQ ID NO: 191 does not simultaneously comprise all of Ser at position 221, Met at position 223, and Gly at position 224. |
| SEQ ID NO: 192 (predicted sequence of β chain of 4400 TCR-A3 without N-terminal signal peptide) | X at position 169 is Cys |
| SEQ ID NO: 197 (α chain of 4400 TCR-J2 with N-terminal signal peptide) | X at position 181 is Cys; X at position 245 is Ser, Ala, Val, Leu, Ile, Pro, Phe, Met, or Trp; preferably wherein X at position 245 is Leu, Ile, or Val; especially preferably wherein X at position 245 is Leu; X at position 247 is Met, Ala, Val, Leu, Ile, Pro, Phe, or Trp; preferably wherein X at position 247 is Leu, Ile, or Val; especially preferably wherein X at position 247 is Ile; and X at position 248 is Gly, Ala, Val, Leu, Ile, Pro, Phe, Met, or Trp; preferably wherein X at position 248 is Leu, Ile, or Val; and especially preferably wherein X at position 248 is Val, wherein SEQ ID NO: 197 does not simultaneously comprise all of Ser at position 245, Met at position 247, and Gly at position 248. |
| SEQ ID NO: 198 (β chain of 4400 TCR-J2 with N-terminal signal peptide) | X at position 188 is Cys |
| SEQ ID NO: 199 (predicted sequence of α chain of 4400 TCR-J2 without N-terminal signal peptide) | X at position 16180 is Cys; X at position 225 is Ser, Ala, Val, Leu, Ile, Pro, Phe, Met, or Trp; preferably wherein X at position 225 is Leu, Ile, or Val; especially preferably wherein X at position 225 is Leu; X at position 227 is Met, Ala, Val, Leu, Ile, Pro, Phe, or Trp; preferably wherein X at position 227 is Leu, Ile, or Val; especially preferably wherein X at position 227 is Ile; and X at position 228 is Gly, Ala, Val, Leu, Ile, Pro, Phe, Met, or Trp; preferably wherein X at position 228 is Leu, Ile, or Val; and especially preferably wherein X at position 228 is Val, wherein SEQ ID NO: 199 does not simultaneously comprise all of Ser at position 225, Met at position 227, and Gly at position 228. |
| SEQ ID NO: 200 (predicted sequence of β chain of 4400 TCR-J2 without N-terminal signal peptide) | X at position 169 is Cys |
| SEQ ID NO: 205 (α chain of 4400 TCR-N4 with N-terminal signal peptide) | X at position 184 is Cys; X at position 248 is Ser, Ala, Val, Leu, Ile, Pro, Phe, Met, or Trp; preferably wherein X at position 248 is Leu, Ile, or Val; especially preferably wherein X at position 248 is Leu; X at position 250 is Met, Ala, Val, Leu, Ile, Pro, Phe, or Trp; preferably wherein X at position 250 is Leu, Ile, or Val; especially preferably wherein X at position 250 is Ile; and X at position 251 is Gly, Ala, Val, Leu, Ile, Pro, Phe, Met, or Trp; preferably wherein X at position 251 is Leu, Ile, or Val; and especially preferably wherein X at position 251 is Val, wherein SEQ ID NO: 205 does not simultaneously comprise all of Ser at position 248, Met at position 250, and Gly at position 251. |
| SEQ ID NO: 206 (β chain of 4400 TCR-N4 with N-terminal signal peptide) | X at position 190 is Cys; |
| SEQ ID NO: 207 (predicted sequence of α chain of 4400 TCR-N4 without N-terminal signal peptide) | X at position 163 is Cys; X at position 227 is Ser, Ala, Val, Leu, Ile, Pro, Phe, Met, or Trp; preferably wherein X at position 227 is Leu, Ile, or Val; especially preferably wherein X at position 227 is Leu; X at position 229 is Met, Ala, Val, Leu, Ile, Pro, Phe, or Trp; preferably wherein X at position 229 is Leu, Ile, or Val; especially preferably wherein X at position 229 is Ile; and X at position 230 is Gly, Ala, Val, Leu, Ile, Pro, Phe, Met, or Trp; |

TABLE 4-continued

| SEQ ID NO: | Definitions of "X" |
| --- | --- |
| | preferably wherein X at position 230 is Leu, Ile, or Val; and especially preferably wherein X at position 230 is Val, wherein SEQ ID NO: 207 does not simultaneously comprise all of Ser at position 227, Met at position 229, and Gly at position 230. |
| SEQ ID NO: 208 (predicted sequence of β chain of 4400 TCR-N4 without N-terminal signal peptide) | X at position 164 is Cys |
| SEQ ID NO: 213 (α chain of 4400 TCR-N12 with N-terminal signal peptide) | X at position 183 is Cys; X at position 247 is Ser, Ala, Val, Leu, Ile, Pro, Phe, Met, or Trp; preferably wherein X at position 247 is Leu, Ile, or Val; especially preferably wherein X at position 247 is Leu; X at position 249 is Met, Ala, Val, Leu, Ile, Pro, Phe, or Trp; preferably wherein X at position 249 is Leu, Ile, or Val; especially preferably wherein X at position 249 is Ile; and X at position 250 is Gly, Ala, Val, Leu, Ile, Pro, Phe, Met, or Trp; preferably wherein X at position 250 is Leu, Ile, or Val; and especially preferably wherein X at position 250 is Val, wherein SEQ ID NO: 213 does not simultaneously comprise all of Ser at position 247, Met at position 249, and Gly at position 250. |
| SEQ ID NO: 214 (β chain of 4400 TCR-N12 with N-terminal signal peptide) | X at position 188 is Cys |
| SEQ ID NO: 215 (predicted sequence of α chain of 4400 TCR-N12 without N-terminal signal peptide) | X at position 161 is Cys; X at position 225 is Ser, Ala, Val, Leu, Ile, Pro, Phe, Met, or Trp; preferably wherein X at position 225 is Leu, Ile, or Val; especially preferably wherein X at position 225 is Leu; X at position 227 is Met, Ala, Val, Leu, Ile, Pro, Phe, or Trp; preferably wherein X at position 227 is Leu, Ile, or Val; especially preferably wherein X at position 227 is Ile; and X at position 228 is Gly, Ala, Val, Leu, Ile, Pro, Phe, Met, or Trp; preferably wherein X at position 228 is Leu, Ile, or Val; and especially preferably wherein X at position 228 is Val, wherein SEQ ID NO: 215 does not simultaneously comprise all of Ser at position 225, Met at position 227, and Gly at position 228. |
| SEQ ID NO: 216 (predicted sequence of β chain of 4400 TCR-N12 without N-terminal signal peptide) | X at position 169 is Cys |
| SEQ ID NO: 221 (α chain of 4400 TCR-N13 with N-terminal signal peptide) | X at position 180 is Cys; X at position 244 is Ser, Ala, Val, Leu, Ile, Pro, Phe, Met, or Trp; preferably wherein X at position 244 is Leu, Ile, or Val; especially preferably wherein X at position 244 is Leu; X at position 246 is Met, Ala, Val, Leu, Ile, Pro, Phe, or Trp; preferably wherein X at position 246 is Leu, Ile, or Val; especially preferably wherein X at position 246 is Ile; and X at position 247 is Gly, Ala, Val, Leu, Ile, Pro, Phe, Met, or Trp; preferably wherein X at position 247 is Leu, Ile, or Val; and especially preferably wherein X at position 247 is Val, wherein SEQ ID NO: 221 does not simultaneously comprise all of Ser at position 244, Met at position 246, and Gly at position 247. |
| SEQ ID NO: 222 (β chain of 4400 TCR-N13 with N-terminal signal peptide) | X at position 188 is Cys |
| SEQ ID NO: 223 (predicted sequence of α chain of 4400 TCR-N13 without N-terminal signal peptide) | X at position 158 is Cys; X at position 222 is Ser, Ala, Val, Leu, Ile, Pro, Phe, Met, or Trp; preferably wherein X at position 222 is Leu, Ile, or Val; especially preferably wherein X at position 222 is Leu; X at position 224 is Met, Ala, Val, Leu, Ile, Pro, Phe, or Trp; preferably wherein X at position 224 is Leu, Ile, or Val; especially preferably wherein X at position 224 is Ile; and X at position 225 is Gly, Ala, Val, Leu, Ile, Pro, Phe, Met, or Trp; preferably wherein X at position 225 is Leu, Ile, or Val; and especially preferably wherein X at position 225 is Val, wherein SEQ ID NO: 223 does not simultaneously comprise all of Ser at position 222, Met at position 224, and Gly at position 225. |

TABLE 4-continued

| SEQ ID NO: | Definitions of "X" |
|---|---|
| SEQ ID NO: 224 (predicted sequence of β chain of 4400 TCR-N13 without N-terminal signal peptide) | X at position 169 is Cys |
| SEQ ID NO: 229 (α chain of 4400 TCR-C with N-terminal signal peptide) | X at position 184 is Cys; X at position 248 is Ser, Ala, Val, Leu, Ile, Pro, Phe, Met, or Trp; preferably wherein X at position 248 is Leu, Ile, or Val; especially preferably wherein X at position 248 is Leu; X at position 250 is Met, Ala, Val, Leu, Ile, Pro, Phe, or Trp; preferably wherein X at position 250 is Leu, Ile, or Val; especially preferably wherein X at position 250 is Ile; and X at position 251 is Gly, Ala, Val, Leu, Ile, Pro, Phe, Met, or Trp; preferably wherein X at position 251 is Leu, Ile, or Val; and especially preferably wherein X at position 251 is Val, wherein SEQ ID NO: 229 does not simultaneously comprise all of Ser at position 248, Met at position 250, and Gly at position 251. |
| SEQ ID NO: 230 (β chain of 4400 TCR-C with N-terminal signal peptide) | X at position 189 is Cys |
| SEQ ID NO: 231 (predicted sequence of α chain of 4400 TCR-C without N-terminal signal peptide) | X at position 163 is Cys; X at position 227 is Ser, Ala, Val, Leu, Ile, Pro, Phe, Met, or Trp; preferably wherein X at position 227 is Leu, Ile, or Val; especially preferably wherein X at position 227 is Leu; X at position 229 is Met, Ala, Val, Leu, Ile, Pro, Phe, or Trp; preferably wherein X at position 229 is Leu, Ile, or Val; especially preferably wherein X at position 229 is Ile; and X at position 230 is Gly, Ala, Val, Leu, Ile, Pro, Phe, Met, or Trp; preferably wherein X at position 230 is Leu, Ile, or Val; and especially preferably wherein X at position 230 is Val, wherein SEQ ID NO: 231 does not simultaneously comprise all of Ser at position 227, Met at position 229, and Gly at position 230. |
| SEQ ID NO: 232 (predicted sequence of β chain of 4400 TCR-C without N-terminal signal peptide) | X at position 170 is Cys |
| SEQ ID NO: 237 (α chain of 4400 TCR-20 with N-terminal signal peptide) | X at position 184 is Cys; X at position 248 is Ser, Ala, Val, Leu, Ile, Pro, Phe, Met, or Trp; preferably wherein X at position 248 is Leu, Ile, or Val; especially preferably wherein X at position 248 is Leu; X at position 250 is Met, Ala, Val, Leu, Ile, Pro, Phe, or Trp; preferably wherein X at position 250 is Leu, Ile, or Val; especially preferably wherein X at position 250 is Ile; and X at position 251 is Gly, Ala, Val, Leu, Ile, Pro, Phe, Met, or Trp; preferably wherein X at position 251 is Leu, Ile, or Val; and especially preferably wherein X at position 251 is Val, wherein SEQ ID NO: 237 does not simultaneously comprise all of Ser at position 248, Met at position 250, and Gly at position 251. |
| SEQ ID NO: 238 (β chain of 4400 TCR-20 with N-terminal signal peptide) | X at position 189 is Cys |
| SEQ ID NO: 239 (predicted sequence of α chain of 4400 TCR-20 without N-terminal signal peptide) | X at position 163 is Cys; X at position 227 is Ser, Ala, Val, Leu, Ile, Pro, Phe, Met, or Trp; preferably wherein X at position 227 is Leu, Ile, or Val; especially preferably wherein X at position 227 is Leu; X at position 229 is Met, Ala, Val, Leu, Ile, Pro, Phe, or Trp; preferably wherein X at position 229 is Leu, Ile, or Val; especially preferably wherein X at position 229 is Ile; and X at position 230 is Gly, Ala, Val, Leu, Ile, Pro, Phe, Met, or Trp; preferably wherein X at position 230 is Leu, Ile, or Val; and especially preferably wherein X at position 230 is Val, wherein SEQ ID NO: 239 does not simultaneously comprise all of Ser at position 227, Met at position 229, and Gly at position 230. |
| SEQ ID NO: 240 (predicted sequence of β chain of 4400 TCR-20 without N-terminal signal peptide) | X at position 170 is Cys |

In an embodiment of the invention, the cysteine-substituted, LVL-modified TCR comprises (a) SEQ ID NO: 61 (α chain constant region of cysteine-substituted, LVL-modified TCR); (b) SEQ ID NO: 62 (β chain constant region of cysteine-substituted, LVL-modified TCR); or (c) both (a) and (b).

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to G13D RAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to G13D RAS (e.g., within the context of any of the HLA Class II molecules described herein), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to G13D RAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 1 (CDR1 of α chain of 4400 TCR-A1), SEQ ID NO: 2 (CDR2 of α chain of 4400 TCR-A1), SEQ ID NO: 3 (CDR3 of α chain of 4400 TCR-A1), SEQ ID NO: 4 (CDR1 of β chain of 4400 TCR-A1), SEQ ID NO: 5 (CDR2 of β chain of 4400 TCR-A1), SEQ ID NO: 6 (CDR3 of β chain of 4400 TCR-A1), SEQ ID NO: 11 (CDR1 of α chain of 4400 TCR-A2), SEQ ID NO: 12 (CDR2 of α chain of 4400 TCR-A2), SEQ ID NO: 13 (CDR3 of α chain of 4400 TCR-A2), SEQ ID NO: 14 (CDR1 of β chain of 4400 TCR-A2), SEQ ID NO: 15 (CDR2 of β chain of 4400 TCR-A2), SEQ ID NO: 16 (CDR3 of β chain of 4400 TCR-A2), SEQ ID NO: 21 (CDR1 of α chain of 4400 TCR-E), SEQ ID NO: 22 (CDR2 of α chain of 4400 TCR-E), SEQ ID NO: 23 (CDR3 of α chain of 4400 TCR-E), SEQ ID NO: 24 (CDR1 of β chain of 4400 TCR-E), SEQ ID NO: 25 (CDR2 of β chain of 4400 TCR-E), SEQ ID NO: 26 (CDR3 of β chain of 4400 TCR-E), SEQ ID NO: 31 (CDR1 of α chain of 4400 TCR-J), SEQ ID NO: 32 (CDR2 of α chain of 4400 TCR-J), SEQ ID NO: 33 (CDR3 of α chain of 4400 TCR-J), SEQ ID NO: 34 (CDR1 of β chain of 4400 TCR-J), SEQ ID NO: 35 (CDR2 of β chain of 4400 TCR-J), SEQ ID NO: 36 (CDR3 of β chain of 4400 TCR-J), SEQ ID NO: 41 (CDR1 of α chain of 4400 TCR-N), SEQ ID NO: 42 (CDR2 of α chain of 4400 TCR-N), SEQ ID NO: 43 (CDR3 of α chain of 4400 TCR-N), SEQ ID NO: 44 (CDR1 of β chain of 4400 TCR-N), SEQ ID NO: 45 (CDR2 of β chain of 4400 TCR-N), SEQ ID NO: 46 (CDR3 of β chain of 4400 TCR-N), SEQ ID NO: 119 (CDR1 of α chain of 4400 TCR-A3), SEQ ID NO: 120 (CDR2 of α chain of 4400 TCR-A3), SEQ ID NO: 121 (CDR3 of α chain of 4400 TCR-A3), SEQ ID NO: 122 (CDR1 of β chain of 4400 TCR-A3), SEQ ID NO: 123 (CDR2 of β chain of 4400 TCR-A3), SEQ ID NO: 124 (CDR3 of β chain of 4400 TCR-A3), SEQ ID NO: 129 (CDR1 of α chain of 4400 TCR-J2), SEQ ID NO: 130 (CDR2 of α chain of 4400 TCR-J2), SEQ ID NO: 131 (CDR3 of α chain of 4400 TCR-J2), SEQ ID NO: 132 (CDR1 of β chain of 4400 TCR-J2), SEQ ID NO: 133 (CDR2 of β chain of 4400 TCR-J2), SEQ ID NO: 134 (CDR3 of β chain of 4400 TCR-J2), SEQ ID NO: 139 (CDR1 of a chain of 4400 TCR-N4), SEQ ID NO: 140 (CDR2 of α chain of 4400 TCR-N4), SEQ ID NO: 141 (CDR3 of α chain of 4400 TCR-N4), SEQ ID NO: 142 (CDR1 of β chain of 4400 TCR-N4), SEQ ID NO: 143 (CDR2 of β chain of 4400 TCR-N4), SEQ ID NO: 144 (CDR3 of (3 chain of 4400 TCR-N4), SEQ ID NO: 149 (CDR1 of α chain of 4400 TCR-N12), SEQ ID NO: 150 (CDR2 of α chain of 4400 TCR-N12), SEQ ID NO: 151 (CDR3 of α chain of 4400 TCR-N12), SEQ ID NO: 152 (CDR1 of β chain of 4400 TCR-N12), SEQ ID NO: 153 (CDR2 of β chain of 4400 TCR-N12), SEQ ID NO: 154 (CDR3 of β chain of 4400 TCR-N12), SEQ ID NO: 159 (CDR1 of α chain of 4400 TCR-N13), SEQ ID NO: 160 (CDR2 of α chain of 4400 TCR-N13), SEQ ID NO: 161 (CDR3 of α chain of 4400 TCR-N13), SEQ ID NO: 162 (CDR1 of β chain of 4400 TCR-N13), SEQ ID NO: 163 (CDR2 of β chain of 4400 TCR-N13), SEQ ID NO: 164 (CDR3 of β chain of 4400 TCR-N13), SEQ ID NO: 169 (CDR1 of a chain of 4400 TCR-C), SEQ ID NO: 170 (CDR2 of α chain of 4400 TCR-C), SEQ ID NO: 171 (CDR3 of α chain of 4400 TCR-C), SEQ ID NO: 172 (CDR1 of β chain of 4400 TCR-C), SEQ ID NO: 173 (CDR2 of β chain of 4400 TCR-C), SEQ ID NO: 174 (CDR3 of β chain of 4400 TCR-C), SEQ ID NO: 179 (CDR1 of α chain of 4400 TCR-20), SEQ ID NO: 180 (CDR2 of α chain of 4400 TCR-20), SEQ ID NO: 181 (CDR3 of α chain of 4400 TCR-20), SEQ ID NO: 182 (CDR1 of β chain of 4400 TCR-20), SEQ ID NO: 183 (CDR2 of β chain of 4400 TCR-20), SEQ ID NO: 184 (CDR3 of β chain of 4400 TCR-20), or a combination thereof. In this regard, the inventive polypeptide can comprise any one or more of the amino acid sequences selected from the group consisting of SEQ ID NOs: 1-6, 11-16, 21-26, 31-36, 41-46, 119-124, 129-134, 139-144, 149-154, 159-164, 169-174, or 179-184. In an embodiment of the invention, the polypeptide comprises the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, W all of SEQ ID NOs: 31-33, (k) all of SEQ ID NOs: 34-36, (l) all of SEQ ID NOs: 31-36, (m) all of SEQ ID NOs: 41-43, (n) all of SEQ ID NOs: 44-46, (o) all of SEQ ID NOs: 41-46, (p) all of SEQ ID NOs: 119-121, (q) all of SEQ ID NOs: 122-124, (r) all of SEQ ID NOs: 119-124, (s) all of SEQ ID NOs: 129-131, (t) all of SEQ ID NOs: 132-134, (u) all of SEQ ID NOs: 129-134, (v) all of SEQ ID NOs: 139-141, (w) all of SEQ ID NOs: 142-144, (x) all of SEQ ID NOs:

139-144, (y) all of SEQ ID NOs: 149-151, (z) all of SEQ ID NOs: 152-154, (aa) all of SEQ ID NOs: 149-154, (bb) all of SEQ ID NOs: 159-161, (cc) all of SEQ ID NOs: 162-164, (dd) all of SEQ ID NOs: 159-164, (ee) all of SEQ ID NOs: 169-171, (ff) all of SEQ ID NOs: 172-174, (gg) all of SEQ ID NOs: 169-174, (hh) all of SEQ ID NOs: 179-181, (ii) all of SEQ ID NOs: 182-184, or (jj) all of SEQ ID NOs: 179-184. In a preferred embodiment, the polypeptide comprises the amino acid sequences of all of (i) SEQ ID NOs: 1-6, (ii) SEQ ID NOs: 11-16, (iii) SEQ ID NOs: 21-26, (iv) SEQ ID NOs: 31-36, (v) SEQ ID NOs: 41-46, (vi) all of SEQ ID NOs: 119-124, (vii) all of SEQ ID NOs: 129-134, (viii) all of SEQ ID NOs: 139-144, (ix) all of SEQ ID NOs: 149-154, (x) all of SEQ ID NOs: 159-164, (xi) all of SEQ ID NOs: 169-174, or (xii) all of SEQ ID NOs: 179-184.

In an embodiment of the invention, the inventive polypeptide can comprise, for instance, the variable region of the inventive TCR comprising a combination of the CDR regions set forth above. In this regard, the polypeptide can comprise the amino acid sequence(s) of (1) SEQ ID NO: 7, (2) SEQ ID NO: 8, (3) SEQ ID NO: 9, (4) SEQ ID NO: 10, (5) SEQ ID NO: 17, (6) SEQ ID NO: 18, (7) SEQ ID NO: 19, (8) SEQ ID NO: 20, (9) SEQ ID NO: 27, (10) SEQ ID NO: 28, (11) SEQ ID NO: 29, (12) SEQ ID NO: 30, (13) SEQ ID NO: 37, (14) SEQ ID NO: 38, (15) SEQ ID NO: 39, (16) SEQ ID NO: 40, (17) SEQ ID NO: 47, (18) SEQ ID NO: 48, (19) SEQ ID NO: 49, (20) SEQ ID NO: 50, (21) SEQ ID NO: 125, (22) SEQ ID NO: 126, (23) SEQ ID NO: 127, (24) SEQ ID NO: 128, (25) SEQ ID NO: 135, (26) SEQ ID NO: 136, (27) SEQ ID NO: 137, (28) SEQ ID NO: 138, (29) SEQ ID NO: 145, (30) SEQ ID NO: 146, (31) SEQ ID NO: 147, (32) SEQ ID NO: 148, (33) SEQ ID NO: 155, (34) SEQ ID NO: 156, (35) SEQ ID NO: 157, (36) SEQ ID NO: 158, (37) SEQ ID NO: 165, (38) SEQ ID NO: 166, (39) SEQ ID NO: 167, (40) SEQ ID NO: 168, (41) SEQ ID NO: 175, (42) SEQ ID NO: 176, (43) SEQ ID NO: 177, (44) SEQ ID NO: 178, (45) SEQ ID NO: 185, (46) SEQ ID NO: 186, (47) SEQ ID NO: 187, (48) SEQ ID NO: 188, (49) both of SEQ ID NOs: 7 and 8, (50) both of SEQ ID NOs: 9 and 10, (51) both of SEQ ID NOs: 17 and 18, (52) both of SEQ ID NOs: 19 and 20, (53) both of SEQ ID NOs: 27 and 28, (54) both of SEQ ID NOs: 29 and 30, (55) both of SEQ ID NOs: 37 and 38, (56) both of SEQ ID NOs: 39 and 40, (57) both of SEQ ID NOs: 47 and 48, (58) both of SEQ ID NOs: 49 and 50, (59) both of SEQ ID NOs: 125 and 126, (60) both of SEQ ID NOs: 127 and 128, (61) both of SEQ ID NOs: 135 and 136, (62) both of SEQ ID NOs: 137 and 138, (63) both of SEQ ID NOs: 145 and 146, (64) both of SEQ ID NOs: 147 and 148, (65) both of SEQ ID NOs: 155 and 156, (66) both of SEQ ID NOs: 157 and 158, (67) both of SEQ ID NOs: 165 and 166, (68) both of SEQ ID NOs: 167 and 168, (69) both of SEQ ID NOs: 175 and 176, (70) both of SEQ ID NOs: 177 and 178, (71) both of SEQ ID NOs: 185 and 186, or (72) both of SEQ ID NOs: 187 and 188. In a preferred embodiment, the polypeptide comprises the amino acid sequences of (a) both of SEQ ID NOs: 7 and 8, (b) both of SEQ ID NOs: 9 and 10, (c) both of SEQ ID NOs: 17 and 18, (d) both of SEQ ID NOs: 19 and 20, (e) both of SEQ ID NOs: 27 and 28, (f) both of SEQ ID NOs: 29 and 30, (g) both of SEQ ID NOs: 37 and 38, (h) both of SEQ ID NOs: 39 and 40, (i) both of SEQ ID NOs: 47 and 48, (j) both of SEQ ID NOs: 49 and 50, (k) both of SEQ ID NOs: 125 and 126, (l) both of SEQ ID NOs: 127 and 128, (m) both of SEQ ID NOs: 135 and 136, (n) both of SEQ ID NOs: 137 and 138, (o) both of SEQ ID NOs: 145 and 146, (p) both of SEQ ID NOs: 147 and 148, (q) both of SEQ ID NOs: 155 and 156, (r) both of SEQ ID NOs: 157 and 158, (s) both of SEQ ID NOs: 165 and 166, (t) both of SEQ ID NOs: 167 and 168, (u) both of SEQ ID NOs: 175 and 176, (v) both of SEQ ID NOs: 177 and 178, (w) both of SEQ ID NOs: 185 and 186, or (x) both of SEQ ID NOs: 187 and 188.

In an embodiment of the invention, the inventive polypeptide can further comprise the constant region of the inventive TCR set forth above. In this regard, the polypeptide can further comprise the amino acid sequence of SEQ ID NO: 63 (WT murine constant region of α chain), SEQ ID NO: 64 (WT murine constant region of β chain), SEQ ID NO: 59 (substituted murine constant region of α chain), SEQ ID NO: 60 (substituted murine constant region of β chain), SEQ ID NO: 61 (α chain constant region of cysteine-substituted, LVL-modified TCR); SEQ ID NO: 62 (β chain constant region of cysteine-substituted, LVL-modified TCR); both SEQ ID NOs: 59 and 60, both SEQ ID NOs: 61 and 62, or both SEQ ID NOs: 63 and 64. Preferably, the polypeptide further comprises the amino acid sequences of both of SEQ ID NOs: 59 and 60, both of SEQ ID NO: 61 and 62, or both of SEQ ID NOs: 63 and 64 in combination with any of the CDR regions or variable regions described herein with respect to other aspects of the invention. In an embodiment of the invention, one or both of SEQ ID NOs: 59 and 60 of the polypeptide are as defined in any one of Tables 2-4.

In an embodiment of the invention, the inventive polypeptide can comprise the entire length of an α or β chain of the TCR described herein. In this regard, the inventive polypeptide can comprise the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, or SEQ ID NO: 244.

Alternatively, the polypeptide of the invention can comprise both chains of the TCRs described herein. For example, the polypeptide may comprise the amino acid sequences of: both of SEQ ID NOs: 65-66, both of SEQ ID NOs: 67-68, both of SEQ ID NOs: 69-70, both of SEQ ID NOs: 71-72, both of SEQ ID NOs: 73-74, both of SEQ ID NOs: 75-76, both of SEQ ID NOs: 77-78, both of SEQ ID NOs: 79-80, both of SEQ ID NOs: 81-82, both of SEQ ID NOs: 83-84, both of SEQ ID NOs: 85-86, both of SEQ ID NOs: 87-88, both of SEQ ID NOs: 89-90, both of SEQ ID NOs: 91-92, both of SEQ ID NOs: 93-94, both of SEQ ID NOs: 95-96, both of SEQ ID NOs: 97-98, both of SEQ ID NOs: 99-100, both of SEQ ID NOs: 101-102, both of SEQ ID NOs: 103-104, both of SEQ ID NOs: 189 and 190, both of SEQ ID NOs: 191 and 192, both of SEQ ID NOs: 193 and 194, both of SEQ ID NOs: 195 and 196, both of SEQ ID NOs: 197 and 198, both of SEQ ID NOs: 199 and 200, both of SEQ ID NOs: 201 and 202, both of SEQ ID NOs: 203 and 204, both of SEQ ID NOs: 205 and 206, both of SEQ ID NOs: 207 and 208, both of SEQ ID NOs: 209 and 210, both of SEQ ID NOs: 211 and 212, both of SEQ ID NOs: 213 and 214, both of SEQ ID NOs: 215 and 216, both of SEQ ID NOs: 217 and 218, both of SEQ ID NOs: 219 and 220, both of SEQ ID NOs: 221 and 222, both of SEQ ID NOs: 223 and 224, both of SEQ ID NOs: 225 and 226, both of SEQ ID NOs: 227 and 228, both of SEQ ID NOs: 229 and 230, both of SEQ ID NOs: 231 and 232, both of SEQ ID NOs: 233 and 234, both of SEQ ID NOs: 235 and 236, both of SEQ ID NOs: 237 and 238, both of SEQ ID NOs: 239 and 240, both of SEQ ID NOs: 241 and 242, or both of SEQ ID NOs: 243 and 244.

For example, the polypeptide of the invention can comprise (a) the amino acid sequence of SEQ ID NO: 65 (α chain of 4400 TCR-A1 with N-terminal signal peptide), wherein: (i) X at position 180 of SEQ ID NO: 65 is Thr or Cys; (ii) X at position 244 of SEQ ID NO: 65 is Ser, Ala, Val, Leu, Ile, Pro, Phe, Met, or Trp; (iii) X at position 246 of SEQ ID NO: 65 is Met, Ala, Val, Leu, Ile, Pro, Phe, or Trp; and (iv) X at position 247 of SEQ ID NO: 65 is Gly, Ala, Val, Leu, Ile, Pro, Phe, Met, or Trp; (b) the amino acid sequence of SEQ ID NO: 66 (β chain of 4400 TCR-A1 with N-terminal signal peptide), wherein X at position 188 of SEQ ID NO: 66 is Ser or Cys; (c) the amino acid sequences of both of SEQ ID NOs: 65 and 66; (d) the amino acid sequence of SEQ ID NO: 67 (predicted sequence of α chain of 4400 TCR-A1 without N-terminal signal peptide), wherein: (i) X at position 158 of SEQ ID NO: 67 is Thr or Cys; (ii) X at position 222 of SEQ ID NO: 67 is Ser, Ala, Val, Leu, Ile, Pro, Phe, Met, or Trp; (iii) X at position 224 of SEQ ID NO: 67 is Met, Ala, Val, Leu, Ile, Pro, Phe, or Trp; and (iv) X at position 225 of SEQ ID NO: 67 is Gly, Ala, Val, Leu, Ile, Pro, Phe, Met, or Trp; (e) the amino acid sequence of SEQ ID NO: 68 (predicted sequence of β chain of 4400 TCR-A1 without N-terminal signal peptide), wherein X at position 169 of SEQ ID NO: 68 is Ser or Cys; (0 the amino acid sequences of both of SEQ ID NOs: 67 and 68; (g) the amino acid sequence of SEQ ID NO: 69 (α chain of cysteine-substituted, LVL-modified 4400 TCR-A1 with N-terminal signal peptide); (h) the amino acid sequence of SEQ ID NO: 70 (β chain of cysteine-substituted, LVL-modified 4400 TCR-A1 with N-terminal signal peptide); (i) the amino acid sequence of SEQ ID NO: 71 (predicted sequence of α chain of cysteine-substituted, LVL-modified 4400 TCR-A1 without N-terminal signal peptide); (j) the amino acid sequence of SEQ ID NO: 72 (predicted sequence of β chain of cysteine-substituted, LVL-modified 4400 TCR-A1 without N-terminal signal peptide); (k) the amino acid sequences of both of SEQ ID NOs: 69 and 70; (l) the amino acid sequences of both of SEQ ID NOs: 71 and 72; (m) the amino acid sequence of SEQ ID NO: 73 (α chain of 4400 TCR-A2 with N-terminal signal peptide), wherein: (i) X at position 180 of SEQ ID NO: 73 is Thr or Cys; (ii) X at position 244 of SEQ ID NO: 73 is Ser, Ala, Val, Leu, Ile, Pro, Phe, Met, or Trp; (iii) X at position 246 of SEQ ID NO: 73 is Met, Ala, Val, Leu, Ile, Pro, Phe, or Trp; and (iv) X at position 247 of SEQ ID NO: 73 is Gly, Ala, Val, Leu, Ile, Pro, Phe, Met, or Trp; (n) the amino acid sequence of SEQ ID NO: 74 (β chain of 4400 TCR-A2 with N-terminal signal peptide), wherein X at position 188 of SEQ ID NO: 74 is Ser or Cys; (o) the amino acid sequences of both of SEQ ID NOs: 73 and 74; (p) the amino acid sequence of SEQ ID NO: 75 (predicted sequence of α chain of 4400 TCR-A2 without N-terminal signal peptide), wherein: (i) X at position 158 of SEQ ID NO: 75 is Thr or Cys; (ii) X at position 222 of SEQ ID NO: 75 is Ser, Ala, Val, Leu, Ile, Pro, Phe, Met, or Trp; (iii) X at position 224 of SEQ ID NO: 75 is Met, Ala, Val, Leu, Ile, Pro, Phe, or Trp; and (iv) X at position 225 of SEQ ID NO: 75 is Gly, Ala, Val, Leu, Ile, Pro, Phe, Met, or Trp; (q) the amino acid sequence of SEQ ID NO: 76 (predicted sequence of β chain of 4400 TCR-A2 without N-terminal signal peptide), wherein X at position 169 of SEQ ID NO: 76 is Ser or Cys; (r) the amino acid sequences of both of SEQ ID NOs: 75 and 76; (s) the amino acid sequence of SEQ ID NO: 77 (α chain of cysteine-substituted, LVL-modified 4400 TCR-A2 with N-terminal signal peptide); (t) the amino acid sequence of SEQ ID NO: 78 (β chain of cysteine-substituted, LVL-modified 4400 TCR-A2 with N-terminal signal peptide); (u) the amino acid sequence of SEQ ID NO: 79 (predicted sequence of α chain of cysteine-substituted, LVL-modified 4400 TCR-A2 without N-terminal signal peptide); (v) the amino acid sequence of SEQ ID NO: 80 (predicted sequence of β chain of cysteine-substituted, LVL-modified 4400 TCR-A2 without N-terminal signal peptide); (w) the amino acid sequences of both of SEQ ID NOs: 77 and 78; (x) the amino acid sequences of both of SEQ ID NOs: 79 and 80; (y) the amino acid sequence of SEQ ID NO: 81 (α chain of 4400 TCR-E with N-terminal signal peptide), wherein: (i) X at position 177 of SEQ ID NO: 81 is Thr or Cys; (ii) X at position 241 of SEQ ID NO: 81 is Ser, Ala, Val, Leu, Ile, Pro, Phe, Met, or Trp; (iii) X at position 243 of SEQ ID NO: 81 is Met, Ala, Val, Leu, Ile, Pro, Phe, or Trp; and (iv) X at position 244 of SEQ ID NO: 81 is Gly, Ala, Val, Leu, Ile, Pro, Phe, Met, or Trp; (z) the amino acid sequence of SEQ ID NO: 82 (β chain of 4400 TCR-E with N-terminal signal peptide), wherein X at position 189 of SEQ ID NO: 82 is Ser or Cys; (aa) the amino acid sequences of both of SEQ ID NOs: 81 and 82; (bb) the amino acid sequence of SEQ ID NO: 83 (predicted sequence of α chain of 4400 TCR-E without N-terminal signal peptide), wherein: (i) X at position 160 of SEQ ID NO: 83 is Thr or Cys; (ii) X at position 224 of SEQ ID NO: 83 is Ser, Ala, Val, Leu, Ile, Pro, Phe, Met, or Trp; (iii) X at position 226 of SEQ ID NO: 83 is Met, Ala, Val, Leu, Ile, Pro, Phe, or Trp; and (iv) X at position 227 of SEQ ID NO: 83 is Gly, Ala, Val, Leu, Ile, Pro, Phe, Met, or Trp; (cc) the amino acid sequence of SEQ ID NO: 84 (predicted sequence of β chain of 4400 TCR-E without N-terminal signal peptide), wherein X at position 170 of SEQ ID NO: 84 is Ser or Cys; (dd) the amino acid sequences of both of SEQ ID NOs: 83 and 84; (ee) the amino acid sequence of SEQ ID NO: 85 (α chain of cysteine-substituted, LVL-modified 4400 TCR-E with N-terminal signal peptide); (ff) the amino acid sequence of SEQ ID NO: 86 (β chain of cysteine-substituted, LVL-modified 4400 TCR-E with N-terminal signal peptide); (gg) the amino acid sequence of SEQ ID NO: 87 (predicted sequence of α chain of cysteine-substituted, LVL-modified 4400 TCR-E without N-terminal signal peptide); (hh) the amino acid sequence of SEQ ID NO: 88 (predicted sequence of β chain of cysteine-substituted, LVL-modified 4400 TCR-E without N-terminal signal peptide); (ii) the amino acid sequences of both of SEQ ID NOs: 85 and 86; (jj) the amino acid sequences of both of SEQ ID NOs: 87 and 88; (kk) the amino acid sequence of SEQ ID NO: 89 (α chain of 4400 TCR-J with N-terminal signal peptide), wherein: (i) X at position 183 of SEQ ID NO: 89 is Thr or Cys; (ii) X at position 247 of SEQ ID NO: 89 is Ser, Ala, Val, Leu, Ile, Pro, Phe, Met, or Trp; (iii) X at position 249 of SEQ ID NO: 89 is Met, Ala, Val, Leu, Ile, Pro, Phe, or Trp; and (iv) X at position 250 of SEQ ID NO: 89 is Gly, Ala, Val, Leu, Ile, Pro, Phe, Met, or Trp; (ll) the amino acid sequence of SEQ ID NO: 90 (β chain of 4400 TCR-J with N-terminal signal peptide), wherein X at position 188 of SEQ ID NO: 90 is Ser or Cys; (mm) the amino acid sequences of both of SEQ ID NOs: 89 and 90; (nn) the amino acid sequence of SEQ ID NO: 91 (predicted sequence of α chain of 4400 TCR-J without N-terminal signal peptide), wherein: (i) X at position 161 of SEQ ID NO: 91 is Thr or Cys; (ii) X at position 225 of SEQ ID NO: 91 is Ser, Ala, Val, Leu, Ile, Pro, Phe, Met, or Trp; (iii) X at position 227 of SEQ ID NO: 91 is Met, Ala, Val, Leu, Ile, Pro, Phe, or Trp; and (iv) X at position 228 of SEQ ID NO: 91 is Gly, Ala, Val, Leu, Ile, Pro, Phe, Met, or Trp; (oo) the amino acid sequence of SEQ ID NO: 92 (predicted sequence of β chain of 4400 TCR-J without N-terminal signal peptide), wherein X at position 169 of SEQ ID NO: 92 is Ser or Cys; (pp) the amino acid sequences of both of SEQ ID NOs: 91 and 92; (qq) the amino acid sequence of SEQ ID NO: 93 (α chain of cysteine-substituted, LVL-modified 4400 TCR-J with N-terminal signal peptide); (rr) the amino acid sequence of SEQ ID NO: 94 (β chain of cysteine-substituted, LVL-modified 4400 TCR-J with N-terminal signal peptide); (ss) the amino acid sequence of SEQ ID NO: 95 (predicted sequence of α chain of cysteine-substituted, LVL-modified 4400 TCR-J without N-terminal signal peptide); (tt) the amino acid sequence of SEQ ID NO: 96 (predicted sequence of β chain of cysteine-substituted, LVL-modified 4400 TCR-J without N-terminal signal peptide); (uu) the amino acid sequences of both of SEQ ID NOs: 93 and 94; (vv) the amino acid sequences of both of SEQ ID NOs: 95 and 96; (ww) the amino acid sequence of SEQ ID NO: 97 (α chain of 4400 TCR-N with N-terminal signal peptide), wherein: (i) X at position 178 of SEQ ID NO: 97 is Thr or Cys; (ii) X at position 242 of SEQ ID NO: 97 is Ser, Ala, Val, Leu, Ile, Pro, Phe, Met, or Trp; (iii) X at position 244 of SEQ ID NO: 97 is Met, Ala, Val, Leu, Ile, Pro, Phe, or Trp; and (iv) X at position 245 of SEQ ID NO: 97 is Gly, Ala, Val, Leu, Ile, Pro, Phe, Met, or Trp; (xx) the amino acid sequence of SEQ ID NO: 98 (β chain of 4400 TCR-N with N-terminal signal peptide), wherein X at position 188 of SEQ ID NO: 98 is Ser or Cys; (yy) the amino acid sequences of both of SEQ ID NOs: 97 and 98; (zz) the amino acid sequence of SEQ ID NO: 99 (predicted sequence of α chain of 4400 TCR-N without N-terminal signal peptide), wherein: (i) X at position 157 of SEQ ID NO: 99 is Thr or Cys; (ii) X at position 221 of SEQ ID NO: 99 is Ser, Ala, Val, Leu, Ile, Pro, Phe, Met, or Trp; (iii) X at position 223 of SEQ ID NO: 99 is Met, Ala, Val, Leu, Ile, Pro, Phe, or Trp; and (iv) X at position 224 of SEQ ID NO: 99 is Gly, Ala, Val, Leu, Ile, Pro, Phe, Met, or Trp; (aaa) the amino acid sequence of SEQ ID NO: 100 (predicted sequence of β chain of 4400 TCR-N without N-terminal signal peptide), wherein X at position 169 of SEQ ID NO: 100 is Ser or Cys; (bbb) the amino acid sequences of both of SEQ ID NOs: 99 and 100; (ccc) the amino acid sequence of SEQ ID NO: 101 (α chain of cysteine-substituted, LVL-modified 4400 TCR-N with N-terminal signal peptide); (ddd) the amino acid sequence of SEQ ID NO: 102 (β chain of cysteine-substituted, LVL-modified 4400 TCR-N with N-terminal signal peptide); (eee) the amino acid sequence of SEQ ID NO: 103 (predicted sequence of α chain of cysteine-substituted, LVL-modified 4400 TCR-N without N-terminal signal peptide); (fff) the amino acid sequence of SEQ ID NO: 104 (predicted sequence of β chain of cysteine-substituted, LVL-modified 4400 TCR-N without N-terminal signal peptide); (ggg) the amino acid sequences of both of SEQ ID NOs: 101 and 102; (hhh) the amino acid sequences of both of SEQ ID NOs: 103 and 104; (iii) the amino acid sequence of SEQ ID NO: 189 (α chain of 4400 TCR-A3 with N-terminal signal peptide), wherein: (i) X at position 176 of SEQ ID NO: 189 is Thr or Cys; (ii) X at position 240 of SEQ ID NO: 189 is Ser, Ala, Val, Leu, Ile, Pro, Phe, Met, or Trp; (iii) X at position 242 of SEQ ID NO: 189 is Met, Ala, Val, Leu, Ile, Pro, Phe, or Trp; and (iv) X at position 243 of SEQ ID NO: 189 is Gly, Ala, Val, Leu, Ile, Pro, Phe, Met, or Trp; (jjj) the amino acid sequence of SEQ ID NO: 190 (β chain of 4400 TCR-A3 with N-terminal signal peptide), wherein X at position 188 of SEQ ID NO: 190 is Ser or Cys; (kkk) the amino acid sequences of both of SEQ ID NOs: 189 and 190; (lll) the amino acid sequence of SEQ ID NO: 191 (predicted sequence of α chain of 4400 TCR-A3 without N-terminal signal peptide), wherein: (i) X at position 157 of SEQ ID NO: 191 is Thr or Cys; (ii) X at position 221 of SEQ ID NO: 191 is Ser, Ala, Val, Leu, Ile, Pro, Phe, Met, or Trp; (iii) X at position 223 of SEQ ID NO: 191 is Met, Ala, Val, Leu, Ile, Pro, Phe, or Trp; and (iv) X at position 224 of SEQ ID NO: 191 is Gly, Ala, Val, Leu, Ile, Pro, Phe, Met, or Trp; (mmm) the amino acid sequence of SEQ ID NO: 192 (predicted sequence of β chain of 4400 TCR-A3 without N-terminal signal peptide), wherein X at position 169 of SEQ ID NO: 192 is Ser or Cys; (nnn) the amino acid sequences of both of SEQ ID NOs: 191 and 192; (ooo) the amino acid sequence of SEQ ID NO: 193 (α chain of cysteine-substituted, LVL-modified 4400 TCR-A3 with N-terminal signal peptide); (ppp) the amino acid sequence of SEQ ID NO: 194 (β chain of cysteine-substituted, LVL-modified 4400 TCR-A3 with N-terminal signal peptide); (qqq) the amino acid sequence of SEQ ID NO: 195 (predicted sequence of α chain of cysteine-substituted, LVL-modified 4400 TCR-A3 without N-terminal signal peptide); (rrr) the amino acid sequence of SEQ ID NO: 196 (predicted sequence of (3 chain of cysteine-substituted, LVL-modified 4400 TCR-A3 without N-terminal signal peptide); (sss) the amino acid sequences of both of SEQ ID NOs: 193 and 194; (ttt) the amino acid sequences of both of SEQ ID NOs: 195 and 196; (uuu) the amino acid sequence of SEQ ID NO: 197 (α chain of 4400 TCR-J2 with N-terminal signal peptide), wherein: (i) X at position 181 of SEQ ID NO: 197 is Thr or Cys; (ii) X at position 245 of SEQ ID NO: 197 is Ser, Ala, Val, Leu, Ile, Pro, Phe, Met, or Trp; (iii) X at position 247 of SEQ ID NO: 197 is Met, Ala, Val, Leu, Ile, Pro, Phe, or Trp; and (iv) X at position 248 of SEQ ID NO: 197 is Gly, Ala, Val, Leu, Ile, Pro, Phe, Met, or Trp; (vvv) the amino acid sequence of SEQ ID NO: 198 (β chain of 4400 TCR-J2 with N-terminal signal peptide), wherein X at position 188 of SEQ ID NO: 198 is Ser or Cys; (www) the amino acid sequences of both of SEQ ID NOs: 197 and 198; (xxx) the amino acid sequence of SEQ ID NO: 199 (predicted sequence of a chain of 4400 TCR-J2 without N-terminal signal peptide), wherein: (i) X at position 161 of SEQ ID NO: 199 is Thr or Cys; (ii) X at position 225 of SEQ ID NO: 199 is Ser, Ala, Val, Leu, Ile, Pro, Phe, Met, or Trp; (iii) X at position 227 of SEQ ID NO: 199 is Met, Ala, Val, Leu, Ile, Pro, Phe, or Trp; and (iv) X at position 228 of SEQ ID NO: 199 is Gly, Ala, Val, Leu, Ile, Pro, Phe, Met, or Trp; (yyy) the amino acid sequence of SEQ ID NO: 200 (predicted sequence of β chain of 4400 TCR-J2 without N-terminal signal peptide), wherein X at position 169 of SEQ ID NO: 200 is Ser or Cys; (zzz) the amino acid sequences of both of SEQ ID NOs: 199 and 200; (aaaa) the amino acid sequence of SEQ ID NO: 201

(α chain of cysteine-substituted, LVL-modified 4400 TCR-J2 with N-terminal signal peptide); (bbbb) the amino acid sequence of SEQ ID NO: 202 (β chain of cysteine-substituted, LVL-modified 4400 TCR-J2 with N-terminal signal peptide); (cccc) the amino acid sequence of SEQ ID NO: 203 (predicted sequence of α chain of cysteine-substituted, LVL-modified 4400 TCR-J2 without N-terminal signal peptide); (dddd) the amino acid sequence of SEQ ID NO: 204 (predicted sequence of β chain of cysteine-substituted, LVL-modified 4400 TCR-J2 without N-terminal signal peptide); (eeee) the amino acid sequences of both of SEQ ID NOs: 201 and 202; (ffff) the amino acid sequences of both of SEQ ID NOs: 203 and 204; (gggg) the amino acid sequence of SEQ ID NO: 205 (α chain of 4400 TCR-N4 with N-terminal signal peptide), wherein: (i) X at position 184 of SEQ ID NO: 205 is Thr or Cys; (ii) X at position 248 of SEQ ID NO: 205 is Ser, Ala, Val, Leu, Ile, Pro, Phe, Met, or Trp; (iii) X at position 250 of SEQ ID NO: 205 is Met, Ala, Val, Leu, Ile, Pro, Phe, or Trp; and (iv) X at position 251 of SEQ ID NO: 205 is Gly, Ala, Val, Leu, Ile, Pro, Phe, Met, or Trp; (hhhh) the amino acid sequence of SEQ ID NO: 206 (β chain of 4400 TCR-N4 with N-terminal signal peptide), wherein X at position 190 of SEQ ID NO: 206 is Ser or Cys; (iiii) the amino acid sequences of both of SEQ ID NOs: 205 and 206; (jjjj) the amino acid sequence of SEQ ID NO: 207 (predicted sequence of α chain of 4400 TCR-N4 without N-terminal signal peptide), wherein: (i) X at position 163 of SEQ ID NO: 207 is Thr or Cys; (ii) X at position 227 of SEQ ID NO: 207 is Ser, Ala, Val, Leu, Ile, Pro, Phe, Met, or Trp; (iii) X at position 229 of SEQ ID NO: 207 is Met, Ala, Val, Leu, Ile, Pro, Phe, or Trp; and (iv) X at position 230 of SEQ ID NO: 207 is Gly, Ala, Val, Leu, Ile, Pro, Phe, Met, or Trp; (kkkk) the amino acid sequence of SEQ ID NO: 208 (predicted sequence of β chain of 4400 TCR-N4 without N-terminal signal peptide), wherein X at position 164 of SEQ ID NO: 208 is Ser or Cys; (llll) the amino acid sequences of both of SEQ ID NOs: 207 and 208; (mmmm) the amino acid sequence of SEQ ID NO: 209 (α chain of cysteine-substituted, LVL-modified 4400 TCR-N4 with N-terminal signal peptide); (nnnn) the amino acid sequence of SEQ ID NO: 210 (β chain of cysteine-substituted, LVL-modified 4400 TCR-N4 with N-terminal signal peptide); (0000) the amino acid sequence of SEQ ID NO: 211 (predicted sequence of α chain of cysteine-substituted, LVL-modified 4400 TCR-N4 without N-terminal signal peptide); (pppp) the amino acid sequence of SEQ ID NO: 212 (predicted sequence of β chain of cysteine-substituted, LVL-modified 4400 TCR-N4 without N-terminal signal peptide); (qqqq) the amino acid sequences of both of SEQ ID NOs: 209 and 210; (rrrr) the amino acid sequences of both of SEQ ID NOs: 211 and 212; (ssss) the amino acid sequence of SEQ ID NO: 213 (α chain of 4400 TCR-N12 with N-terminal signal peptide), wherein: (i) X at position 183 of SEQ ID NO: 213 is Thr or Cys; (ii) X at position 247 of SEQ ID NO: 213 is Ser, Ala, Val, Leu, Ile, Pro, Phe, Met, or Trp; (iii) X at position 249 of SEQ ID NO: 213 is Met, Ala, Val, Leu, Ile, Pro, Phe, or Trp; and (iv) X at position 250 of SEQ ID NO: 213 is Gly, Ala, Val, Leu, Ile, Pro, Phe, Met, or Trp; (tttt) the amino acid sequence of SEQ ID NO: 214 (β chain of 4400 TCR-N12 with N-terminal signal peptide), wherein X at position 188 of SEQ ID NO: 214 is Ser or Cys; (uuuu) the amino acid sequences of both of SEQ ID NOs: 213 and 214; (vvvv) the amino acid sequence of SEQ ID NO: 215 (predicted sequence of α chain of 4400 TCR-N12 without N-terminal signal peptide), wherein: (i) X at position 161 of SEQ ID NO: 215 is Thr or Cys; (ii) X at position 225 of SEQ ID NO: 215 is Ser, Ala, Val, Leu, Ile, Pro, Phe, Met, or Trp; (iii) X at position 227 of SEQ ID NO: 215 is Met, Ala, Val, Leu, Ile, Pro, Phe, or Trp; and (iv) X at position 228 of SEQ ID NO: 215 is Gly, Ala, Val, Leu, Ile, Pro, Phe, Met, or Trp; (wwww) the amino acid sequence of SEQ ID NO: 216 (predicted sequence of β chain of 4400 TCR-N12 without N-terminal signal peptide), wherein X at position 169 of SEQ ID NO: 216 is Ser or Cys; (xxxx) the amino acid sequences of both of SEQ ID NOs: 215 and 216; (yyyy) the amino acid sequence of SEQ ID NO: 217 (α chain of cysteine-substituted, LVL-modified 4400 TCR-N12 with N-terminal signal peptide); (zzzz) the amino acid sequence of SEQ ID NO: 218 (β chain of cysteine-substituted, LVL-modified 4400 TCR-N12 with N-terminal signal peptide); (aaaaa) the amino acid sequence of SEQ ID NO: 219 (predicted sequence of α chain of cysteine-substituted, LVL-modified 4400 TCR-N12 without N-terminal signal peptide); (bbbbb) the amino acid sequence of SEQ ID NO: 220 (predicted sequence of β chain of cysteine-substituted, LVL-modified 4400 TCR-N12 without N-terminal signal peptide); (ccccc) the amino acid sequences of both of SEQ ID NOs: 217 and 218; (ddddd) the amino acid sequences of both of SEQ ID NOs: 219 and 220; (eeeee) the amino acid sequence of SEQ ID NO: 221 (α chain of 4400 TCR-N13 with N-terminal signal peptide), wherein: (i) X at position 180 of SEQ ID NO: 221 is Thr or Cys; (ii) X at position 244 of SEQ ID NO: 221 is Ser, Ala, Val, Leu, Ile, Pro, Phe, Met, or Trp; (iii) X at position 246 of SEQ ID NO: 221 is Met, Ala, Val, Leu, Ile, Pro, Phe, or Trp; and (iv) X at position 247 of SEQ ID NO: 221 is Gly, Ala, Val, Leu, Ile, Pro, Phe, Met, or Trp; (fffff) the amino acid sequence of SEQ ID NO: 222 (β chain of 4400 TCR-N13 with N-terminal signal peptide), wherein X at position 188 of SEQ ID NO: 222 is Ser or Cys; (ggggg) the amino acid sequences of both of SEQ ID NOs: 221 and 222; (hhhhh) the amino acid sequence of SEQ ID NO: 223 (predicted sequence of α chain of 4400 TCR-N13 without N-terminal signal peptide), wherein: (i) X at position 158 of SEQ ID NO: 223 is Thr or Cys; (ii) X at position 222 of SEQ ID NO: 223 is Ser, Ala, Val, Leu, Ile, Pro, Phe, Met, or Trp; (iii) X at position 224 of SEQ ID NO: 223 is Met, Ala, Val, Leu, Ile, Pro, Phe, or Trp; and (iv) X at position 225 of SEQ ID NO: 223 is Gly, Ala, Val, Leu, Ile, Pro, Phe, Met, or Trp; (iiiii) the amino acid sequence of SEQ ID NO: 224 (predicted sequence of β chain of 4400 TCR-N13 without N-terminal signal peptide), wherein X at position 169 of SEQ ID NO: 224 is Ser or Cys; (jjjjj) the amino acid sequences of both of SEQ ID NOs: 223 and 224; (kkkkk) the amino acid sequence of SEQ ID NO: 225 (α chain of cysteine-substituted, LVL-modified 4400 TCR-N13 with N-terminal signal peptide); (lllll) the amino acid sequence of SEQ ID NO: 226 (β chain of cysteine-substituted, LVL-modified 4400 TCR-N13 with N-terminal signal peptide); (mmmmm) the amino acid sequence of SEQ ID NO: 227 (predicted sequence of α chain of cysteine-substituted, LVL-modified 4400 TCR-N13 without N-terminal signal peptide); (nnnnn) the amino acid sequence of SEQ ID NO: 228 (predicted sequence of β chain of cysteine-substituted, LVL-modified 4400 TCR-N13 without N-terminal signal peptide); (ooooo) the amino acid sequences of both of SEQ ID NOs: 225 and 226; (ppppp) the amino acid sequences of both of SEQ ID NOs: 227 and 228; (qqqqq) the amino acid sequence of SEQ ID NO: 229 (α chain of 4400 TCR-C with N-terminal signal peptide), wherein: (i) X at position 184 of SEQ ID NO: 229 is Thr or Cys; (ii) X at position 248 of SEQ ID NO: 229 is Ser, Ala, Val, Leu, Ile, Pro, Phe, Met, or Trp; (iii) X at position 250 of SEQ ID NO: 229 is Met, Ala, Val, Leu, Ile, Pro, Phe, or Trp; and (iv) X at position 251 of SEQ ID NO: 229 is Gly, Ala, Val, Leu, Ile, Pro, Phe, Met, or Trp;

(rrrrr) the amino acid sequence of SEQ ID NO: 230 (β chain of 4400 TCR-C with N-terminal signal peptide), wherein X at position 189 of SEQ ID NO: 230 is Ser or Cys; (sssss) the amino acid sequences of both of SEQ ID NOs: 229 and 230; (ttttt) the amino acid sequence of SEQ ID NO: 231 (pre-dicted sequence of a chain of 4400 TCR-C without N-ter-minal signal peptide), wherein: (i) X at position 163 of SEQ ID NO: 231 is Thr or Cys; (ii) X at position 227 of SEQ ID NO: 231 is Ser, Ala, Val, Leu, Ile, Pro, Phe, Met, or Trp; (iii) X at position 229 of SEQ ID NO: 231 is Met, Ala, Val, Leu, Ile, Pro, Phe, or Trp; and (iv) X at position 230 of SEQ ID NO: 231 is Gly, Ala, Val, Leu, Ile, Pro, Phe, Met, or Trp; (uuuuu) the amino acid sequence of SEQ ID NO: 232 (predicted sequence of β chain of 4400 TCR-C without N-terminal signal peptide), wherein X at position 170 of SEQ ID NO: 232 is Ser or Cys; (vvvvv) the amino acid sequences of both of SEQ ID NOs: 231 and 232; (wwwww) the amino acid sequence of SEQ ID NO: 233 (a chain of cysteine-substituted, LVL-modified 4400 TCR-C with N-terminal signal peptide); (xxxxx) the amino acid sequence of SEQ ID NO: 234 (β chain of cysteine-substituted, LVL-modified 4400 TCR-C with N-terminal signal peptide); (yyyyy) the amino acid sequence of SEQ ID NO: 235 (predicted sequence of α chain of cysteine-substituted, LVL-modified 4400 TCR-C without N-terminal signal peptide); (zzzzz) the amino acid sequence of SEQ ID NO: 236 (predicted sequence of β chain of cysteine-substituted, LVL-modified 4400 TCR-C without N-terminal signal peptide); (aaaaaa) the amino acid sequences of both of SEQ ID NOs: 233 and 234; (bbbbbb) the amino acid sequences of both of SEQ ID NOs: 235 and 236; (cccccc) the amino acid sequence of SEQ ID NO: 237 (α chain of 4400 TCR-20 with N-terminal signal peptide), wherein: (i) X at position 184 of SEQ ID NO: 237 is Thr or Cys; (ii) X at position 248 of SEQ ID NO: 237 is Ser, Ala, Val, Leu, Ile, Pro, Phe, Met, or Trp; (iii) X at position 250 of SEQ ID NO: 237 is Met, Ala, Val, Leu, Ile, Pro, Phe, or Trp; and (iv) X at position 251 of SEQ ID NO: 237 is Gly, Ala, Val, Leu, Ile, Pro, Phe, Met, or Trp; (dddddd) the amino acid sequence of SEQ ID NO: 238 (β chain of 4400 TCR-20 with N-terminal signal peptide), wherein X at position 189 of SEQ ID NO: 238 is Ser or Cys; (eeeeee) the amino acid sequences of both of SEQ ID NOs: 237 and 238; (ffffff) the amino acid sequence of SEQ ID NO: 239 (predicted sequence of α chain of 4400 TCR-20 without N-terminal signal peptide), wherein: (i) X at position 163 of SEQ ID NO: 239 is Thr or Cys; (ii) X at position 227 of SEQ ID NO: 239 is Ser, Ala, Val, Leu, Ile, Pro, Phe, Met, or Trp; (iii) X at position 229 of SEQ ID NO: 239 is Met, Ala, Val, Leu, Ile, Pro, Phe, or Trp; and (iv) X at position 230 of SEQ ID NO: 239 is Gly, Ala, Val, Leu, Ile, Pro, Phe, Met, or Trp; (gggggg) the amino acid sequence of SEQ ID NO: 240 (predicted sequence of β chain of 4400 TCR-20 without N-terminal signal peptide), wherein X at position 170 of SEQ ID NO: 240 is Ser or Cys; (hhhhhh) the amino acid sequences of both of SEQ ID NOs: 239 and 240; (iiiiii) the amino acid sequence of SEQ ID NO: 241 (α chain of cysteine-substituted, LVL-modified 4400 TCR-20 with N-terminal signal peptide); (jjjjjj) the amino acid sequence of SEQ ID NO: 242 (β chain of cysteine-substituted, LVL-modified 4400 TCR-20 with N-terminal signal peptide); (kkkkkk) the amino acid sequence of SEQ ID NO: 243 (predicted sequence of α chain of cysteine-substituted, LVL-modified 4400 TCR-20 without N-terminal signal peptide); (llllll) the amino acid sequence of SEQ ID NO: 244 (pre-dicted sequence of β chain of cysteine-substituted, LVL-modified 4400 TCR-20 without N-terminal signal peptide); (mmmmmm) the amino acid sequences of both of SEQ ID NOs: 241 and 242; or (nnnnnn) the amino acid sequences of both of SEQ ID NOs: 243 and 244. In an embodiment of the invention, one or more of SEQ ID NOs: 65-68, 73-76, 81-84, 89-92, 97-100, 189-192, 197-200, 205-208, 213-216, 221-224, 229-232, and 237-240 of the polypeptide are as defined in any one of Tables 2-4.

An embodiment of the invention provides a protein com-prising at least one of the polypeptides described herein. By "protein" is meant a molecule comprising one or more polypeptide chains.

In an embodiment of the invention, the protein of the invention can comprise (a) a first polypeptide chain com-prising the amino acid sequences of SEQ ID NOs: 1-3 and a second polypeptide chain comprising the amino acid sequences of SEQ ID NOs: 4-6; (b) a first polypeptide chain comprising the amino acid sequences of SEQ ID NOs: 11-13 and a second polypeptide chain comprising the amino acid sequences of SEQ ID NOs: 14-16; (c) a first polypeptide chain comprising the amino acid sequences of SEQ ID NOs: 21-23 and a second polypeptide chain comprising the amino acid sequences of SEQ ID NOs: 24-26; (d) a first polypep-tide chain comprising the amino acid sequences of SEQ ID NOs: 31-33 and a second polypeptide chain comprising the amino acid sequences of SEQ ID NOs: 34-36; (e) a first polypeptide chain comprising the amino acid sequences of SEQ ID NOs: 41-43 and a second polypeptide chain com-prising the amino acid sequences of SEQ ID NOs: 44-46; (f) a first polypeptide chain comprising the amino acid sequences of all of SEQ ID NOs: 119-121 and a second polypeptide chain comprising the amino acid sequences of all of SEQ ID NOs: 122-124; (g) a first polypeptide chain comprising the amino acid sequences of all of SEQ ID NOs: 129-131 and a second polypeptide chain comprising the amino acid sequences of all of SEQ ID NOs: 132-134; (h) a first polypeptide chain comprising the amino acid sequences of all of SEQ ID NOs: 139-141 and a second polypeptide chain comprising the amino acid sequences of all of SEQ ID NOs: 142-144; (i) a first polypeptide chain comprising the amino acid sequences of all of SEQ ID NOs: 149-151 and a second polypeptide chain comprising the amino acid sequences of all of SEQ ID NOs: 152-154; (j) a first polypeptide chain comprising the amino acid sequences of all of SEQ ID NOs: 159-161 and a second polypeptide chain comprising the amino acid sequences of all of SEQ ID NOs: 162-164; (k) a first polypeptide chain comprising the amino acid sequences of all of SEQ ID NOs: 169-171 and a second polypeptide chain comprising the amino acid sequences of all of SEQ ID NOs: 172-174; or (l) a first polypeptide chain comprising the amino acid sequences of all of SEQ ID NOs: 179-181 and a second polypeptide chain comprising the amino acid sequences of all of SEQ ID NOs: 182-184.

In another embodiment of the invention, (i) the first polypeptide chain comprises the amino acid sequence of SEQ ID NO: 7 and the second polypeptide chain comprises the amino acid sequence of SEQ ID NO: 8; (ii) the first polypeptide chain comprises the amino acid sequence of SEQ ID NO: 9 and the second polypeptide chain comprises the amino acid sequence of SEQ ID NO: 10; (iii) the first polypeptide chain comprises the amino acid sequence of SEQ ID NO: 17 and the second polypeptide chain comprises the amino acid sequence of SEQ ID NO: 18; (iv) the first polypeptide chain comprises the amino acid sequence of SEQ ID NO: 19 and the second polypeptide chain comprises the amino acid sequence of SEQ ID NO: 20; (v) the first polypeptide chain comprises the amino acid sequence of SEQ ID NO: 27 and the second polypeptide chain comprises the amino acid sequence of SEQ ID NO: 28; (vi) the first polypeptide chain comprises the amino acid sequence of SEQ ID NO: 29 and the second polypeptide chain comprises the amino acid sequence of SEQ ID NO: 30; (vii) the first polypeptide chain comprises the amino acid sequence of SEQ ID NO: 37 and the second polypeptide chain comprises the amino acid sequence of SEQ ID NO: 38; (viii) the first polypeptide chain comprises the amino acid sequence of SEQ ID NO: 39 and the second polypeptide chain comprises the amino acid sequence of SEQ ID NO: 40; (ix) the first polypeptide chain comprises the amino acid sequence of SEQ ID NO: 47 and the second polypeptide chain comprises the amino acid sequence of SEQ ID NO: 48; (x) the first polypeptide chain comprises the amino acid sequence of SEQ ID NO: 49 and the second polypeptide chain comprises the amino acid sequence of SEQ ID NO: 50; (xi) the first polypeptide chain comprises the amino acid sequence of SEQ ID NO: 125 and the second polypeptide chain comprises the amino acid sequence of SEQ ID NO: 126; (xii) the first polypeptide chain comprises the amino acid sequence of SEQ ID NO: 127 and the second polypeptide chain comprises the amino acid sequence of SEQ ID NO: 128; (xiii) the first polypeptide chain comprises the amino acid sequence of SEQ ID NO: 135 and the second polypeptide chain comprises the amino acid sequence of SEQ ID NO: 136; (xiv) the first polypeptide chain comprises the amino acid sequence of SEQ ID NO: 137 and the second polypeptide chain comprises the amino acid sequence of SEQ ID NO: 138; (xv) the first polypeptide chain comprises the amino acid sequence of SEQ ID NO: 145 and the second polypeptide chain comprises the amino acid sequence of SEQ ID NO: 146; (xvi) the first polypeptide chain comprises the amino acid sequence of SEQ ID NO: 147 and the second polypeptide chain comprises the amino acid sequence of SEQ ID NO: 148; (xvii) the first polypeptide chain comprises the amino acid sequence of SEQ ID NO: 155 and the second polypeptide chain comprises the amino acid sequence of SEQ ID NO: 156; (xviii) the first polypeptide chain comprises the amino acid sequence of SEQ ID NO: 157 and the second polypeptide chain comprises the amino acid sequence of SEQ ID NO: 158; (xix) the first polypeptide chain comprises the amino acid sequence of SEQ ID NO: 165 and the second polypeptide chain comprises the amino acid sequence of SEQ ID NO: 166; (xx) the first polypeptide chain comprises the amino acid sequence of SEQ ID NO: 167 and the second polypeptide chain comprises the amino acid sequence of SEQ ID NO: 168; (xxi) the first polypeptide chain comprises the amino acid sequence of SEQ ID NO: 175 and the second polypeptide chain comprises the amino acid sequence of SEQ ID NO: 176; (xxii) the first polypeptide chain comprises the amino acid sequence of SEQ ID NO: 177 and the second polypeptide chain comprises the amino acid sequence of SEQ ID NO: 178; (xxiii) the first polypeptide chain comprises the amino acid sequence of SEQ ID NO: 185 and the second polypeptide chain comprises the amino acid sequence of SEQ ID NO: 186; or (xxiv) the first polypeptide chain comprises the amino acid sequence of SEQ ID NO: 187 and the second polypeptide chain comprises the amino acid sequence of SEQ ID NO: 188.

The inventive protein may further comprise any of the constant regions described herein with respect to other aspects of the invention. In this regard, in an embodiment of the invention, (i) the first polypeptide chain may further comprise the amino acid sequence of SEQ ID NO: 59 and the second polypeptide chain may further comprise the amino acid sequence of SEQ ID NO: 60; (ii) the first polypeptide chain may further comprise the amino acid sequence of SEQ ID NO: 61 and the second polypeptide chain may further comprise the amino acid sequence of SEQ ID NO: 62; or (ii) the first polypeptide chain may comprise the amino acid sequence of SEQ ID NO: 63 and the second polypeptide chain may comprise the amino acid sequence of SEQ ID NO: 64. In an embodiment of the invention, one or both of SEQ ID NOs: 59 and 60 of the protein are as defined in any one of Tables 2-4.

The inventive protein may comprise a full length α or β chain, as described herein with respect to other aspects of the invention. In this regard, in an embodiment of the invention, (a) the first polypeptide chain comprises the amino acid sequence of SEQ ID NO: 65, wherein: (i) X at position 180 of SEQ ID NO: 65 is Thr or Cys; (ii) X at position 244 of SEQ ID NO: 65 is Ser, Ala, Val, Leu, Ile, Pro, Phe, Met, or Trp; (iii) X at position 246 of SEQ ID NO: 65 is Met, Ala, Val, Leu, Ile, Pro, Phe, or Trp; and (iv) X at position 247 of SEQ ID NO: 65 is Gly, Ala, Val, Leu, Ile, Pro, Phe, Met, or Trp; (b) the second polypeptide chain comprises the amino acid sequence of SEQ ID NO: 66, wherein X at position 188 of SEQ ID NO: 66 is Ser or Cys; (c) both (a) and (b); (d) the first polypeptide chain comprises the amino acid sequence of SEQ ID NO: 67, wherein: (i) X at position 158 of SEQ ID NO: 67 is Thr or Cys; (ii) X at position 222 of SEQ ID NO: 67 is Ser, Ala, Val, Leu, Ile, Pro, Phe, Met, or Trp; (iii) X at position 224 of SEQ ID NO: 67 is Met, Ala, Val, Leu, Ile, Pro, Phe, or Trp; and (iv) X at position 225 of SEQ ID NO: 67 is Gly, Ala, Val, Leu, Ile, Pro, Phe, Met, or Trp; (e) the second polypeptide chain comprises the amino acid sequence of SEQ ID NO: 68, wherein X at position 169 of SEQ ID NO: 68 is Ser or Cys; (0 both (d) and (e); (g) the first polypeptide chain comprises the amino acid sequence of SEQ ID NO: 69; (h) the second polypeptide chain comprises the amino acid sequence of SEQ ID NO: 70; (i) the first polypeptide chain comprises the amino acid sequence of SEQ ID NO: 71; (j) the second polypeptide chain comprises the amino acid sequence of SEQ ID NO: 72; (k) both (g) and (h); (l) both (i) and (j); (m) the first polypeptide chain comprises the amino acid sequence of SEQ ID NO: 73, wherein: (i) X at position 180 of SEQ ID NO: 73 is Thr or Cys; (ii) X at position 244 of SEQ ID NO: 73 is Ser, Ala, Val, Leu, Ile, Pro, Phe, Met, or Trp; (iii) X at position 246 of SEQ ID NO: 73 is Met, Ala, Val, Leu, Ile, Pro, Phe, or Trp; and (iv) X at position 247 of SEQ ID NO: 73 is Gly, Ala, Val, Leu, Ile, Pro, Phe, Met, or Trp; (n) the second polypeptide chain comprises the amino acid sequence of SEQ ID NO: 74, wherein X at position 188 of SEQ ID NO: 74 is Ser or Cys; (o) both (m) and (n); (p) the first polypeptide chain comprises the amino acid sequence of SEQ ID NO: 75, wherein: (i) X at position 158 of SEQ ID NO: 75 is Thr or Cys; (ii) X at position 222 of SEQ ID NO: 75 is Ser, Ala, Val, Leu, Ile, Pro, Phe, Met, or Trp; (iii) X at position 224 of SEQ ID NO: 75 is Met, Ala, Val, Leu, Ile, Pro, Phe, or Trp; and (iv) X at position 225 of SEQ ID NO: 75 is Gly, Ala, Val, Leu, Ile, Pro, Phe, Met, or Trp; (q) the second polypeptide chain comprises the amino acid sequence of SEQ ID NO: 76, wherein X at position 169 of SEQ ID NO: 76 is Ser or Cys; (r) both (p) and (q); (s) the first polypeptide chain comprises the amino acid sequence of SEQ ID NO: 77; (t) the second polypeptide chain comprises the amino acid sequence of SEQ ID NO: 78; (u) the first polypeptide chain comprises the amino acid sequence of SEQ ID NO: 79; (v) the second polypeptide chain comprises the amino acid sequence of SEQ ID NO: 80; (w) both (s) and (t); (x) both (u) and (v); (y) the first polypeptide chain comprises the amino acid sequence of SEQ ID NO: 81, wherein: (i) X at position 177 of SEQ ID NO: 81 is Thr or Cys; (ii) X at position 241 of SEQ ID NO: 81 is Ser, Ala, Val, Leu, Ile, Pro, Phe, Met, or Trp; (iii) X at position 243 of SEQ ID NO: 81 is Met, Ala, Val, Leu, Ile, Pro, Phe, or Trp; and (iv) X at position 244 of SEQ ID NO: 81 is Gly, Ala, Val, Leu, Ile, Pro, Phe, Met, or Trp; (z) the second polypeptide chain comprises the amino acid sequence of SEQ ID NO: 82, wherein X at position 189 of SEQ ID NO: 82 is Ser or Cys; (aa) both (y) and (z); (bb) the first polypeptide chain comprises the amino acid sequence of SEQ ID NO: 83, wherein: (i) X at position 160 of SEQ ID NO: 83 is Thr or Cys; (ii) X at position 224 of SEQ ID NO: 83 is Ser, Ala, Val, Leu, Ile, Pro, Phe, Met, or Trp; (iii) X at position 226 of SEQ ID NO: 83 is Met, Ala, Val, Leu, Ile, Pro, Phe, or Trp; and (iv) X at position 227 of SEQ ID NO: 83 is Gly, Ala, Val, Leu, Ile, Pro, Phe, Met, or Trp; (cc) the second polypeptide chain comprises the amino acid sequence of SEQ ID NO: 84, wherein X at position 170 of SEQ ID NO: 84 is Ser or Cys; (dd) both (bb) and (cc); (ee) the first polypeptide chain comprises the amino acid sequence of SEQ ID NO: 85; (ff) the second polypeptide chain comprises the amino acid sequence of SEQ ID NO: 86; (gg) the first polypeptide chain comprises the amino acid sequence of SEQ ID NO: 87; (hh) the second polypeptide chain comprises the amino acid sequence of SEQ ID NO: 88; (ii) both (ee) and (ff); (jj) both (gg) and (hh); (kk) the first polypeptide chain comprises the amino acid sequence of SEQ ID NO: 89, wherein: (i) X at position 183 of SEQ ID NO: 89 is Thr or Cys; (ii) X at position 247 of SEQ ID NO: 89 is Ser, Ala, Val, Leu, Ile, Pro, Phe, Met, or Trp; (iii) X at position 249 of SEQ ID NO: 89 is Met, Ala, Val, Leu, Ile, Pro, Phe, or Trp; and (iv) X at position 250 of SEQ ID NO: 89 is Gly, Ala, Val, Leu, Ile, Pro, Phe, Met, or Trp; (ll) the second polypeptide chain comprises the amino acid sequence of SEQ ID NO: 90, wherein X at position 188 of SEQ ID NO: 90 is Ser or Cys; (mm) both (kk) and (ll); (nn) the first polypeptide chain comprises the amino acid sequence of SEQ ID NO: 91, wherein: (i) X at position 161 of SEQ ID NO: 91 is Thr or Cys; (ii) X at position 225 of SEQ ID NO: 91 is Ser, Ala, Val, Leu, Ile, Pro, Phe, Met, or Trp; (iii) X at position 227 of SEQ ID NO: 91 is Met, Ala, Val, Leu, Ile, Pro, Phe, or Trp; and (iv) X at position 228 of SEQ ID NO: 91 is Gly, Ala, Val, Leu, Ile, Pro, Phe, Met, or Trp; (oo) the second polypeptide chain comprises the amino acid sequence of SEQ ID NO: 92, wherein X at position 169 of SEQ ID NO: 92 is Ser or Cys; (pp) both (nn) and (oo); (qq) the first polypeptide chain comprises the amino acid sequence of SEQ ID NO: 93; (rr) the second polypeptide chain comprises the amino acid sequence of SEQ ID NO: 94; (ss) the first polypeptide chain comprises the amino acid sequence of SEQ ID NO: 95; (tt) the second polypeptide chain comprises the amino acid sequence of SEQ ID NO: 96; (uu) both (qq) and (rr); (vv) both (ss) and (tt); (ww) the first polypeptide chain comprises the amino acid sequence of SEQ ID NO: 97, wherein: (i) X at position 178 of SEQ ID NO: 97 is Thr or Cys; (ii) X at position 242 of SEQ ID NO: 97 is Ser, Ala, Val, Leu, Ile, Pro, Phe, Met, or Trp; (iii) X at position 244 of SEQ ID NO: 97 is Met, Ala, Val, Leu, Ile, Pro, Phe, or Trp; and (iv) X at position 245 of SEQ ID NO: 97 is Gly, Ala, Val, Leu, Ile, Pro, Phe, Met, or Trp; (xx) the second polypeptide chain comprises the amino acid sequence of SEQ ID NO: 98, wherein X at position 188 of SEQ ID NO: 98 is Ser or Cys; (yy) both (ww) and (xx); (zz) the first polypeptide chain comprises the amino acid sequence of SEQ ID NO: 99, wherein: (i) X at position 157 of SEQ ID NO: 99 is Thr or Cys; (ii) X at position 221 of SEQ ID NO: 99 is Ser, Ala, Val, Leu, Ile, Pro, Phe, Met, or Trp; (iii) X at position 223 of SEQ ID NO: 99 is Met, Ala, Val, Leu, Ile, Pro, Phe, or Trp; and (iv) X at position 224 of SEQ ID NO: 99 is Gly, Ala, Val, Leu, Ile, Pro, Phe, Met, or Trp; (aaa) the second polypeptide chain comprises the amino acid sequence of SEQ ID NO: 100, wherein X at position 169 of SEQ ID NO: 100 is Ser or Cys; (bbb) both (zz) and (aaa); (ccc) the first polypeptide chain comprises the amino acid sequence of SEQ ID NO: 101; (ddd) the second polypeptide chain comprises the amino acid sequence of SEQ ID NO: 102; (eee) the first polypeptide chain comprises the amino acid sequence of SEQ ID NO: 103; (fff) the second polypeptide chain comprises the amino acid sequence of SEQ ID NO: 104; (ggg) both (ccc) and (ddd); (hhh) both (eee) and (fff); (iii) the first polypeptide chain comprises the amino acid sequence of SEQ ID NO: 189, wherein: (i) X at position 176 of SEQ ID NO: 189 is Thr or Cys; (ii) X at position 240 of SEQ ID NO: 189 is Ser, Ala, Val, Leu, Ile, Pro, Phe, Met, or Trp; (iii) X at position 242 of SEQ ID NO: 189 is Met, Ala, Val, Leu, Ile, Pro, Phe, or Trp; and (iv) X at position 243 of SEQ ID NO: 189 is Gly, Ala, Val, Leu, Ile, Pro, Phe, Met, or Trp; (jjj) the second polypeptide chain comprises the amino acid sequence of SEQ ID NO: 190, wherein X at position 188 of SEQ ID NO: 190 is Ser or Cys; (kkk) both (iii) and (jjj); (lll) the first polypeptide chain comprises the amino acid sequence of SEQ ID NO: 191, wherein: (i) X at position 157 of SEQ ID NO: 191 is Thr or Cys; (ii) X at position 221 of SEQ ID NO: 191 is Ser, Ala, Val, Leu, Ile, Pro, Phe, Met, or Trp; (iii) X at position 223 of SEQ ID NO: 191 is Met, Ala, Val, Leu, Ile, Pro, Phe, or Trp; and (iv) X at position 224 of SEQ ID NO: 191 is Gly, Ala, Val, Leu, Ile, Pro, Phe, Met, or Trp; (mmm) the second polypeptide chain comprises the amino acid sequence of SEQ ID NO: 192, wherein X at position 169 of SEQ ID NO: 192 is Ser or Cys; (nnn) both (lll) and (mmm); (ooo) the first polypeptide chain comprises the amino acid sequence of SEQ ID NO: 193; (ppp) the second polypeptide chain comprises the amino acid sequence of SEQ ID NO: 194; (qqq) the first polypeptide chain comprises the amino acid sequence of SEQ ID NO: 195; (rrr) the second polypeptide chain comprises the amino acid sequence of SEQ ID NO: 196; (sss) both (ooo) and (ppp); (ttt) both (qqq) and (rrr); (uuu) the first polypeptide chain comprises the amino acid sequence of SEQ ID NO: 197, wherein: (i) X at position 181 of SEQ ID NO: 197 is Thr or Cys; (ii) X at position 245 of SEQ ID NO: 197 is Ser, Ala, Val, Leu, Ile, Pro, Phe, Met, or Trp; (iii) X at position 247 of SEQ ID NO: 197 is Met, Ala, Val, Leu, Ile, Pro, Phe, or Trp; and (iv) X at position 248 of SEQ ID NO: 197 is Gly, Ala, Val, Leu, Ile, Pro, Phe, Met, or Trp; (vvv) the second polypeptide chain comprises the amino acid sequence of SEQ ID NO: 198, wherein X at position 188 of SEQ ID NO: 198 is Ser or Cys; (www) both (uuu) and (vvv); (xxx) the first polypeptide chain comprises the amino acid sequence of SEQ ID NO: 199, wherein: (i) X at position 161 of SEQ ID NO: 199 is Thr or Cys; (ii) X at position 225 of SEQ ID NO: 199 is Ser, Ala, Val, Leu, Ile, Pro, Phe, Met, or Trp; (iii) X at position 227 of SEQ ID NO: 199 is Met, Ala, Val, Leu, Ile, Pro, Phe, or Trp; and (iv) X at position 228 of SEQ ID NO: 199 is Gly, Ala, Val, Leu, Ile, Pro, Phe, Met, or Trp; (yyy) the second polypeptide chain comprises the amino acid sequence of SEQ ID NO: 200, wherein X at position 169 of SEQ ID NO: 200 is Ser or Cys; (zzz) both (xxx) and (yyy); (aaaa) the first polypeptide chain comprises the amino acid sequence of SEQ ID NO: 201; (bbbb) the second polypeptide chain comprises the amino acid sequence of SEQ ID NO: 202; (cccc) the first polypeptide chain comprises the amino acid sequence of SEQ ID NO: 203; (dddd) the second polypeptide chain comprises the amino acid sequence of SEQ ID NO: 204; (eeee) both (aaaa) and (bbbb); (ffff) both (cccc) and (dddd); (gggg) the first polypeptide chain comprises the amino acid sequence of SEQ ID NO: 205, wherein: (i) X at position 184 of SEQ ID NO: 205 is Thr or Cys; (ii) X at position 248 of SEQ ID NO: 205 is Ser, Ala, Val, Leu, Ile, Pro, Phe, Met, or Trp; (iii) X at position 250 of SEQ ID NO: 205 is Met, Ala, Val, Leu, Ile, Pro, Phe, or Trp; and (iv) X at position 251 of SEQ ID NO: 205 is Gly, Ala, Val, Leu, Ile, Pro, Phe, Met, or Trp; (hhhh) the second polypeptide chain comprises the amino acid sequence of SEQ ID NO: 206, wherein X at position 190 of SEQ ID NO: 206 is Ser or Cys; (iiii) both (gggg) and (hhhh); (jjjj) the first polypeptide chain comprises the amino acid sequence of SEQ ID NO: 207, wherein: (i) X at position 163 of SEQ ID NO: 207 is Thr or Cys; (ii) X at position 227 of SEQ ID NO: 207 is Ser, Ala, Val, Leu, Ile, Pro, Phe, Met, or Trp; (iii) X at position 229 of SEQ ID NO: 207 is Met, Ala, Val, Leu, Ile, Pro, Phe, or Trp; and (iv) X at position 230 of SEQ ID NO: 207 is Gly, Ala, Val, Leu, Ile, Pro, Phe, Met, or Trp; (kkkk) the second polypeptide chain comprises the amino acid sequence of SEQ ID NO: 208, wherein X at position 164 of SEQ ID NO: 208 is Ser or Cys; (llll) both (jjjj) and (kkkk); (mmmm) the first polypeptide chain comprises the amino acid sequence of SEQ ID NO: 209; (nnnn) the second polypeptide chain comprises the amino acid sequence of SEQ ID NO: 210; (0000) the first polypeptide chain comprises the amino acid sequence of SEQ ID NO: 211; (pppp) the second polypeptide chain comprises the amino acid sequence of SEQ ID NO: 212; (qqqq) both (mmmm) and (nnnn); (rrrr) both (0000) and (pppp); (ssss) the first polypeptide chain comprises the amino acid sequence of SEQ ID NO: 213, wherein: (i) X at position 183 of SEQ ID NO: 213 is Thr or Cys; (ii) X at position 247 of SEQ ID NO: 213 is Ser, Ala, Val, Leu, Ile, Pro, Phe, Met, or Trp; (iii) X at position 249 of SEQ ID NO: 213 is Met, Ala, Val, Leu, Ile, Pro, Phe, or Trp; and (iv) X at position 250 of SEQ ID NO: 213 is Gly, Ala, Val, Leu, Ile, Pro, Phe, Met, or Trp; (tttt) the second polypeptide chain comprises the amino acid sequence of SEQ ID NO: 214, wherein X at position 188 of SEQ ID NO: 214 is Ser or Cys; (uuuu) both (ssss) and (tttt); (vvvv) the first polypeptide chain comprises the amino acid sequence of SEQ ID NO: 215, wherein: (i) X at position 161 of SEQ ID NO: 215 is Thr or Cys; (ii) X at position 225 of SEQ ID NO: 215 is Ser, Ala, Val, Leu, Ile, Pro, Phe, Met, or Trp; (iii) X at position 227 of SEQ ID NO: 215 is Met, Ala, Val, Leu, Ile, Pro, Phe, or Trp; and (iv) X at position 228 of SEQ ID NO: 215 is Gly, Ala, Val, Leu, Ile, Pro, Phe, Met, or Trp; (wwww) the second polypeptide chain comprises the amino acid sequence of SEQ ID NO: 216, wherein X at position 169 of SEQ ID NO: 216 is Ser or Cys; (xxxx) both (vvvv) and (wwww); (yyyy) the first polypeptide chain comprises the amino acid sequence of SEQ ID NO: 217; (zzzz) the second polypeptide chain comprises the amino acid sequence of SEQ ID NO: 218; (aaaaa) the first polypeptide chain comprises the amino acid sequence of SEQ ID NO: 219; (bbbbb) the second polypeptide chain comprises the amino acid sequence of SEQ ID NO: 220; (ccccc) both (yyyy) and (zzzz); (ddddd) both (aaaaa) and (bbbbb); (eeeee) the first polypeptide chain comprises the amino acid sequence of SEQ ID NO: 221, wherein: (i) X at position 180 of SEQ ID NO: 221 is Thr or Cys; (ii) X at position 244 of SEQ ID NO: 221 is Ser, Ala, Val, Leu, Ile, Pro, Phe, Met, or Trp; (iii) X at position 246 of SEQ ID NO: 221 is Met, Ala, Val, Leu, Ile, Pro, Phe, or Trp; and (iv) X at position 247 of SEQ ID NO: 221 is Gly, Ala, Val, Leu, Ile, Pro, Phe, Met, or Trp; (fffff) the second polypeptide chain comprises the amino acid sequence of SEQ ID NO: 222, wherein X at position 188 of SEQ ID NO: 222 is Ser or Cys; (ggggg) both (eeeee) and (fffff); (hhhhh) the first polypeptide chain comprises the amino acid sequence of SEQ ID NO: 223, wherein: (i) X at position 158 of SEQ ID NO: 223 is Thr or Cys; (ii) X at position 222 of SEQ ID NO: 223 is Ser, Ala, Val, Leu, Ile, Pro, Phe, Met, or Trp; (iii) X at position 224 of SEQ ID NO: 223 is Met, Ala, Val, Leu, Ile, Pro, Phe, or Trp; and (iv) X at position 225 of SEQ ID NO: 223 is Gly, Ala, Val, Leu, Ile, Pro, Phe, Met, or Trp; (iiiii) the second polypeptide chain comprises the amino acid sequence of SEQ ID NO: 224, wherein X at position 169 of SEQ ID NO: 224 is Ser or Cys; (m) both (hhhhh) and (iiiii); (kkkkk) the first polypeptide chain comprises the amino acid sequence of SEQ ID NO: 225; (lllll) the second polypeptide chain comprises the amino acid sequence of SEQ ID NO: 226; (mmmmm) the first polypeptide chain comprises the amino acid sequence of SEQ ID NO: 227; (nnnnn) the second polypeptide chain comprises the amino acid sequence of SEQ ID NO: 228; (ooooo) both (kkkkk) and (lllll); (ppppp) both (mmmmm) and (nnnnn); (qqqqq) the first polypeptide chain comprises the amino acid sequence of SEQ ID NO: 229, wherein: (i) X at position 184 of SEQ ID NO: 229 is Thr or Cys; (ii) X at position 248 of SEQ ID NO: 229 is Ser, Ala, Val, Leu, Ile, Pro, Phe, Met, or Trp; (iii) X at position 250 of SEQ ID NO: 229 is Met, Ala, Val, Leu, Ile, Pro, Phe, or Trp; and (iv) X at position 251 of SEQ ID NO: 229 is Gly, Ala, Val, Leu, Ile, Pro, Phe, Met, or Trp; (rrrrr) the second polypeptide chain comprises the amino acid sequence of SEQ ID NO: 230, wherein X at position 189 of SEQ ID NO: 230 is Ser or Cys; (sssss) both (qqqqq) and (rrrrr); (ttttt) the first polypeptide chain comprises the amino acid sequence of SEQ ID NO: 231, wherein: (i) X at position 163 of SEQ ID NO: 231 is Thr or Cys; (ii) X at position 227 of SEQ ID NO: 231 is Ser, Ala, Val, Leu, Ile, Pro, Phe, Met, or Trp; (iii) X at position 229 of SEQ ID NO: 231 is Met, Ala, Val, Leu, Ile, Pro, Phe, or Trp; and (iv) X at position 230 of SEQ ID NO: 231 is Gly, Ala, Val, Leu, Ile, Pro, Phe, Met, or Trp; (uuuuu) the second polypeptide chain comprises the amino acid sequence of SEQ ID NO: 232, wherein X at position 170 of SEQ ID NO: 232 is Ser or Cys; (vvvvv) both (ttttt) and (uuuuu); (wwwww) the first polypeptide chain comprises the amino acid sequence of SEQ ID NO: 233; (xxxxx) the second polypeptide chain comprises the amino acid sequence of SEQ ID NO: 234; (yyyyy) the first polypeptide chain comprises the amino acid sequence of SEQ ID NO: 235; (zzzzz) the second polypeptide chain comprises the amino acid sequence of SEQ ID NO: 236; (aaaaaa) both (wwwww) and (xxxxx); (bbbbbb) both (yyyyy) and (zzzzz); (cccccc) the first polypeptide chain comprises the amino acid sequence of SEQ ID NO: 237, wherein: (i) X at position 184 of SEQ ID NO: 237 is Thr or Cys; (ii) X at position 248 of SEQ ID NO: 237 is Ser, Ala, Val, Leu, Ile, Pro, Phe, Met, or Trp; (iii) X at position 250 of SEQ ID NO: 237 is Met, Ala, Val, Leu, Ile, Pro, Phe, or Trp; and (iv) X at position 251 of SEQ ID NO: 237 is Gly, Ala, Val, Leu, Ile, Pro, Phe, Met, or Trp; (dddddd) the second polypeptide chain comprises the amino acid sequence of SEQ ID NO: 238, wherein X at position 189 of SEQ ID NO: 238 is Ser or Cys; (eeeeee) both (cccccc) and (dddddd); (ffffff) the first polypeptide chain comprises the amino acid sequence of SEQ ID NO: 239, wherein: (i) X at position 163 of SEQ ID NO: 239 is Thr or Cys; (ii) X at position 227 of SEQ ID NO: 239 is Ser, Ala, Val, Leu, Ile, Pro, Phe, Met, or Trp; (iii) X at position 229 of SEQ ID NO: 239 is Met, Ala, Val, Leu, Ile, Pro, Phe, or Trp; and (iv) X at position 230 of SEQ ID NO: 239 is Gly, Ala, Val, Leu, Ile, Pro, Phe, Met, or Trp; (gggggg) the second polypeptide chain comprises the amino acid sequence of SEQ ID NO: 240, wherein X at position 170 of SEQ ID NO: 240 is Ser or Cys; (hhhhhh) both (fffff) and (gggggg); (iiiiii) the first polypeptide chain comprises the amino acid sequence of SEQ ID NO: 241; (jjjjjj) the second polypeptide chain comprises the amino acid sequence of SEQ ID NO: 242; (kkkkkk) the first polypeptide chain comprises the amino acid sequence of SEQ ID NO: 243; (llllll) the second polypeptide chain comprises the amino acid sequence of SEQ ID NO: 244; (mmmmmm) both (iiiiii) and (jjjjjj); or (nnnnnn) both (kkkkkk) and (llllll). In an embodiment of the invention, one or more of SEQ ID NOs: 65-68, 73-76, 81-84, 89-92, 97-100, 189-192, 197-200, 205-208, 213-216, 221-224, 229-232, and 237-240 of the protein are as defined in any one of Tables 2-4.

The protein of the invention can be a TCR. Alternatively, if, for example, the protein comprises a single polypeptide chain comprising the amino acid sequences of both the TCR α and β chains, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the a chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. The linker peptide may be a cleavable linker peptide. For example, the linker peptide may be a furin-SGSG-P2A linker peptide comprising the amino acid sequence of RAKRSGS-GATNFSLLKQAGDVEENPGP (SEQ ID NO: 105). Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fc, Fab, or F(ab)₂' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to the G13D RAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, about 50%, about 75%, about 80%, about 90%, about 95%, about 96%, about 97%, about 98%, about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, or SEQ ID NO: 244, both of SEQ ID NOs: 65-66, both of SEQ ID NOs: 67-68, both of SEQ ID NOs: 69-70, both of SEQ ID NOs: 71-72, both of SEQ ID NOs: 73-74, both of SEQ ID NOs: 75-76, both of SEQ ID NOs: 77-78, both of SEQ ID NOs: 79-80, both of SEQ ID NOs: 81-82, both of SEQ ID NOs: 83-84, both of SEQ ID NOs: 85-86, both of SEQ ID NOs: 87-88, both of SEQ ID NOs: 89-90, both of SEQ ID NOs: 91-92, both of SEQ ID NOs: 93-94, both of SEQ ID NOs: 95-96, both of SEQ ID NOs: 97-98, both of SEQ ID NOs: 99-100, both of SEQ ID NOs: 101-102, both of SEQ ID NOs: 103-104, both of SEQ ID NOs: 189 and 190, both of SEQ ID NOs: 191 and 192, both of SEQ ID NOs: 193 and 194, both of SEQ ID NOs: 195 and 196, both of SEQ ID NOs: 197 and 198, both of SEQ ID NOs: 199 and 200, both of SEQ ID NOs: 201 and 202, both of SEQ ID NOs: 203 and 204, both of SEQ ID NOs: 205 and 206, both of SEQ ID NOs: 207 and 208, both of SEQ ID NOs: 209 and 210, both of SEQ ID NOs: 211 and 212, both of SEQ ID NOs: 213 and 214, both of SEQ ID NOs: 215 and 216, both of SEQ ID NOs: 217 and 218, both of SEQ ID NOs: 219 and 220, both of SEQ ID NOs: 221 and 222, both of SEQ ID NOs: 223 and 224, both of SEQ ID NOs: 225 and 226, both of SEQ ID NOs: 227 and 228, both of SEQ ID NOs: 229 and 230, both of SEQ ID NOs: 231 and 232, both of SEQ ID NOs: 233 and 234, both of SEQ ID NOs: 235 and 236, both of SEQ ID NOs: 237 and 238, both of SEQ ID NOs: 239 and 240, both of SEQ ID NOs: 241 and 242, or both of SEQ ID NOs: 243 and 244.

Also, for instance, the inventive TCRs, polypeptides, or proteins can consist essentially of the amino acid sequence(s) of (1) SEQ ID NO: 7, (2) SEQ ID NO: 8, (3) SEQ ID NO: 9, (4) SEQ ID NO: 10, (5) SEQ ID NO: 17, (6) SEQ ID NO: 18, (7) SEQ ID NO: 19, (8) SEQ ID NO: 20, (9) SEQ ID NO: 27, (10) SEQ ID NO: 28, (11) SEQ ID NO: 29, (12) SEQ ID NO: 30, (13) SEQ ID NO: 37, (14) SEQ ID NO: 38, (15) SEQ ID NO: 39, (16) SEQ ID NO: 40, (17) SEQ ID NO: 47, (18) SEQ ID NO: 48, (19) SEQ ID NO: 49, (20)

SEQ ID NO: 50, (21) SEQ ID NO: 125, (22) SEQ ID NO: 126, (23) SEQ ID NO: 127, (24) SEQ ID NO: 128, (25) SEQ ID NO: 135, (26) SEQ ID NO: 136, (27) SEQ ID NO: 137, (28) SEQ ID NO: 138, (29) SEQ ID NO: 145, (30) SEQ ID NO: 146, (31) SEQ ID NO: 147, (32) SEQ ID NO: 148, (33) SEQ ID NO: 155, (34) SEQ ID NO: 156, (35) SEQ ID NO: 157, (36) SEQ ID NO: 158, (37) SEQ ID NO: 165, (38) SEQ ID NO: 166, (39) SEQ ID NO: 167, (40) SEQ ID NO: 168, (41) SEQ ID NO: 175, (42) SEQ ID NO: 176, (43) SEQ ID NO: 177, (44) SEQ ID NO: 178, (45) SEQ ID NO: 185, (46) SEQ ID NO: 186, (47) SEQ ID NO: 187, (48) SEQ ID NO: 188, (49) both of SEQ ID NOs: 7 and 8, (50) both of SEQ ID NOs: 9 and 10, (51) both of SEQ ID NOs: 17 and 18, (52) both of SEQ ID NOs: 19 and 20, (53) both of SEQ ID NOs: 27 and 28, (54) both of SEQ ID NOs: 29 and 30, (55) both of SEQ ID NOs: 37 and 38, (56) both of SEQ ID NOs: 39 and 40, (57) both of SEQ ID NOs: 47 and 48, (58) both of SEQ ID NOs: 49 and 50, (59) both of SEQ ID NOs: 125 and 126, (60) both of SEQ ID NOs: 127 and 128, (61) both of SEQ ID NOs: 135 and 136, (62) both of SEQ ID NOs: 137 and 138, (63) both of SEQ ID NOs: 145 and 146, (64) both of SEQ ID NOs: 147 and 148, (65) both of SEQ ID NOs: 155 and 156, (66) both of SEQ ID NOs: 157 and 158, (67) both of SEQ ID NOs: 165 and 166, (68) both of SEQ ID NOs: 167 and 168, (69) both of SEQ ID NOs: 175 and 176, (70) both of SEQ ID NOs: 177 and 178, (71) both of SEQ ID NOs: 185 and 186, or (72) both of SEQ ID NOs: 187 and 188. Furthermore, the inventive TCRs, polypeptides, or proteins can consist essentially of the amino acid sequences of (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, (l) all of SEQ ID NOs: 31-36, (m) all of SEQ ID NOs: 41-43, (n) all of SEQ ID NOs: 44-46, (o) all of SEQ ID NOs: 41-46, (p) all of SEQ ID NOs: 119-121, (q) all of SEQ ID NOs: 122-124, (r) all of SEQ ID NOs: 119-124, (s) all of SEQ ID NOs: 129-131, (t) all of SEQ ID NOs: 132-134, (u) all of SEQ ID NOs: 129-134, (v) all of SEQ ID NOs: 139-141, (w) all of SEQ ID NOs: 142-144, (x) all of SEQ ID NOs: 139-144, (y) all of SEQ ID NOs: 149-151, (z) all of SEQ ID NOs: 152-154, (aa) all of SEQ ID NOs: 149-154, (bb) all of SEQ ID NOs: 159-161, (cc) all of SEQ ID NOs: 162-164, (dd) all of SEQ ID NOs: 159-164, (ee) all of SEQ ID NOs: 169-171, (ff) all of SEQ ID NOs: 172-174, (gg) all of SEQ ID NOs: 169-174, (hh) all of SEQ ID NOs: 179-181, (ii) all of SEQ ID NOs: 182-184, or (jj) all of SEQ ID NOs: 179-184. The TCRs, polypeptides, and proteins of the invention can be of any length, i.e., can comprise any number of amino acids, provided that the TCRs, polypeptides, or proteins retain their biological activity, e.g., the ability to specifically bind to G13D RAS; detect cancer in a mammal; or treat or prevent cancer in a mammal, etc. For example, the polypeptide can be in the range of from about 50 to about 5000 amino acids long, such as about 50, about 70, about 75, about 100, about 125, about 150, about 175, about 200, about 300, about 400, about 500, about 600, about 700, about 800, about 900, about 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitro-phenylalanine, 4-chlorophenylalanine, 4-carboxyphenylala-nine, β-phenylserine β-hydroxyphenylalanine, phenylgly-cine, α-naphthylalanine, cyclohexylalanine, cyclohexylglycine, indoline-2-carboxylic acid, 1,2,3,4-tetra-hydroisoquinoline-3-carboxylic acid, aminomalonic acid, aminomalonic acid monoamide, N'-benzyl-N'-methyl-ly-sine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobu-tyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual,* 4th ed., Cold Spring Harbor Press, Cold Spring Harbor, NY (2012). Alternatively, the TCRs, poly-peptides, and/or proteins described herein can be synthe-sized by any of a variety of commercial entities. In this respect, the inventive TCRs, polypeptides, and proteins can be synthetic, recombinant, isolated, and/or purified. An embodiment of the invention provides an isolated or purified TCR, polypeptide, or protein encoded by any of the nucleic acids or vectors described herein with respect to other aspects of the invention. Another embodiment of the inven-tion provides an isolated or purified TCR, polypeptide, or protein that results from expression of any of the nucleic acids or vectors described herein in a cell. Still another embodiment of the invention provides a method of produc-ing any of the TCRs, polypeptides, or proteins described herein, the method comprising culturing any of the host cells or populations of host cells described herein so that the TCR, polypeptide, or protein is produced.

Included in the scope of the invention are conjugates, e.g., bioconjugates, comprising any of the inventive TCRs, poly-peptides, or proteins (including any of the functional por-tions or variants thereof), nucleic acids, recombinant expres-sion vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligo-nucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate link-age, instead of the phosphodiester found between the nucleotides of an unmodified oligonucleotide. In an embodi-ment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recom-binant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

In an embodiment of the invention, the nucleic acid comprises the nucleotide sequence of SEQ ID NO: 114 (4400 TCR-E), SEQ ID NO: 115 (4400 TCR-J), SEQ ID NO: 116 (4400 TCR-N), SEQ ID NO: 117 (4400 TCR-A1), or SEQ ID NO: 118 (4400 TCR-A2).

The nucleic acids can be constructed based on chemical synthesis and/or enzymatic ligation reactions using proce-dures known in the art. See, for example, Green and Sam-brook et al., supra. For example, a nucleic acid can be chemically synthesized using naturally occurring nucleo-tides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodoura-cil, hypoxanthine, xanthine, 4-acetylcytosine, 5-(carboxy-hydroxymethyl) uracil, 5-carboxymethylaminomethyl-2-thiouridine, 5-carboxymethylaminomethyluracil, dihydrouracil, β-D-galactosylqueosine, inosine, N6-isopen-tenyladenine, 1-methylguanine, 1-methylinosine, 2,2-dim-ethylguanine, 2-methyladenine, 2-methylguanine, 3-methyl-cytosine, 5-methylcytosine, N6-substituted adenine, 7-methylguanine, 5-methylaminomethyluracil, 5-methoxyaminomethyl-2-thiouracil, β-D-mannosylqueo-sine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocyto-sine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from any of a variety of com-mercial entities.

The nucleic acid can comprise any nucleotide sequence which encodes any of the TCRs, polypeptides, or proteins described herein. In an embodiment of the invention, the nucleic acid comprises a codon-optimized nucleotide sequence encoding any of the TCRs, polypeptides, or pro-teins described herein. Without being bound to any particu-lar theory or mechanism, it is believed that codon optimi-zation of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimi-zation of the nucleotide sequence may also reduce secondary mRNA structures that would interfere with translation, thus increasing translation efficiency.

The invention also provides a nucleic acid comprising a nucleotide sequence which is complementary to the nucleo-tide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

An embodiment of the invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 47 and 48; 48 and 47; 49 and 50; 50 and 49; 125 and 126; 126 and 125; 127 and 128; 128 and 127; 135 and 136; 136 and 135; 137 and 138; 138 and 137; 145 and 146; 146 and 145; 147 and 148; 148 and 147; 155 and 156; 156 and 155; 157 and 158; 158 and 157; 165 and 166; 166 and 165; 167 and 168; 168 and 167; 175 and 176; 176 and 175; 177 and 178; 178 and 177; 185 and 186; 186 and 185; 187 and 188; 188 and 187; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; 86 and 85; 87 and 88; 88 and 87; 89 and 90; 90 and 89; 91 and 92; 92 and 91; 93 and 94; 94 and 93; 95 and 96; 96 and 95; 97 and 98; 98 and 97; 99 and 100; 100 and 99; 101 and 102; 102 and 101; 103 and 104; 104 and 103; 189 and 190; 190 and 189; 191 and 192; 192 and 191; 193 and 194; 194 and 193; 195 and 196; 196 and 195; 197 and 198; 198 and 197; 199 and 200; 200 and 199; 201 and 202; 202 and 201; 203 and 204; 204 and 203; 205 and 206; 206 and 205; 207 and 208; 208 and 207; 209 and 210; 210 and 209; 211 and 212; 212 and 211; 213 and 214; 214 and 213; 215 and 216; 216 and 215; 217 and 218; 218 and 217; 219 and 220; 220 and 219; 221 and 222; 222 and 221; 223 and 224; 224 and 223; 225 and 226; 226 and 225; 227 and 228; 228 and 227; 229 and 230; 230 and 229; 231 and 232; 232 and 231; 233 and 234; 234 and 233; 235 and 236; 236 and 235; 237 and 238; 238 and 237; 239 and 240; 240 and 239; 241 and 242; 242 and 241; 243 and 244; or 244 and 243.

In an embodiment of the invention, the isolated or purified nucleic acid further comprises a third nucleotide sequence interposed between the first and second nucleotide sequence, wherein the third nucleotide sequence encodes a cleavable linker peptide. In an embodiment of the invention, the cleavable linker peptide comprises the amino acid sequence of RAKRSGSGATNFSLLKQAGDVEENPGP (SEQ ID NO: 105).

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the PBLUESCRIPT series (Stratagene, LaJolla, CA), the pET series (Novagen, Madison, WI), the pGEX series (Pharmacia Biotech, Uppsala, Sweden), and the pEX series (CLONTECH reagents, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (CLONTECH reagents). Examples of animal expression vectors include pEUK-C1, pMAM and pMAMneo (CLONTECH reagents). Preferably, the recombinant expression vector is a viral vector, e.g., a retroviral vector. In an especially preferred embodiment, the recombinant expression vector is an MSGV1 vector. In an embodiment of the invention, the recombinant expression vector is a transposon or a lentiviral vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

Another embodiment of the invention further provides a host cell comprising any of the nucleic acids or recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5a cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell. In an embodiment of the invention, the host cell is a human lymphocyte. In another embodiment of the invention, the host cell is selected from the group consisting of a T cell, a natural killer T (NKT) cell, an invariant natural killer T (iNKT) cell, and a natural killer (NK) cell. Still another embodiment of the invention provides a method of producing a host cell expressing a TCR that has antigenic specificity for the peptide of MTEYKLVVVGAGDVGK-SALTIQLIQ (SEQ ID NO: 252), the method comprising contacting a cell with any of the vectors described herein under conditions that allow introduction of the vector into the cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., J. Immunother., 26:332-42 (2003); and Riddell et al., J. Immunol. Methods, 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified.

The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, $22^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell (or population thereof) expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., G13D RAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are suitable sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to G13D RAS or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to G13D RAS, such that the TCR (or related inventive polypeptide or protein), when expressed by a cell, is able to mediate an immune response against a target cell expressing G13D RAS. In this regard, an embodiment of the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides a method of inducing an immune response against a cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, in an amount effective to induce an immune response against the cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, for use in inducing an immune response against a cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive method of detecting cancer, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic adenocarcinoma. In an embodiment of the invention, the cancer expresses a mutated human RAS amino acid sequence with a substitution of glycine at position 13 with aspartic acid, wherein the mutated human RAS amino acid sequence is a mutated human KRAS, a mutated human HRAS, or a mutated human NRAS amino acid sequence, and wherein position 13 is defined by reference to the WT human KRAS, WT human HRAS, or WT human NRAS protein, respectively. The mutated human KRAS, mutated human HRAS, and mutated human NRAS expressed by the cancer may be as described herein with respect to other aspects of the invention.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of anti-G13D RAS TCRs from the TIL of colorectal cancer patient 4400.

TILs from tumor fragments from colorectal cancer patient 4400 were independently screened for reactivity against RAS G13D. TIL from tumor fragments (numbered F1-F8, F10-F16, and F18-F22) from patient 4400 (effector cells) were co-cultured with DC (target cells). The DC were (i) transfected with mRNA encoding full length (FL) G13D KRAS (variant B) or the corresponding FL wild-type (WT) KRAS (variant B); (ii) pulsed with G13D 25-mer peptide MTEYKLVVVGAGDVGKSALTIQLIQ (SEQ ID NO: 252) or the corresponding WT 25-mer peptide MTEYKLVVVGAGGVGKSALTIQLIQ (SEQ ID NO: 253); or (iii) cultured with G13D ME "mix" (containing a combination of three predicted minimal epitopes from the mutated peptide). Effector cells (i) co-cultured with DC treated with DMSO or (ii) cultured alone (T cell only) served as negative controls. Effector cells treated with anti-CD3/CD28 antibodies served as a positive control.

Reactivity was tested by IFNγ-secretion using ELISpot assay (FIG. 1) and by measuring the expression of one or both of 4-1BB and OX40 by flow cytometry assay gated on (i) CD3+/CD4+ cells (FIG. 2A) or (ii) CD3+/CD8+ cells (FIG. 2B). Reactive cells were observed following co-culture of the TIL from tumor fragments F15, F16, F21, and F22 with DCs which had been pulsed with the G13D 25-mer peptide or transduced with the full length G13D KRAS protein.

Enriched populations of TIL from tumor fragments F15, F16, F21, and F22 were screened for reactivity as follows. TIL from tumor fragments F15 and F16 were untreated or treated as follows: F16 TIL were stimulated in vitro (IVS) with DC pulsed with G13D 25-mer peptide, or F15 and F16 TIL were combined, activated (as described for FIGS. 1 and 2A-2B), sorted for CD4+/41BB+/OX40+ expression and underwent a rapid expansion protocol (REP). TIL from tumor fragments F21 and F22 were combined, sorted for CD4+/41BB+/OX40+ or CD8+/41BB+/OX40+ expression, and underwent REP. The REP was carried out as follows. After sorting, cells were seeded in T25 flasks and rapidly expanded by adding 2e7 irradiated feeder cells in 20 ml T cell medium supplemented with 3000 IU/ml IL-2 and 30 ug/ml anti-CD3 antibody (Ab) (OKT3). Cells were grown for 11-16 days. The treated TIL were co-cultured with the target cells described for the experiments of FIGS. 1 and 2A-2B. The controls were also as described for the experiments of FIGS. 1 and 2A-2B. Reactivity was tested by measuring the expression of one or both of 4-1BB and OX40 by flow cytometry assay. The results are shown in FIG. 3. Reactive cells were single-cell sorted by fluorescence activated cell sorting (FACS) into 96-well plates and were sequenced to provide TCR alpha and TCR beta chains for 4400 TCR-A1, 4400 TCR-A2, 4400 TCR-B1, and 4400 TCR-B2.

The avidity of the enriched populations of the TIL identified as reactive in FIG. 3 was tested as follows. The TILs were co-cultured with DC pulsed with various concentrations of G13D 25-mer peptide or the corresponding WT 25-mer peptide. Reactivity was tested by IFNγ-secretion using ELISpot assay. The results are shown in FIGS. 4A-4B. FIG. 4A shows the results obtained with TIL from tumor fragment F16 following G13D IVS (FIG. 4A). FIG. 4B shows the results obtained with TIL from tumor fragments F15 and F16 following activation, sorting for CD4+/41BB+/OX40+ and REP (FIG. 4B).

Another four TCRs (4400 TCR-E, 4400 TCR-J, 4400 TCR-N, and TCR-C) were discovered by sorting and sequencing T cells directly from the tumor, without in vitro cell culture, briefly as follows. These TCR sequences were obtained by sorting T cells from a single-cell suspension of the fresh tumor digest and performing single-cell TCR sequencing coupled with RNA sequencing. 14 TCRs were selected because their transcriptional phenotype resembled those of neoantigen-reactive T cells observed in other patients. When those 14 TCR plasmids were introduced into healthy donor PBL and screened against the patient's potential neoantigens (tumor mutation-encoded peptides and tandem minigenes), four were reactive against mutant KRAS, namely 4400 TCR-E, 4400 TCR-J, 4400 TCR-N, and 4400 TCR-C.

Another TCR (TCR-20) was identified by phenotype sorting and sequencing T cells directly from the patient's peripheral blood (PBL).

Five TCRs (TCR-A3, TCR-J2, TCR-N4, TCR-N12, and TCR-N13) were identified by in vitro-stimulation (IVS) of the T cells directly obtained from the tumor (tumor-infiltrating T lymphocytes-TIL) or without in vitro cell culture.

The isolated TCRs are shown in Table 5.

TABLE 5

| TCR Name | Beta Chain | Alpha Chain |
|---|---|---|
| 4400 TCR-A1 | TRBV28*01 + TRBJ2-2*01 + TRBD2*01 | TRAV12-3*01/02 + TRAJ34*01 |
| 4400 TCR-A2 | TRBV28*01 + TRBJ2-2*01 + TRBD2*01 | TRAV12-3*01/02 + TRAJ34*01 |
| 4400 TCR-E | TRBV25-1*01 + TRBJ2-3*01 | TRAV26-1*01 |
| 4400 TCR-J | TRBV28*01 + TRBJ2-2*01 | TRAV12-3*01 |
| 4400 TCR-N | TRBV28*01 + TRBJ2-2*01 | TRAV5*01 |
| 4400 TCR-A3 | TRBV28*01 + TRBJ2-2*01 + TRBD2*01 | TRAV26-2*01 + TRAJ40*01 |
| 4400 TCR-J2 | TRBV28*01 + TRBJ2-2*01 | TRAV9-2*01 + TRAJ28*01 |
| 4400 TCR-N4 | TRBV28*01 + TRBJ1-2*01 + TRBD1*01 | TRAV14/DV4*01 + TRAJ44*01 |
| 4400 TCR-N12 | TRBV28*01 + TRBJ2-2*01 | TRAV12-3*01 + TRAJ45*01 |
| 4400 TCR-N13 | TRBV28*01 + TRBJ2-2*01 | TRAV12-3*01/02 + TRAJ34*01 |
| 4400 TCR-C | TRBV28 + TRBJ1-6 | TRAV14/DV4 + TRAJ44 |
| 4400 TCR-20 | TRBV28*01 + TRBJ1-5*01 | TRAV14/DV4*01 + TRAJ6*01 |

The amino acid sequences of the alpha and beta chain variable regions are shown in Table 6. The CDRs are underlined. The N-terminal signal peptides are in bold font.

TABLE 6

| TCR Name | TCR chain | Amino acid sequence |
|---|---|---|
| 4400 TCR-A1 | Variable α (Predicted | QKEVEQDPGPLSVPEGAIVSLNCTYS<u>NSAFQY</u>FMWYRQYSRK GPELLMY<u>TYSSGN</u>KEDGRFTAQVDKSSKYISLFIRDSQPSDSAT |

TABLE 6-continued

| TCR Name | TCR chain | Amino acid sequence |
|---|---|---|
| | sequence without N-terminal signal peptide) | YLCAMRANTDKLIFGTGTRLQVFP (SEQ ID NO: 7) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASRLGNTGELFFGEGSRLTVL (SEQ ID NO: 8) |
| | Variable α (With N-terminal signal peptide) | MMKSLRVLLVILWLQLSWVWSQQKEVEQDPGPLSVPEGAI VSLNCTYSNSAFQYFMWYRQYSRKGPELLMYTYSSGNKEDG RFTAQVDKSSKYISLFIRDSQPSDSATYLCAMRANTDKLIFGTG TRLQVFP (SEQ ID NO: 9) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASRLGNTGELFFGEGS RLTVL (SEQ ID NO: 10) |
| 4400 TCR-A2 | Variable α (Predicted sequence without N-terminal signal peptide) | QKEVEQDPGPLSVPEGAIVSLNCTYSNSAFQYFMWYRQYSRK GPELLMYTYSSGNKEDGRFTAQVDKSSKYISLFIRDSQPSDSAT YLCAMRANTDKLIFGTGTRLQVFP (SEQ ID NO: 17) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASRQGNTGELFFGEGSRLTVL (SEQ ID NO: 18) |
| | Variable α (With N-terminal signal peptide) | MMKSLRVLLVILWLQLSWVWSQQKEVEQDPGPLSVPEGAI VSLNCTYSNSAFQYFMWYRQYSRKGPELLMYTYSSGNKEDG RFTAQVDKSSKYISLFIRDSQPSDSATYLCAMRANTDKLIFGTG TRLQVFP (SEQ ID NO: 19) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASRQGNTGELFFGEGS RLTVL (SEQ ID NO: 20) |
| 4400 TCR-E | Variable α (Predicted sequence without N-terminal signal peptide) | DAKTTQPPSMDCAEGRAANLPCNHSTISGNEYVYWYRQIHSQ GPQYIIHGLKNNETNEMASLIITEDRKSSTLILPHATLRDTAVY YCIVRVAKSGANNLFFGTGTRLTVIP (SEQ ID NO: 27) |
| | Variable β (Predicted sequence without N-terminal signal peptide) | EADIYQTPRYLVIGTGKKITLECSQTMGHDKMYWYQQDPGME LHLIHYSYGVNSTEKGDLSSESTVSRIRTEHFPLTLESARPSHTS QYLCASSGLTYTDTQYFGPGTRLTVL (SEQ ID NO: 28) |
| | Variable α (With N-terminal signal peptide) | MRLVARVTVFLTFGTIIDAKTTQPPSMDCAEGRAANLPCNHS TISGNEYVYWYRQIHSQGPQYIIHGLKNNETNEMASLIITEDRK SSTLILPHATLRDTAVYYCIVRVAKSGANNLFFGTGTRLTVIP (SEQ ID NO: 29) |
| | Variable β (With N-terminal signal peptide) | MAIRLLCYMGFYFLGAGLMEADIYQTPRYLVIGTGKKITLEC SQTMGHDKMYWYQQDPGMELHLIHYSYGVNSTEKGDLSSES TVSRIRTEHFPLTLESARPSHTSQYLCASSGLTYTDTQYFGPGT RLTVL (SEQ ID NO: 30) |
| 4400 TCR-J | Variable α (Predicted sequence without N-terminal signal peptide) | QKEVEQDPGPLSVPEGAIVSLNCTYSNSAFQYFMWYRQYSRK GPELLMYTYSSGNKEDGRFTAQVDKSSKYISLFIRDSQPSDSAT YLCAMSYSGGGADGLTFGKGTHLIIQP (SEQ ID NO: 37) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASSQGNTGELFFGEGSRLTVL (SEQ ID NO: 38) |
| | Variable α (With N-terminal signal peptide) | MMKSLRVLLVILWLQLSWVWSQQKEVEQDPGPLSVPEGAI VSLNCTYSNSAFQYFMWYRQYSRKGPELLMYTYSSGNKEDG RFTAQVDKSSKYISLFIRDSQPSDSATYLCAMSYSGGGADGLT FGKGTHLIIQP (SEQ ID NO: 39) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASSQGNTGELFFGEGS RLTVL (SEQ ID NO: 40) |

TABLE 6-continued

| TCR Name | TCR chain | Amino acid sequence |
|---|---|---|
| 4400 TCR-N | Variable α (Predicted sequence without N-terminal signal peptide) | GEDVEQSLFLSVREGDSSVINCTYTDSSSTYLYWYKQEPGAGL QLLTYIFSNMDMKQDQRLTVLLNKKDKHLSLRIADTQTGDSAI YFCAPGGYNKLIFGAGTRLAVHP (SEQ ID NO: 47) |
| | Variable ß (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASRIGNTGELFFGEGSRLTVL (SEQ ID NO: 48) |
| | Variable α (With N-terminal signal peptide) | MKTFAGFSFLFLWLQLDCMSRGEDVEQSLFLSVREGDSSVI NCTYTDSSSTYLYWYKQEPGAGLQLLTYIFSNMDMKQDQRLT VLLNKKDKHLSLRIADTQTGDSAIYFCAPGGYNKLIFGAGTRL AVHP (SEQ ID NO: 49) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASRIGNTGELFFGEGS RLTVL (SEQ ID NO: 50) |
| 4400 TCR-A3 | Variable α (Predicted sequence without N-terminal signal peptide) | KTTQPNSMESNEEEPVHLPCNHSTISGTDYIHWYRQLPSQGPE YVIHGLTSNVNNRMASLAIAEDRKSSTLILHRATLRDAAVYYC ILRAPSGTYKYIFGTGTRLKVLA (SEQ ID NO: 125) |
| | Variable β (Predicted sequence without N-terminal signal peptide) | DVKVTQSSRYLVKRTGEKVFLECVQDMDHENMFWYRQD PGLGLRLIYFSYDVKMKEKGDIPEGYSVSREKKERFSLILE SASTNQTSMYLCASRQGNTGELFFGEGSRLTVL (SEQ ID NO: 126) |
| | Variable α (With N-terminal signal peptide) | MKLVTSITVLLSLGIMGDAKTTQPNSMESNEEEPVHLPCNHS TISGTDYIHWYRQLPSQGPEYVIHGLTSNVNNRMASLAIAEDR KSSTLILHRATLRDAAVYYCILRAPSGTYKYIFGTGTRLKVLA (SEQ ID NO: 127) |
| | Variable β (With N-terminal signal peptide) | MAIRLLCRVAFCFLAVGLVDVKVTQSSRYLVKRTGEKV FLECVQDMDHENMFWYRQDPGLGLRLIYFSYDVKMKEK GDIPEGYSVSREKKERFSLILESASTNQTSMYLCASRQGNT GELFFGEGSRLTVL (SEQ ID NO: 128) |
| 4400 TCR-J2 | Variable α (Predicted sequence without N-terminal signal peptide) | NSVTQMEGPVTLSEEAFLTINCTYTATGYPSLFWYVQYPGEGL QLLLKATKADDKGSNKGFEATYRKETTSFHLEKGSVQVSDSA VYFCALRLSGAGSYQLTFGKGTKLSVIP (SEQ ID NO: 135) |
| | Variable β (Predicted sequence without N-terminal signal peptide) | DVKVTQSSRYLVKRTGEKVFLECVQDMDHENMFWYRQD PGLGLRLIYFSYDVKMKEKGDIPEGYSVSREKKERFSLILE SASTNQTSMYLCASSQGNTGELFFGEGSRLTVL (SEQ ID NO: 136) |
| | Variable α (With N-terminal signal peptide) | MNYSPGLVSLILLLLGRTRGNSVTQMEGPVTLSEEAFLTINC TYTATGYPSLFWYVQYPGEGLQLLLKATKADDKGSNKGFEAT YRKETTSFHLEKGSVQVSDSAVYFCALRLSGAGSYQLTFGKGT KLSVIP (SEQ ID NO: 137) |
| | Variable β (With N-terminal signal peptide) | MAIRLLCRVAFCFLAVGLVDVKVTQSSRYLVKRTGEKV FLECVQDMDHENMFWYRQDPGLGLRLIYFSYDVKMKEK GDIPEGYSVSREKKERFSLILESASTNQTSMYLCASSQGNT GELFFGEGSRLTVL (SEQ ID NO: 138) |
| 4400 TCR-N4 | Variable α (Predicted sequence without N-terminal signal peptide) | QKITQTQPGMFVQEKEAVTLDCTYDTSDPSYGLFWYKQPSSG EMIFLIYQGSYDQQNATEGRYSLNFQKARKSANLVISASQLGD SAMYFCAMRERSGTASKLTFGTGTRLQVTL (SEQ ID NO: 145) |
| | Variable β (Predicted sequence without N-terminal signal peptide) | SRYLVKRTGEKVFLECVQDMDHENMFWYRQDPGLGLRLIYFS YDVKMKEKGDIPEGYSVSREKKERFSLILESASTNQTSMYLCA SSLGVGSNYGYTFGSGTRLTVV (SEQ ID NO: 146) |
| | Variable α (With N-terminal signal peptide) | MSLSSLLKVVTASLWLGPGIAQKITQTQPGMFVQEKEAVTL DCTYDTSDPSYGLFWYKQPSSGEMIFLIYQGSYDQQNATEGRY SLNFQKARKSANLVISASQLGDSAMYFCAMRERSGTASKLTF GTGTRLQVTL (SEQ ID NO: 147) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASSLGVGSNYGYTFGS GTRLTVV (SEQ ID NO: 148) |

TABLE 6-continued

| TCR Name | TCR chain | Amino acid sequence |
|---|---|---|
| 4400 TCR-N12 | Variable α (Predicted sequence without N-terminal signal peptide) | QKEVEQDPGPLSVPEGAIVSLNCTYSNSAFQYFMWYRQYSRK GPELLMYTYSSGNKEDGRFTAQVDKSSKYISLFIRDSQPSDSAT YLCAMSYSGGGADGLTFGKGTHLIIQP (SEQ ID NO: 155) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASSTGNTGELFFGEGSRLTVL (SEQ ID NO: 156) |
| | Variable α (With N-terminal signal peptide) | MMKSLRVLLVILWLQLSWVWSQQKEVEQDPGPLSVPEGAI VSLNCTYSNSAFQYFMWYRQYSRKGPELLMYTYSSGNKEDG RFTAQVDKSSKYISLFIRDSQPSDSATYLCAMSYSGGGADGLT FGKGTHLIIQP (SEQ ID NO: 157) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASSTGNTGELFFGEGS RLTVL (SEQ ID NO: 158) |
| 4400 TCR-N13 | Variable α (Predicted sequence without N-terminal signal peptide) | QKEVEQDPGPLSVPEGAIVSLNCTYSNSAFQYFMWYRQYS RKGPELLMYTYSSGNKEDGRFTAQVDKSSKYISLFIRDSQP SDSATYLCAMRANTDKLIFGTGTRLQVFP (SEQ ID NO: 165) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASRVGNTGELFFGEGSRLTVL (SEQ ID NO: 166) |
| | Variable α (With N-terminal signal peptide) | MMKSLRVLLVILWLQLSWVWSQQKEVEQDPGPLSVPEGAI VSLNCTYSNSAFQYFMWYRQYSRKGPELLMYTYSSGNKEDG RFTAQVDKSSKYISLFIRDSQPSDSATYLCAMRANTDKLIFGTG TRLQVFP (SEQ ID NO: 167) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASRVGNTGELFFGEGS RLTVL (SEQ ID NO: 168) |
| 4400 TCR-C | Variable α (Predicted sequence without N-terminal signal peptide) | QKITQTQPGMFVQEKEAVTLDCTYDTSDPSYGLFWYKQPSSG EMIFLIYQGSYDQQNATEGRYSLNFQKARKSANLVISASQLGD SAMYFCAMRERTGTASKLTFGTGTRLQVTL (SEQ ID NO: 175) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASSPGTENSPLHFGNGTRLTVT (SEQ ID NO: 176) |
| | Variable α (With N-terminal signal peptide) | MSLSSLLKVVTASLWLGPGIAQKITQTQPGMFVQEKEAVTL DCTYDTSDPSYGLFWYKQPSSGEMIFLIYQGSYDQQNATEGRY SLNFQKARKSANLVISASQLGDSAMYFCAMRERTGTASKLTF GTGTRLQVTL (SEQ ID NO: 177) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASSPGTENSPLHFGNG TRLTVT (SEQ ID NO: 178) |
| 4400 TCR-20 | Variable α (Predicted sequence without N-terminal signal peptide) | QKITQTQPGMFVQEKEAVTLDCTYDTSDPSYGLFWYKQPSSG EMIFLIYQGSYDQQNATEGRYSLNFQKARKSANLVISASQLGD SAMYFCAMRERSGGSYIPTFGRGTSLIVHP (SEQ ID NO: 185) |
| | Variable β (Predicted sequence without N-terminal signal peptide) | DVKVTQSSRYLVKRTGEKVFLECVQDMDHENMFWYRQDPGL GLRLIYFSYDVKMKEKGDIPEGYSVSREKKERFSLILESASTNQ TSMYLCASSLGTFNQPQHFGDGTRLSIL (SEQ ID NO: 186) |
| | Variable α (With N-terminal signal peptide) | MHLSSLLKVVTASLWLGPGIAQKITQTQPGMFVQEKEAVTL DCTYDTSDPSYGLFWYKQPSSGEMIFLIYQGSYDQQNATEGRY SLNFQKARKSANLVISASQLGDSAMYFCAMRERSGGSYIPTFG RGTSLIVHP (SEQ ID NO: 187) |
| | Variable β (With N-terminal signal peptide) | MAIRLLCRVAFCFLAVGLVDVKVTQSSRYLVKRTGEKVFLE CVQDMDHENMFWYRQDPGLGLRLIYFSYDVKMKEKGDIPEG YSVSREKKERFSLILESASTNQTSMYLCASSLGTFNQPQHFGDG TRLSIL (SEQ ID NO: 188) |

Example 2

This example demonstrates the construction of retroviral vectors encoding the respective TCRs of Example 1.

Nucleotide sequences encoding the variable regions of the α and β chains of the 4400 TCR-A1 (SEQ ID NO: 117), 4400 TCR-A2 (SEQ ID NO: 118), 4400 TCR-E (SEQ ID NO: 114), 4400 TCR-J (SEQ ID NO: 115), 4400 TCR-N (SEQ ID NO: 116), 4400 TCR-A3, 4400 TCR-J2, 4400 TCR-N4, 4400 TCR-N12, 4400 TCR-N13, 4400 TCR-C, or 4400 TCR-20 of Table 6 were obtained and codon-optimized. The TCRβ VDJ regions were fused to the mouse TCRβ constant chain. The TCRα VJ regions were fused to the mouse TCRα constant chain. Without being bound to a particular theory or mechanism, it is believed that replacing the constant regions of the human TCRα and TCRβ chains with the corresponding murine constant regions improves TCR expression and functionality (Cohen et al., Cancer Res., 66(17): 8878-86 (2006)).

In addition, the murine TCRα and TCRβ constant chains were cysteine-modified. Transmembrane hydrophobic mutations were introduced into the murine TCRα constant chain. Without being bound to a particular theory or mechanism, it is believed that these modifications result in preferential pairing of the introduced TCR chains and enhanced TCR surface expression and functionality (Cohen et al., Cancer Res., 67(8):3898-903 (2007); Haga-Friedman et al., J. Immu., 188: 5538-5546 (2012)). The full length α and β chains of each of the four TCRs, including these modifications to the constant region, are shown in Table 7. In Table 7, the CDRs are underlined, and the modified amino acid residues of the constant region are underlined and in bold.

TABLE 7

| SEQ ID NO: | Sequence |
|---|---|
| SEQ ID NO: 69 (Cys-substituted, LVL-modified 4400 TCR-A1 α chain with N-terminal signal peptide) | MMKSLRVLLVILWLQLSWVWSQQKEVEQDPGPLSVPEGAIVSLNCTYSN SAFQYFMWYRQYSRKGPELLMYTYSSGNKEDGRFTAQVDKSSKYISLFI RDSQPSDSATYLCAMRANTDKLIFGTGTRLQVFPNIQNPEPAVYQLKDPR SQDSTLCLFTDFDSQINVPKTMESGTFITDKCVLDMKAMDSKSNGAIAWS NQTSFTCQDIFKETNATYPSSDVPCDATLTEKSFETDMNLNFQNLLVIVL RILLLKVAGFNLLMTLRLWSS |
| SEQ ID NO: 70 (Cys-substituted, LVL-modified 4400 TCR-A1 β chain with N-terminal signal peptide) | MAIRLLCRVAFCFLAVGLVDVKVTQSSRYLVKRTGEKVFLECVQDMDH ENMFWYRQDPGLGLRLIYFSYDVKMKEKGDIPEGYSVSREKKERFSLILE SASTNQTSMYLCASRLGNTGELFFGEGSRLTVLEDLRNVTPPKVSLFEPS KAEIANKQKATLVCLARGFFPDHVELSWWVNGKEVHSGVCTDPQAYKE SNYSYCLSSRLRVSATFWHNPRNHFRCQVQFHGLSEEDKWPEGSPKPVT QNISAEAWGRADCGITSASYQQGVLSATILYEILLGKATLYAVLVSTLVV MAMVKRKNS |
| SEQ ID NO: 71 (Cys-substituted, LVL-modified 4400 TCR-A1 α chain predicted sequence without N-terminal signal peptide) | QKEVEQDPGPLSVPEGAIVSLNCTYSNSAFQYFMWYRQYSRKGPELLMY TYSSGNKEDGRFTAQVDKSSKYISLFIRDSQPSDSATYLCAMRANTDKLIF GTGTRLQVFPNIQNPEPAVYQLKDPRSQDSTLCLFTDFDSQINVPKTMES GTFITDKCVLDMKAMDSKSNGAIAWSNQTSFTCQDIFKETNATYPSSDVP CDATLTEKSFETDMNLNFQNLLVIVLRILLLKVAGFNLLMTLRLWSS |
| SEQ ID NO: 72 (Cys-substituted, LVL-modified 4400 TCR-A1 β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASRLGNT GELFFGEGSRLTVLEDLRNVTPPKVSLFEPSKAEIANKQKATLVCLARGFF PDHVELSWWVNGKEVHSGVCTDPQAYKESNYSYCLSSRLRVSATFWHN PRNHFRCQVQFHGLSEEDKWPEGSPKPVTQNISAEAWGRADCGITSASY QQGVLSATILYEILLGKATLYAVLVSTLVVMAMVKRKNS |
| SEQ ID NO: 77 (Cys-substituted, LVL-modified 4400 TCR-A2 α chain with N-terminal signal peptide) | MMKSLRVLLVILWLQLSWVWSQQKEVEQDPGPLSVPEGAIVSLNCTYSN SAFQYFMWYRQYSRKGPELLMYTYSSGNKEDGRFTAQVDKSSKYISLFI RDSQPSDSATYLCAMRANTDKLIFGTGTRLQVFPNIQNPEPAVYQLKDPR SQDSTLCLFTDFDSQINVPKTMESGTFITDKCVLDMKAMDSKSNGAIAWS NQTSFTCQDIFKETNATYPSSDVPCDATLTEKSFETDMNLNFQNLLVIVL RILLLKVAGFNLLMTLRLWSS |
| SEQ ID NO: 78 (Cys-substituted, LVL-modified 4400 TCR-A2 β chain with N-terminal signal peptide) | MAIRLLCRVAFCFLAVGLVDVKVTQSSRYLVKRTGEKVFLECVQDMDH ENMFWYRQDPGLGLRLIYFSYDVKMKEKGDIPEGYSVSREKKERFSLILE SASTNQTSMYLCASRQGNTGELFFGEGSRLTVLEDLRNVTPPKVSLFEPS KAEIANKQKATLVCLARGFFPDHVELSWWVNGKEVHSGVCTDPQAYKE SNYSYCLSSRLRVSATFWHNPRNHFRCQVQFHGLSEEDKWPEGSPKPVT QNISAEAWGRADCGITSASYQQGVLSATILYEILLGKATLYAVLVSTLVV MAMVKRKNS |
| SEQ ID NO: 79 (Cys-substituted, LVL-modified 4400 TCR-A2 α chain predicted sequence without N-terminal signal peptide) | QKEVEQDPGPLSVPEGAIVSLNCTYSNSAFQYFMWYRQYSRKGPELLMY TYSSGNKEDGRFTAQVDKSSKYISLFIRDSQPSDSATYLCAMRANTDKLIF GTGTRLQVFPNIQNPEPAVYQLKDPRSQDSTLCLFTDFDSQINVPKTMES GTFITDKCVLDMKAMDSKSNGAIAWSNQTSFTCQDIFKETNATYPSSDVP CDATLTEKSFETDMNLNFQNLLVIVLRILLLKVAGFNLLMTLRLWSS |
| SEQ ID NO: 80 (Cys-substituted, LVL-modified 4400 TCR-A2 β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASRQGNT GELFFGEGSRLTVLEDLRNVTPPKVSLFEPSKAEIANKQKATLVCLARGFF PDHVELSWWVNGKEVHSGVCTDPQAYKESNYSYCLSSRLRVSATFWHN PRNHFRCQVQFHGLSEEDKWPEGSPKPVTQNISAEAWGRADCGITSASY QQGVLSATILYEILLGKATLYAVLVSTLVVMAMVKRKNS |

TABLE 7-continued

| SEQ ID NO: | Sequence |
| --- | --- |
| SEQ ID NO: 85<br>(Cys-substituted, LVL-<br>modified 4400 TCR-E α<br>chain with N-terminal<br>signal peptide) | MRLVARVTVFLTFGTIIDAKTTQPPSMDCAEGRAANLPCNHSTISGNEYV<br>YWYRQIHSQGPQYIIHGLKNNETNEMASLIITEDRKSSTLILPHATLRDTA<br>VYYCIVRVAKSGANNLFFGTGTRLTVIPNIQNPEPAVYQLKDPRSQDSTL<br>CLFTDFDSQINVPKTMESGTFITDKCVLDMKAMDSKSNGAIAWSNQTSFT<br>CQDIFKETNATYPSSDVPCDATLTEKSFETDMNLNFQNLLVIVLRILLLKV<br>AGFNLLMTLRLWSS |
| SEQ ID NO: 86<br>(Cys-substituted, LVL-<br>modified 4400 TCR-E β<br>chain with N-terminal<br>signal peptide) | MAIRLLCYMGFYFLGAGLMEADIYQTPRYLVIGTGKKITLECSQTMGHD<br>KMYWYQQDPGMELHLIHYSYGVNSTEKGDLSSESTVSRIRTEHFPLTLES<br>ARPSHTSQYLCASSGLTYTDTQYFGPGTRLTVLEDLRNVTPPKVSLFEPSK<br>AEIANKQKATLVCLARGFFPDHVELSWWVNGKEVHSGVCTDPQAYKES<br>NYSYCLSSRLRVSATFWHNPRNHFRCQVQFHGLSEEDKWPEGSPKPVTQ<br>NISAEAWGRADCGITSASYQQGVLSATILYEILLGKATLYAVLVSTLVVM<br>AMVKRKNS |
| SEQ ID NO: 87<br>(Cys-substituted, LVL-<br>modified 4400 TCR-E α<br>chain predicted sequence<br>without N-terminal<br>signal peptide) | DAKTTQPPSMDCAEGRAANLPCNHSTISGNEYVYWYRQIHSQGPQYIIHG<br>LKNNETNEMASLIITEDRKSSTLILPHATLRDTAVYYCIVRVAKSGANNLF<br>FGTGTRLTVIPNIQNPEPAVYQLKDPRSQDSTLCLFTDFDSQINVPKTMES<br>GTFITDKCVLDMKAMDSKSNGAIAWSNQTSFTCQDIFKETNATYPSSDVP<br>CDATLTEKSFETDMNLNFQNLLVIVLRILLLKVAGFNLLMTLRLWSS |
| SEQ ID NO: 88<br>(Cys-substituted, LVL-<br>modified 4400 TCR-E β<br>chain predicted sequence<br>without N-terminal<br>signal peptide) | EADIYQTPRYLVIGTGKKITLECSQTMGHDKMYWYQQDPGMELHLIHYS<br>YGVNSTEKGDLSSESTVSRIRTEHFPLTLESARPSHTSQYLCASSGLTYTD<br>TQYFGPGTRLTVLEDLRNVTPPKVSLFEPSKAEIANKQKATLVCLARGFF<br>PDHVELSWWVNGKEVHSGVCTDPQAYKESNYSYCLSSRLRVSATFWHN<br>PRNHFRCQVQFHGLSEEDKWPEGSPKPVTQNISAEAWGRADCGITSASY<br>QQGVLSATILYEILLGKATLYAVLVSTLVVMAMVKRKNS |
| SEQ ID NO: 93<br>(Cys-substituted, LVL-<br>modified 4400 TCR-J α<br>chain with N-terminal<br>signal peptide) | MMKSLRVLLVILWLQLSWVWSQQKEVEQDPGPLSVPEGAIVSLNCTYSN<br>SAFQYFMWYRQYSRKGPELLMYTYSSGNKEDGRFTAQVDKSSKYISLFI<br>RDSQPSDSATYLCAMSYSGGGADGLTFGKGTHLIIQPNIQNPEPAVYQLK<br>DPRSQDSTLCLFTDFDSQINVPKTMESGTFITDKCVLDMKAMDSKSNGAI<br>AWSNQTSFTCQDIFKETNATYPSSDVPCDATLTEKSFETDMNLNFQNLLV<br>IVLRILLLKVAGFNLLMTLRLWSS |
| SEQ ID NO: 94<br>(Cys-substituted, LVL-<br>modified 4400 TCR-J β<br>chain with N-terminal<br>signal peptide) | MAIRLLCRVAFCFLAVGLVDVKVTQSSRYLVKRTGEKVFLECVQDMDH<br>ENMFWYRQDPGLGLRIYFSYDVKMKEKGDIPEGYSVSREKKERFSLILE<br>SASTNQTSMYLCASSQGNTGELFFGEGSRLTVLEDLRNVTPPKVSLFEPS<br>KAEIANKQKATLVCLARGFFPDHVELSWWVNGKEVHSGVCTDPQAYKE<br>SNYSYCLSSRLRVSATFWHNPRNHFRCQVQFHGLSEEDKWPEGSPKPVT<br>QNISAEAWGRADCGITSASYQQGVLSATILYEILLGKATLYAVLVSTLVV<br>MAMVKRKNS |
| SEQ ID NO: 95<br>(Cys-substituted, LVL-<br>modified 4400 TCR-J α<br>chain predicted sequence<br>without N-terminal<br>signal peptide) | QKEVEQDPGPLSVPEGAIVSLNCTYSNSAFQYFMWYRQYSRKGPELLMY<br>TYSSGNKEDGRFTAQVDKSSKYISLFIRDSQPSDSATYLCAMSYSGGGAD<br>GLTFGKGTHLIIQPNIQNPEPAVYQLKDPRSQDSTLCLFTDFDSQINVPKT<br>MESGTFITDKCVLDMKAMDSKSNGAIAWSNQTSFTCQDIFKETNATYPSS<br>DVPCDATLTEKSFETDMNLNFQNLLVIVLRILLLKVAGFNLLMTLRLWSS |
| SEQ ID NO: 96<br>(Cys-substituted, LVL-<br>modified 4400 TCR-J β<br>chain predicted sequence<br>without N-terminal<br>signal peptide) | DVKVTQSSRYLVKRTGEKVFLECVQDMDHENMFWYRQDPGLGLRLIYF<br>SYDVKMKEKGDIPEGYSVSREKKERFSLILESASTNQTSMYLCASSQGNT<br>GELFFGEGSRLTVLEDLRNVTPPKVSLFEPSKAEIANKQKATLVCLARGFF<br>PDHVELSWWVNGKEVHSGVCTDPQAYKESNYSYCLSSRLRVSATFWHN<br>PRNHFRCQVQFHGLSEEDKWPEGSPKPVTQNISAEAWGRADCGITSASY<br>QQGVLSATILYEILLGKATLYAVLVSTLVVMAMVKRKNS |
| SEQ ID NO: 101<br>(Cys-substituted, LVL-<br>modified 4400 TCR-N α<br>chain with N-terminal<br>signal peptide) | MKTFAGFSFLFLWLQLDCMSRGEDVEQSLFLSVREGDSSVINCTYTDSSS<br>TYLYWYKQEPGAGLQLLTYIFSNMDMKQDQRLTVLLNKKDKHLSLRIA<br>DTQTGDSAIYFCAPGGYNKLIFGAGTRLAVHPNIQNPEPAVYQLKDPRSQ<br>DSTLCLFTDFDSQINVPKTMESGTFITDKCVLDMKAMDSKSNGAIAWSN<br>QTSFTCQDIFKETNATYPSSDVPCDATLTEKSFETDMNLNFQNLLVIVLRI<br>LLLKVAGFNLLMTLRLWSS |
| SEQ ID NO: 102<br>(Cys-substituted, LVL-<br>modified 4400 TCR-N β<br>chain with N-terminal<br>signal peptide) | MAIRLLCRVAFCFLAVGLVDVKVTQSSRYLVKRTGEKVFLECVQDMDH<br>ENMFWYRQDPGLGLRLIYFSYDVKMKEKGDIPEGYSVSREKKERFSLILE<br>SASTNQTSMYLCASRIGNTGELFFGEGSRLTVLEDLRNVTPPKVSLFEPSK<br>AEIANKQKATLVCLARGFFPDHVELSWWVNGKEVHSGVCTDPQAYKES<br>NYSYCLSSRLRVSATFWHNPRNHFRCQVQFHGLSEEDKWPEGSPKPVTQ<br>NISAEAWGRADCGITSASYQQGVLSATILYEILLGKATLYAVLVSTLVVM<br>AMVKRKNS |

TABLE 7-continued

| SEQ ID NO: | Sequence |
|---|---|
| SEQ ID NO: 103 (Cys-substituted, LVL-modified 4400 TCR-N α chain predicted sequence without N-terminal signal peptide) | GEDVEQSLFLSVREGDSSVINCTYTDSSSTYLYWYKQEPGAGLQLLTYIFS NMDMKQDQRLTVLLNKKDKHLSLRIADTQTGDSAIYFCAPGGYNKLIFG AGTRLAVHPNIQNPEPAVYQLKDPRSQDSTLCLFTDFDSQINVPKTMESG TFITDKCVLDMKAMDSKSNGAIAWSNQTSFTCQDIFKETNATYPSSDVPC DATLTEKSFETDMNLNFQNLLVIVLRILLLKVAGFNLLMTLRLWSS |
| SEQ ID NO: 104 (Cys-substituted, LVL-modified 4400 TCR-N β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASRIGNT GELFFGEGSRLTVLEDLRNVTPPKVSLFEPSKAEIANKQKATLVCLARGFF PDHVELSWWVNGKEVHSGVCTDPQAYKESNYSYCLSSRLRVSATFWHN PRNHFRCQVQFHGLSEEDKWPEGSPKPVTQNISAEAWGRADCGITSASY QQGVLSATILYEILLGKATLYAVLVSTLVVMAMVKRKNS |
| SEQ ID NO: 193 (Cys-substituted, LVL-modified 4400 TCR-A3 α chain with N-terminal signal peptide) | MKLVTSITVLLSLGIMGDAKTTQPNSMESNEEEPVHLPCNHSTISGTDYIH WYRQLPSQGPEYVIHGLTSNVNNRMASLAIAEDRKSSTLILHRATLRDAA VYYCILRAPSGTYKYIFGTGTRLKVLANIQNPEPAVYQLKDPRSQDSTLC LFTDFDSQINVPKTMESGTFITDKCVLDMKAMDSKSNGAIAWSNQTSFTC QDIFKETNATYPSSDVPCDATLTEKSFETDMNLNFQNLLVIVLRILLLKVA GFNLLMTLRLWSS |
| SEQ ID NO: 194 (Cys-substituted, LVL-modified 4400 TCR-A3 β chain with N-terminal signal peptide) | MAIRLLCRVAFCFLAVGLVDVKVTQSSRYLVKRTGEKVFLECVQDM DHENMFWYRQDPGLGLRLIYFSYDVKMKEKGDIPEGYSVSREKKER FSLILESASTNQTSMYLCASRQGNTGELFFGEGSRLTVLEDLRNVTPP KVSLFEPSKAEIANKQKATLVCLARGFFPDHVELSWWVNGKEVHSG VCTDPQAYKESNYSYCLSSRLRVSATFWHNPRNHFRCQVQFHGLSE EDKWPEGSPKPVTQNISAEAWGRADCGITSASYQQGVLSATILYEILL GKATLYAVLVSTLVVMAMVKRKNS |
| SEQ ID NO: 195 (Cys-substituted, LVL-modified 4400 TCR-A3 α chain predicted sequence without N-terminal signal peptide) | KTTQPNSMESNEEEPVHLPCNHSTISGTDYIHWYRQLPSQGPEYVIHGLTS NVNNRMASLAIAEDRKSSTLILHRATLRDAAVYYCILRAPSGTYKYIFGT GTRLKVLANIQNPEPAVYQLKDPRSQDSTLCLFTDFDSQINVPKTMESGT FITDKCVLDMKAMDSKSNGAIAWSNQTSFTCQDIFKETNATYPSSDVPCD ATLTEKSFETDMNLNFQNLLVIVLRILLLKVAGFNLLMTLRLWSS |
| SEQ ID NO: 196 (Cys-substituted, LVL-modified 4400 TCR-A3 β chain predicted sequence without N-terminal signal peptide) | DVKVTQSSRYLVKRTGEKVFLECVQDMDHENMFWYRQDPGLGLRL IYFSYDVKMKEKGDIPEGYSVSREKKERFSLILESASTNQTSMYLCAS RQGNTGELFFGEGSRLTVLEDLRNVTPPKVSLFEPSKAEIANKQKATL VCLARGFFPDHVELSWWVNGKEVHSGVCTDPQAYKESNYSYCLSS RLRVSATFWHNPRNHFRCQVQFHGLSEEDKWPEGSPKPVTQNISAE AWGRADCGITSASYQQGVLSATILYEILLGKATLYAVLVSTLVVMA MVKRKNS |
| SEQ ID NO: 201 (Cys-substituted, LVL-modified 4400 TCR-J2 α chain with N-terminal signal peptide) | MNYSPGLVSLILLLLGRTRGNSVTQMEGPVTLSEEAFLTINCTYTATGYPS LFWYVQYPGEGLQLLLKATKADDKGSNKGFEATYRKETTSFHLEKGSV QVSDSAVYFCALRLSGAGSYQLTFGKGTKLSVIPNIQNPEPAVYQLKDPR SQDSTLCLFTDFDSQINVPKTMESGTFITDKCVLDMKAMDSKSNGAIAWS NQTSFTCQDIFKETNATYPSSDVPCDATLTEKSFETDMNLNFQNLLVIVL RILLLKVAGFNLLMTLRLWSS |
| SEQ ID NO: 202 (Cys-substituted, LVL-modified 4400 TCR-J2 β chain with N-terminal signal peptide) | MAIRLLCRVAFCFLAVGLVDVKVTQSSRYLVKRTGEKVFLECVQDM DHENMFWYRQDPGLGLRLIYFSYDVKMKEKGDIPEGYSVSREKKER FSLILESASTNQTSMYLCASSQGNTGELFFGEGSRLTVLEDLRNVTPP KVSLFEPSKAEIANKQKATLVCLARGFFPDHVELSWWVNGKEVHSG VCTDPQAYKESNYSYCLSSRLRVSATFWHNPRNHFRCQVQFHGLSE EDKWPEGSPKPVTQNISAEAWGRADCGITSASYQQGVLSATILYEILL GKATLYAVLVSTLVVMAMVKRKNS |
| SEQ ID NO: 203 (Cys-substituted, LVL-modified 4400 TCR-J2 α chain predicted sequence without N-terminal signal peptide) | NSVTQMEGPVTLSEEAFLTINCTYTATGYPSLFWYVQYPGEGLQLLLKAT KADDKGSNKGFEATYRKETTSFHLEKGSVQVSDSAVYFCALRLSGAGSY QLTFGKGTKLSVIPNIQNPEPAVYQLKDPRSQDSTLCLFTDFDSQINVPKT MESGTFITDKCVLDMKAMDSKSNGAIAWSNQTSFTCQDIFKETNATYPSS DVPCDATLTEKSFETDMNLNFQNLLVIVLRILLLKVAGFNLLMTLRLWSS |
| SEQ ID NO: 204 (Cys-substituted, LVL-modified 4400 TCR-J2 β chain predicted sequence without N-terminal signal peptide) | DVKVTQSSRYLVKRTGEKVFLECVQDMDHENMFWYRQDPGLGLRL IYFSYDVKMKEKGDIPEGYSVSREKKERFSLILESASTNQTSMYLCAS SQGNTGELFFGEGSRLTVLEDLRNVTPPKVSLFEPSKAEIANKQKATL VCLARGFFPDHVELSWWVNGKEVHSGVCTDPQAYKESNYSYCLSS RLRVSATFWHNPRNHFRCQVQFHGLSEEDKWPEGSPKPVTQNISAE AWGRADCGITSASYQQGVLSATILYEILLGKATLYAVLVSTLVVMA MVKRKNS |
| SEQ ID NO: 209 (Cys-substituted, LVL-modified 4400 TCR-N4 | MSLSSLLKVVTASLWLGPGIAQKITQTQPGMFVQEKEAVTLDCTYDTSDP SYGLFWYKQPSSGEMIFLIYQGSYDQQNATEGRYSLNFQKARKSANLVIS ASQLGDSAMYFCAMRERSGTASKLTFGTGTRLQVTLNIQNPEPAVYQLK |

TABLE 7-continued

| SEQ ID NO: | Sequence |
|---|---|
| α chain with N-terminal signal peptide) | DPRSQDSTLCLFTDFDSQINVPKTMESGTFITDKCVLDMKAMDSKSNGAI AWSNQTSFTCQDIFKETNATYPSSDVPCDATLTEKSFETDMNLNFQNLLV IVLRILLLLKVAGFNLLMTLRLWSS |
| SEQ ID NO: 210 (Cys-substituted, LVL-modified 4400 TCR-N4 β chain with N-terminal signal peptide) | MAIRLLCRVAFCFLAVGLVDVKVTQSSRYLVKRTGEKVFLECVQD<u>MDH</u> <u>ENMFWYRQDPGLGLRLIYFSYDVKMKEKGDIPEGYSVSREKKERFSLILE</u> SASTNQTSMYLC<u>ASSLGVGSNYGYTF</u>GSGTRLTVVEDLRNVTPPKVSLFE PSKAEIANKQKATLVCLARGFFPDHVELSWWVNGKEVHSGVCTDPQAY KESNYSYCLSSRLRVSATFWHNPRNHFRCQVQFHGLSEEDKWPEGSPKP VTQNISAEAWGRADCGITSASYQQGVLSATILYEILLGKATLYAVLVSTL VVMAMVKRKNS |
| SEQ ID NO: 211 (Cys-substituted, LVL-modified 4400 TCR-N4 α chain predicted sequence without N-terminal signal peptide) | QKITQTQPGMFVQEKEAVTLDCTYDT<u>SDPSYG</u>LFWYKQPSSGEMIFLIY<u>Q</u> <u>GSYDQQN</u>ATEGRYSLNFQKARKSANL<u>VIS</u>ASQLGDSAMYFC<u>AMRERSGT</u> <u>ASKLT</u>FGTGTRLQVTLNIQNPEPAVYQLKDPRSQDSTLCLFTDFDSQINVP KTMESGTFITDKCVLDMKAMDSKSNGAIAWSNQTSFTCQDIFKETNATY PSSDVPCDATLTEKSFETDMNLNFQNLLV IVLRILLLLKVAGFNLLMTLRL WSS |
| SEQ ID NO: 212 (Cys-substituted, LVL-modified 4400 TCR-N4 β chain predicted sequence without N-terminal signal peptide) | SRYLVKRTGEKVFLECVQD<u>MDHEN</u>MFWYRQDPGLGLRLIYFSYDVKMK EKGDIPEGYSVSREKKERF<u>SLILE</u>SASTNQTSMYLCASSLGVGSNYGYTFG SGTRLTVVEDLRNVTPPKVSLFEPSKAEIANKQKATLVCLARGFFPDHVE LSWWVNGKEVHSGVCTDPQAYKESNYSYCLSSRLRVSATFWHNPRNHF RCQVQFHGLSEEDKWPEGSPKPVTQNISAEAWGRADCGITSASYQQGVL SATILYEILLGKATLYAVLVSTLVVMAMVKRKNS |
| SEQ ID NO: 217 (Cys-substituted, LVL-modified 4400 TCR-N12 α chain with N-terminal signal peptide) | MMKSLRVLLVILWLQLSWVWSQQKEVEQDPGPLSVPEGAIVSLNCT YSNSAF<u>QY</u>FMWYRQYSRKGPELLMYT<u>YSSGNKEDGRFTAQVDKSS</u> KY<u>ISLF</u>IRDSQPSDSATYLCAMSYSGGG<u>ADG</u>LTFGKGTHLIIQPNIQNP EPAVYQLKDPRSQDSTLCL<u>FTDFDSQ</u>INVPKTMESGTFITDKCVLDM KAMDSKSNGAIAWSNQTSFTCQDIFKETNATYPSSDVPCDATL<u>T</u>EKS FETDMNLNFQNLLV IVLRILLLLKVAGFNLLMTLRLWSS |
| SEQ ID NO: 218 (Cys-substituted, LVL-modified 4400 TCR-N12 β chain with N-terminal signal peptide) | MAIRLLCRVAFCFLAVGLVDVKVTQSSRYLVKRTGEKVFLECVQD<u>MDH</u> <u>ENMFWYRQDPGLGLRLIYFSYDVKMKEKGDIPEGYSVSREKKERFSLILE</u> SASTNQTSMYLC<u>ASSTGNTGELFF</u>GEGSRLTVLEDLRNVTPPKVSLFEPSK AEIANKQKATL<u>V</u>CLARGFFPDHVELSWWVNGKEVHSGVCTDPQAYKES NYSYCLSSRLRVSATFWHNPRNHFRCQVQFHGLSEEDKWPEGSPKPVTQ NISAEAWGRADCGITSASYQQGVLSATILYEILLGKATLYAVLVSTLVVM AMVKRKNS |
| SEQ ID NO: 219 (Cys-substituted, LVL-modified 4400 TCR-N12 α chain predicted sequence without N-terminal signal peptide) | QKEVEQDPGPLSVPEGAIVSLNCTYS<u>NSAFQY</u>FMWYRQYSRKGPELLMY <u>TYSSGNKEDGRFTAQVDKSS</u>KYISLF<u>IRDSQPSDSATYLCAMSYSGGGAD</u> <u>GLTFGKGTHLI</u>IQPNIQNPEPAVYQLKDPRSQDSTLCLFTDFDSQINVPKT MESGTFITDKCVLDMKAMDSKSNGAIAWSNQTSFTCQDIFKETNATYPSS DVPCDATLTEKSFETDMNLNFQNLLV IVLRILLLLKVAGFNLLMTLRLWSS |
| SEQ ID NO: 220 (Cys-substituted, LVL-modified 4400 TCR-N12 β chain predicted sequence without N-terminal signal peptide) | DVKVTQSSRYLVKRTGEKVFLECVQD<u>MDHEN</u>MFWYRQDPGLGLRLIYF <u>SYDVKMKEKGDIPEGYSVSREKKERFSLILE</u>SASTNQTSMYLC<u>ASSTGNT</u> <u>GELFF</u>GEGSRLTVLEDLRNVTPPKVSLFEPSKAEIANKQKATLVCLARGFF PDHVELSWWVNGKEVHSGVCTDPQAYKESNYSYCLSSRLRVSATFWHN PRNHFRCQVQFHGLSEEDKWPEGSPKPVTQNISAEAWGRADCGITSASY QQGVLSATILYEILLGKATLYAVLVSTLVVMAMVKRKNS |
| SEQ ID NO: 225 (Cys-substituted, LVL-modified 4400 TCR-N13 α chain with N-terminal signal peptide) | MMKSLRVLLVILWLQLSWVWSQQKEVEQDPGPLSVPEGAIVSLNCT YS<u>NSAFQY</u>FMWYRQYSRKGPELLMYTYSSGNKEDGRFTAQVDKSS KY<u>ISLF</u>IRDSQPSDSATYL<u>CAMRANTDKLIF</u>GTGTRLQVFPNIQNPEPA VYQLKDPRSQDSTLCLFTDFDSQINVPKTMESGTFITDKCVLDMKAM DSKSNGAIAWSNQTSFTCQDIFKETNATYPSSDVPCDATLTEKSFETD MNLNFQNLLV IVLRILLLLKVAGFNLLMTLRLWSS |
| SEQ ID NO: 226 (Cys-substituted, LVL-modified 4400 TCR-N13 β chain with N-terminal signal peptide) | MAIRLLCRVAFCFLAVGLVDVKVTQSSRYLVKRTGEKVFLECVQD<u>MDH</u> <u>EN</u>MFWYRQDPGLGLRLIYF<u>SYDVKMK</u>EKGDIPEGYSVSREKKERF<u>SLILE</u> SASTNQTSMYLCASRVGN<u>TGELFF</u>GEGSRLTVLEDLRNVTPPKVSLFEPS KAEIANKQKATLVCLARGFFPDHVELSWWVNGKEVHSGVCTDPQAYKE SNYSYCLSSRLRVSATFWHNPRNHFRCQVQFHGLSEEDKWPEGSPKPVT QNISAEAWGRADCGITSASYQQGVLSATILYEILLGKATLYAVLVSTLVV MAMVKRKNS |
| SEQ ID NO: 227 (Cys-substituted, LVL-modified 4400 TCR-N13 α chain predicted sequence without N-terminal signal peptide) | QKEVEQDPGPLSVPEGAIVSLNCTYS<u>NSAFQY</u>FMWYRQYSRKGPELL MY<u>TYSSGNKEDGRFTAQVDKSS</u>KYISLFIRDSQPSDSATYL<u>CAMRAN</u> <u>TDKLIF</u>GTGTRLQVFPNIQNPEPAVYQLKDPRSQDSTLCLFTDFDSQI NVPKTMESGTFITDKCVLDMKAMDSKSNGAIAWSNQTSFTCQDIFK ETNATYPSSDVPCDATLTEKSFETDMNLNFQNLLV IVLRILLLLKVAGF NLLMTLRLWSS |

TABLE 7-continued

| SEQ ID NO: | Sequence |
|---|---|
| SEQ ID NO: 228 (Cys-substituted, LVL-modified 4400 TCR-N13 β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASRVGNT GELFFGEGSRLTVLEDLRNVTPPKVSLFEPSKAEIANKQKATLVCLARGFF PDHVELSWWVNGKEVHSGVCTDPQAYKESNYSYCLSSRLRVSATFWHN PRNHFRCQVQFHGLSEEDKWPEGSPKPVTQNISAEAWGRADCGITSASY QQGVLSATILYEILLGKATLYAVLVSTLVVMAMVKRKNS |
| SEQ ID NO: 233 (Cys-substituted, LVL-modified 4400 TCR-C α chain with N-terminal signal peptide) | MSLSSLLKVVTASLWLGPGIAQKITQTQPGMFVQEKEAVTLDCTYDTSDP SYGLFWYKQPSSGEMIFLIYQGSYDQQNATEGRYSLNFQKARKSANLVIS ASQLGDSAMYFCAMRERTGTASKLTFGTGTRLQVTLNIQNPEPAVYQLK DPRSQDSTLCLFTDFDSQINVPKTMESGTFITDKCVLDMKAMDSKSNGAI AWSNQTSFTCQDIFKETNATYPSSDVPCDATLTEKSFETDMNLNFQNLLV IVLRILLLKVAGFNLLMTLRLWSS |
| SEQ ID NO: 234 (Cys-substituted, LVL-modified 4400 TCR-C β chain with N-terminal signal peptide) | MAIRLLCRVAFCFLAVGLVDVKVTQSSRYLVKRTGEKVFLECVQDMDH ENMFWYRQDPGLGLRLIYFSYDVKMKEKGDIPEGYSVSREKKERFSLILE SASTNQTSMYLCASSPGTENSPLHFGNGTRLTVTEDLRNVTPPKVSLFEPS KAEIANKQKATLVCLARGFFPDHVELSWWVNGKEVHSGVCTDPQAYKE SNYSYCLSSRLRVSATFWHNPRNHFRCQVQFHGLSEEDKWPEGSPKPVT QNISAEAWGRADCGITSASYQQGVLSATILYEILLGKATLYAVLVSTLVV MAMVKRKNS |
| SEQ ID NO: 235 (Cys-substituted, LVL-modified 4400 TCR-C α chain predicted sequence without N-terminal signal peptide) | QKITQTQPGMFVQEKEAVTLDCTYDTSDPSYGLFWYKQPSSGEMIFLIYQ GSYDQQNATEGRYSLNFQKARKSANLVISASQLGDSAMYFCAMRERTG TASKLTFGTGTRLQVTLNIQNPEPAVYQLKDPRSQDSTLCLFTDFDSQINV PKTMESGTFITDKCVLDMKAMDSKSNGAIAWSNQTSFTCQDIFKETNAT YPSSDVPCDATLTEKSFETDMNLNFQNLLVIVLRILLLKVAGFNLLMTLR LWSS |
| SEQ ID NO: 236 (Cys-substituted, LVL-modified 4400 TCR-C β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASSPGTE NSPLHFGNGTRLTVTEDLRNVTPPKVSLFEPSKAEIANKQKATLVCLARG FFPDHVELSWWVNGKEVHSGVCTDPQAYKESNYSYCLSSRLRVSATFW HNPRNHFRCQVQFHGLSEEDKWPEGSPKPVTQNISAEAWGRADCGITSA SYQQGVLSATILYEILLGKATLYAVLVSTLVVMAMVKRKNS |
| SEQ ID NO: 241 (Cys-substituted, LVL-modified 4400 TCR-20 α chain with N-terminal signal peptide) | MHLSSLLKVVTASLWLGPGIAQKITQTQPGMFVQEKEAVTLDCTYDTSD PSYGLFWYKQPSSGEMIFLIYQGSYDQQNATEGRYSLNFQKARKSANLVI SASQLGDSAMYFCAMRERSGGSYIPTFGRGTSLIVHPNIQNPEPAVYQLK DPRSQDSTLCLFTDFDSQINVPKTMESGTFITDKCVLDMKAMDSKSNGAI AWSNQTSFTCQDIFKETNATYPSSDVPCDATLTEKSFETDMNLNFQNLLV IVLRILLLKVAGFNLLMTLRLWSS |
| SEQ ID NO: 242 (Cys-substituted, LVL-modified 4400 TCR-20 β chain with N-terminal signal peptide) | MAIRLLCRVAFCFLAVGLVDVKVTQSSRYLVKRTGEKVFLECVQDMDH ENMFWYRQDPGLGLRLIYFSYDVKMKEKGDIPEGYSVSREKKERFSLILE SASTNQTSMYLCASSLGTFNQPQHFGDGTRLSILEDLRNVTPPKVSLFEPS KAEIANKQKATLVCLARGFFPDHVELSWWVNGKEVHSGVCTDPQAYKE SNYSYCLSSRLRVSATFWHNPRNHFRCQVQFHGLSEEDKWPEGSPKPVT QNISAEAWGRADCGITSASYQQGVLSATILYEILLGKATLYAVLVSTLVV MAMVKRKNS |
| SEQ ID NO: 243 (Cys-substituted, LVL-modified 4400 TCR-20 α chain predicted sequence without N-terminal signal peptide) | QKITQTQPGMFVQEKEAVTLDCTYDTSDPSYGLFWYKQPSSGEMIFLIYQ GSYDQQNATEGRYSLNFQKARKSANLVISASQLGDSAMYFCAMRERSG GSYIPTFGRGTSLIVHPNIQNPEPAVYQLKDPRSQDSTLCLFTDFDSQINVP KTMESGTFITDKCVLDMKAMDSKSNGAIAWSNQTSFTCQDIFKETNATY PSSDVPCDATLTEKSFETDMNLNFQNLLVIVLRILLLKVAGFNLLMTLRL WSS |
| SEQ ID NO: 244 (Cys-substituted, LVL-modified 4400 TCR-20 β chain predicted sequence without N-terminal signal peptide) | DVKVTQSSRYLVKRTGEKVFLECVQDMDHENMFWYRQDPGLGLRLIYF SYDVKMKEKGDIPEGYSVSREKKERFSLILESASTNQTSMYLCASSLGTF NQPQHFGDGTRLSILEDLRNVTPPKVSLFEPSKAEIANKQKATLVCLARG FFPDHVELSWWVNGKEVHSGVCTDPQAYKESNYSYCLSSRLRVSATFW HNPRNHFRCQVQFHGLSEEDKWPEGSPKPVTQNISAEAWGRADCGITSA SYQQGVLSATILYEILLGKATLYAVLVSTLVVMAMVKRKNS |

Nucleotide sequences encoding the variable regions of the α and β chains of the 4400 TCR-A1, 4400 TCR-A2, 4400 TCR-E, 4400 TCR-J, 4400 TCR-N, 4400 TCR-A3, 4400 TCR-J2, 4400 TCR-N4, 4400 TCR-N12, 4400 TCR-N13, 4400 TCR-C, or 4400 TCR-20 of Table 7 were independently cloned into a MSGV1-based retroviral vectors with the following expression cassette configuration: 5'NcoI-VDJβ-mCβ-Furin/SerGly/P2A-VJα-mCα-EcoRI3'. To facilitate cloning of the TCR expression cassette into the MSGV1 vector 5'NcoI site, the second amino acid in the N-terminal signal peptide of the TCRVβ chain was changed to an alanine (A).

The TCRβ and TCRα chains were separated by a Furin Ser/Gly P2A linker peptide (SEQ ID NO: 105). Without being bound to a particular theory or mechanism, it is believed that the linker peptide provides comparable expression efficiency of the two chains (Szymczak et al., *Nat. Biotechnol.*, 22(5):589-94 (2004)).

The TCR expression cassette of the retroviral vector encoded, from 5' to 3', the TCRβ and TCRα chains separated by the linker peptide. The amino acid sequence encoded by the TCR expression cassette for each respective TCR is shown in Table 8. In Table 8, the CDRs are underlined, the constant regions are italicized, and the linker peptide is shown in bold.

TABLE 8

| TCR Name | Amino acid sequence encoded by TCR Expression Cassette |
|---|---|
| 4400 TCR-A1 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASRLGNTGELFFGEGSRLTVLEDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNSRAKRSGSGATNFSLLKQAGDVEENPGPMMKS LRVLLVILWLQLSWVWSQQKEVEQDPGPLSVPEGAIVSLNCTYSNSAFQYFMWY RQYSRKGPELLMYTYSSGNKEDGRFTAQVDKSSKYISLFIRDSQPSDSATYLCAM RANTDKLIFGTGTRLQVFPNIQNPEPAVYQLKDPRSQDSTLCLFTDFDSQINVPKTM ESGTFITDKCVLDMKAMDSKSNGAIAWSNQTSFTCQDIFKETNATYPSSDVPCDATLT EKSFETDMNLNFQNLLVIVLRILLLKVAGFNLLMTLRLWSS (SEQ ID NO: 108) |
| 4400 TCR-A2 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASRQGNTGELFFGEGSRLTVLEDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNSRAKRSGSGATNFSLLKQAGDVEENPGPMMKS LRVLLVILWLQLSWVWSQQKEVEQDPGPLSVPEGAIVSLNCTYSNSAFQYFMWY RQYSRKGPELLMYTYSSGNKEDGRFTAQVDKSSKYISLFIRDSQPSDSATYLCAM RANTDKLIFGTGTRLQVFPNIQNPEPAVYQLKDPRSQDSTLCLFTDFDSQINVPKTM ESGTFITDKCVLDMKAMDSKSNGAIAWSNQTSFTCQDIFKETNATYPSSDVPCDATLT EKSFETDMNLNFQNLLVIVLRILLLKVAGFNLLMTLRLWSS (SEQ ID NO: 109) |
| 4400 TCR-E | MAIRLLCYMGFYFLGAGLMEADIYQTPRYLVIGTGKKITLECSQTMGHDKMYW YQQDPGMELHLIHYSYGVNSTEKGDLSSESTVSRIRTEHFPLTLESARPSHTSQYL CASSGLTYTDTQYFGPGTRLTVLEDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNSRAKRSGSGATNFSLLKQAGDVEENPGPMRLV ARVTVFLTFGTIIDAKTTQPPSMDCAEGRAANLPCNHSTISGNEYVYWYRQIHSQ GPQYIIHGLKNNETNEMASLIITEDRKSSTLILPHATLRDTAVYYCIVRVAKSGAN NLFFGTGTRLTVIPNIQNPEPAVYQLKDPRSQDSTLCLFTDFDSQINVPKTMESGTFIT DKCVLDMKAMDSKSNGAIAWSNQTSFTCQDIFKETNATYPSSDVPCDATLTEKSFETD MNLNFQNLLVIVLRILLLKVAGFNLLMTLRLWSS (SEQ ID NO: 110) |
| 4400 TCR-J | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSQGNTGELFFGEGSRLTVLEDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNSRAKRSGSGATNFSLLKQAGDVEENPGPMMKS LRVLLVILWLQLSWVWSQQKEVEQDPGPLSVPEGAIVSLNCTYSNSAFQYFMWY RQYSRKGPELLMYTYSSGNKEDGRFTAQVDKSSKYISLFIRDSQPSDSATYLCAM SYSGGGADGLTFGKGTHLIIQPNIQNPEPAVYQLKDPRSQDSTLCLFTDFDSQINVPK TMESGTFITDKCVLDMKAMDSKSNGAIAWSNQTSFTCQDIFKETNATYPSSDVPCDAT LTEKSFETDMNLNFQNLLVIVLRILLLKVAGFNLLMTLRLWSS (SEQ ID NO: 111) |
| 4400 TCR-N | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASRIGNTGELFFGEGSRLTVLEDLRNVTPPKVSLFEPSKAEIANKQKATLVCLARG FFPDHVELSWWVNGKEVHSGVCTDPQAYKESNYSYCLSSRLRVSATFWHNPRNHFRC QVQFHGLSEEDKWPEGSPKPVTQNISAEAWGRADCGITSASYQQGVLSATILYEILLGK ATLYAVLVSTLVVMAMVKRKNSRAKRSGSGATNFSLLKQAGDVEENPGPMKTFA GFSFLFLWLQLDCMSRGEDVEQSLFLSVREGDSSVINCTYTDSSSTYLYWYKQEP GAGLQLLTYIFSNMDMKQDQRLTVLLNKKDKHLSLRIADTQTGDSAIYFCAPGG YNKLIFGAGTRLAVHPNIQNPEPAVYQLKDPRSQDSTLCLFTDFDSQINVPKTMESG TFITDKCVLDMKAMDSKSNGAIAWSNQTSFTCQDIFKETNATYPSSDVPCDATLTEKS FETDMNLNFQNLLVIVLRILLLKVAGFNLLMTLRLWSS (SEQ ID NO: 112) |
| 4400 TCR-A3 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASRQGNTGELFFGEGSRLTVLEDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNSRAKRSGSGATNFSLLKQAGDVEENPGPMKLV TSITVLLSLGIMGDAKTTQPNSMESNEEEPVHLPCNHSTISGTDYIHWYRQLPSQG PEYVIHGLTSNVNNRMASLAIAEDRKSSTLILHRATLRDAAVYYCILRAPSGTYK YIFGTGTRLKVLANIQNPEPAVYQLKDPRSQDSTLCLFTDFDSQINVPKTMESGTFIT |

TABLE 8-continued

| TCR Name | Amino acid sequence encoded by TCR Expression Cassette |
|---|---|
| | *DKCVLDMKAMDSKSNGAIAWSNQTSFTCQDIFKETNATYPSSDVPCDATLTEKSFETD MNLNFQNLLVIVLRILLLKVAGFNLLMTLRLWSS* (SEQ ID NO: 245) |
| 4400 TCR-J2 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSQGNTGELFFGEGSRLTVL*EDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNS*RAKRSGSGATNFSLLKQAGDVEENPGP*MNYS PGLVSLILLLLGRTRGNSVTQMEGPVTLSEEAFLTINCTYTATGYPSLFWYVQYP GEGLQLLLKATKADDKGSNKGFEATYRKETTSFHLEKGSVQVSDSAVYFCALRL SGAGSYQLTFGKGTKLSVIPNIQNPEPAVYQLKDPRSQDSTLCLFTDFDSQINVPKT MESGTFITDKCVLDMKAMDSKSNGAIAWSNQTSFTCQDIFKETNATYPSSDVPCDATL TEKSFETDMNLNFQNLLVIVLRILLLKVAGFNLLMTLRLWSS* (SEQ ID NO: 246) |
| 4400 TCR-N4 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSLGVGSNYGYTFGSGTRLTVV*EDLRNVTPPKVSLFEPSKAEIANKQKATLVCL ARGFFPDHVELSWWVNGKEVHSGVCTDPQAYKESNYSYCLSSRLRVSATFWHNPRNH FRCQVQFHGLSEEDKWPEGSPKPVTQNISAEAWGRADCGITSASYQQGVLSATILYEIL LGKATLYAVLVSTLVVMAMVKRKNS*RAKRSGSGATNFSLLKQAGDVEENPGP*MS LSSLLKVVTASLWLGPGIAQKITQTQPGMFVQEKEAVTLDCTYDTSDPSYGLFW YKQPSSGEMIFLIYQGSYDQQNATEGRYSLNFQKARKSANLVISASQLGDSAMYF CAMRERSGTASKLTFGTGTRLQVTLNIQNPEPAVYQLKDPRSQDSTLCLFTDFDSQI NVPKTMESGTFITDKCVLDMKAMDSKSNGAIAWSNQTSFTCQDIFKETNATYPSSDVP CDATLTEKSFETDMNLNFQNLLVIVLRILLLKVAGFNLLMTLRLWSS* (SEQ ID NO: 247) |
| 4400 TCR-N12 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSTGNTGELFFGEGSRLTVL*EDLRNVTPPKVSLFEPSKAEIANKQKATLVCLARG FFPDHVELSWWVNGKEVHSGVCTDPQAYKESNYSYCLSSRLRVSATFWHNPRNHFRC QVQFHGLSEEDKWPEGSPKPVTQNISAEAWGRADCGITSASYQQGVLSATILYEILLGK ATLYAVLVSTLVVMAMVKRKNS*RAKRSGSGATNFSLLKQAGDVEENPGP*MMKSL RVLLVILWLQLSWVWSQQKEVEQDPGPLSVPEGAIVSLNCTYSNSAFQYFMWY RQYSRKGPELLMYTYSSGNKEDGRFTAQVDKSSKYISLFIRDSQPSDSATYLCAM SYSGGGADGLTFGKGTHLI*IQPNIQNPEPAVYQLKDPRSQDSTLCLFTDFDSQINVPK TMESGTFITDKCVLDMKAMDSKSNGAIAWSNQTSFTCQDIFKETNATYPSSDVPCDAT LTEKSFETDMNLNFQNLLVIVLRILLLKVAGFNLLMTLRLWSS* (SEQ ID NO: 248) |
| 4400 TCR-N13 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASRVGNTGELFFGEGSRLTVL*EDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNS*RAKRSGSGATNFSLLKQAGDVEENPGP*MMKS LRVLLVILWLQLSWVWSQQKEVEQDPGPLSVPEGAIVSLNCTYSNSAFQYFMWY RQYSRKGPELLMYTYSSGNKEDGRFTAQVDKSSKYISLFIRDSQPSDSATYLCAM RANTDKLIFGTGTRLQVFPNIQNPEPAVYQLKDPRSQDSTLCLFTDFDSQINVPKTM ESGTFITDKCVLDMKAMDSKSNGAIAWSNQTSFTCQDIFKETNATYPSSDVPCDATLT EKSFETDMNLNFQNLLVIVLRILLLKVAGFNLLMTLRLWSS* (SEQ ID NO: 249) |
| 4400 TCR-C | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSPGTENSPLHFGNGTRLTVT*EDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNS*RAKRSGSGATNFSLLKQAGDVEENPGP*MSLS SLLKVVTASLWLGPGIAQKITQTQPGMFVQEKEAVTLDCTYDTSDPSYGLFWYK QPSSGEMIFLIYQGSYDQQNATEGRYSLNFQKARKSANLVISASQLGDSAMYFCA MRERTGTASKLTFGTGTRLQVTLNIQNPEPAVYQLKDPRSQDSTLCLFTDFDSQINV PKTMESGTFITDKCVLDMKAMDSKSNGAIAWSNQTSFTCQDIFKETNATYPSSDVPCD ATLTEKSFETDMNLNFQNLLVIVLRILLLKVAGFNLLMTLRLWSS* (SEQ ID NO: 250) |
| 4400 TCR-20 | MAIRLLCRVAFCFLAVGLVDVKVTQSSRYLVKRTGEKVFLECVQDMDHENMFW YRQDPGLGLRLIYFSYDVKMKEKGDIPEGYSVSREKKERFSLILESASTNQTSMY LCASSLGTFNQPQHFGDGTRLSIL*EDLRNVTPPKVSLFEPSKAEIANKQKATLVCLAR GFFPDHVELSWWVNGKEVHSGVCTDPQAYKESNYSYCLSSRLRVSATFWHNPRNHFR CQVQFHGLSEEDKWPEGSPKPVTQNISAEAWGRADCGITSASYQQGVLSATILYEILLG KATLYAVLVSTLVVMAMVKRKNS*RAKRSGSGATNFSLLKQAGDVEENPGP*MHLS SLLKVVTASLWLGPGIAQKITQTQPGMFVQEKEAVTLDCTYDTSDPSYGLFWYK QPSSGEMIFLIYQGSYDQQNATEGRYSLNFQKARKSANLVISASQLGDSAMYFCA MRERSGGSYIPTFGRGTSLIVHPNIQNPEPAVYQLKDPRSQDSTLCLFTDFDSQINVP KTMESGTFITDKCVLDMKAMDSKSNGAIAWSNQTSFTCQDIFKETNATYPSSDVPCDA TLTEKSFETDMNLNFQNLLVIVLRILLLKVAGFNLLMTLRLWSS* (SEQ ID NO: 251) |

Example 3

This example demonstrates that Jurkat cells transfected with mRNA encoding the 4400 TCR-A1 or 4400 TCR-A2 of Example 2 specifically recognize G13D.

Effector cells were a Jurkat cell line stably expressing luciferase under the transcriptional control of an NFAT promotor and also stably expressing the CD4 co-receptor. These cells were virally transduced with mRNA encoding a TCR alpha and beta chain generated according to the sequencing described for FIG. 3 (Example 1). The TCR was the 4400 TCR-A1 or 4400 TCR-A2 of Example 2 or the 4400 TCR-B1 or 4400 TCR-B2 identified in Example 1.

Transcription under the control of an NFAT promoter is activated by TCR stimulation. TCR stimulation increases intracellular calcium concentration and activates calcium channels. It is believed that the NFAT protein is then dephosporylated by calmoduin and translocates to the nucleus where it binds with the NFAT promoter sequence and activates downstream gene expression. By providing luciferase under the transcriptional control of an NFAT promoter, luciferase is expected to be expressed only when the TCR is stimulated by the target antigen.

Target cells were DC (i) transfected with full length G13D KRAS mRNA (G13D FL) (variant B) or the corresponding full length WT KRAS mRNA (WT FL) (variant B); pulsed with the G13D 25-mer peptide (G13D Mut LP) or the corresponding WT 25-mer peptide (G13 WT LP) of Example 1. Transfected cells co-cultured with DC treated with DMSO and Jurkat cells without TCR transfection served as negative controls.

The effector cells were co-cultured with target cells. Luciferase expression was measured by measuring luminescence units (FIG. 5). The results show that Jurkat cells transfected with 4400 TCR-A1 or 4400 TCR-A2 specifically recognize G13D.

Example 4

This example demonstrates that healthy donor PBL independently transduced with the retroviral vector encoding the 4400 TCR-A1, 4400 TCR-A2, 4400 TCR-E, 4400 TCR-J, or 4400 TCR-N of Example 2 specifically recognize G13D.

Effector cells were healthy donor PBL independently transduced with the retroviral vector encoding the 4400 TCR-A1, 4400 TCR-A2, 4400 TCR-E, 4400 TCR-J, or 4400 TCR-N of Example 2 or the 4400 TCR-B1 or 4400 TCR-B2.

Target cells were DC (i) transduced with full length G13D KRAS mRNA (G13D FL) (variant B) or the corresponding full length WT KRAS mRNA (WT FL) (variant B); (ii) pulsed with G13D 25-mer peptide (G13D Mut LP) or the corresponding WT 25-mer peptide (G13 WT LP) of Example 1; or (iii) pulsed with G12D 25-mer peptide (G12D Mut LP) or G12V 25-mer peptide (G12V Mut LP).

The effector cells were co-cultured with the target cells. Reactivity was tested by IFNγ-secretion using ELISpot assay (FIG. 6) and by measuring the expression of one or both of 4-1BB and OX40 by flow cytometry assay gated on (i) CD3+/mTCR+/CD8+ cells (FIG. 7A) or (ii) CD3+/mTCR+/CD4+ cells (FIG. 7B).

Example 5

This example demonstrates that the TCRs expressed by the retroviral vectors of Example 2 recognize G13D RAS presented by a HLA-DQ heterodimer.

The MHC Class II molecules expressed by Patient 4400 were determined using exome and mRNA sequencing. The expressed MHC Class II molecules are shown in FIG. 8.

HEK cells (target cells) were untransfected (control) or independently transfected with the HLA heterodimers shown in FIG. 8 (alpha and beta) and then were pulsed with the G13D 25-mer peptide of Example 1. The effector cells were healthy donor PBL independently transduced with the retroviral vector encoding the 4400 TCR-A1, 4400 TCR-A2, 4400 TCR-E, 4400 TCR-J, or 4400 TCR-N of Example 2. Effector cells cultured in the presence of anti-CD3/anti-CD28 Dynabeads served as a positive control. Reactivity was tested by IFNγ-secretion using ELISpot assay (FIG. 8) and by measuring the expression of one or both of 4-1BB and OX40 by flow cytometry assay gated on CD3+/mTCR+/CD4+ cells (FIG. 9).

As shown in FIGS. 8-9, reactivity was observed upon co-culture of the effector cells with target cells transduced with the HLA-DQA1*05:01/HLA-DQB1*03:01 heterodimer.

Example 6

This example demonstrates the avidity of the TCRs expressed by the retroviral vectors of Example 2.

Healthy donor PBL (effector cells) were independently transduced with the retroviral vector of Example 2 encoding the 4400 TCR-A1, 4400 TCR-A2, 4400 TCR-E, 4400 TCR-J, or 4400 TCR-N.

Autologous DCs (target cells) were loaded with the G13D 25-mer peptide or the corresponding WT 25-mer peptide of Example 1 at one of the various concentrations shown in FIGS. 10A-10C, 11A-11C, 12A-12C, 13A-13C, and 14A-14C. The cells were washed twice and co-cultured overnight with transduced cells at a ratio of 6e4 DC:5e4 T cells. Reactivity was tested by IFNγ-secretion using ELISpot assay (FIGS. 10A, 11A, 12A, 13A, and 14A) and by measuring the expression of one or both of 4-1BB and OX40 by flow cytometry assay gated on CD3+/mTCR+/CD4+ cells (FIGS. 10B, 11B, 12B, 13B, and 14B) or gated on CD3+/mTCR+/CD8+ cells (FIGS. 10C, 11C, 12C, 13C, and 14C).

Example 7

This example demonstrates that Jurkat cells transfected with 4400 TCR-A1, 4400 TCR-A2, 4400 TCR-A3, 4400 TCR-E, 4400 TCR-J2, 4400 TCR-N4, 4400 TCR-N12, or 4400 TCR-N13 of Example 2 specifically recognize G13D.

Effector cells were a Jurkat-NFAT-firefly luciferase CD4+/CD8+ cell line (described in Example 3) independently virally transduced with a retroviral vector encoding or one of the following TCRs described in Example 2: 4400 TCR-A1, 4400 TCR-A2, 4400 TCR-E, 4400 TCR-A3, 4400 TCR-J, 4400 TCR-J2, 4400 TCR-N, 4400 4400 TCR-N4, 4400 TCR-N12, or 4400 TCR-N13.

Target cells were DC autologous to Patient 4400 (i) transfected overnight with full length G13D KRAS mRNA (G13D FL) (variant B) or the corresponding full length WT KRAS mRNA (WT FL) (variant B); (ii) pulsed with the G13D 25-mer peptide (G13D Mut LP) or the corresponding WT 25-mer peptide (G13 WT LP) of Example 1. Mock transduction was used as a negative control.

Effector cells were co-cultured with target cells for 5 hours followed by lysis in the presence of luciferin reagent. Luminescence was then measured as described in Example 3. The results are shown in FIG. 15. The results show that Jurkat-NFAT firefly luciferase cells transfected with 4400 TCR-A1, 4400 TCR-A2, 4400 TCR-E, TCR-J, 4400 TCR-A3, 4400 TCR-J2, 4400 TCR-N, 4400 4400 TCR-N4, 4400 TCR-N12, or 4400 TCR-N13 specifically recognize G13D.

Example 8

This example demonstrates that the TCRs expressed by the retroviral vectors of Example 2 recognize G13D RAS presented by a HLA-DQ heterodimer.

The MHC Class II molecules expressed by Patient 4400 were determined using exome and mRNA sequencing. The expressed MHC Class II molecules are shown in FIG. 16.

COS7 cells (target cells) were independently transfected with the HLA heterodimers shown in FIG. 16 (alpha and beta) or with HLA DRA1 only and then were pulsed with the G13D 25-mer peptide of Example 1. The effector cells were the same as those described in Example 7. Effector cells were co-cultured with target cells for 5 hours. The cells were then tested for luciferase activity, as explained in Example 3. Untransduced Jurkat-NFAT firefly luciferase cells co-cultured with the same target cells served as a negative control. The results are shown in FIG. 16. As shown in FIG. 16, reactivity was observed upon co-culture of the effector cells with target cells transduced with the HLA-DQA1*05:01/HLA-DQB1*03:01 heterodimer.

Example 9

This example demonstrates the avidity of the TCRs expressed by the retroviral vectors of Example 2.

The effector cells were the same as those described in Example 7. Target cells were DCs autologous to Patient 4400 loaded with the G13D 25-mer peptide or the corresponding WT 25-mer peptide of Example 1 at one of the various concentrations shown in FIGS. 17A-17K. The cells were washed twice and co-cultured for 5 hours with the effector cells at a ratio of 6e4 target cells:1.5e5 effector cells. The cells were then tested for luciferase activity, as explained in Example 3.

The results are shown in FIGS. 17A-17J. FIG. 17K shows the results obtained following a control experiment, namely the same experiment as that which was carried out for FIGS. 17A-17J, except that the Jurkat-NFAT firefly luciferase cell line was virally transduced with a control plasmid (a backbone plasmid without the gene encoding a TCR). The results showed that the cells transduced with 4400 TCR-A1 (17A), 4400 TCR-A2 (17B), 4400 TCR-A3 (17C), 4400 TCR-J (17D), 4400 TCR-J2 (17E), 4400 TCR-E (17F), 4400 TCR-N (17G), 4400 TCR-N4 (17H), 4400 TCR-N12 (17I), or 4400 TCR-N13 (17J) specifically and avidly recognize G13D.

Example 10

This example demonstrates that the 4400 TCR-C and 4400 TCR-20 expressed by the retroviral vectors of Example 2 recognize G13D RAS presented by a HLA-DQ heterodimer.

COS7 cells (target cells) were transfected with the HLA-DQA1*05:01 and HLA-DQB1*03:01 heterodimer and then were pulsed with the G13D 25-mer peptide of Example 1. Effector cells were a Jurkat-NFAT-firefly luciferase CD4+/CD8+ cell line (described in Example 3) independently virally transduced with a retroviral vector encoding the 4400 ICR-C or 4400 TCR-20 described in Example 2. Effector cells were co-cultured with target cells for 5 hours. The cells were then tested for luciferase activity, as explained in Example 3. The effector cells were co-cultured with untransfected COS7 loaded with G13D 25-mer peptide as a negative control. The results are shown in FIG. 18. As shown in FIG. 18, reactivity was observed upon co-culture of the effector cells with target cells transduced with the HLA-DQA1*05:01/HLA-DQB1*03:01 heterodimer.

Example 11

This example demonstrates that healthy donor PBL independently transduced with the retroviral vector encoding the 4400 TCR-C or 4400 TCR-20 of Example 2 specifically recognize G13D.

Effector cells were healthy donor PBL independently transduced with the retroviral vector encoding the 4400 TCR-C or 4400 TCR-20 of Example 2. Target cells were autologous DC pre-loaded with G13D 25-mer peptide (G13D) or the corresponding WT 25-mer peptide of Example 1 at one of the various concentrations shown in FIGS. 19A-19D. The target cells were washed twice and co-cultured overnight with the effector cells at a ratio of 6e4 target cells:1e5 effector cells.

Reactivity was tested by measuring the expression of one or both of 4-1BB and OX40 by flow cytometry assay gated on (i) CD3+/mTCR+/CD8+ cells (FIGS. 19B and 19D) or (ii) CD3+/mTCR+/CD4+ cells (FIGS. 19A and 19C).

The results showed that PBL independently transduced with the retroviral vector encoding the 4400 TCR-C (FIGS. 19A-19B) or 4400 TCR-20 (FIGS. 19C-19D) of Example 2 specifically recognized G13D.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

---

The invention claimed is:

1. An isolated or purified T-cell receptor (TCR) having antigenic specificity for a mutated human RAS amino acid sequence with a substitution of glycine at position 13 with aspartic acid, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, wherein position 13 is defined by reference to the wild-type human KRAS, wild-type human HRAS, or wild-type human NRAS protein, respectively, and wherein the TCR comprises:

(a) all of SEQ ID NOs: 1-6,
(b) all of SEQ ID NOs: 11-16,
(c) all of SEQ ID NOs: 21-26,
(d) all of SEQ ID NOs: 31-36,
(e) all of SEQ ID NOs: 41-46,
(f) all of SEQ ID NOs: 119-124,
(g) all of SEQ ID NOs: 129-134,
(h) all of SEQ ID NOs: 139-144,
(i) all of SEQ ID NOs: 149-154,
(j) all of SEQ ID NOs: 159-164,
(k) all of SEQ ID NOs: 169-174, or
(l) all of SEQ ID NOs: 179-184.

2. An isolated or purified polypeptide comprising a functional portion of the TCR of claim 1, wherein the functional portion comprises the amino acid sequences of:

(a) all of SEQ ID NOs: 1-6,
(b) all of SEQ ID NOs: 11-16,
(c) all of SEQ ID NOs: 21-26,
(d) all of SEQ ID NOs: 31-36,
(e) all of SEQ ID NOs: 41-46,
(f) all of SEQ ID NOs: 119-124,
(g) all of SEQ ID NOs: 129-134,
(h) all of SEQ ID NOs: 139-144,
(i) all of SEQ ID NOs: 149-154,
(j) all of SEQ ID NOs: 159-164,
(k) all of SEQ ID NOs: 169-174, or
(l) all of SEQ ID NOs: 179-184.

3. An isolated or purified protein, comprising:

(a) a first polypeptide chain comprising the amino acid sequences of SEQ ID NOs: 1-3 and a second polypeptide chain comprising the amino acid sequences of SEQ ID NOs: 4-6;

(b) a first polypeptide chain comprising the amino acid sequences of SEQ ID NOs: 11-13 and a second polypeptide chain comprising the amino acid sequences of SEQ ID NOs: 14-16;

(c) a first polypeptide chain comprising the amino acid sequences of SEQ ID NOs: 21-23 and a second polypeptide chain comprising the amino acid sequences of SEQ ID NOs: 24-26;

(d) a first polypeptide chain comprising the amino acid sequences of SEQ ID NOs: 31-33 and a second polypeptide chain comprising the amino acid sequences of SEQ ID NOs: 34-36;

(e) a first polypeptide chain comprising the amino acid sequences of SEQ ID NOs: 41-43 and a second polypeptide chain comprising the amino acid sequences of SEQ ID NOs: 44-46;

(f) a first polypeptide chain comprising the amino acid sequences of all of SEQ ID NOs: 119-121 and a second polypeptide chain comprising the amino acid sequences of all of SEQ ID NOs: 122-124;

(g) a first polypeptide chain comprising the amino acid sequences of all of SEQ ID NOs: 129-131 and a second polypeptide chain comprising the amino acid sequences of all of SEQ ID NOs: 132-134;

(h) a first polypeptide chain comprising the amino acid sequences of all of SEQ ID NOs: 139-141 and a second polypeptide chain comprising the amino acid sequences of all of SEQ ID NOs: 142-144;

(i) a first polypeptide chain comprising the amino acid sequences of all of SEQ ID NOs: 149-151 and a second polypeptide chain comprising the amino acid sequences of all of SEQ ID NOs: 152-154;

(j) a first polypeptide chain comprising the amino acid sequences of all of SEQ ID NOs: 159-161 and a second polypeptide chain comprising the amino acid sequences of all of SEQ ID NOs: 162-164;

(k) a first polypeptide chain comprising the amino acid sequences of all of SEQ ID NOs: 169-171 and a second polypeptide chain comprising the amino acid sequences of all of SEQ ID NOs: 172-174; or (l) a first polypeptide chain comprising the amino acid sequences of all of SEQ ID NOs: 179-181 and a second polypeptide chain comprising the amino acid sequences of all of SEQ ID NOs: 182-184.

4. An isolated or purified nucleic acid comprising a nucleotide sequence encoding the TCR according to claim 1.

5. An isolated or purified nucleic acid comprising, from 5' to 3', a first nucleotide sequence and a second nucleotide sequence, wherein the first and second nucleotide sequence, respectively, encode the amino sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 47 and 48; 48 and 47; 49 and 50; 50 and 49; 125 and 126; 126 and 125; 127 and 128; 128 and 127; 135 and 136; 136 and 135; 137 and 138; 138 and 137; 145 and 146; 146 and 145; 147 and 148; 148 and 147; 155 and 156; 156 and 155; 157 and 158; 158 and 157; 165 and 166; 166 and 165; 167 and 168; 168 and 167; 175 and 176; 176 and 175; 177 and 178; 178 and 177; 185 and 186; 186 and 185; 187 and 188; 188 and 187; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; 86 and 85; 87 and 88; 88 and 87; 89 and 90; 90 and 89; 91 and 92; 92 and 91; 93 and 94; 94 and 93; 95 and 96; 96 and 95; 97 and 98; 98 and 97; 99 and 100; 100 and 99; 101 and 102; 102 and 101; 103 and 104; 104 and 103; 189 and 190; 190 and 189; 191 and 192; 192 and 191; 193 and 194; 194 and 193; 195 and 196; 196 and 195; 197 and 198; 198 and 197; 199 and 200; 200 and 199; 201 and 202; 202 and 201; 203 and 204; 204 and 203; 205 and 206; 206 and 205; 207 and 208; 208 and 207; 209 and 210; 210 and 209; 211 and 212; 212 and 211; 213 and 214; 214 and 213; 215 and 216; 216 and 215; 217 and 218; 218 and 217; 219 and 220; 220 and 219; 221 and 222; 222 and 221; 223 and 224; 224 and 223; 225 and 226; 226 and 225; 227 and 228; 228 and 227; 229 and 230; 230 and 229; 231 and 232; 232 and 231; 233 and 234; 234 and 233; 235 and 236; 236 and 235; 237 and 238; 238 and 237; 239 and 240; 240 and 239; 241 and 242; 242 and 241; 243 and 244; or 244 and 243.

6. The isolated or purified nucleic acid according to claim 5, further comprising a third nucleotide sequence interposed between the first and second nucleotide sequence, wherein the third nucleotide sequence encodes a cleavable linker peptide.

7. The isolated or purified nucleic acid according to claim 6, wherein the cleavable linker peptide comprises the amino acid sequence of RAKRSGSGATNFSLLKQAGDVEEN-PGP (SEQ ID NO: 105).

8. A recombinant expression vector comprising the nucleic acid according to claim 4.

9. The recombinant expression vector according to claim 8, which is a transposon or a lentiviral vector.

10. An isolated or purified TCR, polypeptide, or protein encoded by the nucleic acid according to claim 4.

11. An isolated or purified TCR, polypeptide, or protein that results from expression of the nucleic acid according to claim 4 in a cell.

12. An in vitro method of producing a host cell expressing a TCR that has antigenic specificity for the peptide of MTEYKLVVVGAGDVGKSALTIQLIQ (SEQ ID NO: 252), the method comprising contacting a cell with the vector according to claim 8 under conditions that allow introduction of the vector into the cell.

13. An isolated or purified host cell comprising the nucleic acid according to claim 4.

14. The host cell according to claim 13, wherein the cell is a human lymphocyte.

15. The host cell according to claim 13, wherein the cell is selected from the group consisting of a T cell, a natural killer T (NKT) cell, an invariant natural killer T (iNKT) cell, and a natural killer (NK) cell.

16. An isolated or purified population of cells comprising the host cell according to claim 13.

17. A method of producing a TCR, the method comprising culturing the host cell according to claim 13 so that the TCR is produced.

18. A pharmaceutical composition comprising (a) the population of cells according to claim 16 and (b) a pharmaceutically acceptable carrier.

19. A method of detecting the presence of cancer in a mammal, the method comprising:

(a) contacting a sample comprising cells of the cancer with the TCR according to claim 1, thereby forming a complex; and (b) detecting the complex, wherein detection of the complex is indicative of the presence of cancer in the mammal.

20. A method of inducing an immune response against cancer in a mammal, the method comprising administering to the mammal the population of cells according to claim 16 in an amount effective to induce the immune response against cancer in the mammal.

21. A method of treating or preventing cancer in a mammal, the method comprising administering to the mammal the population of cells according to claim 16 in an amount effective to treat or prevent cancer in the mammal.

* * * * *